(12) United States Patent
Smith et al.

(10) Patent No.: US 10,544,399 B2
(45) Date of Patent: *Jan. 28, 2020

(54) HIGHLY EFFICIENT INFLUENZA MATRIX (M1) PROTEINS

(71) Applicant: Novavax, Inc., Gaithersburg, MD (US)

(72) Inventors: Gale Smith, Germantown, MD (US); Yingyun Wu, Clarksburg, MD (US); Michael J. Massare, Mt. Airy, MD (US); Peter M. Pushko, Frederick, MD (US); Margaret Nathan, Montgomery Village, MD (US); Thomas Kort, Germantown, MD (US); Robin Robinson, Dickerson, MD (US)

(73) Assignee: Novavax, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/928,385

(22) Filed: Mar. 22, 2018

(65) Prior Publication Data

US 2019/0062713 A1 Feb. 28, 2019

Related U.S. Application Data

(63) Continuation of application No. 15/287,433, filed on Oct. 6, 2016, now Pat. No. 9,951,317, which is a continuation of application No. 14/628,513, filed on Feb. 23, 2015, now Pat. No. 9,464,276, which is a continuation of application No. 13/280,043, filed on Oct. 24, 2011, now Pat. No. 8,992,939, which is a continuation of application No. 13/032,571, filed on Feb. 22, 2011, now abandoned, which is a continuation of application No. 12/832,657, filed on Jul. 8, 2010, now abandoned, which is a continuation of application No. 12/558,844, filed on Sep. 14, 2009, now abandoned, which is a continuation-in-part of application No. 12/340,186, filed on Dec. 19, 2008, now Pat. No. 8,506,967, which is a continuation-in-part of application No. 11/582,540, filed on Oct. 18, 2006, now Pat. No. 8,080,255, which is a continuation-in-part of application No. 10/617,569, filed on Jul. 11, 2003, now Pat. No. 8,592,197.

(60) Provisional application No. 61/015,440, filed on Dec. 20, 2007, provisional application No. 60/845,495, filed on Sep. 19, 2006, provisional application No. 60/832,116, filed on Jul. 21, 2006, provisional application No. 60/831,196, filed on Jul. 17, 2006, provisional application No. 60/800,006, filed on May 15, 2006, provisional application No. 60/780,847, filed on Mar. 10, 2006, provisional application No. 60/727,513, filed on Oct. 18, 2005, provisional application No. 61/096,561, filed on Sep. 12, 2008.

(51) Int. Cl.
*C12N 7/00* (2006.01)
*C12N 9/24* (2006.01)
*A61K 39/12* (2006.01)
*C07K 14/005* (2006.01)
*A61K 39/00* (2006.01)

(52) U.S. Cl.
CPC ............... *C12N 7/00* (2013.01); *A61K 39/12* (2013.01); *C07K 14/005* (2013.01); *C12N 9/2402* (2013.01); *C12Y 302/01018* (2013.01); *A61K 2039/5258* (2013.01); *A61K 2039/55505* (2013.01); *A61K 2039/55555* (2013.01); *C07K 2319/01* (2013.01); *C07K 2319/03* (2013.01); *C12N 2710/14143* (2013.01); *C12N 2760/16122* (2013.01); *C12N 2760/16123* (2013.01); *C12N 2760/16134* (2013.01); *C12N 2760/16151* (2013.01); *C12N 2760/16171* (2013.01); *C12N 2760/16222* (2013.01); *C12N 2760/16223* (2013.01); *C12N 2760/16251* (2013.01); *C12N 2770/20022* (2013.01); *C12N 2770/20023* (2013.01); *C12N 2770/20051* (2013.01); *C12N 2800/22* (2013.01)

(58) Field of Classification Search
None
See application file for complete search history.

(56) References Cited

U.S. PATENT DOCUMENTS

| | | |
|---|---|---|
| 4,552,758 A | 11/1985 | Murphy et al. |
| 6,224,882 B1 | 5/2001 | Smith et al. |
| 6,649,372 B1 | 11/2003 | Palese et al. |
| 7,556,940 B2 | 7/2009 | Galarza et al. |
| 7,763,450 B2 | 7/2010 | Robinson et al. |
| 8,080,255 B2 | 12/2011 | Smith et al. |
| 8,506,967 B2 | 8/2013 | Smith et al. |

(Continued)

FOREIGN PATENT DOCUMENTS

| | | |
|---|---|---|
| EP | 0870508 A1 | 10/1998 |
| EP | 1644037 B1 | 12/2011 |

(Continued)

OTHER PUBLICATIONS

Latham et al. J Virol. vol. 75, pp. 6154-6165 (Year: 2001).*

(Continued)

*Primary Examiner* — Shanon A. Foley
*Assistant Examiner* — Myron G Hill
(74) *Attorney, Agent, or Firm* — Cooley LLP

(57) ABSTRACT

This invention discloses a method of increasing production of virus-like particles comprising expressing an avian influenza matrix protein. The invention also comprises methods of making and using said VLPs.

20 Claims, 66 Drawing Sheets

Specification includes a Sequence Listing.

(56) References Cited

U.S. PATENT DOCUMENTS

| | | | |
|---|---|---|---|
| 8,551,756 B2 * | 10/2013 | Smith | A61K 39/145 435/235.1 |
| 8,592,197 B2 | 11/2013 | Robinson et al. | |
| 8,951,537 B2 | 2/2015 | Smith et al. | |
| 8,992,939 B2 * | 3/2015 | Smith | A61K 39/12 424/209.1 |
| 9,050,290 B2 | 6/2015 | Smith et al. | |
| 9,144,607 B2 | 9/2015 | Robinson et al. | |
| 9,180,180 B2 | 11/2015 | Smith et al. | |
| 9,464,276 B2 | 10/2016 | Smith et al. | |
| 9,474,799 B2 | 10/2016 | Robinson et al. | |
| 9,623,104 B2 | 4/2017 | Smith et al. | |
| 9,694,066 B2 | 7/2017 | Smith et al. | |
| 9,937,253 B2 | 4/2018 | Smith et al. | |
| 9,956,280 B2 | 5/2018 | Robinson et al. | |
| 2003/0035814 A1 | 2/2003 | Kawaoka et al. | |
| 2005/0009008 A1 | 1/2005 | Robinson et al. | |
| 2006/0263804 A1 | 11/2006 | Robinson et al. | |
| 2007/0184526 A1 | 8/2007 | Smith et al. | |
| 2010/0129401 A1 | 5/2010 | Smith et al. | |
| 2012/0207786 A1 | 8/2012 | Smith et al. | |
| 2013/0039938 A1 | 2/2013 | Smith et al. | |
| 2013/0177587 A1 | 7/2013 | Robinson et al. | |
| 2013/0295135 A1 | 11/2013 | Smith et al. | |
| 2014/0193447 A1 | 7/2014 | Smith et al. | |
| 2015/0306206 A1 | 10/2015 | Robinson et al. | |
| 2015/0307849 A1 | 10/2015 | Smith et al. | |
| 2015/0374813 A1 | 12/2015 | Smith et al. | |

FOREIGN PATENT DOCUMENTS

| | | |
|---|---|---|
| WO | WO 95/22989 A1 | 8/1995 |
| WO | WO 96/10633 A1 | 4/1996 |
| WO | WO 96/37624 A1 | 11/1996 |
| WO | WO 01/00684 A1 | 1/2001 |
| WO | WO 02/00885 A2 | 1/2002 |
| WO | WO 03/048348 A2 | 6/2003 |
| WO | WO 03/051835 A2 | 6/2003 |
| WO | WO 2005/020889 A2 | 3/2005 |

OTHER PUBLICATIONS

"New Strain of Avian Influenza Now Found to Infect Humans," Medscape [online] (Mar. 22, 2006) htttp://www.medscape.com/viewarticle/528258_print.

"Section 1. Past Achievements and Future Needs," Vaccines, Vaccination and the Immune Response, pp. 1-45, by Gordon Ada, Alistair Ramsay (1997).

Ali et al., "Influenza Virus Assembly: Effect of Influenza Virus Glycoproteins on the Membrane Association of M1 Protein," J. Virol. 74:8709-8719 (2000).

Avalos et al., "Association of Influenza Virus NP and M1 Proteins with Cellular Cytoskeletal Elements in Influenza Virus-Infected Cells," J. Virol. 71:2947-2958 (1997).

Belser et al., "The ferret as a model organism to study influenza A virus infection," Dis. Model. Mech. 4(5):575-579 (2011).

Bender et al., "Characterization of the Surface Proteins of Influenza A (H5N1) Viruses Isolated from Humans in 1997-1998," Virology 254:115-123 (1999).

Berglund et al., "Immunization with Recombinant Semlike Forest Virus Induces Protection Against Influenza Challenge in Mice," Vaccine 17:497-507 (1999).

Bright et al., "Cross-Clade Protective Immune Responses to Influenza Viruses with H5N1 HA and NA Elicited by an Influenza Virus-Like Particle," PLOS One, Public Library of Science 3:1501 (2008).

Bucher et al., "Incorporation of Influenza Virus M-Protein into Liposomes," J. Virol. 36:586-590 (1980).

Bucher et al., "M Protein (M1) of Influenza Virus: Antigenic Analysis and Intracellular Localization with Monoclonal Antibodies," J. Virol. 63:3622-3633 (1989).

Bullido et al., "Several Protein Regions Contribute to Determine the Nuclear and Cytoplasmic Localization of the Influenza A Virus Nucleoprotein," J. Gen. Virol. 81:135-142 (2000).

Burleigh et al., "Influenza A Viruses with Mutations in the M1 Helix Six Domain Display a Wide Variety of Morphological Phenotypes," J. Virol. 79(2):1262-1270 (2005).

Castrucci et al., "Reverse Genetics System for Generation of an Influenza A Virus Mutant Containing a Deletion of the Carboxyl-Terminal Residue of M2 Protein," J. Virol. 69:2725-2728 (1995).

Chambers et al., "A single dose of killed Mycobacterium bovis BCG in a novel class of adjuvant (Novasome™) protects guinea pigs from lethal tuberculosis," Vaccine 22:1063-1071 (2004).

Chen et al., "Avian flu: H5N1 virus outbreak in migratory waterfowl," Nature 436:191-192 (2005).

Chen et al., "Comparison of the ability of viral protein-expressing plasmid DNAs to protect against influenza," Vaccine 16:1544-1549 (1998).

Chen et al., "Enhanced protection against a lethal influenza virus challenge by immunization with both hemagglutinin- and neuraminidase- expressing DNAs," Vaccine 17:653-659 (1999).

Chen et al., "The Evolution of H5N1 Influenza Viruses in Ducks in Southern China," Proc. Natl. Acad. Sci. USA 101:10452-10457 (2004).

Chen et al., "Influenza Virus Hemagglutinin and Neuraminidase, but Not the Matrix Protein, Are Required for Assembly and Budding of Plasmid-Derived Virus-Like Particles," J. Virol. 81(3):7111-7123 (2007).

Cox and Coulter, "Adjuvants—A Classification and Review of Their Modes of Action," Vaccine 15:248-256 (1997).

Crawford et al., "Baculovirus-Derived Hemagglutinin Vaccines Protect Against Lethal Influenza Infections by Avian H5 and H7 Subtypes," Vaccine 17:2265-2274 (1999).

Crowther et al., "Three-Dimensional Structure of Hepatitis B. Virus Core Particles Determined by Electron Cryomicroscopy," Cell 77:943-950 (1994).

Das et al., "Structural basis for suppression of a host antoviral response by influenza A virus," Proc. Natl. Acad. Sci. USA 105:13093-13098 (2008).

Database UniProt [Online] Oct. 1, 2004 (Oct. 1, 2004), Hongbo Z et al.: "Matrix protein 1" XP002526328 retrieved from http://www.uniprot.org/uniprot/q6b3p4 Database accession No. Q6B3P4.

Database UniProt [Online] Jul. 11, 2006 (Jul. 11, 2006), Hoffmann E et al.: "Hemagglutinin" XP002526332 retrieved from http://www.uniprot.org/uniprot/q195d4 Database accession No. Q195D4.

Database UniProt [Online] Sep. 13, 2005 (Sep. 13, 2005), Chen H et al.: "Neuramidase" XP002526329 retrieved from http://www.uniprot.org/uniprot/q4fb59 Database accession No. Q4FB59.

Database UniProt [Online] Aug. 16, 2004 (Aug. 16, 2004), Li Ks et al.: "Hemagglutinin" XP002526330 retrieved from http://www.uniprot.org/uniprot/q6dq47 Database accession No. Q6DQ47.

Database UniProt [Online] Oct. 25, 2004 (Oct. 25, 2004), Li Ks et al.: "Neuramidase" XP002526331 retrieved from http://www.uniprot.org/uniprot/q6dph6 Database accession No. Q6DPH6.

Ebel, Search Report and Written Opinion, 9 pages, from Singapore Patent Appl. No. 200701731-2 (dated Feb. 25, 2010).

Elster et al., "Influenza Virus MI Protein Binds to RNA Through Its Nuclear Localization Signal", J. Gen. Virol. 78:1589-1956 (1997).

Enami and Enami, "Influenza Virus Hemagglutinin and Neuraminidase Glycoproteins Stimulate the Membrane Association of the Matrix Protein," J. Virol. 70:6653-6657 (1996).

Fodor et al., "Rescue of Influenza A Virus from Recombinant DNA," J. Virol. 73:9679-9682 (1999).

Galarza et al., "Virus-Like Particle (VLP) Conferred Complete Protection Against a Lethal Influenza Virus Challenge," Viral Immunol. 18:244-251 (2005).

Galarza et al., "Virus-Like Particle Vaccine Conferred Complete Protection Against a Lethal Influenza Virus Challenge," Viral Immunol. 18:365-372 (2005).

Germann et al., "Mitigation Strategies for Pandemic Influenza in the United States," Proc. Natl. Acad. Sci. USA 103:5935-5940 (2006).

Gómez-Puertas et al., "Efficient Formation of Influenza Virus-Like Particles: Dependence on the Expression Levels of Viral Proteins," J. Gen. Virol. 80:1635-1645 (1999).

(56) References Cited

OTHER PUBLICATIONS

Gómez-Puertas et al., "Influenza Virus Matrix Protein is the Major Driving Force in Virus Budding," J. Virol. 74:11538-11547 (2000).
Gregoriadis et al., "Vaccine Entrapment in Liposomes," Methods 19:156-162 (1999).
Gupta et al., "Adjuvant properties of non-phospholipid liposomes (Novasomes) in experimental animals for human vaccine antigens," Vaccine 14:219-225 (1996).
Hatta and Kawaoka, "A clue to the molecular mechanism of virulence of highly pathogenic H5N1 avian influenza viruses isolated in 2004," Virus 55:55-62 (2005) abstract attached.
Hatta et al., "Special topic, Mechanism of infection, Mechanism of defense, Pathogenesis of Hong Kong H5N1 influenza virus, Why did avian influenza viruses affected humans?" Cell Technol. 21(2):192-197 (2002).
Heiduschat, "Supplementary European Search Report," 12 pages, from EP Appl. No. 06826264.1, European Patent Office, Munich, Germany (dated May 28, 2009).
Hirata Clinic, "Influenza Q&A," http://web.archive.org/web/20010427013049//http://www5a.biglobe.ne.jp/~hiracli/QA.htm (2001).
Hoffmann et al., "A DNA Transfection System for Generation of Influenza A Virus from Eight Plasmids," Proc. Natl. Acad. Sci. USA 97:6108-6113 (2000).
Huylebroeck et al., "High-level transient expression of influenza virus proteins from a series of SV40 late and early replacement vectors," Gene 66:163-181 (1988).
Itamura, "Development of influenza vaccines against newly emerging A/H5N1 virus," Nippon Rinsho 58:255-264 (2000) abstract front.
Johansson, "Immunization with Influenza A Virus Hemagglutinin and Neuraminidase Produced in Recobinant Baculovirus Results in a Balanced and Broadened Immune Response Superior to Conventional Vaccine," Vaccine 17:2073-2080 (1999).
Korsman, "Vaccines," Chapter 6, pp. 127-149 in: Influenza Report 2006; Eds. Bernd Sebastian Kamps, Christian Hoffmann and Wolfgang Preiser; Mar. 24, 2006.
Kretzschmar et al., "Membrane Association of Influenza Virus Matrix Protein Does Not Require Specific Hydrophobic Domains or the Viral Glycoproteins," Virol. 220:37-45 (1996).
Kuroda et al., "Expression of the Influenza virus Haemagglutinin in Insect Cells by a Baculovirus Vector," EMBO J. 5:1359-1365 (1986).
Lakey et al., "Recombinant Baculovirus Influenza A Hemagglutinin Vaccines are Well Tolerated and Immunogenic in Healthy Adults" J. Infect. Dis. 174:838-841 (1996).
Latham and Galarza, "Formation of Wild-Type and Chimeric Influenza Virus-Like Particles Following Simultaneous Expression of Only Four Structural Proteins," J. Virol. 75:6154-6165 (2001).
Li et al., "Chimeric Influenza Virus Induces Neutralizing Antibodies and Cytotoxic T Cells Against Human Immunodeficiency Virus Type 1," J. Virol. 67:6659-6666 (1993).
Li et al., "Genesis of a highly pathogenic and potentially pandemic H5N1 influenza virus in eastern Asia," Nature 430:209-213 (2004).
Li et al., "Recombinant Influenza A Virus Vaccines for the Pathogenic Human A/Hong Kong/97 (H5N1 Viruses)," J. Infect. Dis. 179:1132-1138 (1999).
Li et al., Matrix protein 1 [Influenza A virus (A/Dk/HN/5806/2003(H5N1))], Genbank AAT70589.1 published on Jul. 16, 2004.
Lin et al., "Avian-to-human transmission of H9N2 subtype influenza A viruses: Relationship between H9N2 and H5N1 human isolates," Proc. Natl. Acad. Sci. USA 97(17):9654-9658 (2000).
Logrippo, "Investigations of the use of beta-propiolactone in virus inactivation," Ann. N.Y. Acad. Sci. 83:578-594 (1960).
Lyles et al. "Subunit Interactions of Vesicular Stomatitis Virus Envelope Glycoprotein Stablilized by Binding to Viral Matrix Protein," J. Virol. 66:349-358 (1992).
Matassov et al., "A Novel intranasal Virus-Like Particle (VLP) Vaccine Designed to Protect against the Pandemic 1918 Influenza A Virus (H1N1)," Viral Immunol. 20:441-452 (2007).

Matsuda, "Notice of Reasons for Rejection," 3 pages, Japan Patent Appl. No. 2006-518925, with 4 page translation (dated Mar. 17, 2010).
Mena et al., "Rescue of a Synthetic Chloramphenicol Acetyltransferase RNA into Influenza Virus-Like Particles Obtained from Recombinant Plasmids," J. Virol. 70:5016-5024 (1996).
Murphy and Webster, Orthomyxoviruses, Fields Virology, Third Edition, vol. 1, pp. 1397-1445 (1996).
NCBI Accession No. CY014173, "Influenza A virus (A/Indonesia/5/2005 (H5N1)) segment 7 sequence," 3 pages (available Aug. 30, 2006).
Nerome et al., "Development of a new type of influenza subunit vaccine made by muramyldipeptide-liposome: enhancement of humoral and cellular immune responses," Vaccine 8:503-509 (1990).
Neumann et al., "An Improved Reverse Genetics System for Influenza A Virus Generation and its Implications for Vaccine Production," Proc. Natl. Acad. Sci. USA 102:16825-16829 (2005).
Neumann et al., "Generation of Influenza A Viruses Entirely from Cloned cDNAs," Proc. Natl. Acad. Sci. USA 96:9345-9350 (1999).
Neumann et al., "Plasmid-Driven Formation of Influenza Virus-Like Particles," J. Virol. 74:547-551 (2000).
Olsen et al., "Immunogenicity and Efficacy of Baculovirus-Expressed and DNA-Based Equine Influenza Virus Hemagglutinin Vaccines in Mice," Vaccine 15:1149-1156 (1997).
Ottolini et al,. "The cotton rat provides a useful small-animal model for the study of influenza virus pathogenesis," J. Gen. Virol. 86(Pt 10):2823-2830 (2005).
Palese, "Making Better Influenza Vaccines?" Emerg. Infect. Dis. 12:61-65 (2006).
Park et al., "The M2 Ectodomain is Important for Its Incorporation into Influenza A Virions," J. Virol. 72(3):2449-2455 (1998).
Park, Man-Seong, et al., "Engineered Viral Vaccine Constructs with Dual Specificity: Avian Influenza and Newcastle Disease," Proc. Natl. Acad. Sci. USA 103:8203-8208 (2006).
Pattnaik et al., "Formation of Influenza Virus particles Lacking Hemagglutinin on the Viral Envelope," J. Virol. 60:994-1001 (1986).
Peiris et al., "Cocirculation of Avian H-N2 and Contemporary "Human" H3N2 Influenza A Viruses in Pigs in Southeastern China: Potential for Genetic Reassortment?" J. Virol. 75:9679-9686 (2001).
Peradze et al., "Anti-influenza prophylactic formulations," 1986, Moscow, Meditsina, pp. 218-225.
Piedra et al., "Herd Immunity in Adults Against Influenza-Related Illnesses with use of the Trivalent-Live Attenuated Influenza Vaccine (CAIV-T) in Children," Vaccine 23:1540-1548 (2005).
Pleschka et al., "A Plasmid-Based Reverse Genetics System for Influenza A Virus," J. Virol. 70:4188-4192 (1996).
Plotnicky et al., "The immunodominant influenza matrix T cell epitope recognized in human induces influenza protection in HLA-A2/K$^b$ transgenic mice," Virology 309:320-329 (2003).
Pumpens and Grens, "Artificial Genes for Chimeric Virus-Like Particles," Artificial DNA (Khudyakov, Y.E., and Fields, H.A., Eds.) pp. 249-327, CRC Press, New York (2003).
Pushko et al., "Influenza Virus-Like Particles Comprised of the HA, NA, and M1 proteins of H9N2 Influenza Virus Induce Protective Immune Responses in BALB/c Mice," Vaccine 23:5751-5759 (2005).
Pushko et al., "Replicon-Helper Systems from Attenuated Venezuelan Equine Encephalitis Virus: Expression of Heterologous Genes in Vitro and Immunization Against Heterologous Pathogens in Vivo," Virology 239:389-401 (1997).
Roldao et al., "Virus-like particles in vaccine development," Expert Rev. Vaccines 9(10):1149-1176 (2010).
Saito et al., "Characterization of a human H9N2 influenza virus isolated in Hong Kong," Vaccine 20:125-133 (2001).
Search Report, SG appl. No. 2014012868, 7 pages (dated Feb. 15, 2016).
Slepushkin et al., "Protection of Mice Against Influenza A Virus Challenge by Vaccination With Baculovirus-Expressed M2 Protein," Vaccine 13:1399-1402 (1995).
Smith et al., U.S. Appl. No. 12/558,844, filed Sep. 14, 2009.
Smith et al., U.S. Appl. No. 12/832,657, filed Jul. 8, 2010.
St. Angelo et al., "Two of the Three Influenza Viral Polymerase Proteins Expressed by Using Baculovirus Vectors Form a Complex in Insect Cells," J. Virol. 61:361-365 (1987).

(56) References Cited

OTHER PUBLICATIONS

The Patent Office of the People's Republic of China, "The Decision of Final Rejection of the Application," 4 pages, from China Patent Appl. No. 200480026152.3 (dated May 20, 2010).

Tian et al., "Study and Use of Avian Flu H5 and H9 Bivalent Inactivated Vaccines (Strains H5N1 Re-1 and H9N2 Re-2)," Symposia of the 6th Symposium of the Branch of Biotechnology of Veterinary and Animal Husbandry of Chinese Association of Animal Science and Veterinary Medicine and the Branch of Veterinary Immunology of Chinese Society for Immunologypp. 42-47 (2005.

Tobita et al., "Spontaneous Excretion of Virus from MDCK Cells Persistently Infected with Influenza Virus A/PR/8/34," J. Gen. Virol. 78:563-566 (1997).

Treanor et al., "Evaluation of a Recombinant Hemagglutinin Expressed in Insect Cells as an Influenza Vaccine in Young an Elderly Adults," J. Infect. Dis. 173:1467-1470 (1996).

Treanor et al., "Safety and Immunogenicity of an Inactivated Subvirion Influenza A (H5N1) Vaccine," N. Engl. J. Med. 354:1343-1351 (2006).

Tsuji et al, "Recombinant Sindbis Viruses Expressing a Cytotoxic T-Lymphocyte Epitope of a Malaria Parasite or of Influenza Virus Elicit Protection Against the Corresponding Pathogen in Mice," J. Virol. 72:6907-6910 (1998).

Ulmer et al., "Heterologous Protection Against Influenza by Injection of DNA Encoding a Viral Protein," Science 259:1745-1749 (1993).

Ulmer et al., "Protective CD4+ and CD8+ T Cells against Influenza Virus Induced by Vaccination with Nucleoprotein DNA," J. Virol. 72:5648-5653 (1998).

UniProt Accession No. Q6DPY4 Matrix protein 1 of Influenza A virus A/Ck/Indonesia/4/2004(H5N1)), Aug. 16, 2004, 6 pages, http://www.uniprot.org/uniprot/Q6DPY4.

UniProt Accession No. Q1WDM0, Hemagglutinin of Influenza A virus (A/Anhui/1/2005(H5N1)), May 2, 2006, http://www.uniprot.org/uniprot/Q1WDM0.

UniProt Accession No. Q4FB63, Neuraminidase of Influenza A virus (A/BarheadedGoose/Qinghai/60/05(H5N1)), Aug. 30, 2005, http://www.uniprot.org/uniprot/Q4FB63.

Unknown, Rinsho to Kenkyuu 81:1899-1903 (2004).

Watanabe et al., "Immunogenicity and Protective Efficacy of Replication-Incompetent Influenza Virus-Like Particles," J. Virol. 76:767-773 (2002).

Watatabe et al., "Influenza A Virus Can Undergo Multiple Cycles of Replication without M2 Ion Channel Activity," J. Virol. 75(12):5656-5662 (2001).

Welsh, "Examiner's first report on patent application No. 2004268510," 3 pages, from Australian Patent Appl. No. 2004268510 (dated Feb. 5, 2010).

Wiebke, "Communication pursuant to Article 94(3) EPC," 4 pages, from EP Appl. No. 04786052.3, European Patent Office, Munich, Germany (mailed Mar. 19, 2010).

Wiebke, "Communication pursuant to Article 94(3) EPC," 7 pages, from EP Appl. No. 04786052.3, European Patent Office, Munich, Germany (mailed Sep. 15, 2008).

Wiebke, "European Search Report," 8 pages, from EP Appl. No. 10010286.2, European Patent Office, Munich, Germany (dated May 23, 2011).

Wiebke, "Supplementary European Search Report," 6 pages, from EP Appl. No. 04786052.3, European Patent Office, Munich, Germany (dated Mar. 26, 2008).

Wood et al., "Preparation of Vaccines Against H5N1 Influenza," Vaccine, 20:S84-S87 (2002).

Written Opinion, SG appl. No. 2014012868, 7 pages (dated Feb. 15, 2016).

Yasuda et al., "Growth Control of Influenza A Virus by MI Protein: Analysis of Transfectant Viruses Carrying the Chimeric M Gene," J. Virol. 68:8141-8146 (1994).

Ye et al., "Nucleus-Targeting Domain of the Matrix Protein (MI) of Influenza Virus," J. Virol. 69:1964-1970 (1995).

Zhang and Lamb, "Characterization of the Membrane Association of the Influenza Virus Matrix Protein in Living Cells," Virol. 225:225-266 (1996).

Zhao et al., "The M1 and NP Proteins of Influenza A Virus Form Homo- but not Heterooligomeric Complexes when Coexpressed in BHK-21 Cells," J. Gen. Virol. 79:2435-2446 (1998).

Zhou et al., "Generation of Cytotoxic and Humoral Immune-Responses by Non-replicative Recombinant Semlike Forest Virus," Proc. Natl. Acad. Sci. USA 92:3009-3013 (1995).

Zitzow et al., "Pathogenesis of Avian Influenza A (H5N1) Viruses in Ferrets," J. Virol. 76(9):4420-4439 (2002).

* cited by examiner

Fig. 1

ATGAATCCAAATCAAAAGATAATAGCACTTGGCTCCTGTTTCTATAACTATTGGACAATATG
TTTACTCATGCAGAATTGCCATCTTAGCAACGACTATGACACTACATTTCAATGAATGTACCA
ACCCATCGAACAATCAAGCAGTGCCATGTGAACCAATCATATAGAAGAGGAACATAACAGAG
ATAGTGCATTTCAATTAATACTACCATACAGACAGGAACAAGTTCTCCTAAAGTAGCAGATACAA
GAATTGGTCAAAACCGCATGTCAAATTACAGGGTTCGGCCCTTTCTCCAAGGACAACTCAA
TTAGGCTTTCTGCAGGCGGGATATTTGGGTGACAAGAGACCTTATGTATGTGTGGGTCTT
GGTAAATGTTACCAATTTGCACTTGGGCAGGGAACCACTTTGAACAACAAACACTCAAATGG
CACAATACATGATAGGAGTCCCCCATAGAACCCTTTTAATGAACGAGTGGGTTCCATTTC
ATTTGGGACCAAACAAGTGTGCATAGCATGTCCAGCTCAAGCTGCCATGGGAAGGCA
TGGTTACATGTTTCTGTCACTGGGCGATGATAGACAAATGCGACTCCTAGCAATCATTATGATGC
GATGCTTACCCACACTATTGGTTCATCGTCTAAGACAATCATCCCAGAACTCAGGAGTCAGAAT
GCGTTGCATCGACTTGTACACTTGTAATGACTGATGCAGTGCATCAGGAGTGCAAGGCT
GATACTAAAATACTATTCATTACAGAAGGGAAAATTGTCCACATTGGTCCACTGTCAGGAAAG
TGCTCAGGAATGTGGAGGATGTCCTGTTACCCCGGTATCCAGAAGTTAGATGTGTTTGCA
CAGACAATTGCAAGGGCTCCAATAGGACTTGTTGGCGACACACCCAAGAAATGACGATAGCTCCAG
GATTCTAGTTATGTGTCCAGGGATCCTAATAACGAGAGAACAATCAAGAAAGAGATTGGCGCTGGCCT
CAGCAGTAACTGCAGGGATCCTAATAACGGATCGGACCAACAATCAAGAAGATTCGGCGCTCTGTAT
TTGACAATGGAATGATGTTGGTTGCATGGGACGGACCAAGTCACAGTCACAAATAAATAGGCA
GAGACTTTCAGGGTCGTTGGTGGTTGGACTACGGCTCTCGGGTATTCTGGTATATTCTCTGTTGAAGGAAAAA
AGTCATAGTTGACAGTGATAACTGGTCTCGGGAGTTGATAACGAGGAGACCACAGGAGACCAGAGTA
CCTGCATCAACAGGTGTTTTTATGTCGAGTTGATAAGAGGAGACCACAGGAGACCAGAGTA
TGGTGGACTTCAAATACCATCATTCGTATTTTCTCGACTCAGCTACCTACGAACGAACAGGTTC
ATGGGCCCATGCAGCCGAATATCAATTCATGTCTATATAA

```
ATGAGTCTTCTAACCGAGGTCGAAACGTACGTTCTCTCTATCATCAGGCCCCTCAA
AGCCGAGATGGCGCAGAGACTTGAGGATGTTTTTGCAGGGAAGAACACAGATCTTGAGCTC
TCATGGAATGGCTAAAGACAAGACCAATCCTGTCACCTCTGACTAAGGGATTTTAGGGTTT
GTGTTCACGGCTCACCGTGCCAGTGAGCGAGGACTGCAGCGTAGACGATTTGTCCAAAATGC
CCTAAATGGGAATGGAGAGCCAAACAACATGGACAGGGCAGTTAAACTATACAAGAAGCTGA
AGAGGGAAATGACATTCCATGGAGCAAGGAAGTTGCACTCAGTTACTCAACTGGTGCGCTT
GCCACTTGCCATGGCTCCATATACAACGGATGGAAACAGTGACCACGGTCCCACAGGCACATGG
CCTAGTATGTGCCACTTGTGAACAGATTCCTGATGCCCACCAGATGGTACTAGCCAAGCACTACGGCT
CGACTACCACCAACCCACTAATCAGGCATGAGAACAGATGGCAGGCAGAATGGAGTCCAGTGCAAG
AAGGCCATGGAGCAGATGGCTGGATCAAGTGAGGACAATTGGGACTCACCCTAGTTCCAGTGCAG
TCAGGCTAGGCAAATGGTGCAGGCTATGAGGACAATTTGCAGGCTTACCGAAAGCGGATGGGAGTGGAGTGCAAATG
GTCTAAAAGATGATCTTATTGAAAAATTTCGAGGCTTACCAGAAACGGATGGGAGTGGAGTGCAAATG
CAGAGATTCAAGTGA
```

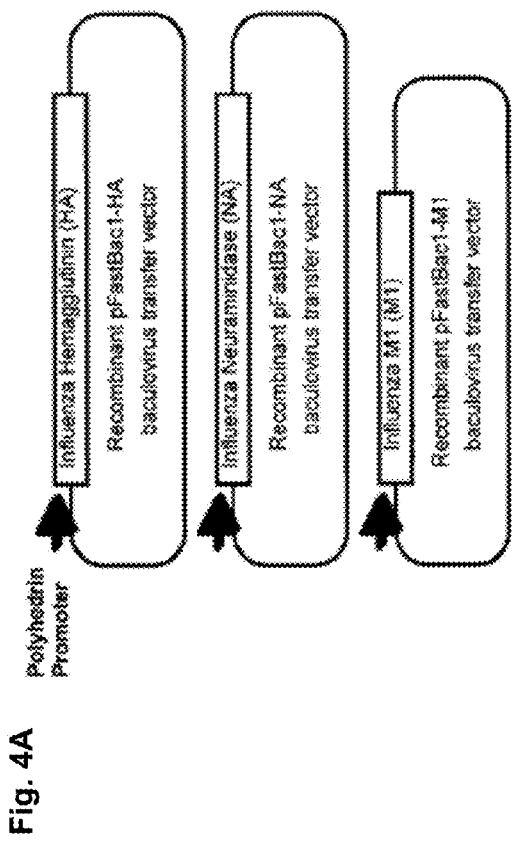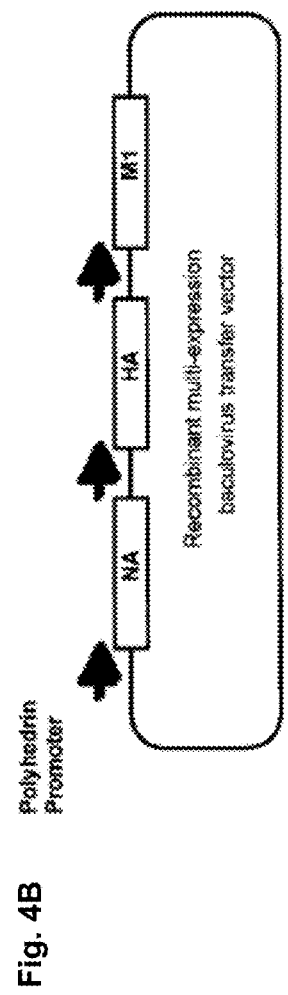
Fig. 4A
Fig. 4B

Fig. 11

| Study Day | -1 | 0 | 27 | 28 | 54 |
|---|---|---|---|---|---|
| | Pre-bleed | Primary Immunization | Primary Bleed | Booster Immunization | Secondary Bleed |

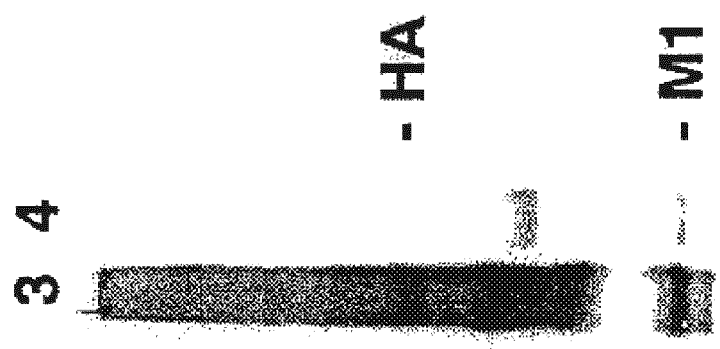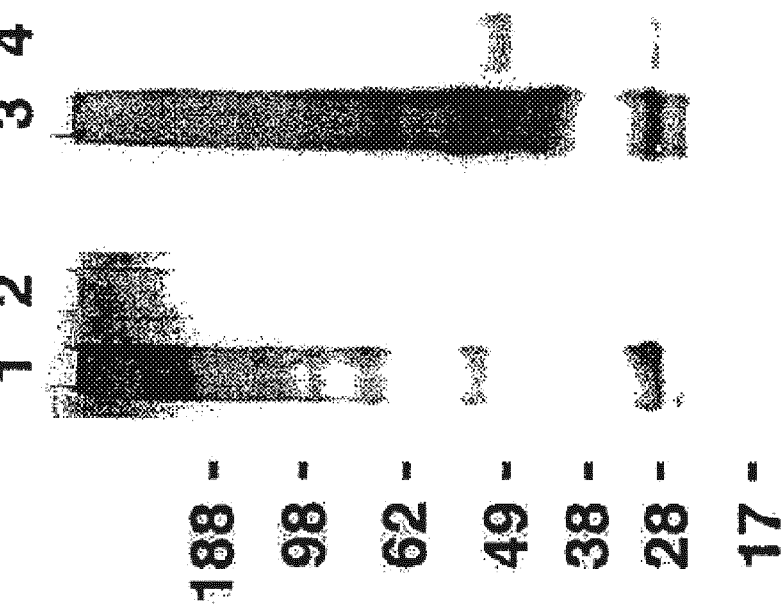

Fig. 16

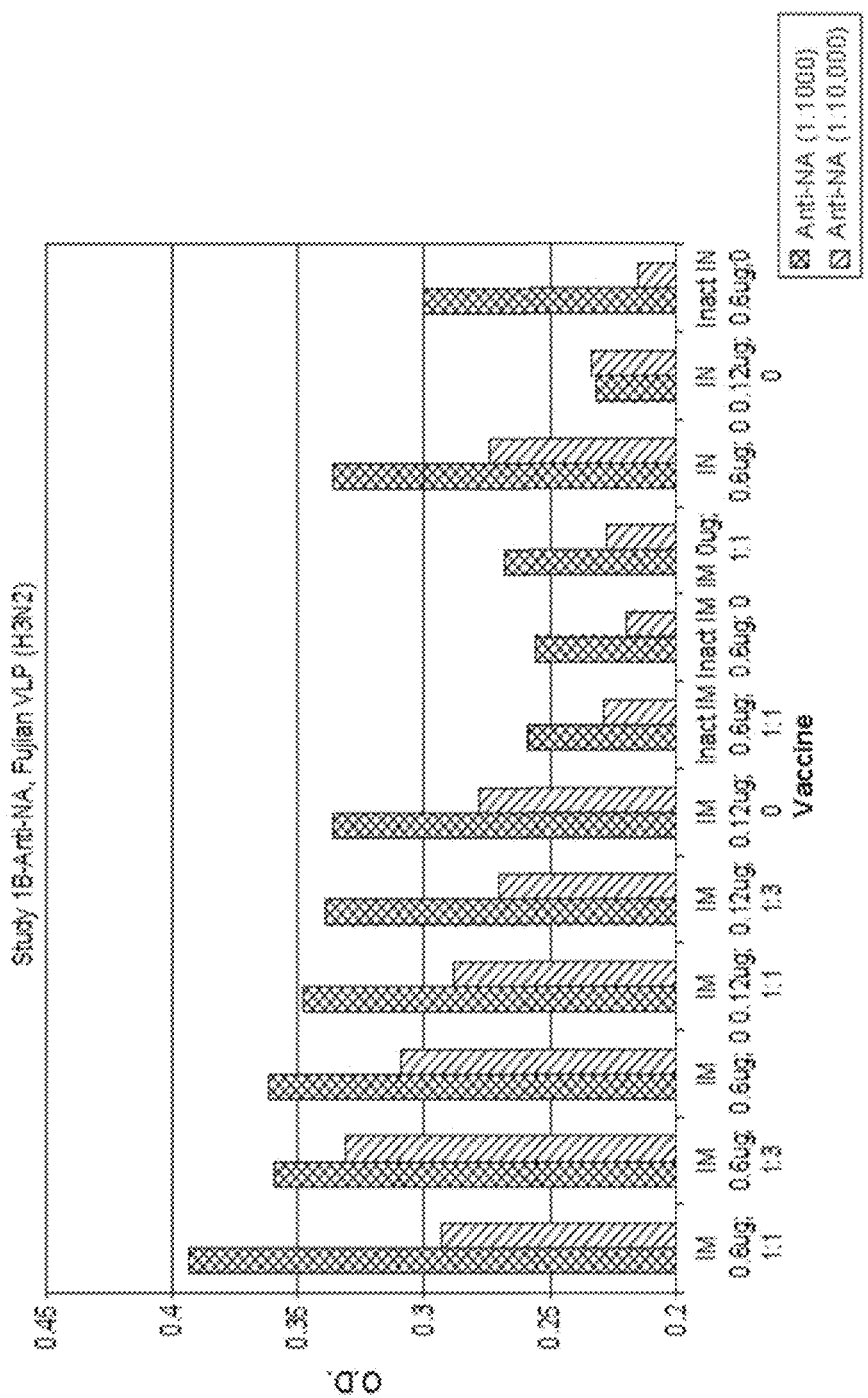

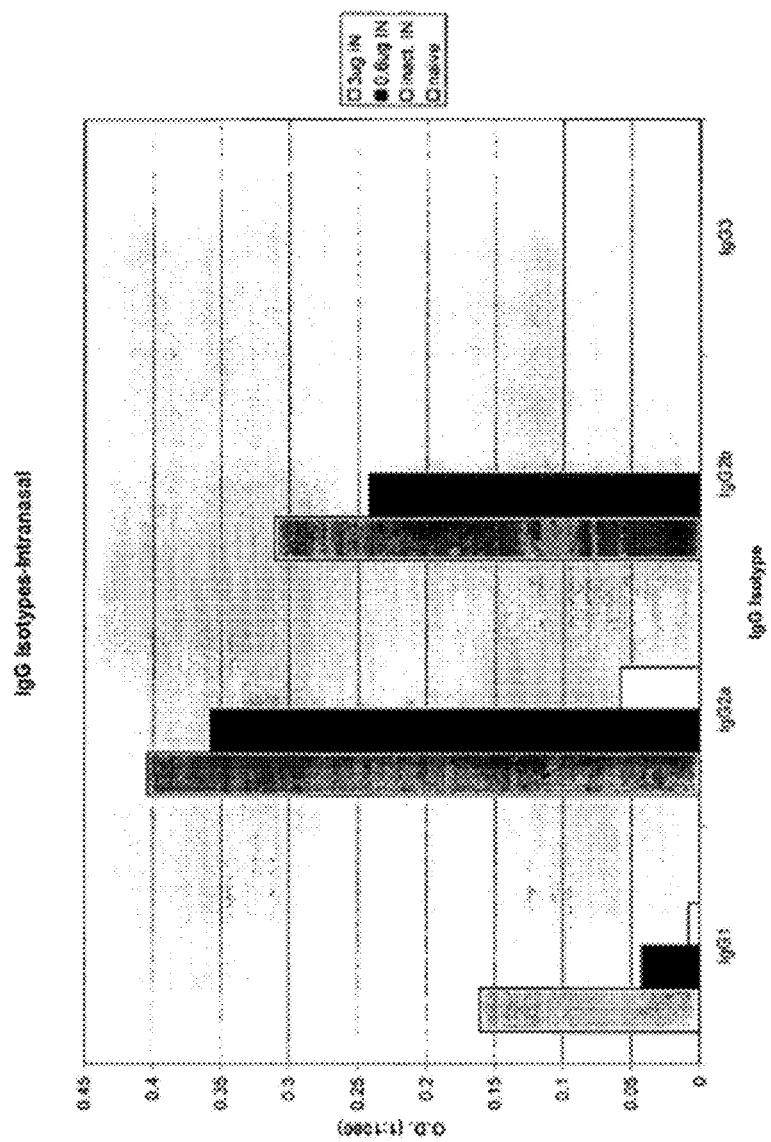

Fig. 22

H9N2 VLP Dose Response Ferrets

Fig. 23

Table X. Hemagglutinin-Inhibition Titers-Ferrets

| Vaccine | H3N2 | | | | H1N1 |
|---|---|---|---|---|---|
| | CA/04 | Fuj/02 | Well/01 | Pan/99 | NC/99 |
| Intramuscular | | | | | |
| VLP (15 ug) | 640 | 905 | 508 | 40 | 10 |
| VLP (3 ug) | 160 | 640 | 226 | 57 | 10 |
| VLP (0.6 ug) | 50 | 320 | 143 | 67 | 10 |
| VLP (0.12 ug) | 10 | 184 | 70 | 50 | 10 |
| rHA (15 ug) | 80 | 254 | 143 | 56 | 10 |
| Mock | 10 | 10 | 10 | 10 | 10 |

Fig. 29

Virus Titers - Novavax H9N2 Vaccine Study
(A/HK/1073/99-$10^6$ $EID_{50}$ i.n. challenge)

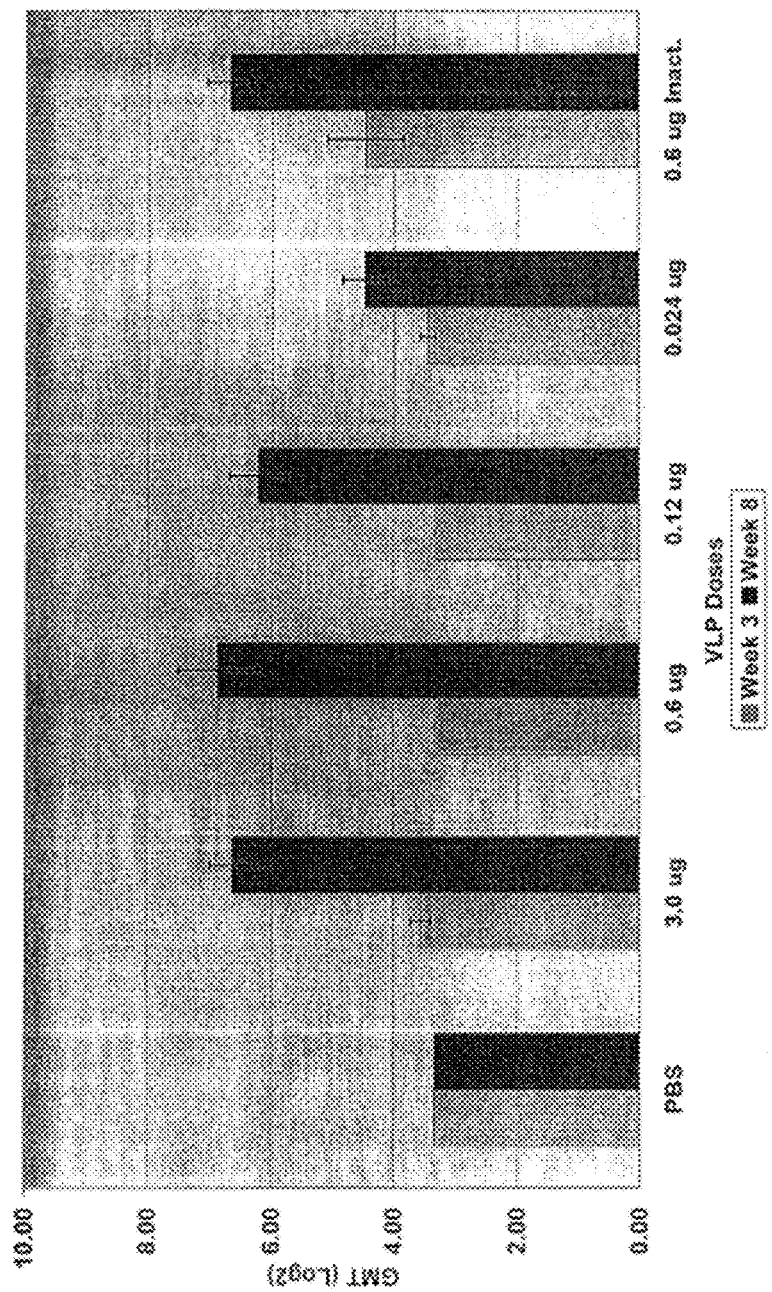

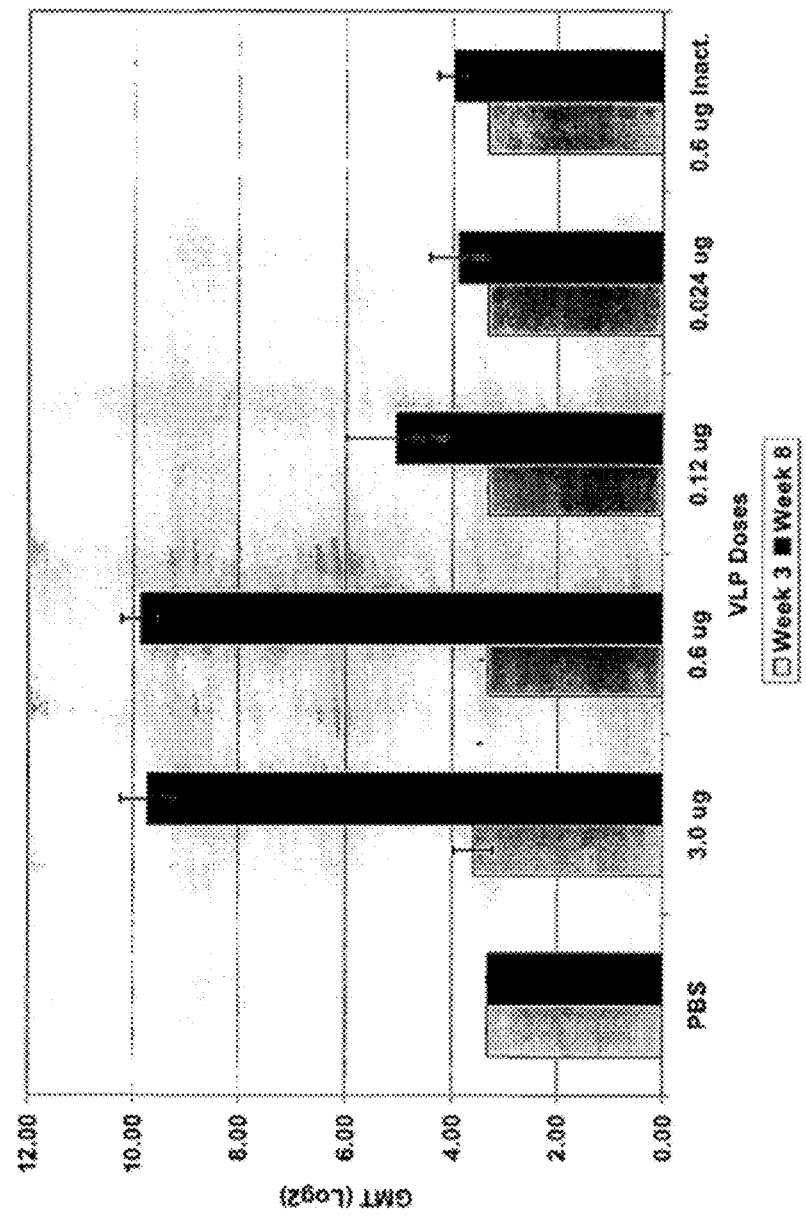

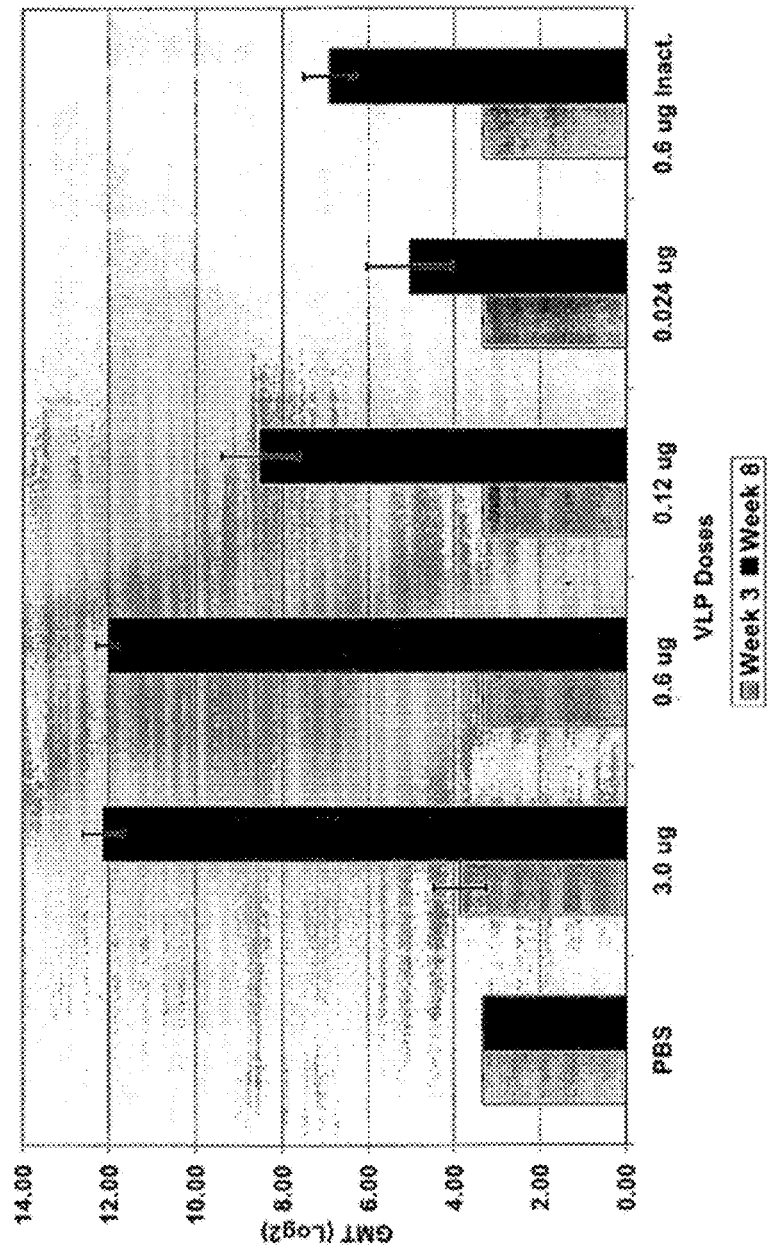

Fig. 30G

HI titer to A/New York/55/2004 (H3N2) after intramuscular inoculation with H3H2 VLPs

Fig. 35

```
   1 MFIFLLFLTL TSGSDLDRCT TFDDVQAPNY TQHTSSMRGV YYPDEIFRSD TLYLTQDLFL
  61 PFYSNVTGFH TINHTFGNPV IPFKDGIYFA ATEKSNVVRG WVFGSTMNNK SQSVIINNS
 121 TNVVIRACNF ELCDNPFFAV SKPMGTQTHT MIFDNAFNCT FEYISDAFSL DVSEKSGNFK
 181 HLREFVFKNK DGFLYVYKGY QPIDVVRDLP SGFNTLKPIF KLPLGINITN FRAILTAFSP
 241 AQDIWGTSAA AYFVGYLKPT TMLKYDENG TITDAVDCSQ NPLAELKCSV KSFEIDKGIY
 301 QTSNFRVVPS GDVVRFPNIT NLCPFGEVFN ATKFPSVYAW ERKKISMCVA DYSVLYNSTF
 361 FSTFKCYGVS ATKLNDLCFS NVYADSFVVK GDDVRQIAPG QTGVIADYNY KLPDDFMGCV
 421 LAWNTRNIDA TSTGNYNYKY RYLRHGKLRP FERDISNVPF SPDGKPCTPP ALNCYWPLND
 481 YGFYTTTGIG YQPYRVVVLS FELLNAPATV CGPKLSTDLI KNQCVNFNFN GLTGTGVLTP
 541 SSKRFQPFQQ FGRDVSDFTD SVRDPKTSEI LDISPCSFGG VSVITPGTNA SSEVAVLYQD
 601 VNCTDVSTAI HADQLTPAWR IYSTGNNVFQ TQAGCLIGAE HVDTSYECDI PIGAGICASY
 661 HTVSLLRSTS QKSIVAYTMS LGADSSIAYS NNTIAIPTNF SISITTEVMP VSMAKTSVDC
 721 NMYICGDSTE CANLLLQYGS FCTQLNRALS GIAAEQDRNT REVFAQVKQM YKTPTLKYFG
 781 GFNFSQILPD PLKPTKRSFI EDLLFNKVTL ADAGFMKQYG ECLGDINARD LICAQKFNGL
 841 TVLPPLLTDD MIAAYTAALV SGTATAGWTF GAGAALQIPF AMQMAYRFNG IGVTQNVLYE
 901 NQKQIANQFN KAISQIQESL TTTSTALGKL QDVVNQNAQA LNTLVKQLSS NFGAISSVLN
 961 DILSRLDKVE AEVQIDRLIT GRLQSLQTYV TQQLIRAAEI RASANLAATK MSECVLGQSK
1021 RVDFCGKGYH LMSFPQAAPH GVVFLHVTYV PSQERNFTTA PAICHEGKAY FPREGVFVFN
1081 GTSWFITQRN FFSPQIITTD NTFVSGNCDV VIGIINNTVY DPLQPELDSF KEELDKYFKN
1141 HTSPDVDLGD ISGINASVVN IQKEIDRLNE VAKNLNESLI DLQELGKYEQ YIKWPQILSI
1201 YSTVASSLAL AIMMAGLSLW MCSNGSLQCR ICI (SEQ ID NO. 10)
```

Fig. 36

1 MSLITEVETYVLSIIPSGPLKAETAQKLEDVFAGKMTDLEALMEWLKTRP
 51 ILSPITKGILGFVFTLTVPSERGLQRRRFVQNALNGNGDPNNMDRAVKLY
101 KKLKREITFHGAKEVSLSYSTGALASCMGLIYNRMGTVTTEVAFGLVCAT
151 CEQIADSQHRSHRQMATITNPLIRHENRMVLASTTAKAMEQMAGSSEQAA
201 EAMEVANQARQMVQAMRTIGTHPNSSAGLRDNLLENLQAYQKRMGVQMQR
251 FK (SEQ ID NO. 3)

Influenza B/Florida/4/06 VLP Constructs

Influenza B/Florida/4/06

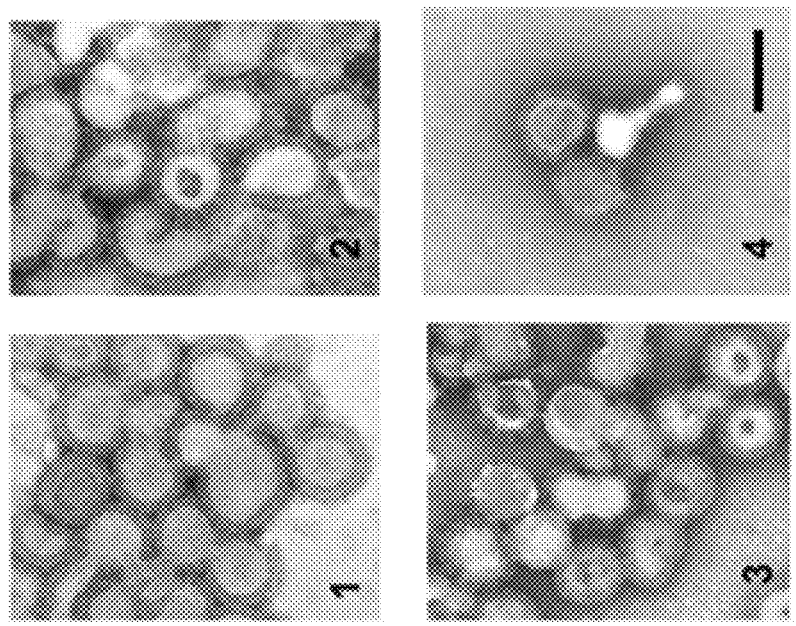
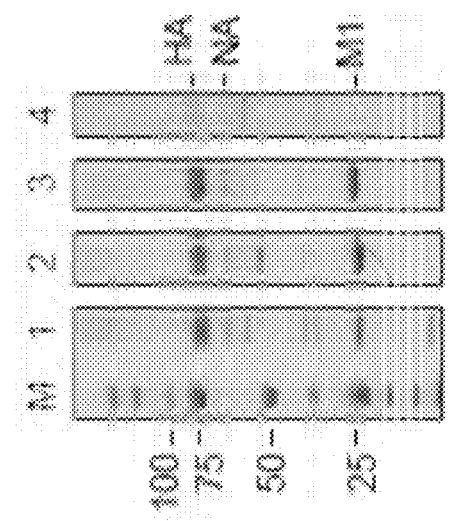
Fig. 52B
Fig. 52A

SEQUENCE LISTING

```
<160> NUMBER OF SEQ ID NOS: 80

<210> SEQ ID NO 1
<211> LENGTH: 1404
<212> TYPE: DNA
<213> ORGANISM: Influenza A virus

<400> SEQUENCE: 1
atgaatccaa atcaaaagat aatagcactt ggctctgttt ctataactat tgcgacaata      60
tgtttactca tgcagattgc catcttagca acgactatga cactacattt caatgaatgt     120
```

-continued

```
accaacccat cgaacaatca agcagtgcca tgtgaaccaa tcataataga aaggaacata    180
acagagatag tgcatttgaa taatactacc atagagaagg aaagttgtcc taaagtagca    240
gaatacaaga attggtcaaa accgcaatgt caaattacag ggttcgcccc tttctccaag    300
gacaactcaa ttaggctttc tgcaggcggg gatatttggg tgacaagaga accttatgta    360
tcgtgcggtc ttggtaaatg ttaccaattt gcacttgggc agggaaccac tttgaacaac    420
aaacactcaa atggcacaat acatgatagg agtccccata gaaccctttt aatgaacgag    480
ttgggtgttc catttcattt gggaaccaaa caagtgtgca tagcatggtc cagctcaagc    540
tgccatgatg ggaaggcatg gttacatgtt tgtgtcactg ggatgataag aaatgcgact    600
gctagcatca tttatgatgg gatgcttacc gacagtattg gttcatggtc taagaacatc    660
ctcagaactc aggagtcaga atgcgtttgc atcaatggaa cttgtacagt agtaatgact    720
gatggaagtg catcaggaag ggctgatact aaaatactat tcattagaga agggaaaatt    780
gtccacattg gtccactgtc aggaagtgct cagcatgtgg aggaatgctc ctgttacccc    840
cggtatccag aagttagatg tgtttgcaga gacaattgga agggctccaa tagacccgtg    900
ctatatataa atgtggcaga ttatagtgtt gattctagtt atgtgtgctc aggacttgtt    960
ggcgacacac caagaaatga cgatagctcc agcagcagta actgcaggga tcctaataac   1020
gagagagggg gcccaggagt gaaagggtgg gcctttgaca atggaaatga tgtttggatg   1080
ggacgaacaa tcaagaaaga ttcgcgctct ggttatgaga ctttcagggt cgttggtggt   1140
tggactacgg ctaattccaa gtcacaaata aataggcaag tcatagttga cagtgataac   1200
tggtctgggt attctggtat attctctgtt gaaggaaaaa cctgcatcaa caggtgtttt   1260
tatgtggagt tgataagagg gagaccacag gagaccagag tatggtggac ttcaaatagc   1320
atcattgtat tttgtggaac ttcaggtacc tatggaacag gctcatggcc cgatggagcg   1380
aatatcaatt tcatgtctat ataa                                          1404
```
<210> SEQ ID NO 2
<211> LENGTH: 1683
<212> TYPE: DNA
<213> ORGANISM: Influenza A virus

<400> SEQUENCE: 2
```
atggaaacaa tatcactaat aactatacta ctagtagtaa cagcaagcaa tgcagataaa     60
atctgcatcg gccaccagtc aacaaactcc acagaaactg tggacacgct aacagaaacc    120
aatgttcctg tgacacatgc caaagaattg ctccacacag agcataatgg aatgctgtgt    180
gcaacaagcc tgggacatcc cctcattcta gacacatgca ctattgaagg actagtctat    240
ggcaaccctt cttgtgacct gctgttggga ggaagagaat ggtcctacat cgtcgaaaga    300
tcatcagctg taaatggaac gtgttaccct gggaatgtag aaaacctaga ggaactcagg    360
acacttttta gttccgctag ttcctaccaa agaatccaaa tcttcccaga cacaacctgg    420
aatgtgactt acactggaac aagcagagca tgttcaggtt cattctacag gagtatgaga    480
tggctgactc aaaagagcgg tttttaccct gttcaagacg cccaatacac aaataacagg    540
ggaaagagca ttcttttcgt gtggggcata catcacccac ccacctatac cgagcaaaca    600
aatttgtaca taagaaacga cacaacaaca agcgtgacaa cagaagattt gaataggacc    660
ttcaaaccag tgatagggcc aaggcccctt gtcaatggtc tgcagggaag aattgattat    720
tattggtcgg tactaaaacc aggccaaaca ttgcgagtac gatccaatgg gaatctaatt    780
gctccatggt atggacacgt tctttcagga gggagccatg gaagaatcct gaagactgat    840
```

| | | | |
|---|---|---|---|
| ttaaaaggtg | gtaattgtgt | agtgcaatgt cagactgaaa aaggtggctt aaacagtaca | 900 |
| ttgccattcc | acaatatcag | taaatatgca tttggaacct gccccaaata tgtaagagtt | 960 |
| aatagtctca | aactggcagt | cggtctgagg aacgtgcctg ctagatcaag tagaggacta | 1020 |
| tttggagcca | tagctggatt | catagaagga ggttggccag gactagtcgc tggctggtat | 1080 |
| ggtttccagc | attcaaatga | tcaaggggtt ggtatggctg cagataggga ttcaactcaa | 1140 |
| aaggcaattg | ataaaataac | atccaaggtg aataatatag tcgacaagat gaacaagcaa | 1200 |
| tatgaaataa | ttgatcatga | attcagtgag gttgaaacta gactcaatat gatcaataat | 1260 |
| aagattgatg | accaaataca | agacgtatgg gcatataatg cagaattgct agtactactt | 1320 |
| gaaaatcaaa | aaacactcga | tgagcatgat gcgaacgtga acaatctata taacaaggtg | 1380 |
| aagagggcac | tgggctccaa | tgctatggaa gatgggaaag gctgtttcga gctataccat | 1440 |
| aaatgtgatg | atcagtgcat | ggaaacaatt cggaacggga cctataatag agaaaagtat | 1500 |
| agagaggaat | caagactaga | aaggcagaaa atagagggg ttaagctgga atctgaggga | 1560 |
| acttacaaaa | tcctcaccat | ttattcgact gtcgcctcat ctcttgtgct tgcaatgggg | 1620 |
| tttgctgcct | tcctgttctg | ggccatgtcc aatggatctt gcagatgcaa catttgtata | 1680 |
| taa | | | 1683 |

<210> SEQ ID NO 3
<211> LENGTH: 759
<212> TYPE: DNA
<213> ORGANISM: Influenza A virus

<400> SEQUENCE: 3

| | | | |
|---|---|---|---|
| atgagtcttc | taaccgaggt | cgaaacgtac gttctctcta tcatcccatc aggccccctc | 60 |
| aaagccgaga | tcgcgcagag | acttgaggat gttttttgcag ggaagaacac agatcttgag | 120 |
| gctctcatgg | aatggctaaa | gacaagacca atcctgtcac ctctgactaa ggggatttta | 180 |
| gggtttgtgt | tcacgctcac | cgtgcccagt gagcgaggac tgcagcgtag acgatttgtc | 240 |
| caaaatgccc | taaatgggaa | tggagaccca acaacatgg acagggcagt taaactatac | 300 |
| aagaagctga | agagggaaat | gacattccat ggagcaaagg aagttgcact cagttactca | 360 |
| actggtgcgc | ttgccagttg | catgggtctc atatacaacc ggatgggaac agtgaccaca | 420 |
| gaagtggctc | ttgcctagt | atgtgccact tgtgaacaga ttgctgatgc ccaacatcgg | 480 |
| tcccacaggc | agatggcgac | taccaccaac ccactaatca ggcatgagaa cagaatggta | 540 |
| ctagccagca | ctacgctaa | ggccatggag cagatggctg gatcaagtga gcaggcagca | 600 |
| gaagccatgg | aagtcgcaag | tcaggctagg caaatggtgc aggctatgag gacaattggg | 660 |
| actcacccta | gttccagtgc | aggtctaaaa gatgatctta ttgaaaattt gcaggcttac | 720 |
| cagaaacgga | tgggagtgca | aatgcagaga ttcaagtga | 759 |

<210> SEQ ID NO 4
<211> LENGTH: 31
<212> TYPE: DNA
<213> ORGANISM: Influenza A virus

<400> SEQUENCE: 4

| | |
|---|---|
| aacggtccga tggagaaaat agtgcttctt c | 31 |

<210> SEQ ID NO 5
<211> LENGTH: 33
<212> TYPE: DNA

```
<213> ORGANISM: Influenza A virus

<400> SEQUENCE: 5
aaagctttta aatgcaaatt ctgcattgta acg                                    33

<210> SEQ ID NO 6
<211> LENGTH: 32
<212> TYPE: DNA
<213> ORGANISM: Influenza A virus

<400> SEQUENCE: 6
aacggtccga tgaatccaaa tcagaagata at                                     32

<210> SEQ ID NO 7
<211> LENGTH: 32
<212> TYPE: DNA
<213> ORGANISM: Influenza A virus

<400> SEQUENCE: 7
aaagcttcta cttgtcaatg gtgaatggca ac                                     32

<210> SEQ ID NO 8
<211> LENGTH: 30
<212> TYPE: DNA
<213> ORGANISM: Influenza A virus

<400> SEQUENCE: 8
aacggtccga tgagtcttct aaccgaggtc                                        30

<210> SEQ ID NO 9
<211> LENGTH: 31
<212> TYPE: DNA
<213> ORGANISM: Influenza A virus

<400> SEQUENCE: 9 aaagcttttca cttgaatcgc tgcatctgca c                                     31

<210> SEQ ID NO 10
<211> LENGTH: 1707
<212> TYPE: DNA
<213> ORGANISM: Influenza virus

<400> SEQUENCE: 10
atggagaaaa tagtgcttct tcttgcaata gtcagtcttg ttaaaagtga tcagatttgc       60
attggttacc atgcaaacaa ttcaacagag caggttgaca caatcatgga aaagaacgtt      120
actgttacac atgcccaaga catactggaa agacacaca  acgggaagct ctgcgatcta      180
gatggagtga agcctctaat tttaagagat tgtagtgtag ctggatggct cctcgggaac      240
ccaatgtgtg acgaattcat caatgtaccg gaatggtctt acatagtgga aaggccaat      300 ccaaccaatg acctctgtta cccagggagt tcaacgact  atgaagaact gaaacaccta      360
ttgagcagaa taaccatttt tgagaaaatt caaatcatcc ccaaaagttc ttggtccgat      420
catgaagcct catcaggagt gagctcagca tgtccatacc tgggaagtcc ctcctttttt      480
agaaatgtgg tatggcttat caaaagaac agtacatacc caacaataaa gaaaagctac      540
aataatacca ccaagaaga tcttttggta ctgtggggaa ttcaccatcc taatgatgcg      600
gcagagcaga caggctata  tcaaaaccca accacctata tttccattgg gacatcaaca      660
ctaaaccaga gattggtacc aaaaatagct actagatcca agtaaacgg gcaaagtgga      720 aggatggagt tcttctggac aatttaaaa cctaatgatg caatcaactt cgagagtaat      780
```

```
ggaaatttca ttgctccaga atatgcatac aaaattgtca agaaagggga ctcagcaatt      840
atgaaaagtg aattggaata tggtaactgc aacaccaagt gtcaaactcc aatgggggcg      900
ataaactcta gtatgccatt ccacaacata caccctctca ccatcgggga atgccccaaa      960
tatgtgaaat caaacagatt agtccttgca acagggctca gaaatagccc tcaaagagag     1020
agcagaagaa aaagagagg actatttgga gctatagcag gttttataga gggaggatgg       1080
cagggaatgg tagatggttg gtatgggtac caccatagca atgagcaggg gagtgggtac     1140
gctgcagaca aagaatccac tcaaaaggca atagatggag tcaccaataa ggtcaactca     1200
atcattgaca aaatgaacac tcagtttgag gccgttggaa gggaatttaa taacttagaa     1260
aggagaatag agaatttaaa caagaagatg gaagacgggt ttctagatgt ctggacttat     1320
aatgccgaac ttctggttct catggaaaat gagagaactc tagactttca tgactcaaat     1380
gttaagaacc tctacgacaa ggtccgacta cagcttaggg ataatgcaaa ggagctgggt     1440
aacggttgtt tcgagttcta tcacaaatgt gataatgaat gtatggaaag tataagaaac     1500
ggaacgtaca actatccgca gtattcagaa gaagcaagat taaaaagaga ggaaataagt     1560
ggggtaaaat tggaatcaat aggaacttac caaatactgt caatttattc aacagtggcg     1620
agttccctag cactggcaat catgatggct ggtctatctt tatggatgtg ctccaatgga     1680
tcgttacaat gcagaatttg catttaa                                         1707

<210> SEQ ID NO 11
<211> LENGTH: 1350
<212> TYPE: DNA
<213> ORGANISM: Influenza virus

<400> SEQUENCE: 11
atgaatccaa atcagaagat aataaccatt ggatcaatct gtatggtaat tggaatagtt       60
agcttaatgt tacaaattgg gaacatgatc tcaatatggg tcagtcattc aattcagaca      120
gggaatcaac accaagctga atcaatcagc aatactaacc ctcttactga gaaagctgtg      180
gcttcagtaa cattagcggg caattcatct ctttgcccca ttagaggatg gctgtacac       240 agtaaggaca caatataag gatcggttcc aaggggatg tgtttgttat tagagagccg        300
ttcatctcat gctcccacct ggaatgcaga actttcttct tgactcaggg agccttgctg      360
aatgacaagc actccaacgg gactgtcaaa gacagaagcc ctcacagaac attaatgagt     420
tgtcctgtgg gtgaggctcc ctctccatat aactcaaggt ttgagtctgt tgcttggtca      480
gcaagtgctt gccatgatgg caccagttgg ttgacaattg gaatttctgg cccagacaat     540
gaggctgtgg ctgtattgaa atacaatggc ataatacag acactatcaa gagttggagg      600
aacaacatac tgagaactca gagtctgaa tgtgcatgtg taaatggctc ttgctttact      660
gtaatgactg atggaccaag tgatgggcag gcatcatata gatcttcaa aatggaaaaa      720 ggaaaagtgg tcaaatcagt cgaattggat gctcctaatt atcactatga ggaatgctcc     780
tgttatcctg atgccggcga aatcacatgt gtttgcaggg ataattggca tggctcaaat     840
aggccatggg tatcttttca tcaaaatttg gagtatcaaa taggatatat atgcagtgga     900
gttttcggag acaatccacg ccccaatgat ggaacaggta gttgtggccc gatgtcccct     960 aacgggcat atgggtaaa agggttttca tttaaatacg gcaatggtgt ttggatcggg      1020
agaaccaaaa gcactaattc caggagcggc tttgaaatga tttgggatcc aaatgggtgg     1080
actggaacgg acagtagctt ttcagtgaaa caagatagag tagcaataac tgattggtca    1140
```

```
ggatatagcg ggagttttgt ccagcatcca gaactgacag gattagattg cataagacct    1200
tgtttctggg ttgagttaat cagagggcgg cccaaagaga gcacaatttg gactagtggg    1260
agcagcatat cttttgtgg tgtaaatagt gacactgtga gttggtcttg ccagacggt     1320 gctgagttgc cattcaccat tgacaagtag                                     1350

<210> SEQ ID NO 12
<211> LENGTH: 759
<212> TYPE: DNA
<213> ORGANISM: Influenza virus

<400> SEQUENCE: 12
atgagtcttc taaccgaggt cgaaacgtac gttctctcta tcatcccgtc aggccccctc      60
aaagccgaga tcgcgcagaa acttgaagat gtctttgcag gaagaacac cgatctcgag     120 gctctcatgg agtggctgaa gacaagacca atcctgtcac ctctgactaa agggattttg    180
ggatttgtat tcacgctcac cgtgcccagt gagcgaggac tgcagcgtag acgctttgtc    240
cagaatgccc taaatggaaa tggagatcca ataatatgg atagggcagt taagctatat    300
aagaagctga aaagagaaat aacattccat ggggctaaag aggtttcact cagctactca    360
accggtgcac ttgccagttg catgggtctc atatacaaca ggatgggaac ggtgactacg    420
gaagtggctt ttggcctagt gtgtgccact tgtgagcaga ttgcagattc acagcatcgg    480
tctcacaggc agatggcaac tatcaccaac ccactaatca ggcatgaaaa cagaatggtg    540
ctggccagca ctacagctaa ggctatggag cagatggcgg gatcaagtga gcaggcagcg    600
gaagccatgg aggtcgctaa tcaggctagg cagatggtgc aggcaatgag gacaattgga    660
actcatccta actctagtgc tggtctgaga gataatcttc ttgaaaattt gcaggcctac    720
cagaaacgaa tgggagtgca gatgcagcga ttcaagtga                           759

<210> SEQ ID NO 13
<211> LENGTH: 30
<212> TYPE: DNA
<213> ORGANISM: Influenza A virus

<400> SEQUENCE: 13
aggatccatg aagactatca ttgctttgag                                      30

<210> SEQ ID NO 14
<211> LENGTH: 32
<212> TYPE: DNA
<213> ORGANISM: Influenza A virus

<400> SEQUENCE: 14
aggtacctca aatgcaaatg ttgcacctaa tg                                   32

<210> SEQ ID NO 15
<211> LENGTH: 72
<212> TYPE: DNA
<213> ORGANISM: Influenza A virus

<400> SEQUENCE: 15
ggggacaagt ttgtacaaaa aagcaggctt agaaggagat agaaccatga atccaaatca      60
aaagataata ac                                                         72

<210> SEQ ID NO 16
<211> LENGTH: 57
<212> TYPE: DNA
<213> ORGANISM: Influenza A virus
```

<400> SEQUENCE: 16 gggaccact tgtacaaga aagctgggtc ctatataggc atgagattga tgtccgc         57

<210> SEQ ID NO 17
<211> LENGTH: 38
<212> TYPE: DNA
<213> ORGANISM: Influenza A virus

<400> SEQUENCE: 17
aaagaattca tgagtcttct aaccgaggtc gaaacgta                             38

<210> SEQ ID NO 18
<211> LENGTH: 38
<212> TYPE: DNA
<213> ORGANISM: Influenza A virus

<400> SEQUENCE: 18
aaattcgaat tactccagct ctatgctgac aaaatgac                             38

<210> SEQ ID NO 19
<211> LENGTH: 57
<212> TYPE: DNA
<213> ORGANISM: Influenza A virus

<400> SEQUENCE: 19
agaatcatga gtcttctaac cgaggtcgaa acgcctatca gaaacgaatg ggggtgc       57

<210> SEQ ID NO 20
<211> LENGTH: 38
<212> TYPE: DNA
<213> ORGANISM: Influenza A virus

<400> SEQUENCE: 20
aaattcgaat tactccagct ctatgctgac aaaatgac                             38

<210> SEQ ID NO 21
<211> LENGTH: 30
<212> TYPE: DNA
<213> ORGANISM: Influenza A virus

<400> SEQUENCE: 21
agaattcatg gcgtcccaag gcaccaaacg                                       30

<210> SEQ ID NO 22
<211> LENGTH: 50
<212> TYPE: DNA
<213> ORGANISM: Influenza A virus

<400> SEQUENCE: 22
agcggccgct taattgtcgt actcctctgc attgtctccg aagaaataag                50

<210> SEQ ID NO 23
<211> LENGTH: 35
<212> TYPE: DNA
<213> ORGANISM: Influenza B virus

<400> SEQUENCE: 23
agaattcatg aaggcaataa ttgtactact catgg                                 35

<210> SEQ ID NO 24
<211> LENGTH: 47
<212> TYPE: DNA

<213> ORGANISM: Influenza B virus

<400> SEQUENCE: 24
agcggccgct tatagacaga tggagcaaga aacattgtct ctggaga        47

<210> SEQ ID NO 25
<211> LENGTH: 31
<212> TYPE: DNA
<213> ORGANISM: Influenza B virus

<400> SEQUENCE: 25
agaattcatg ctaccttcaa ctatacaaac g        31

<210> SEQ ID NO 26
<211> LENGTH: 40
<212> TYPE: DNA
<213> ORGANISM: Influenza B virus

<400> SEQUENCE: 26
agcggccgct tacagagcca tatcaacacc tgtgacagtg        40

<210> SEQ ID NO 27
<211> LENGTH: 568
<212> TYPE: PRT
<213> ORGANISM: Artificial Sequence
<220> FEATURE:
<223> OTHER INFORMATION: Vac2-hac-opt derived from codon-optimized HA
      Gene of A/Indonesia/5/05 virus

<400> SEQUENCE: 27

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
        260                 265                 270

Val Lys Lys Gly Asp Ser Ala Ile Met Lys Ser Glu Leu Glu Tyr Gly
    275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 28
<211> LENGTH: 572
<212> TYPE: PRT
<213> ORGANISM: Artificial Sequence
<220> FEATURE:
<223> OTHER INFORMATION: Vac2-hac-spc-opt derived from codon-optimized
      HA Gene of A/Indonesia/5/05 virus

<400> SEQUENCE: 28

Met Pro Leu Tyr Lys Leu Leu Asn Val Leu Trp Leu Val Ala Val Ser
1               5                   10                  15

-continued

Asn Ala Ile Pro Asp Gln Ile Cys Ile Gly Tyr His Ala Asn Asn Ser
                20                  25                  30

Thr Glu Gln Val Asp Thr Ile Met Glu Lys Asn Val Thr Val Thr His
            35                  40                  45

Ala Gln Asp Ile Leu Glu Lys Thr His Asn Gly Lys Leu Cys Asp Leu
 50                  55                  60

Asp Gly Val Lys Pro Leu Ile Leu Arg Asp Cys Ser Val Ala Gly Trp
 65                  70                  75                  80

Leu Leu Gly Asn Pro Met Cys Asp Glu Phe Ile Asn Val Pro Glu Trp
                 85                  90                  95

Ser Tyr Ile Val Glu Lys Ala Asn Pro Thr Asn Asp Leu Cys Tyr Pro
                100                 105                 110

Gly Ser Phe Asn Asp Tyr Glu Glu Leu Lys His Leu Leu Ser Arg Ile
            115                 120                 125

Asn His Phe Glu Lys Ile Gln Ile Ile Pro Lys Ser Ser Trp Ser Asp
130                 135                 140

His Glu Ala Ser Ser Gly Val Ser Ser Ala Cys Pro Tyr Leu Gly Ser
145                 150                 155                 160

Pro Ser Phe Phe Arg Asn Val Val Trp Leu Ile Lys Lys Asn Ser Thr
                165                 170                 175

Tyr Pro Thr Ile Lys Lys Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Arg Leu Tyr Gln Asn Pro Thr Thr Tyr Ile Ser Ile Gly Thr Ser Thr
210                 215                 220

Leu Asn Gln Arg Leu Val Pro Lys Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Ala Ile Met Lys Ser Glu
        275                 280                 285

Leu Glu Tyr Gly Asn Cys Asn Thr Lys Cys Gln Thr Pro Met Gly Ala
290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Ser Arg Arg Lys Lys Arg Gly Leu
            340                 345                 350

Phe Gly Ala Ile Ala Gly Phe Ile Glu Gly Gly Trp Gln Gly Met Val
        355                 360                 365

Asp Gly Trp Tyr Gly Tyr His His Ser Asn Glu Gln Gly Ser Gly Tyr
370                 375                 380

Ala Ala Asp Lys Glu Ser Thr Gln Lys Ala Ile Asp Gly Val Thr Asn
385                 390                 395                 400

Lys Val Asn Ser Ile Ile Asp Lys Met Asn Thr Gln Phe Glu Ala Val
                405                 410                 415

Gly Arg Glu Phe Asn Asn Leu Glu Arg Arg Ile Glu Asn Leu Asn Lys
            420                 425                 430

```
Lys Met Glu Asp Gly Phe Leu Asp Val Trp Thr Tyr Asn Ala Glu Leu
        435                 440                 445

Leu Val Leu Met Glu Asn Glu Arg Thr Leu Asp Phe His Asp Ser Asn
    450                 455                 460

Val Lys Asn Leu Tyr Asp Lys Val Arg Leu Gln Leu Arg Asp Asn Ala
465                 470                 475                 480

Lys Glu Leu Gly Asn Gly Cys Phe Glu Phe Tyr His Lys Cys Asp Asn
                485                 490                 495

Glu Cys Met Glu Ser Ile Arg Asn Gly Thr Tyr Asn Tyr Pro Gln Tyr
            500                 505                 510

Ser Glu Glu Ala Arg Leu Lys Arg Glu Glu Ile Ser Gly Val Lys Leu
        515                 520                 525

Glu Ser Ile Gly Thr Tyr Gln Ile Leu Ser Ile Tyr Ser Thr Val Ala
    530                 535                 540

Ser Ser Leu Ala Leu Ala Ile Met Met Ala Gly Leu Ser Leu Trp Met
545                 550                 555                 560

Cys Ser Asn Gly Ser Leu Gln Cys Arg Ile Cys Ile
                565                 570

<210> SEQ ID NO 29
<211> LENGTH: 570
<212> TYPE: PRT
<213> ORGANISM: Artificial Sequence
<220> FEATURE:
<223> OTHER INFORMATION: Vac2-hac-sph9-opt derived from codon-optimized
      HA Gene of A/Indonesia/5/05 virus

<400> SEQUENCE: 29

Met Glu Thr Ile Ser Leu Ile Thr Ile Leu Leu Val Val Thr Ala Ser
1               5                   10                  15

Asn Ala Asp Gln Ile Cys Ile Gly Tyr His Ala Asn Asn Ser Thr Glu
            20                  25                  30

Gln Val Asp Thr Ile Met Glu Lys Asn Val Thr Val Thr His Ala Gln
        35                  40                  45

Asp Ile Leu Glu Lys Thr His Asn Gly Lys Leu Cys Asp Leu Asp Gly
    50                  55                  60

Val Lys Pro Leu Ile Leu Arg Asp Cys Ser Val Ala Gly Trp Leu Leu
65                  70                  75                  80

Gly Asn Pro Met Cys Asp Glu Phe Ile Asn Val Pro Glu Trp Ser Tyr
                85                  90                  95

Ile Val Glu Lys Ala Asn Pro Thr Asn Asp Leu Cys Tyr Pro Gly Ser
            100                 105                 110

Phe Asn Asp Tyr Glu Glu Leu Lys His Leu Leu Ser Arg Ile Asn His
        115                 120                 125

Phe Glu Lys Ile Gln Ile Ile Pro Lys Ser Ser Trp Ser Asp His Glu
    130                 135                 140

Ala Ser Ser Gly Val Ser Ser Ala Cys Pro Tyr Leu Gly Ser Pro Ser
145                 150                 155                 160

Phe Phe Arg Asn Val Val Trp Leu Ile Lys Lys Asn Ser Thr Tyr Pro
                165                 170                 175

Thr Ile Lys Lys Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
        195                 200                 205

Tyr Gln Asn Pro Thr Thr Tyr Ile Ser Ile Gly Thr Ser Thr Leu Asn
    210                 215                 220
```

Gln Arg Leu Val Pro Lys Ile Ala Thr Arg Ser Lys Val Asn Gly Gln
225                 230                 235                 240

Ser Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Ala Ile Met Lys Ser Glu Leu Glu
        275                 280                 285

Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Ser Arg Arg Lys Lys Arg Gly Leu Phe Gly
            340                 345                 350

Ala Ile Ala Gly Phe Ile Glu Gly Gly Trp Gln Gly Met Val Asp Gly
        355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Ile Arg Asn Gly Thr Tyr Asn Tyr Pro Gln Tyr Ser Glu
            500                 505                 510

Glu Ala Arg Leu Lys Arg Glu Glu Ile Ser Gly Val Lys Leu Glu Ser
        515                 520                 525

Ile Gly Thr Tyr Gln Ile Leu Ser Ile Tyr Ser Thr Val Ala Ser Ser
    530                 535                 540

Leu Ala Leu Ala Ile Met Met Ala Gly Leu Ser Leu Trp Met Cys Ser
545                 550                 555                 560

Asn Gly Ser Leu Gln Cys Arg Ile Cys Ile
                565                 570

<210> SEQ ID NO 30
<211> LENGTH: 564
<212> TYPE: PRT
<213> ORGANISM: Artificial Sequence
<220> FEATURE:
<223> OTHER INFORMATION: Vac2-hac-cs-opt derived from codon-optimized HA
      Gene of A/Indonesia/5/05 virus

<400> SEQUENCE: 30

Met Glu Lys Ile Val Leu Leu Leu Ala Ile Val Ser Leu Val Lys Ser

-continued

```
1               5                   10                  15
Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
            85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
            165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
            195                 200                 205

Asn Pro Thr Thr Tyr Ile Ser Ile Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Ser Arg Gly Leu Phe Gly Ala Ile Ala Gly Phe Ile
            340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
            405                 410                 415

Arg Arg Ile Glu Asn Leu Asn Lys Lys Met Glu Asp Gly Phe Leu Asp
            420                 425                 430
```

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
                500                 505                 510

Glu Glu Ile Ser Gly Val Lys Leu Glu Ser Ile Gly Thr Tyr Gln Ile
            515                 520                 525

Leu Ser Ile Tyr Ser Thr Val Ala Ser Ser Leu Ala Leu Ala Ile Met
530                 535                 540

Met Ala Gly Leu Ser Leu Trp Met Cys Ser Asn Gly Ser Leu Gln Cys
545                 550                 555                 560

Arg Ile Cys Ile

<210> SEQ ID NO 31
<211> LENGTH: 449
<212> TYPE: PRT
<213> ORGANISM: Artificial Sequence
<220> FEATURE:
<223> OTHER INFORMATION: Vac2-naj-opt derived from unmodified,
      codon-optimized NA Gene of A/Indonesia/5/05 virus

<400> SEQUENCE: 31

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln His Gln Ala Glu Ser
        35                  40                  45

Ile Ser Asn Thr Asn Pro Leu Thr Glu Lys Ala Val Ala Ser Val Thr
    50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

-continued

```
Gly Pro Ser Asp Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
            245                 250                 255

Glu Glu Cys Ser Cys Tyr Pro Asp Ala Gly Glu Ile Thr Cys Val Cys
        260                 265                 270

Arg Asp Asn Trp His Gly Ser Asn Arg Pro Trp Val Ser Phe Asn Gln
    275                 280                 285

Asn Leu Glu Tyr Gln Ile Gly Tyr Ile Cys Ser Gly Val Phe Gly Asp
290                 295                 300

Asn Pro Arg Pro Asn Asp Gly Thr Gly Ser Cys Gly Pro Met Ser Pro
305                 310                 315                 320

Asn Gly Ala Tyr Gly Val Lys Gly Phe Ser Phe Lys Tyr Gly Asn Gly
            325                 330                 335

Val Trp Ile Gly Arg Thr Lys Ser Thr Asn Ser Arg Ser Gly Phe Glu
        340                 345                 350

Met Ile Trp Asp Pro Asn Gly Trp Thr Gly Thr Asp Ser Ser Phe Ser
    355                 360                 365

Val Lys Gln Asp Ile Val Ala Ile Thr Asp Trp Ser Gly Tyr Ser Gly
370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
            405                 410                 415

Trp Thr Ser Gly Ser Ser Ile Ser Phe Cys Gly Val Asn Ser Asp Thr
        420                 425                 430

Val Ser Trp Ser Trp Pro Asp Gly Ala Glu Leu Pro Phe Thr Ile Asp
    435                 440                 445

Lys

<210> SEQ ID NO 32
<211> LENGTH: 252
<212> TYPE: PRT
<213> ORGANISM: Artificial Sequence
<220> FEATURE:
<223> OTHER INFORMATION: Vac2-mc-opt derived from unmodified,
      codon-optimized M1 Gene of A/Indonesia/5/05 virus

<400> SEQUENCE: 32

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
            85                  90                  95

Val Lys Leu Tyr Lys Lys Leu Lys Arg Glu Ile Thr Phe His Gly Ala
        100                 105                 110

Lys Glu Val Ser Leu Ser Tyr Ser Thr Gly Ala Leu Ala Ser Cys Met
    115                 120                 125
```

```
Gly Leu Ile Tyr Asn Arg Met Gly Thr Val Thr Thr Glu Val Ala Phe
            130                 135                 140
Gly Leu Val Cys Ala Thr Cys Glu Gln Ile Ala Asp Ser Gln His Arg
145                 150                 155                 160
Ser His Arg Gln Met Ala Thr Ile Thr Asn Pro Leu Ile Arg His Glu
                165                 170                 175
Asn Arg Met Val Leu Ala Ser Thr Thr Ala Lys Ala Met Glu Gln Met
            180                 185                 190
Ala Gly Ser Ser Glu Gln Ala Ala Glu Ala Met Glu Val Ala Asn Gln
        195                 200                 205
Ala Arg Gln Met Val Gln Ala Met Arg Thr Ile Gly Thr His Pro Asn
    210                 215                 220
Ser Ser Ala Gly Leu Arg Asp Asn Leu Leu Glu Asn Leu Gln Ala Tyr
225                 230                 235                 240
Gln Lys Arg Met Gly Val Gln Met Gln Arg Phe Lys
                245                 250

<210> SEQ ID NO 33
<211> LENGTH: 564
<212> TYPE: PRT
<213> ORGANISM: Artificial Sequence
<220> FEATURE:
<223> OTHER INFORMATION: VN1203-ha-cs-opt derived from codon-optimized
      HA Gene of A/Viet Nam/1203/04

<400> SEQUENCE: 33

Met Glu Lys Ile Val Leu Leu Phe Ala Ile Val Ser Leu Val Lys Ser
1               5                   10                  15
Asp Gln Ile Cys Ile Gly Tyr His Ala Asn Asn Ser Thr Glu Gln Val
            20                  25                  30
Asp Thr Ile Met Glu Lys Asn Val Thr Val Thr His Ala Gln Asp Ile
        35                  40                  45
Leu Glu Lys Thr His Asn Gly Lys Leu Cys Asp Leu Asp Gly Val Lys
    50                  55                  60
Pro Leu Ile Leu Arg Asp Cys Ser Val Ala Gly Trp Leu Leu Gly Asn
65                  70                  75                  80
Pro Met Cys Asp Glu Phe Ile Asn Val Pro Glu Trp Ser Tyr Ile Val
                85                  90                  95
Glu Lys Ala Asn Pro Ala Asn Asp Leu Cys Tyr Pro Gly Asp Phe Asn
            100                 105                 110
Asp Tyr Glu Glu Leu Lys His Leu Leu Ser Arg Ile Asn His Phe Glu
        115                 120                 125
Lys Ile Gln Ile Ile Pro Lys Asn Ser Trp Ser Ser His Glu Ala Ser
    130                 135                 140
Leu Gly Val Ser Ser Ala Cys Pro Tyr Gln Gly Lys Ser Ser Phe Phe
145                 150                 155                 160
Arg Asn Val Val Trp Leu Ile Lys Lys Asn Ala Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Arg Leu Tyr Gln
        195                 200                 205
Asn Pro Thr Thr Tyr Ile Ser Val Gly Thr Ser Thr Leu Asn Gln Arg
    210                 215                 220
Leu Val Pro Lys Ile Ala Thr Arg Ser Lys Val Asn Gly Gln Asn Gly
```

```
            225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Leu Glu Tyr Gly
                275                 280                 285

Asn Cys Asn Thr Lys Cys Gln Thr Pro Met Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
                355                 360                 365

Ser Asn Glu Gln Gly Ser Gly Tyr Ala Ala Asp Lys Glu Ser Thr Gln
                370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
                435                 440                 445

Thr Leu Asp Phe His Asp Ser Asn Val Lys Asn Leu Tyr Asp Lys Val
                450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
                500                 505                 510

Glu Glu Ile Ser Gly Val Lys Leu Glu Ser Ile Gly Thr Tyr Gln Ile
                515                 520                 525

Leu Ser Ile Tyr Ser Thr Val Ala Ser Ser Leu Ala Leu Ala Ile Met
                530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 34
<211> LENGTH: 572
<212> TYPE: PRT
<213> ORGANISM: Artificial Sequence
<220> FEATURE:
<223> OTHER INFORMATION: VN1203-ha-spc-opt derived from codon-optimized
      HA Gene of A/Viet Nam/1203/04

<400> SEQUENCE: 34

Met Pro Leu Tyr Lys Leu Leu Asn Val Leu Trp Leu Val Ala Val Ser
1               5                   10                  15

Asn Ala Ile Pro Asp Gln Ile Cys Ile Gly Tyr His Ala Asn Asn Ser
```

```
                 20                  25                  30
Thr Glu Gln Val Asp Thr Ile Met Glu Lys Asn Val Thr Val Thr His
             35                  40                  45
Ala Gln Asp Ile Leu Glu Lys Thr His Asn Gly Lys Leu Cys Asp Leu
 50                  55                  60
Asp Gly Val Lys Pro Leu Ile Leu Arg Asp Cys Ser Val Ala Gly Trp
 65                  70                  75                  80
Leu Leu Gly Asn Pro Met Cys Asp Glu Phe Ile Asn Val Pro Glu Trp
                 85                  90                  95
Ser Tyr Ile Val Glu Lys Ala Asn Pro Ala Asn Asp Leu Cys Tyr Pro
                100                 105                 110
Gly Asp Phe Asn Asp Tyr Glu Glu Leu Lys His Leu Leu Ser Arg Ile
                115                 120                 125
Asn His Phe Glu Lys Ile Gln Ile Ile Pro Lys Asn Ser Trp Ser Ser
                130                 135                 140
His Glu Ala Ser Leu Gly Val Ser Ser Ala Cys Pro Tyr Gln Gly Lys
145                 150                 155                 160
Ser Ser Phe Phe Arg Asn Val Val Trp Leu Ile Lys Lys Asn Asn Ala
                165                 170                 175
Tyr Pro Thr Ile Lys Arg Ser Tyr Asn Asn Thr Asn Gln Glu Asp Leu
                180                 185                 190
Leu Val Leu Trp Gly Ile His His Pro Asn Asp Ala Ala Glu Gln Thr
                195                 200                 205
Arg Leu Tyr Gln Asn Pro Thr Thr Tyr Ile Ser Val Gly Thr Ser Thr
                210                 215                 220
Leu Asn Gln Arg Leu Val Pro Lys Ile Ala Thr Arg Ser Lys Val Asn
225                 230                 235                 240
Gly Gln Asn Gly Arg Met Glu Phe Phe Trp Thr Ile Leu Lys Pro Asn
                245                 250                 255
Asp Ala Ile Asn Phe Glu Ser Asn Gly Asn Phe Ile Ala Pro Glu Tyr
                260                 265                 270
Ala Tyr Lys Ile Val Lys Lys Gly Asp Ser Ala Ile Met Lys Ser Glu
                275                 280                 285
Leu Glu Tyr Gly Asn Cys Asn Thr Lys Cys Gln Thr Pro Met Gly Ala
                290                 295                 300
Ile Asn Ser Ser Met Pro Phe His Asn Ile His Pro Leu Thr Ile Gly
305                 310                 315                 320
Glu Cys Pro Lys Tyr Val Lys Ser Asn Arg Leu Val Leu Ala Thr Gly
                325                 330                 335
Leu Arg Asn Ser Pro Gln Arg Glu Arg Arg Lys Lys Arg Gly Leu
                340                 345                 350
Phe Gly Ala Ile Ala Gly Phe Ile Glu Gly Gly Trp Gln Gly Met Val
                355                 360                 365
Asp Gly Trp Tyr Gly Tyr His His Ser Asn Glu Gln Gly Ser Gly Tyr
                370                 375                 380
Ala Ala Asp Lys Glu Ser Thr Gln Lys Ala Ile Asp Gly Val Thr Asn
385                 390                 395                 400
Lys Val Asn Ser Ile Ile Asp Lys Met Asn Thr Gln Phe Glu Ala Val
                405                 410                 415
Gly Arg Glu Phe Asn Asn Leu Glu Arg Arg Ile Glu Asn Leu Asn Lys
                420                 425                 430
Lys Met Glu Asp Gly Phe Leu Asp Val Trp Thr Tyr Asn Ala Glu Leu
                435                 440                 445
```

```
Leu Val Leu Met Glu Asn Glu Arg Thr Leu Asp Phe His Asp Ser Asn
    450                 455                 460
Val Lys Asn Leu Tyr Asp Lys Val Arg Leu Gln Leu Arg Asp Asn Ala
465                 470                 475                 480
Lys Glu Leu Gly Asn Gly Cys Phe Glu Phe Tyr His Lys Cys Asp Asn
                485                 490                 495
Glu Cys Met Glu Ser Val Arg Asn Gly Thr Tyr Asp Tyr Pro Gln Tyr
            500                 505                 510
Ser Glu Glu Ala Arg Leu Lys Arg Glu Glu Ile Ser Gly Val Lys Leu
        515                 520                 525
Glu Ser Ile Gly Thr Tyr Gln Ile Leu Ser Ile Tyr Ser Thr Val Ala
    530                 535                 540
Ser Ser Leu Ala Leu Ala Ile Met Val Ala Gly Leu Ser Leu Trp Met
545                 550                 555                 560
Cys Ser Asn Gly Ser Leu Gln Cys Arg Ile Cys Ile
                565                 570

<210> SEQ ID NO 35
<211> LENGTH: 570
<212> TYPE: PRT
<213> ORGANISM: Artificial Sequence
<220> FEATURE:
<223> OTHER INFORMATION: VN1203-ha-sph9-opt derived from codon-optimized
      HA Gene of A/Viet Nam/1203/04

<400> SEQUENCE: 35

Met Glu Thr Ile Ser Leu Ile Thr Ile Leu Leu Val Val Thr Ala Ser
1               5                   10                  15

Asn Ala Asp Gln Ile Cys Ile Gly Tyr His Ala Asn Asn Ser Thr Glu
            20                  25                  30

Gln Val Asp Thr Ile Met Glu Lys Asn Val Thr Val Thr His Ala Gln
        35                  40                  45

Asp Ile Leu Glu Lys Thr His Asn Gly Lys Leu Cys Asp Leu Asp Gly
    50                  55                  60

Val Lys Pro Leu Ile Leu Arg Asp Cys Ser Val Ala Gly Trp Leu Leu
65                  70                  75                  80

Gly Asn Pro Met Cys Asp Glu Phe Ile Asn Val Pro Glu Trp Ser Tyr
                85                  90                  95

Ile Val Glu Lys Ala Asn Pro Ala Asn Asp Leu Cys Tyr Pro Gly Asp
            100                 105                 110

Phe Asn Asp Tyr Glu Glu Leu Lys His Leu Leu Ser Arg Ile Asn His
        115                 120                 125

Phe Glu Lys Ile Gln Ile Ile Pro Lys Asn Ser Trp Ser Ser His Glu
    130                 135                 140

Ala Ser Leu Gly Val Ser Ser Ala Cys Pro Tyr Gln Gly Lys Ser Ser
145                 150                 155                 160

Phe Phe Arg Asn Val Val Trp Leu Ile Lys Lys Asn Asn Ala Tyr Pro
                165                 170                 175

Thr Ile Lys Arg Ser Tyr Asn Asn Thr Asn Gln Glu Asp Leu Leu Val
            180                 185                 190

Leu Trp Gly Ile His His Pro Asn Asp Ala Ala Glu Gln Thr Arg Leu
        195                 200                 205

Tyr Gln Asn Pro Thr Thr Tyr Ile Ser Val Gly Thr Ser Thr Leu Asn
    210                 215                 220

Gln Arg Leu Val Pro Lys Ile Ala Thr Arg Ser Lys Val Asn Gly Gln
```

```
            225                 230                 235                 240
Asn Gly Arg Met Glu Phe Phe Trp Thr Ile Leu Lys Pro Asn Asp Ala
                245                 250                 255

Ile Asn Phe Glu Ser Asn Gly Asn Phe Ile Ala Pro Glu Tyr Ala Tyr
            260                 265                 270

Lys Ile Val Lys Lys Gly Asp Ser Ala Ile Met Lys Ser Glu Leu Glu
        275                 280                 285

Tyr Gly Asn Cys Asn Thr Lys Cys Gln Thr Pro Met Gly Ala Ile Asn
    290                 295                 300

Ser Ser Met Pro Phe His Asn Ile His Pro Leu Thr Ile Gly Glu Cys
305                 310                 315                 320

Pro Lys Tyr Val Lys Ser Asn Arg Leu Val Leu Ala Thr Gly Leu Arg
                325                 330                 335

Asn Ser Pro Gln Arg Glu Arg Arg Lys Lys Arg Gly Leu Phe Gly
            340                 345                 350

Ala Ile Ala Gly Phe Ile Glu Gly Gly Trp Gln Gly Met Val Asp Gly
            355                 360                 365

Trp Tyr Gly Tyr His His Ser Asn Glu Gln Gly Ser Gly Tyr Ala Ala
    370                 375                 380

Asp Lys Glu Ser Thr Gln Lys Ala Ile Asp Gly Val Thr Asn Lys Val
385                 390                 395                 400

Asn Ser Ile Ile Asp Lys Met Asn Thr Gln Phe Glu Ala Val Gly Arg
                405                 410                 415

Glu Phe Asn Asn Leu Glu Arg Arg Ile Glu Asn Leu Asn Lys Lys Met
            420                 425                 430

Glu Asp Gly Phe Leu Asp Val Trp Thr Tyr Asn Ala Glu Leu Leu Val
        435                 440                 445

Leu Met Glu Asn Glu Arg Thr Leu Asp Phe His Asp Ser Asn Val Lys
    450                 455                 460

Asn Leu Tyr Asp Lys Val Arg Leu Gln Leu Arg Asp Asn Ala Lys Glu
465                 470                 475                 480

Leu Gly Asn Gly Cys Phe Glu Phe Tyr His Lys Cys Asp Asn Glu Cys
                485                 490                 495

Met Glu Ser Val Arg Asn Gly Thr Tyr Asp Tyr Pro Gln Tyr Ser Glu
            500                 505                 510

Glu Ala Arg Leu Lys Arg Glu Glu Ile Ser Gly Val Lys Leu Glu Ser
        515                 520                 525

Ile Gly Thr Tyr Gln Ile Leu Ser Ile Tyr Ser Thr Val Ala Ser Ser
    530                 535                 540

Leu Ala Leu Ala Ile Met Val Ala Gly Leu Ser Leu Trp Met Cys Ser
545                 550                 555                 560

Asn Gly Ser Leu Gln Cys Arg Ile Cys Ile
                565                 570

<210> SEQ ID NO 36
<211> LENGTH: 1707
<212> TYPE: DNA
<213> ORGANISM: Influenza virus

<400> SEQUENCE: 36
atggagaaaa tagtgcttct ttttgcaata gtcagtcttg ttaaaagtga tcagatttgc     60
attggttacc atgcaaacaa ctcgacagag caggttgaca caataatgga aaagaacgtt    120
actgttacac atgcccaaga catactggaa aagaaacaca cgggaagct ctgcgatcta    180
```

-continued

```
gatggagtga agcctctaat tttgagagat tgtagcgtag ctggatggct cctcggaaac    240
ccaatgtgtg acgaattcat caatgtgccg gaatggtctt acatagtgga gaaggccaat    300
ccagtcaatg acctctgtta cccaggggat ttcaatgact atgaagaatt gaaacaccta    360
ttgagcagaa taaaccattt tgagaaaatt cagatcatcc ccaaaagttc ttggtccagt    420
catgaagcct cattaggggt gagctcagca tgtccatacc agggaaagtc ctcctttttc    480
agaaatgtgg tatggcttat caaaaagaac agtacatacc caacaataaa gaggagctac    540
aataatacca accaagaaga tcttttggta ctgtggggga ttcaccatcc taatgatgcg    600
gcagagcaga caaagctcta tcaaaaccca accacctata tttccgttgg gacatcaaca    660
ctaaaccaga gattggtacc aagaatagct actagatcca aagtaaacgg gcaaagtgga    720
aggatggagt tcttctggac aattttaaag ccgaatgatg caatcaactt cgagagtaat    780
ggaaatttca ttgctccaga atatgcatac aaaattgtca agaaagggga ctcaacaatt    840
atgaaaagtg aattggaata tggtaactgc aacaccaagt gtcaaactcc aatgggggcg    900
ataaactcta gcatgccatt ccacaatata caccctctca ccattgggga atgcccccaaa    960
tatgtgaaat caaacagatt agtccttgcg actgggctca gaaatagccc tcaaagagag   1020
agaagaagaa aaaagagagg attatttgga gctatagcag gttttataga gggaggatgg   1080
cagggaatgg tagatggttg gtatgggtac caccatagca atgagcaggg gagtgggtac   1140
gctgcagaca aagaatccac tcaaaaggca atagatggag tcaccaataa ggtcaactcg   1200
atcattgaca aaatgaacac tcagtttgag gccgttggaa gggaatttaa caacttagaa   1260
aggagaatag agaatttaaa caagaagatg gaagacgggt tcctagatgt ctggacttat   1320
aatgctgaac ttctggttct catggaaaat gagagaactc tagactttca tgactcaaat   1380
gtcaagaacc tttacgacaa ggtccgacta cagcttaggg ataatgcaaa ggagctgggt   1440
aacggttgtt tcgagttcta tcataaatgt gataatgaat gtatggaaag tgtaagaaat   1500
ggaacgtatg actacccgca gtattcagaa gaagcgagac taaaaagaga ggaaataagt   1560
ggagtaaaat tggaatcaat aggaatttac caaatactgt caatttattc tacagtggcg   1620
agttccctag cactggcaat catggtagct ggtctatcct tatggatgtg ctccaatgga   1680
tcgttacaat gcagaatttg catttaa                                         1707

<210> SEQ ID NO 37
<211> LENGTH: 1750
<212> TYPE: DNA
<213> ORGANISM: Influenza A virus

<400> SEQUENCE: 37
agtgtgatgg atatctgcag aattcgccct taggcgcgcc atggagaaaa tagtgcttct     60
ttttgcaata gtcagtcttg ttaaaagtga tcagatttgc attggttacc atgcaaacaa    120
ctcgacagag caggttgaca caataatgga aaagaacgtt actgttacac atgcccaaga    180
catactggaa aagaaacaca acgggaagct ctgcgatcta gatggagtga agcctctaat    240
tttgagagat tgtagcgtag ctggatggct cctcggaaac ccaatgtgtg acgaattcat    300
caatgtgccg gaatggtctt acatagtgga gaaggccaat ccagtcaatg acctctgtta    360
cccaggggat ttcaatgact atgaagaatt gaaacaccta ttgagcagaa taaaccattt    420
tgagaaaatt cagatcatcc ccaaaagttc ttggtccagt catgaagcct cattaggggt    480
gagctcagca tgtccatacc agggaaagtc ctcctttttc agaaatgtgg tatggcttat    540
caaaaagaac agtacatacc caacaataaa gaggagctac aataatacca accaagaaga    600
```

```
tcttttggta ctgtggggga ttcaccatcc taatgatgcg gcagagcaga caaagctcta    660
tcaaaaccca accacctata tttccgttgg gacatcaaca ctaaaccaga gattggtacc    720
aagaatagct actagatcca aagtaaacgg gcaaagtgga aggatggagt tcttctggac    780
aattttaaag ccgaatgatg caatcaactt cgagagtaat ggaaatttca ttgctccaga    840
atatgcatac aaaattgtca agaaaggggga ctcaacaatt atgaaaagtg aattggaata    900
tggtaactgc aacaccaagt gtcaaactcc aatgggggcg ataaactcta gcatgccatt    960
ccacaatata caccctctca ccattgggga atgccccaaa tatgtgaaat caaacagatt   1020
agtccttgcg actgggctca gaaatagccc tcaaagagag agaagaagaa aaagagagg    1080 attatttgga gctatagcag gttttataga gggaggatgg cagggaatgg tagatggttg    1140
gtatgggtac caccatagca atgagcaggg gagtgggtac gctgcagaca agaatccac    1200 tcaaaaggca atagatggag tcaccaataa ggtcaactcg atcattgaca aaatgaacac   1260
tcagtttgag gccgttggaa gggaatttaa caacttagaa aggagaatag agaatttaaa   1320
caagaagatg gaagacgggt tcctagatgt ctggacttat aatgctgaac ttctggttct   1380
catggaaaat gagagaactc tagactttca tgactcaaat gtcaagaacc tttacgacaa   1440
ggtccgacta cagcttaggg ataatgcaaa ggagctgggt aacggttgtt tcgagttcta   1500
tcataaatgt gataatgaat gtatggaaag tgtaagaaat ggaacgtatg actacccgca   1560
gtattcagaa gaagcgagac taaaaagaga ggaaataagt ggagtaaaat ggaatcaat   1620 aggaatttac caaatactgt caatttattc tacagtggcg agttccctag cactggcaat   1680
catggtagct ggtctatcct tatggatgtg ctccaatggg tcgttacaat gcagaatttg   1740
catttaagcg                                                          1750
```

<210> SEQ ID NO 38
<211> LENGTH: 1350
<212> TYPE: DNA
<213> ORGANISM: Influenza virus

<400> SEQUENCE: 38

```
atgaatccaa atcagaagat aataaccatc ggatcaatct gtatggtaac tggaatagtt     60
agcttaatgt tacaaattgg gaacatgatc tcaatatggg tcagtcattc aattcacaca    120
gggaatcaac accaatctga accaatcagc aatactaatt ttcttactga aaaagctgtg    180
gcttcagtaa aattagcggg caattcatct ctttgcccca ttaacggatg ggctgtatac    240
agtaaggaca acagtataag gatcggttcc aaggggggatg tgtttgttat aagagagccg    300
ttcatctcat gctcccactt ggaatgcaga actttctttt tgactcaggg agccttgctg    360
aatgacaagc actccaatgg gactgtcaaa gacagaagcc ctcacagaac attaatgagt    420
tgtcctgtgg gtgaggctcc ctccccatat aactcaaggt ttgagtctgt tgcttggtca    480
gcaagtgctt gccatgatgg caccagttgg ttgacgattg aattctggcc ccagacaat    540 ggggctgtgg ctgtattgaa atacaatggc ataataacag acactatcaa gagttggagg    600
aacaacatac tgagaactca agagtctgaa tgtgcatgtg taaatggctc ttgctttact    660
gtaatgactg acggaccaag taatggtcag gcatcacata tagatcttca aatggaaaaa    720
gggaaagtgg ttaaatcagt cgaattggat gctcctaatt atcactatga ggaatgctcc    780
tgttatccta atgccggaga aatcacatgt gtgtgcaggg ataattggca tggctcaaat    840
cggccatggg tatctttcaa tcaaaatttg gagtatcaaa taggatatat atgcagtgga    900
```

```
gttttcggag acaatccacg ccccaatgat ggaacaggta gttgtggtcc ggtgtcctct    960 aacgggcat  atgggtaaa  agggttttca tttaaatacg gcaatggtgt ctggatcggg   1020
agaaccaaaa gcactaattc caggagcggc tttgaaatga tttgggatcc aaatgggtgg   1080
actgaaacgg acagtagctt ttcagtgaaa caagatatcg tagcaataac tgattggtca   1140
ggatatagcg ggagttttgt ccagcatcca gaactgacag gactagattg cataagacct   1200
tgtttctggg ttgagttgat cagagggcgc cccaaagaga gcacaatttg gactagtggg   1260
agcagcatat cttttgtgg  tgtaaatagt gacactgtgg gttggtcttg ccagacggt    1320 gccgagttgc cattcaccat tgacaagtag                                    1350
```

<210> SEQ ID NO 39
<211> LENGTH: 1400
<212> TYPE: DNA
<213> ORGANISM: Influenza A virus

<400> SEQUENCE: 39

```
ccgggatgaa tccaaatcag aagataataa ccatcggatc aatctgtatg gtaactggaa     60
tagttagctt aatgttacaa attgggaaca tgatctcaat atgggtcagt cattcaattc    120
acacagggaa tcaacaccaa tctgaaccaa tcagcaatac taattttctt actgagaaag    180
ctgtggcttc agtaaaatta gcgggcaatt catctctttg ccccattaac ggatgggctg    240
tatacagtaa ggacaacagt ataaggatcg gttccaaggg ggatgtgttt gttataagag    300
agccgttcat ctcatgctcc cacttggaat gcagaacttt cttttttgact cagggagcct    360 cgctgaatga caagcactcc aatgggactg tcaaagacag aagccctcac agaacattaa    420
tgagttgtcc tgtgggtgag gctccctccc catataactc aaggtttgag tctgttgctt    480
ggtcagcaag tgcttgccat gatggcacca gttggttgac gattggaatt ctggcccag    540 acaatgggc  tgtggctgta ttgaaataca atggcataat aacagacact atcaagagtt    600
ggaggaacaa catactgaga actcaagagt ctgaatgtgc atgtgtaaat ggctcttgct    660
ttactgtaat gactgacgga ccaagtaatg gtcaggcatc acataagatc ttcaaaatgg    720
aaaaagggaa agtggttaaa tcagtcgaat tggatgctcc taattatcac tatgaggaat    780
gctcctgtta tcctaatgcc ggagaaatca catgtgtgtg cagggataat tggcatggct    840
caaatcggcc atgggtatct ttcaatcaaa atttggagta tcaaataggaa tatatatgca    900 gtggagtttt cggagacaat ccacgcccca atgatggaac aggtagttgt ggtccggtgt    960
cctctaacgg ggcatatggg gtaaaagggt tttcatttaa atacggcaat ggtgtctgga   1020
tcgggagaac caaaagcact aattccagga gcggctttga atgatttgg  gatccaaatg   1080 ggtggactga acggacagt  agcttttcag tgaaacaaga tatcgtagca ataactgatt   1140
ggtcaggata tagcgggagt tttgtccagc atccagaact gacaggacta gattgcataa   1200
gaccttgttt ctgggttgag ttgatcagag ggcggcccaa agagagcaca atttggacta   1260
gtgggagcag catatctttt tgtggtgtaa atagtgacac tgtgggttgg tcttggccag   1320
acggtgctga gttgccattc accattgaca gtagggggcc ctcgagtaag ggcgaattcc   1380
agcacactgg cggccgttac                                               1400
```

<210> SEQ ID NO 40
<211> LENGTH: 759
<212> TYPE: DNA
<213> ORGANISM: Influenza A virus

<400> SEQUENCE: 40

```
atgagtcttc taaccgaggt cgaaacgtac gttctctcta tcatcccgtc aggcccctc      60 aaagccgaga tcgcacagaa acttgaagat gtctttgcag gaaagaacac cgatctcgag     120
gctctcatgg agtggctaaa gacaagacca atcctgtcac ctctgactaa agggatttg     180 ggatttgtat tcacgctcac cgtgcccagt gagcgaggac tgcagcgtag acgctttgtc     240
cagaatgccc taaatggaaa tggagatcca ataatatgg ataggcagt taagctatat     300 aagaagctga aaagagaaat aacattccat ggggctaagg aggtcgcact cagctactca     360
accggtgcac ttgccagttg catgggtctc atatacaaca ggatgggaac ggtgactacg     420
gaagtggctt ttggcctagt gtgtgccact tgtgagcaga ttgcagattc acagcatcgg     480
tctcacagac agatggcaac tatcaccaac ccactaatca gacatgagaa cagaatggtg     540
ctggccagca ctacagctaa ggctatggag cagatggcgg atcaagtga gcaggcagcg     600 gaagccatgg agatcgctaa tcaggctagg cagatggtgc aggcaatgag gacaattggg     660
actcatccta actctagtgc tggtctgaga gataatcttc ttgaaaattt gcaggcctac     720
cagaaacgaa tgggagtgca gatgcagcga ttcaagtga                            759

<210> SEQ ID NO 41
<211> LENGTH: 793
<212> TYPE: DNA
<213> ORGANISM: Influenza virus

```
ggcaagctgt gcgacctgga cggtgtcaag cccctgatcc tgcgtgactg ctccgtggct    240
ggttggctgc tgggtaaccc catgtgcgac gagttcatca acgtgcccga gtggtcctac    300
atcgtggaga aggctaaccc caccaacgac ctgtgctacc ccggttcctt caacgactac    360
gaggagctga agcacctgct gtcccgtatc aaccacttcg agaagatcca gatcatcccc    420
aagtcctctt ggtccgacca cgaggcttcc tccggtgtct cctccgcttg cccctacctg    480
ggttccccct ccttcttccg taacgtggtg tggctgatca agaagaactc cacctacccc    540
accatcaaga gtcctacaa caacaccaac caggaggacc tgctggtcct gtggggtatc    600
caccacccca cgacgctgc cgagcagacc cgtctgtacc agaacccac cacctacatc     660 tccatcggca cctccaccct gaaccagcgt ctggtgccca gatcgctac ccgttccaag     720 gtgaacggcc agtccggtcg tatggagttc ttctggacca tcctgaagcc taacgacgct    780
atcaacttcg agtccaacgg caacttcatc gctcccgagt acgcttacaa gatcgtgaag    840
aagggcgact ccgctatcat gaagtccgag ctggagtacg gtaactgcaa caccaagtgc    900
cagaccccca tgggtgctat caactcctcc atgcccttcc acaacatcca ccccctgacc    960
atcggcgagt gccccaagta cgtgaagtcc aaccgtctgg tgctggctac cggtctgcgt   1020
aactcccccc agcgcgagtc ccgtcgtaag aagcgtggtc tgttcggcgc tatcgctggt   1080
ttcatcgagg gcggttggca gggcatggtg acggatggt acggttacca ccactctaac    1140
gagcagggtt ccggttacgc tgctgacaag gagtccaccc agaaggctat cgacggcgtc   1200
accaacaagg tgaactccat catcgacaag atgaacaccc agttcgaggc tgtgggtcgt   1260
gagttcaaca acctcgagcg tcgtatcgag aacctgaaca agaagatgga ggacggtttc   1320
ctggacgtgt ggacctacaa cgccgagctg ctggtgctga tggagaacga gcgtaccctg   1380
gacttccacg actccaacgt gaagaacctg tacgacaagg tccgcctgca gctgcgtgac   1440
aacgctaagg agctgggtaa cggttgcttc gagttctacc acaagtgcga caacgagtgc   1500
atggagtcca tccgtaacgg cacctacaac taccccagt actccgagga ggctcgtctg   1560
aagcgtgagg agatctccgg cgtgaagctc gagtccatcg aacctacca gatcctgtcc   1620 atctactcca ccgtggcttc ctccctggct ctggctatca tgatggctgg tctgtccctg   1680
tggatgtgct ccaacggttc cctgcagtgc cgtatctgca tctaatgaaa gcttgagctc   1740
```

<210> SEQ ID NO 43
<211> LENGTH: 568
<212> TYPE: PRT
<213> ORGANISM: Influenza A virus

<400> SEQUENCE: 43

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95
```

-continued

```
Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
```

515                 520                 525
Thr Tyr Gln Ile Leu Ser Ile Tyr Ser Thr Val Ala Ser Ser Leu Ala
            530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 44
<211> LENGTH: 1716
<212> TYPE: DNA
<213> ORGANISM: Artificial Sequence
<220> FEATURE:
<223> OTHER INFORMATION: Influenza HA gene optimized for expression in
      insect cell expression system

<400> SEQUENCE: 44

```
ggatccgcca ccatggagaa gatcgtgctg ctgctggcta tcgtgtccct ggtgaagtcc      60
gaccagatct gcatcggtta ccacgctaac aactccaccg agcaggtgga caccatcatg     120
gagaagaacg tcaccgtgac ccacgctcag gacatcctcg aaaagaccca caacggcaag     180
ctgtgcgacc tggacggtgt caagcccctg atcctgcgtg actgctccgt ggctggttgg     240
ctgctgggta cccccatgtg cgacgagttc atcaacgtgc ccgagtggtc ctacatcgtg     300
gagaaggcta cccccaccaa cgacctgtgc taccccggtt ccttcaacga ctacgaggag     360
ctgaagcacc tgctgtcccg tatcaaccac ttcgagaaga tccagatcat ccccaagtcc     420
tcttggtccg accacgaggc ttcctccggt gtctcctccg cttgccccta cctgggttcc     480
ccctccttct ccgtaacgt ggtgtggctg atcaagaaga actccaccta ccccaccatc     540
aagaagtcct acaacaacac caaccaggag gacctgctgg tcctgtgggg tatccaccac     600
cccaacgacg ctgccgagca gacccgtctg taccagaacc ccaccaccta catctccatc     660
ggcacctcca ccctgaacca gcgtctggtg cccaagatcg ctacccgttc caaggtgaac     720
ggccagtccg gtcgtatgga gttcttctgg accatcctga agcctaacga cgctatcaac     780
ttcgagtcca cggcaacttt catcgctccc gagtacgctt acaagatcgt gaagaagggc     840
gactccgcta tcatgaagtc cgagctggag tacggtaact gcaacaccaa gtgccagacc     900
cccatgggtg ctatcaactc ctccatgccc ttccacaaca tccaccccct gaccatcggc     960
gagtgcccca gtacgtgaa gtccaaccgt ctggtgctgg ctaccggtct gcgtaactcc    1020
ccccagcgcg agtcccgtgg tctgttcggc gctatcgctg gtttcatcga gggcggttgg    1080
cagggcatgg tggacggatg gtacggttac caccactcta acgagcaggg ttccggttac    1140
gctgctgaca aggagtccac ccagaaggct atcgacggcg tcaccaacaa ggtgaactcc    1200
atcatcgaca agatgaacac ccagttcgag gctgtgggtc gtgagttcaa caacctcgag    1260
cgtcgtatcg agaacctgaa caagaagatg gaggacggtt tcctggacgt gtggacctac    1320
aacgccgagc tgctggtgct gatggagaac gagcgtaccc tggacttcca cgactccaac    1380
gtgaagaacc tgtacgacaa ggtccgcctg cagctgcgtg acaacgctaa ggagctgggt    1440
aacggttgct tcgagttcta ccacaagtgc gacaacgagt gcatggagtc catccgtaac    1500
ggcacctaca actacccca gtactccgag gaggctcgtc tgaagcgtga ggagatctcc    1560
ggcgtgaagc tcgagtccat cggaacctac cagatcctgt ccatctactc caccgtggct    1620
tcctccctgg ctctggctat catgatggct ggtctgtccc tgtggatgtg ctccaacggt    1680
tccctgcagt gccgtatctg catctaatga aagctt                              1716
```

<210> SEQ ID NO 45
<211> LENGTH: 564
<212> TYPE: PRT
<213> ORGANISM: Influenza A virus

<400> SEQUENCE: 45

| | | | | | | | | | | | | | | | |
|---|---|---|---|---|---|---|---|---|---|---|---|---|---|---|---|
| Met | Glu | Lys | Ile | Val | Leu | Leu | Ala | Ile | Val | Ser | Leu | Val | Lys | Ser | |
| 1 | | | | 5 | | | | | 10 | | | | | 15 | |
| Asp | Gln | Ile | Cys | Ile | Gly | Tyr | His | Ala | Asn | Asn | Ser | Thr | Glu | Gln | Val |
| | | | 20 | | | | | 25 | | | | | 30 | | |
| Asp | Thr | Ile | Met | Glu | Lys | Asn | Val | Thr | Val | Thr | His | Ala | Gln | Asp | Ile |
| | | 35 | | | | | 40 | | | | | 45 | | | |
| Leu | Glu | Lys | Thr | His | Asn | Gly | Lys | Leu | Cys | Asp | Leu | Asp | Gly | Val | Lys |
| | 50 | | | | | 55 | | | | | 60 | | | | |
| Pro | Leu | Ile | Leu | Arg | Asp | Cys | Ser | Val | Ala | Gly | Trp | Leu | Leu | Gly | Asn |
| 65 | | | | | 70 | | | | | 75 | | | | | 80 |
| Pro | Met | Cys | Asp | Glu | Phe | Ile | Asn | Val | Pro | Glu | Trp | Ser | Tyr | Ile | Val |
| | | | | 85 | | | | | 90 | | | | | 95 | |
| Glu | Lys | Ala | Asn | Pro | Thr | Asn | Asp | Leu | Cys | Tyr | Pro | Gly | Ser | Phe | Asn |
| | | | 100 | | | | | 105 | | | | | 110 | | |
| Asp | Tyr | Glu | Glu | Leu | Lys | His | Leu | Leu | Ser | Arg | Ile | Asn | His | Phe | Glu |
| | | 115 | | | | | 120 | | | | | 125 | | | |
| Lys | Ile | Gln | Ile | Ile | Pro | Lys | Ser | Ser | Trp | Ser | Asp | His | Glu | Ala | Ser |
| | 130 | | | | | 135 | | | | | 140 | | | | |
| Ser | Gly | Val | Ser | Ser | Ala | Cys | Pro | Tyr | Leu | Gly | Ser | Pro | Ser | Phe | Phe |
| 145 | | | | | 150 | | | | | 155 | | | | | 160 |
| Arg | Asn | Val | Val | Trp | Leu | Ile | Lys | Lys | Asn | Ser | Thr | Tyr | Pro | Thr | Ile |
| | | | | 165 | | | | | 170 | | | | | 175 | |
| Lys | Lys | Ser | Tyr | Asn | Asn | Thr | Asn | Gln | Glu | Asp | Leu | Leu | Val | Leu | Trp |
| | | | 180 | | | | | 185 | | | | | 190 | | |
| Gly | Ile | His | His | Pro | Asn | Asp | Ala | Ala | Glu | Gln | Thr | Arg | Leu | Tyr | Gln |
| | | 195 | | | | | 200 | | | | | 205 | | | |
| Asn | Pro | Thr | Thr | Tyr | Ile | Ser | Ile | Gly | Thr | Ser | Thr | Leu | Asn | Gln | Arg |
| | 210 | | | | | 215 | | | | | 220 | | | | |
| Leu | Val | Pro | Lys | Ile | Ala | Thr | Arg | Ser | Lys | Val | Asn | Gly | Gln | Ser | Gly |
| 225 | | | | | 230 | | | | | 235 | | | | | 240 |
| Arg | Met | Glu | Phe | Phe | Trp | Thr | Ile | Leu | Lys | Pro | Asn | Asp | Ala | Ile | Asn |
| | | | | 245 | | | | | 250 | | | | | 255 | |
| Phe | Glu | Ser | Asn | Gly | Asn | Phe | Ile | Ala | Pro | Glu | Tyr | Ala | Tyr | Lys | Ile |
| | | | 260 | | | | | 265 | | | | | 270 | | |
| Val | Lys | Lys | Gly | Asp | Ser | Ala | Ile | Met | Lys | Ser | Glu | Leu | Glu | Tyr | Gly |
| | | 275 | | | | | 280 | | | | | 285 | | | |
| Asn | Cys | Asn | Thr | Lys | Cys | Gln | Thr | Pro | Met | Gly | Ala | Ile | Asn | Ser | Ser |
| | 290 | | | | | 295 | | | | | 300 | | | | |
| Met | Pro | Phe | His | Asn | Ile | His | Pro | Leu | Thr | Ile | Gly | Glu | Cys | Pro | Lys |
| 305 | | | | | 310 | | | | | 315 | | | | | 320 |
| Tyr | Val | Lys | Ser | Asn | Arg | Leu | Val | Leu | Ala | Thr | Gly | Leu | Arg | Asn | Ser |
| | | | | 325 | | | | | 330 | | | | | 335 | |
| Pro | Gln | Arg | Glu | Ser | Arg | Gly | Leu | Phe | Gly | Ala | Ile | Ala | Gly | Phe | Ile |
| | | | 340 | | | | | 345 | | | | | 350 | | |
| Glu | Gly | Gly | Trp | Gln | Gly | Met | Val | Asp | Gly | Trp | Tyr | Gly | Tyr | His | His |
| | | 355 | | | | | 360 | | | | | 365 | | | |
| Ser | Asn | Glu | Gln | Gly | Ser | Gly | Tyr | Ala | Ala | Asp | Lys | Glu | Ser | Thr | Gln |

| | | | | | | | | | | | |
|---|---|---|---|---|---|---|---|---|---|---|---|
| | | 370 | | | | 375 | | | | 380 | |
| Lys | Ala | Ile | Asp | Gly | Val | Thr | Asn | Lys | Val | Asn | Ser | Ile | Ile | Asp | Lys |
| 385 | | | | 390 | | | | 395 | | | | 400 |

Lys Ala Ile Asp Gly Val Thr Asn Lys Val Asn Ser Ile Ile Asp Lys
385                     390                    395                    400

Met Asn Thr Gln Phe Glu Ala Val Gly Arg Glu Phe Asn Asn Leu Glu
                 405                   410                    415

Arg Arg Ile Glu Asn Leu Asn Lys Lys Met Glu Asp Gly Phe Leu Asp
            420                    425                    430

Val Trp Thr Tyr Asn Ala Glu Leu Leu Val Leu Met Glu Asn Glu Arg
                 435                   440                  445

Thr Leu Asp Phe His Asp Ser Asn Val Lys Asn Leu Tyr Asp Lys Val
     450                    455                    460

Arg Leu Gln Leu Arg Asp Asn Ala Lys Glu Leu Gly Asn Gly Cys Phe
465                    470                   475                    480

Glu Phe Tyr His Lys Cys Asp Asn Glu Cys Met Glu Ser Ile Arg Asn
                 485                   490                  495

Gly Thr Tyr Asn Tyr Pro Gln Tyr Ser Glu Glu Ala Arg Leu Lys Arg
            500                    505                    510

Glu Glu Ile Ser Gly Val Lys Leu Glu Ser Ile Gly Thr Tyr Gln Ile
         515                    520                    525

Leu Ser Ile Tyr Ser Thr Val Ala Ser Ser Leu Ala Leu Ala Ile Met
     530                    535                    540

Met Ala Gly Leu Ser Leu Trp Met Cys Ser Asn Gly Ser Leu Gln Cys
545                    550                   555                    560

Arg Ile Cys Ile

```
<210> SEQ ID NO 46
<211> LENGTH: 1383
<212> TYPE: DNA
<213> ORGANISM: Artificial Sequence
<220> FEATURE:
<223> OTHER INFORMATION: Influenza NA gene optimized for expression in
      insect cell expression system

<400> SEQUENCE: 46
```

| | | | | | |
|---|---|---|---|---|---|
| ggtaccggat | ccgccaccat | gaacccccaac | cagaagatca | tcaccatcgg | ctccatctgc | 60 |
| atggtgatcg | gtatcgtgtc | cctgatgctg | cagatcggta | acatgatctc | catctgggtg | 120 |
| tcccactcca | tccagaccgg | taaccagcac | caggctgagt | ccatctccaa | caccaacccc | 180 |
| ctgaccgaga | aggctgtggc | ttccgtgacc | ctggctggta | actcctccct | gtgccccatc | 240 |
| cgtggttggg | ctgtgcactc | caaggacaac | aacatccgca | tcggttccaa | gggtgacgtg | 300 |
| ttcgtgatcc | gtgagccctt | catctcctgc | tcccacctcg | agtgccgtac | cttcttcctg | 360 |
| acccaaggtg | ctctgctgaa | cgacaagcac | tccaacggca | ccgtgaagga | ccgttccccc | 420 |
| caccgtaccc | tgatgtcctg | ccccgtgggc | gaggctccct | ccccctacaa | ctcccgtttc | 480 |
| gagtccgtgg | cttggtccgc | ttccgcttgc | cacgacggca | cctcttggct | gaccatcggt | 540 |
| atctccggtc | ccgacaacga | ggctgtcgct | gtgctgaagt | acaacggcat | catcaccgac | 600 |
| accatcaagt | cctggcgtaa | caacatcctg | cgtacccagg | agtccgagtg | cgcttgcgtg | 660 |
| aacggttcct | gcttcaccgt | gatgaccgac | ggtccctccg | acggccaggc | ttcctacaag | 720 |
| atcttcaaga | tggagaaggg | caaggtggtg | aagtccgtgg | agctggacgc | tcccaactac | 780 |
| cactacgagg | agtgctcttg | ctaccccgac | gctggcgaga | tcacctgcgt | gtgccgtgac | 840 |
| aactggcacg | gttccaaccg | tccctgggtg | tccttcaacc | agaacctcga | gtaccagatc | 900 |
| ggttacatct | gctccggcgt | gttcggtgac | aaccccgtc | ccaacgacgg | aaccggttcc | 960 |

```
tgcggtccca tgtcccccaa cggtgcttac ggtgtcaagg gcttctcctt caagtacggt   1020
aacggtgtct ggatcggtcg taccaagtcc accaactccc gctccggttt cgagatgatc   1080
tgggacccca acggttggac cggcaccgac tcttccttct ccgtgaagca ggacatcgtg   1140
gctatcaccg actggtccgg ttactccggt tccttcgtgc agcaccccga gctgaccggt   1200
ctggactgca ttcgtccctg cttctgggtg gagctgatcc gtggtcgtcc caaggagtcc   1260
accatctgga cctccggctc ctccatctct tctgcggtg tgaactccga caccgtgtcc   1320
tggtcctggc ccgacggtgc cgagctgccc ttcaccatcg acaagtaatg aaagcttgag   1380
ctc                                                                1383
```

<210> SEQ ID NO 47
<211> LENGTH: 449
<212> TYPE: PRT
<213> ORGANISM: Influenza A virus

<400> SEQUENCE: 47

```
Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln His Gln Ala Glu Ser
        35                  40                  45

Ile Ser Asn Thr Asn Pro Leu Thr Glu Lys Ala Val Ala Ser Val Thr
    50                  55                  60

Leu Ala Gly Asn Ser Ser Leu Cys Pro Ile Arg Gly Trp Ala Val His
65                  70                  75                  80

Ser Lys Asp Asn Asn Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Glu Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asp Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285
```

```
Asn Leu Glu Tyr Gln Ile Gly Tyr Ile Cys Ser Gly Val Phe Gly Asp
    290                 295                 300
Asn Pro Arg Pro Asn Asp Gly Thr Gly Ser Cys Gly Pro Met Ser Pro
305                 310                 315                 320
Asn Gly Ala Tyr Gly Val Lys Gly Phe Ser Phe Lys Tyr Gly Asn Gly
                325                 330                 335
Val Trp Ile Gly Arg Thr Lys Ser Thr Asn Ser Arg Ser Gly Phe Glu
            340                 345                 350
Met Ile Trp Asp Pro Asn Gly Trp Thr Gly Thr Asp Ser Ser Phe Ser
        355                 360                 365
Val Lys Gln Asp Ile Val Ala Ile Thr Asp Trp Ser Gly Tyr Ser Gly
    370                 375                 380
Ser Phe Val Gln His Pro Glu Leu Thr Gly Leu Asp Cys Ile Arg Pro
385                 390                 395                 400
Cys Phe Trp Val Glu Leu Ile Arg Gly Arg Pro Lys Glu Ser Thr Ile
                405                 410                 415
Trp Thr Ser Gly Ser Ser Ile Ser Phe Cys Gly Val Asn Ser Asp Thr
            420                 425                 430
Val Ser Trp Ser Trp Pro Asp Gly Ala Glu Leu Pro Phe Thr Ile Asp
        435                 440                 445
Lys

<210> SEQ ID NO 48
<211> LENGTH: 792
<212> TYPE: DNA
<213> ORGANISM: Artificial Sequence
<220> FEATURE:
<223> OTHER INFORMATION: Influenza M1 gene optimized for expression in
      insect cell expression system

<400> SEQUENCE: 48
ggtaccggat ccgccaccat gtccctgctg accgaggtgg agacctacgt gctgtccatc      60
atcccctccg gtcctctgaa ggctgagatc gctcagaagc tcgaggacgt tttcgctggc     120
aagaacaccg acctcgaggc tctgatggag tggctcaaga cccgtcccat cctgtccccc     180
ctgaccaagg gtatcctggg tttcgtgttc accctgaccg tgccctccga gcgtggtctg     240
cagcgtcgtc gtttcgtgca gaacgctctg aacggtaacg tgaccccaa caacatggac      300 cgtgctgtga agctgtacaa gaagctgaag cgcgagatca ccttccacgg tgctaaggag     360
gtgtccctgt cctactccac cggtgctctg gctagctgca tgggcctgat ctacaaccgt     420
atgggcaccg tgaccaccga ggtggccttc ggtctggtct cgctacctg cgagcagatc      480 gctgactccc agcaccgttc ccaccgtcag atggctacca tcaccaaccc cctgatccgt     540
cacgagaacc gtatggtgct ggcttccacc accgctaagg ctatggagca gatggctggt     600
tcctccgagc aggctgctga ggccatggag gtggccaacc aggctcgtca gatggtgcag     660
gctatgcgta ccatcggcac ccaccccaac tcctccgctg tctgcgtga caacctgctc      720 gagaacctgc aggcttacca gaagcgtatg ggagtccaga tgcagcgctt caagtaatga     780
aagcttgagc tc                                                          792

<210> SEQ ID NO 49
<211> LENGTH: 252
<212> TYPE: PRT
<213> ORGANISM: Influenza A virus

<400

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250

<210> SEQ ID NO 50
<211> LENGTH: 1736
<212> TYPE: DNA
<213> ORGANISM: Artificial Sequence
<220> FEATURE:
<223> OTHER INFORMATION: Influenza HA gene optimized for expression in
      insect cell expression system

<400> SEQUENCE: 50
ggtaccggat ccctcgagat ggagaagatc gtgctgctgc tggctatcgt gtccctggtg      60
aagtccgacc agatctgcat cggttaccac gctaacaact ccaccgagca ggtggacacc    120
atcatggaga gaacgtcac cgtgacccac gctcaggaca tcctggaaaa gacccacaac     180
ggcaagctgt gcgacctgga cggtgtcaag cccctgatcc tgcgtgactg ctccgtggct    240
ggttggctgc tgggtaaccc catgtgcgac gagttcatca acgtgcccga gtggtcctac    300
atcgtggaga aggctaaccc cgctaacgac ctgtgctacc ccggtaactt caacgactac    360
gaggagctga agcacctgct gtcccgtatc aaccacttcg agaagatcca gatcatcccc    420
aagtcctctt ggtccgacca cgaggcttcc tccggtgtct cctccgcttg cccataccag    480
ggcaccccat ctttcttccg taacgtggtg tggctgatca agaagaacaa cacctacccc    540
accatcaagc gttcctacaa caacaccaac caggaggacc tgctgatcct gtggggtatc    600
```

```
caccactcca acgacgctgc cgagcagacc aagctgtacc agaaccccac cacctacatc    660
tccgtgggca cctccaccct gaaccagcgt ctggtgccca agatcgctac ccgttccaag    720
gtgaacggcc agtccggtcg tatggacttc ttctggacca tcctgaagcc taacgacgct    780
atcaacttcg agtccaacgg caacttcatc gctcccgagt acgcttacaa gatcgtgaag    840
aagggcgact ccgctatcgt caagtccgag gtggagtacg gtaactgcaa caccaagtgc    900
cagaccccca tcggtgctat caactcctcc atgcccttcc acaacatcca ccccctgacc    960
atcggcgagt gccccaagta cgtgaagtcc aacaagctgg tgctggctac cggtctgcgt   1020
aactcccccc tgcgtgagcg tggtctgttc ggcgctatcg ctggtttcat cgagggcggt   1080
tggcagggca tggtggacgg ttggtacggt taccaccaca gcaacgagca gggttccggt   1140
tacgctgctg acaaggagtc cacccagaag gctatcgacg gcgtcaccaa caaggtgaac   1200
tccatcatcg acaagatgaa cacccagttc gaggctgtgg gtcgtgagtt caacaacctg   1260
gagcgtcgta tcgagaacct gaacaagaag atggaggacg gtttcctgga cgtgtggacc   1320
tacaacgccg agctgctggt gctgatggag aacgagcgta ccctggactt ccacgactct   1380
aacgtgaaga acctgtacga caaggtccgc ctgcagctgc gtgacaacgc taaggagctg   1440
ggtaacggtt gcttcgagtt ctaccacaag tgcgacaacg agtgcatgga gtccgtgcgt   1500
aacggcacct acgactaccc ccagtactcc gaggaggctc gtctgaagcg tgaggagatc   1560
tccggcgtga gctggagtc catcggcacc taccagatcc tgtccatcta ctccaccgtg   1620
gcttcctccc tggctctggc tatcatggtg gctggtctgt ccctgtggat gtgctccaac   1680
ggttccctgc agtgccgtat ctgcatctaa taatgaggcg cgccaagctt gagctc       1736
```

<210> SEQ ID NO 51
<211> LENGTH: 563
<212> TYPE: PRT
<213> ORGANISM: Influenza A virus

<400> SEQUENCE: 51

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175
```

```
Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
            210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Val Lys Ser Glu Val Glu Tyr Gly
                275                 280                 285

Asn Cys Asn Thr Lys Cys Gln Thr Pro Ile Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Gly Leu Phe Gly Ala Ile Ala Gly Phe Ile Glu
                340                 345                 350

Gly Gly Trp Gln Gly Met Val Asp Gly Trp Tyr Gly Tyr His His Ser
                355                 360                 365

Asn Glu Gln Gly Ser Gly Tyr Ala Ala Asp Lys Glu Ser Thr Gln Lys
                370                 375                 380

Ala Ile Asp Gly Val Thr Asn Lys Val Asn Ser Ile Ile Asp Lys Met
385                 390                 395                 400

Asn Thr Gln Phe Glu Ala Val Gly Arg Glu Phe Asn Asn Leu Glu Arg
                405                 410                 415

Arg Ile Glu Asn Leu Asn Lys Lys Met Glu Asp Gly Phe Leu Asp Val
                420                 425                 430

Trp Thr Tyr Asn Ala Glu Leu Leu Val Leu Met Glu Asn Glu Arg Thr
                435                 440                 445

Leu Asp Phe His Asp Ser Asn Val Lys Asn Leu Tyr Asp Lys Val Arg
                450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Val Arg Asn Gly
                485                 490                 495

Thr Tyr Asp Tyr Pro Gln Tyr Ser Glu Glu Ala Arg Leu Lys Arg Glu
                500                 505                 510

Glu Ile Ser Gly Val Lys Leu Glu Ser Ile Gly Thr Tyr Gln Ile Leu
                515                 520                 525

Ser Ile Tyr Ser Thr Val Ala Ser Ser Leu Ala Leu Ala Ile Met Val
                530                 535                 540

Ala Gly Leu Ser Leu Trp Met Cys Ser Asn Gly Ser Leu Gln Cys Arg
545                 550                 555                 560

Ile Cys Ile

<210> SEQ ID NO 52
<211> LENGTH: 1738
<212> TYPE: DNA
<213> ORGANISM: Artificial Sequence
```

<220> FEATURE:
<223> OTHER INFORMATION: Influenza HA gene optimized for expression in
      insect cell expression system

<400> SEQUENCE: 52

```
cgggcgcgga gcggccgcat ggagaagatc gtgctgctgc tggctatcgt gtctctggtc      60
aagtccgacc agatctgcat cggttaccac gctaacaact ccaccgagca ggtggacacc     120
atcatggaga gaacgtcac cgtgacccac gctcaggaca tcctcgaaaa gacccacaac     180
ggcaagctgt gcgacctgga cggcgtgaag ccctgatcc tgcgtgactg ctccgtggct     240
ggttggctgc tgggtaaccc catgtgcgac gagttcctca acgtgcccga gtggtcctac     300
atcgtggaga agatcaaccc cgctaacgac ctgtgctacc ccggtaactt caacgactac     360
gaggagctga agcacctgct gtcccgtatc aaccacttcg agaagatcca gatcatcccc     420
aagtcctctt ggtccgacca cgaggcttcc tccggtgtct cctccgcttg cccataccag     480
ggccgttctt ccttcttccg caacgtggtg tggctgatca agaagaacaa cgcctacccc     540
accatcaagc gttcctacaa caacaccaac caggaggacc tgctggtcct gtggggtatc     600
caccacccca cgacgctgc cgagcagacc cgtctgtacc agaaccccac cacctacatc     660
tccgtgggca cctctaccct gaaccagcgt ctggtgccca gatcgctac ccgttccaag     720
gtgaacggcc agtccggtcg tatggagttc ttctggacca tcctgaagcc taacgacgct     780
atcaacttcg agtccaacgg caacttcatc gctcccgaga cgcttacaa gatcgtgaag     840
aagggcgact ccaccatcat gaagtccgag ctggagtacg gcaactgcaa cactaagtgc     900
cagaccccca tcggtgctat caactcctcc atgcccttcc acaacatcca ccccctgact     960
atcggcgagt gccccaagta cgtgaagtcc aaccgtctgg tgctggctac cggtctgcgt    1020
aactcccccc agatcgagac tgtggtctg ttcggcgcta tcgctggttt catcgagggc    1080
ggttggcagg gcatggtgga cggttggtac ggttaccacc actctaacga gcagggttcc    1140
ggttacgctc tgacaagga gtctacccag aaggctatcg acggcgtcac caacaaggtg    1200
aactccatca tcgacaagat gaacacccag ttcgaggctg tgggtcgtga gttcaacaac    1260
ctcgaacgtc gtatcgagaa cctgaacaag aagatggagg acggttttcct ggacgtgtgg    1320
acctacaacg ccgagctgct ggtgctgatg gagaacgagc gtaccctgga cttccacgac    1380
tccaacgtga gaacctgta cgacaaggtc cgcctgcagc tgcgtgacaa cgctaaggag    1440
ctgggtaacg gttgcttcga gttctaccac cgttgcgaca acgagtgcat ggagtccgtg    1500
cgtaacggca cctacgacta ccccagtac tccgaggagg ctcgtctgaa gcgtgaggag    1560
atctccggtg tcaagctcga atccatcgga acctaccaga tcctgtccat ctactccacc    1620
gtggcttcct ccctggctct ggctatcatg gtggctggtc tgtccctgtg gatgtgctcc    1680
aacggttccc tgcagtgccg tatctgcatc taataatgag gcgcgccaag cttgtcga      1738
```

<210> SEQ ID NO 53
<211> LENGTH: 564
<212> TYPE: PRT
<213> ORGANISM: Influenza A virus

<400> SEQUENCE: 53

```
Met Glu Lys Ile Val Leu Leu Leu Ala Ile Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
```

```
                35                  40                  45
Leu Glu Lys Thr His Asn Gly Lys Leu Cys Asp Leu Asp Gly Val Lys
 50                  55                  60
Pro Leu Ile Leu Arg Asp Cys Ser Val Ala Gly Trp Leu Leu Gly Asn
 65                  70                  75                  80
Pro Met Cys Asp Glu Phe Leu Asn Val Pro Glu Trp Ser Tyr Ile Val
                 85                  90                  95
Glu Lys Ile Asn Pro Ala Asn Asp Leu Cys Tyr Pro Gly Asn Phe Asn
                100                 105                 110
Asp Tyr Glu Glu Leu Lys His Leu Leu Ser Arg Ile Asn His Phe Glu
                115                 120                 125
Lys Ile Gln Ile Ile Pro Lys Ser Ser Trp Ser Asp His Glu Ala Ser
                130                 135                 140
Ser Gly Val Ser Ser Ala Cys Pro Tyr Gln Gly Arg Ser Ser Phe Phe
145                 150                 155                 160
Arg Asn Val Val Trp Leu Ile Lys Lys Asn Asn Ala Tyr Pro Thr Ile
                165                 170                 175
Lys Arg Ser Tyr Asn Asn Thr Asn Gln Glu Asp Leu Leu Val Leu Trp
                180                 185                 190
Gly Ile His His Pro Asn Asp Ala Ala Glu Gln Thr Arg Leu Tyr Gln
                195                 200                 205
Asn Pro Thr Thr Tyr Ile Ser Val Gly Thr Ser Thr Leu Asn Gln Arg
210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Asn Ala Tyr Lys Ile
                260                 265                 270
Val Lys Lys Gly Asp Ser Thr Ile Met Lys Ser Glu Leu Glu Tyr Gly
                275                 280                 285
Asn Cys Asn Thr Lys Cys Gln Thr Pro Ile Gly Ala Ile Asn Ser Ser
                290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Ile Glu Thr Arg Gly Leu Phe Gly Ala Ile Ala Gly Phe Ile
                340                 345                 350
Glu Gly Gly Trp Gln Gly Met Val Asp Gly Trp Tyr Gly Tyr His His
                355                 360                 365
Ser Asn Glu Gln Gly Ser Gly Tyr Ala Ala Asp Lys Glu Ser Thr Gln
                370                 375                 380
Lys Ala Ile Asp Gly Val Thr Asn Lys Val Asn Ser Ile Ile Asp Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
                420                 425                 430
Val Trp Thr Tyr Asn Ala Glu Leu Leu Val Leu Met Glu Asn Glu Arg
                435                 440                 445
Thr Leu Asp Phe His Asp Ser Asn Val Lys Asn Leu Tyr Asp Lys Val
450                 455                 460
```

```
Arg Leu Gln Leu Arg Asp Asn Ala Lys Glu Leu Gly Asn Gly Cys Phe
465                 470                 475                 480

Glu Phe Tyr His Arg Cys Asp Asn Glu Cys Met Glu Ser Val Arg Asn
            485                 490                 495

Gly Thr Tyr Asp Tyr Pro Gln Tyr Ser Glu Glu Ala Arg Leu Lys Arg
        500                 505                 510

Glu Glu Ile Ser Gly Val Lys Leu Glu Ser Ile Gly Thr Tyr Gln Ile
            515                 520                 525

Leu Ser Ile Tyr Ser Thr Val Ala Ser Ser Leu Ala Leu Ala Ile Met
            530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 54
<211> LENGTH: 1422
<212> TYPE: DNA
<213> ORGANISM: Artificial Sequence
<220> FEATURE:
<223> OTHER INFORMATION: Influenza NA gene optimized for expression in
      insect cell expression system

<400> SEQUENCE: 54

```
accgtcccac catcgggcgc ggatccctcg agatgaaccc caaccagaag atcatcacca      60
tcggctccat ctgcatggtg atcggtatcg tgtccctgat gctgcagatc ggtaacatga     120
tctccatctg ggtgtcccac tccatccaga ccggtaacca cgtcaggcc gagcccatct      180 ccaacaccaa gttcctcacc gagaaggctg tggcttccgt gaccctggct ggtaactcct     240
ccctgtgccc catctccggt tgggctgtgt actccaagga caactccatc cgtatcggtt     300
cccgtggtga cgtgttcgtg atccgtgagc ccttcatctc ctgctcccac ctcgaatgcc     360
gtaccttctt cctgacccag ggtgctctgc tgaacgacaa gcactccaac ggcaccgtga     420
aggaccgttc cccccaccgt accctgatgt cctgccccgt gggcgaggct ccctcccct      480 acaactcccg tttcgagtcc gtggcttggt ccgcttccgc ttgccacgac ggcacctctt     540
ggctgaccat cggtatctcc ggtcccgaca cggtgctgt ggctgtgctg aagtacaacg      600
gcatcatcac cgacaccatc aagtcctggc gtaacaacat cctgcgtacc caagagtccg     660
agtgcgcttg cgtgaacggt tcctgcttca ccgtgatgac cgacggtccc tccaacggcc     720
aggcttccta caagatcttc aagatggaga agggcaaggt ggtgaagtcc gtggagctgg     780
acgctcccaa ctaccactac gaggagtgct cttgctaccc cgacgctggc gagatcacct     840
gcgtgtgccg tgacaactgg cacggttcca accgtccctg ggtgtccttc aaccagaacc     900
tcgaatacca gatcggttac atctgctccg gcgtgttcgg tgacaacccc gtcccaacg      960 acggaaccgg ttcctgcggt cccgtgtccc caacggtgc ttacggtgtc aagggcttct    1020
ccttcaagta cggtaacggt gtctggatcg gtcgtaccaa gtccaccaac tcccgctccg    1080
gtttcgagat gatctgggac cccaacggtt ggaccggcac cgactcttcc ttctccgtga    1140
agcaggacat cgtggctatc accgactggt ccggttactc cggttccttc gtgcagcacc    1200
ccgagctgac cggtctggac tgtatccgtc cctgcttctg ggtggagctg atccgtggtc    1260
gtcccaagga gtccaccatc tggacctccg gctcctccat ctctttctgc ggtgtgaact    1320
ccgacaccgt gtcctggtcc tggcccgacg gtgccgagct gcccttcacc atcgacaagt    1380
aataatgaat cgatttgtcg agaagtacta gaggatcata at                        1422
```

<210> SEQ ID NO 55
<211> LENGTH: 449
<212> TYPE: PRT
<213> ORGANISM: Influenza A virus

<400> SEQUENCE: 55

```
Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ile
            20                  25                  30

Trp Val Ser His Ser Ile Gln Thr Gly Asn Gln Arg Gln Ala Glu Pro
        35                  40                  45

Ile Ser Asn Thr Lys Phe Leu Thr Glu Lys Ala Val Ala Ser Val Thr
    50                  55                  60

Leu Ala Gly Asn Ser Ser Leu Cys Pro Ile Ser Gly Trp Ala Val Tyr
65                  70                  75                  80

Ser Lys Asp Asn Ser Ile Arg Ile Gly Ser Arg Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser Tyr Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Pro
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Ser Phe Ser
        355                 360                 365

Val Lys Gln Asp Ile Val Ala Ile Thr Asp Trp Ser Gly Tyr Ser Gly
```

| | 370 | | 375 | | | 380 | | | | |
|---|---|---|---|---|---|---|---|---|---|---|

Ser Phe Val Gln His Pro Glu Leu Thr Gly Leu Asp Cys Ile Arg Pro
385                390                395                400

Cys Phe Trp Val Glu Leu Ile Arg Gly Arg Pro Lys Glu Ser Thr Ile
            405                410                415

Trp Thr Ser Gly Ser Ser Ile Ser Phe Cys Gly Val Asn Ser Asp Thr
            420                425                430

Val Ser Trp Ser Trp Pro Asp Gly Ala Glu Leu Pro Phe Thr Ile Asp
            435                440                445

Lys

<210> SEQ ID NO 56
<211> LENGTH: 1750
<212> TYPE: DNA
<213> ORGANISM: Influenza A virus

<400> SEQUENCE: 56

| | | | | | |
|---|---|---|---|---|---|
| attcgccctt | aacggtccga | tggagaaaat | agtgcttctt | cttgcaatag | tcagtcttgt | 60 |
| taaaagtgat | cagatttgca | ttggttacca | tgcaaacaat | tcaacagagc | aggttgacac | 120 |
| aatcatggaa | agaacgtta | ctgttacaca | tgcccaagac | atactggaaa | agacacacaa | 180 |
| cgggaagctc | tgcgatctag | atggagtgaa | gcctctaatt | ttaagagatt | gtagtgtagc | 240 |
| tggatggctc | ctcgggaacc | caatgtgtga | cgaattcatc | aatgtaccgg | aatggtctta | 300 |
| catagtggag | aaggccaatc | caaccaatga | cctctgttac | ccagggagtt | caacgacta | 360 |
| tgaagaactg | aaacacctat | tgagcagaat | aaaccatttt | gagaaaattc | aaatcatccc | 420 |
| caaaagttct | tggtccgatc | atgaagcctc | atcaggagtg | agctcagcat | gtccatacct | 480 |
| gggaagtccc | tcctttttta | gaaatgtggt | atggcttatc | aaaaagaaca | gtacataccc | 540 |
| aacaataaag | aaaagctaca | ataataccaa | ccaagaagat | cttttggtac | tgtggggaat | 600 |
| tcaccatcct | aatgatgcgg | cagagcagac | aaggctatat | caaaacccaa | ccacctatat | 660 |
| ttccattggg | acatcaacac | taaaccagag | attggtacca | aaaatagcta | ctagatccaa | 720 |
| agtaaacggg | caaagtggaa | ggatggagtt | cttctggaca | ttttaaaac | ctaatgatgc | 780 |
| aatcaacttc | gagagtaatg | gaaatttcat | tgctccagaa | tatgcataca | aaattgtcaa | 840 |
| gaaaggggac | tcagcaatta | tgaaaagtga | attggaatat | ggtaactgca | acaccaagtg | 900 |
| tcaaactcca | atgggggcga | taaactctag | tatgccattc | cacaacatac | accctctcac | 960 |
| catcggggaa | tgccccaaat | atgtgaaatc | aaacagatta | gtccttgcaa | cagggctcag | 1020 |
| aaatagccct | caaagagaga | gcagaagaaa | aaagagagga | ctatttggag | ctatagcagg | 1080 |
| ttttatagag | ggaggatggc | agggaatggt | agatggttgg | tatgggtacc | accatagcaa | 1140 |
| tgagcagggg | agtgggtacg | ctgcagacaa | agaatccact | caaaaggcaa | tggatggagt | 1200 |
| caccaataag | gtcaactcaa | tcattgacaa | aatgaacact | cagtttgagg | ccgttggaag | 1260 |
| ggaatttaat | aacttagaaa | ggagaataga | gaatttaaac | aagaagatgg | aagacgggtt | 1320 |
| tctagatgtc | tggacttata | atgccgaact | tctggttctc | atggaaaatg | agagaactct | 1380 |
| agactttcat | gactcaaatg | ttaagaacct | ctacgacaag | gtccgactac | agcttaggga | 1440 |
| taatgcaaag | gagctgggta | acggttgttt | cgagttctat | cacaaatgtg | ataatgaatg | 1500 |
| tatggaaagt | ataagaaacg | gaacgtgcaa | ctatccgcag | tattcagaag | aagcaagatt | 1560 |
| aaaaagagag | gaaataagtg | gggtaaaatt | ggaatcaata | ggaacttacc | aaatactgtc | 1620 |
| aatttattca | acagtggcga | gttccctagc | actggcaatc | atgatggctg | gtctatcttt | 1680 |

```
atggatgtgc tccaatggat cgttacaatg cagaatttgc atttaaaagc tttaagggcg    1740
aattccagca                                                            1750
```

<210> SEQ ID NO 57
<211> LENGTH: 568
<212> TYPE: PRT
<213> ORGANISM: Influenza A virus

<400> SEQUENCE: 57

| | | | | | | | | | | | | | | |
|---|---|---|---|---|---|---|---|---|---|---|---|---|---|---|
| Met | Glu | Lys | Ile | Val | Leu | Leu | Ala | Ile | Val | Ser | Leu | Val | Lys | Ser |
| 1 | | | | 5 | | | | | 10 | | | | | 15 |
| Asp | Gln | Ile | Cys | Ile | Gly | Tyr | His | Ala | Asn | Asn | Ser | Thr | Glu | Gln | Val |
| | | | 20 | | | | | 25 | | | | | 30 | | |
| Asp | Thr | Ile | Met | Glu | Lys | Asn | Val | Thr | Val | Thr | His | Ala | Gln | Asp | Ile |
| | | | | 35 | | | | | 40 | | | | | 45 | |
| Leu | Glu | Lys | Thr | His | Asn | Gly | Lys | Leu | Cys | Asp | Leu | Asp | Gly | Val | Lys |
| | 50 | | | | | 55 | | | | | 60 | | | | |
| Pro | Leu | Ile | Leu | Arg | Asp | Cys | Ser | Val | Ala | Gly | Trp | Leu | Leu | Gly | Asn |
| 65 | | | | | 70 | | | | | 75 | | | | | 80 |
| Pro | Met | Cys | Asp | Glu | Phe | Ile | Asn | Val | Pro | Glu | Trp | Ser | Tyr | Ile | Val |
| | | | | 85 | | | | | 90 | | | | | 95 | |
| Glu | Lys | Ala | Asn | Pro | Thr | Asn | Asp | Leu | Cys | Tyr | Pro | Gly | Ser | Phe | Asn |
| | | | | 100 | | | | | 105 | | | | | 110 | |
| Asp | Tyr | Glu | Glu | Leu | Lys | His | Leu | Leu | Ser | Arg | Ile | Asn | His | Phe | Glu |
| | | | 115 | | | | | 120 | | | | | 125 | | |
| Lys | Ile | Gln | Ile | Ile | Pro | Lys | Ser | Ser | Trp | Ser | Asp | His | Glu | Ala | Ser |
| | 130 | | | | | 135 | | | | | 140 | | | | |
| Ser | Gly | Val | Ser | Ser | Ala | Cys | Pro | Tyr | Leu | Gly | Ser | Pro | Ser | Phe | Phe |
| 145 | | | | | 150 | | | | | 155 | | | | | 160 |
| Arg | Asn | Val | Val | Trp | Leu | Ile | Lys | Lys | Asn | Ser | Thr | Tyr | Pro | Thr | Ile |
| | | | | 165 | | | | | 170 | | | | | 175 | |
| Lys | Lys | Ser | Tyr | Asn | Asn | Thr | Asn | Gln | Glu | Asp | Leu | Leu | Val | Leu | Trp |
| | | | 180 | | | | | 185 | | | | | 190 | | |
| Gly | Ile | His | His | Pro | Asn | Asp | Ala | Ala | Glu | Gln | Thr | Arg | Leu | Tyr | Gln |
| | | | 195 | | | | | 200 | | | | | 205 | | |
| Asn | Pro | Thr | Thr | Tyr | Ile | Ser | Ile | Gly | Thr | Ser | Thr | Leu | Asn | Gln | Arg |
| | 210 | | | | | 215 | | | | | 220 | | | | |
| Leu | Val | Pro | Lys | Ile | Ala | Thr | Arg | Ser | Lys | Val | Asn | Gly | Gln | Ser | Gly |
| 225 | | | | | 230 | | | | | 235 | | | | | 240 |
| Arg | Met | Glu | Phe | Phe | Trp | Thr | Ile | Leu | Lys | Pro | Asn | Asp | Ala | Ile | Asn |
| | | | | 245 | | | | | 250 | | | | | 255 | |
| Phe | Glu | Ser | Asn | Gly | Asn | Phe | Ile | Ala | Pro | Glu | Tyr | Ala | Tyr | Lys | Ile |
| | | | | 260 | | | | | 265 | | | | | 270 | |
| Val | Lys | Lys | Gly | Asp | Ser | Ala | Ile | Met | Lys | Ser | Glu | Leu | Glu | Tyr | Gly |
| | | | 275 | | | | | 280 | | | | | 285 | | |
| Asn | Cys | Asn | Thr | Lys | Cys | Gln | Thr | Pro | Met | Gly | Ala | Ile | Asn | Ser | Ser |
| | | | 290 | | | | | 295 | | | | | 300 | | |
| Met | Pro | Phe | His | Asn | Ile | His | Pro | Leu | Thr | Ile | Gly | Glu | Cys | Pro | Lys |
| 305 | | | | | 310 | | | | | 315 | | | | | 320 |
| Tyr | Val | Lys | Ser | Asn | Arg | Leu | Val | Leu | Ala | Thr | Gly | Leu | Arg | Asn | Ser |
| | | | | 325 | | | | | 330 | | | | | 335 | |
| Pro | Gln | Arg | Glu | Ser | Arg | Arg | Lys | Lys | Arg | Gly | Leu | Phe | Gly | Ala | Ile |
| | | | 340 | | | | | 345 | | | | | 350 | | |

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Met Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Cys Asn Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
            530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 58
<211> LENGTH: 568
<212> TYPE: PRT
<213> ORGANISM: Influenza A virus

<400> SEQUENCE: 58

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asp His Glu Ala Ser
            130                 135                 140

Ser Gly Val Ser Ser Ala Cys Pro Tyr Leu Gly Ser Pro Ser Phe Phe
145                 150                 155                 160

```
Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

<210> SEQ ID NO 59
<211> LENGTH: 5
<212> TYPE: PRT
<213> ORGANISM: Influenza virus

<400> SEQUENCE: 59

Arg Arg Arg Lys Arg
1               5

<210> SEQ ID NO 60
<211> LENGTH: 4
<212> TYPE: PRT
<213> ORGANISM: Artificial Sequence
<220> FEATURE:
<223> OTHER INFORMATION: Mutated HA cleavage site

<400> SEQUENCE: 60

Arg Glu Ser Arg
1

<210> SEQ ID NO 61
<211> LENGTH: 4
<212> TYPE: PRT
<213> ORGANISM: Influenza virus

<400> SEQUENCE: 61

Tyr Lys Lys Leu
1

<210> SEQ ID NO 62
<211> LENGTH: 1233
<212> TYPE: PRT
<213> ORGANISM: Artificial Sequence
<220> FEATURE:
<223> OTHER INFORMATION: SARS coronavirus (SARS-CoV) Urbani strain spike
      (S) protein with with Indonesia H5N1 HA transmembrane and carboxyl
      terminal domain

<400> SEQUENCE: 62

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

```
Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Arg Asp
            195                 200                 205

Leu Pro Ser Gly Phe Asn Thr Leu Lys Pro Ile Phe Lys Leu Pro Leu
            210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
            290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
            370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
            450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
            530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590
```

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
            690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
            770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
            930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
            995                1000                1005

Thr Lys Met Ser Glu Cys Val Leu Gly Gln Ser Lys Arg Val Asp

```
                    1010                1015                1020

Phe Cys Gly Lys Gly Tyr His Leu Met Ser Phe Pro Gln Ala Ala
    1025                1030                1035

Pro His Gly Val Val Phe Leu His Val Thr Tyr Val Pro Ser Gln
    1040                1045                1050

Glu Arg Asn Phe Thr Thr Ala Pro Ala Ile Cys His Glu Gly Lys
    1055                1060                1065

Ala Tyr Phe Pro Arg Glu Gly Val Phe Val Phe Asn Gly Thr Ser
    1070                1075                1080

Trp Phe Ile Thr Gln Arg Asn Phe Phe Ser Pro Gln Ile Ile Thr
    1085                1090                1095

Thr Asp Asn Thr Phe Val Ser Gly Asn Cys Asp Val Val Ile Gly
    1100                1105                1110

Ile Ile Asn Asn Thr Val Tyr Asp Pro Leu Gln Pro Glu Leu Asp
    1115                1120                1125

Ser Phe Lys Glu Glu Leu Asp Lys Tyr Phe Lys Asn His Thr Ser
    1130                1135                1140

Pro Asp Val Asp Leu Gly Asp Ile Ser Gly Ile Asn Ala Ser Val
    1145                1150                1155

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
    1175                1180                1185

Glu Gln Tyr Ile Lys Trp Pro Gln Ile Leu Ser Ile Tyr Ser Thr
    1190                1195                1200

Val Ala Ser Ser Leu Ala Leu Ala Ile Met Met Ala Gly Leu Ser
    1205                1210                1215

Leu Trp Met Cys Ser Asn Gly Ser Leu Gln Cys Arg Ile Cys Ile
    1220                1225                1230

<210> SEQ ID NO 63
<211> LENGTH: 1255
<212> TYPE: PRT
<213> ORGANISM: SARS coronavirus

<400> SEQUENCE: 63

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140
```

-continued

```
Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
            165                 170                 175

Gly Asn Phe Lys His Leu Arg Glu Phe Val Phe Lys Asn Lys Asp Gly
                180                 185                 190

Phe Leu Tyr Val Tyr Lys Gly Tyr Gln Pro Ile Asp Val Val Arg Asp
            195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
            245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
    515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
```

```
                       565                 570                 575
Ser Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
                595                 600                 605

Ala Ile His Ala Asp Gln Leu Thr Pro Ala Trp Arg Ile Tyr Ser Thr
            610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
                675                 680                 685

Tyr Ser Asn Asn Thr Ile Ala Ile Pro Thr Asn Phe Ser Ile Ser Ile
            690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
                755                 760                 765

Gln Met Tyr Lys Thr Pro Thr Leu Lys Tyr Phe Gly Gly Phe Asn Phe
            770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
            850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
            930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
                980                 985                 990
```

Gln Leu Ile Arg Ala Ala Glu Ile Arg Ala Ser Ala Asn Leu Ala Ala
995 1000 1005

Thr Lys Met Ser Glu Cys Val Leu Gly Gln Ser Lys Arg Val Asp
1010 1015 1020

Phe Cys Gly Lys Gly Tyr His Leu Met Ser Phe Pro Gln Ala Ala
1025 1030 1035

Pro His Gly Val Val Phe Leu His Val Thr Tyr Val Pro Ser Gln
1040 1045 1050

Glu Arg Asn Phe Thr Thr Ala Pro Ala Ile Cys His Glu Gly Lys
1055 1060 1065

Ala Tyr Phe Pro Arg Glu Gly Val Phe Val Phe Asn Gly Thr Ser
1070 1075 1080

Trp Phe Ile Thr Gln Arg Asn Phe Phe Ser Pro Gln Ile Ile Thr
1085 1090 1095

Thr Asp Asn Thr Phe Val Ser Gly Asn Cys Asp Val Val Ile Gly
1100 1105 1110

Ile Ile Asn Asn Thr Val Tyr Asp Pro Leu Gln Pro Glu Leu Asp
1115 1120 1125

Ser Phe Lys Glu Glu Leu Asp Lys Tyr Phe Lys Asn His Thr Ser
1130 1135 1140

Pro Asp Val Asp Leu Gly Asp Ile Ser Gly Ile Asn Ala Ser Val
1145 1150 1155

Val Asn Ile Gln Lys Glu Ile Asp Arg Leu Asn Glu Val Ala Lys
1160 1165 1170

Asn Leu Asn Glu Ser Leu Ile Asp Leu Gln Glu Leu Gly Lys Tyr
1175 1180 1185

Glu Gln Tyr Ile Lys Trp Pro Trp Tyr Val Trp Leu Gly Phe Ile
1190 1195 1200

Ala Gly Leu Ile Ala Ile Val Met Val Thr Ile Leu Leu Cys Cys
1205 1210 1215

Met Thr Ser Cys Cys Ser Cys Leu Lys Gly Ala Cys Ser Cys Gly
1220 1225 1230

Ser Cys Cys Lys Phe Asp Glu Asp Asp Ser Glu Pro Val Leu Lys
1235 1240 1245

Gly Val Lys Leu His Tyr Thr
1250 1255

<210> SEQ ID NO 64
<211> LENGTH: 462
<212> TYPE: PRT
<213> ORGANISM: Respiratory syncytial virus

<400> SEQUENCE: 64

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu

```
                    85                  90                  95
Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln
    450                 455                 460

<210> SEQ ID NO 65
<211> LENGTH: 1420
<212> TYPE: DNA
<213> ORGANISM: Influenza A virus

<400> SEQUENCE: 65
```

```
atgaatccaa atcaaaagat aataacgatt ggctctgttt ctctcaccat ttccacaata    60
tgcttcttca tgcaaattgc catcttgata actactgtaa cattgcattt caagcaatat   120
gaattcaact cccccccaaa caaccaagtg atgctgtgtg aaccaacaat aatagaaaga   180
aacataacag agatagtgta tctgaccaac accaccatag agaaggaaat atgccccaaa   240
ctagcagaat acagaaattg gtcaaagccg caatgtaaca ttacaggatt tgcacctttt   300
tctaaggaca attcgattag ctttccgct ggtggggaca tctgggtgac aagagaacct   360
tatgtgtcat gcgatcctga caagtgttat caatttgccc ttgggcaggg aacaacacta   420
aacaacgtgc attcaaatga cacagtacat gataggaccc cttatcggac cctattgatg   480
aatgagttag gtgttccatt tcatctgggg accaagcaag tgtgcatagc atggtccagc   540
tcaagttgtc acgatggaaa agcatggctg catgtttgtg taacggggga tgataaaaat   600
gcaactgcta gcttcattta caatgggagg cttgtagata gtattgtttc atggtccaaa   660
gaaatcctca ggacccagga gtcagaatgc gtttgtatca atggaacttg tacagtagta   720
ataactgatg ggagtgcttc aggaaaagct gatactaaaa tactattcat tgaggagggg   780
aaaatcgttc atactagcac attgtcagga agtgctcagc atgtcgagga gtgctcctgc   840
tatcctcgat atcctggtgt cagatgtgtc tgcagagaca actggaaagg ctccaatagg   900
cccatagtag atataaacat aaaggattat agcattgttt ccagttatgt gtgctcagga   960
cttgttggag acacacccag aaaaaacgac agctccagca gtagccattg cttggatcct  1020
aacaatgaag aaggtggtca tggagtgaaa ggctgggcct ttgatgatgg aaatgacgtg  1080
tggatgggaa gaacgatcag cgagaagtta cgctcaggat atgaaaacctt caaagtcatt  1140
gaaggctggt ccaaccctaa ttccaaattg cagataaata ggcaagtcat agttgacaga  1200
ggtaataggt ccggttattc tggtattttc tctgttgaag caaaagctg catcaatcgg  1260
tgcttttatg tggagttgat aaggggaaga aaagaggaaa ctgaagtctt gtggacctca  1320
aacagtattg ttgtgttttg tggcacctca ggtacatatg aacaggctc atggcctgat  1380
ggggcggata tcaatctcat gcctatataa gctttcgcaa                        1420
```

<210> SEQ ID NO 66
<211> LENGTH: 469
<212> TYPE: PRT
<213> ORGANISM: Influenza A virus

<400> SEQUENCE: 66

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125
```

```
Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Leu Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

<210> SEQ ID NO 67
<211> LENGTH: 1502
<212> TYPE: DNA
<213> ORGANISM: Influenza B virus

<400> SEQUENCE: 67

```
actgaggcaa ataggccaaa aatgaacaat gctaccttca actatacaaa cgttaaccct      60
atttctcaca tcagggggag tgttattatc actatatgtg tcagcttcat tgtcatactt     120
```

-continued

```
actatattcg gatatattgc taaaattttc acaaacagaa ataactgcac caataatgcc    180
attggattgt gcaaacgcat caaatgttca ggctgtgaac cgttctgcag caaaaggggt    240
gacacttctt ctcccagaac cggagtggac ataccctcgt ttatcttgcc cgggctcaac    300
ctttcagaaa gcactcctaa ttagccccca tagattcgga gaaaccaaag gaaactcagc    360
tcccttgata taagggaac cttttattgc ttgtggacca acggaatgca aacactttgc    420
tctaacccat tatgcagctc aaccagggg atactacaat ggaacaagag aagacagaaa    480
caagctgagg catctaattt cagtcaaatt gggcaaaatc ccaacagtag aaaactccat    540
tttccatatg gcagcttgga gcgggtccgc atgccatgat ggtaaagaat ggacatatat    600
cggagttgat ggccccgaca gtaatgcatt actcaaaata aaatatggag aagcatatac    660
tgacacatac cattcctatg caaaaaacat cctaaggaca caagaaagtg cctgcaattg    720
catcggggga gattgttatc ttatgataac tgatggccca gcttcaggga ttagtgaatg    780
cagattcctt aagattcgag agggccgaat aataaaagaa atatttccaa caggaagagt    840
aaaacatact gaggaatgca catgcggatt tgccagcaac aaaaaccatag aatgtgcttg    900
tagagataac agttacacag caaaaagacc ctttgtcaaa ttaaatgtgg agactgatac    960
agcggaaata agattgatgt gcacagagac ttatttggac cccccagac caatgatgg    1020
aagcataaca gggccttgcg aatctgatgg ggacaaaggg agtggaggca tcaagggagg    1080
atttgttcat caaagaatgg catccaagat tggaaggtgg tactctcgaa cgatgtctaa    1140
aactaaaaga atggggatgg gactgtatgt aaagtatgat ggagacccat ggactgacag    1200
tgaagcccctt gctcttagtg gagtaatggt ttcgatggaa gaacctggtt ggtattcctt    1260
tggcttcgaa ataaaagata gaaatgtga tgtcccctgt attgggatag aaatggtaca    1320
tgatggtggg aaaacgactt ggcactcagc agcaacagcc atttactgtt taatgggctc    1380
aggacaactg ctgtgggaca ctgtcacagg tgttgatatg gctctgtaat ggaggaatgg    1440
ttgagtctgt tctaaaccct tgttcctat tttgtttgaa caattgtcct tactgagctt    1500
aa                                                                  1502
```

<210> SEQ ID NO 68
<211> LENGTH: 466
<212> TYPE: PRT
<213> ORGANISM: Influenza B virus

<400> SEQUENCE: 68

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Gln Thr Glu Ile Thr Ala Pro
        35                  40                  45

Ile Met Pro Leu Asp Cys Ala Asn Ala Ser Asn Val Gln Ala Val Asn
    50                  55                  60

Arg Ser Ala Ala Lys Gly Val Thr Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Thr Glu Cys Lys
        115                 120                 125
```

His Phe Ala Leu Thr His Tyr Ala Ala Gln Pro Gly Gly Tyr Tyr Asn
            130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
                180                 185                 190

Val Asp Gly Pro Asp Ser Asn Ala Leu Leu Lys Ile Lys Tyr Gly Glu
            195                 200                 205

Ala Tyr Thr Asp Thr Tyr His Ser Tyr Ala Lys Asn Ile Leu Arg Thr
210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
                260                 265                 270

His Thr Glu Glu Cys Thr Cys Gly Phe Ala Ser Asn Lys Thr Ile Glu
            275                 280                 285

Cys Ala Cys Arg Asp Asn Ser Tyr Thr Ala Lys Arg Pro Phe Val Lys
290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asn Asp Gly Ser Ile Thr Gly Pro
                325                 330                 335

Cys Glu Ser Asp Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
355                 360                 365

Met Ser Lys Thr Lys Arg Met Gly Met Gly Leu Tyr Val Lys Tyr Asp
370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
                420                 425                 430

Gly Gly Lys Thr Thr Trp His Ser Ala Ala Thr Ala Ile Tyr Cys Leu
            435                 440                 445

Met Gly Ser Gly Gln Leu Leu Trp Asp Thr Val Thr Gly Val Asp Met
    450                 455                 460

Ala Leu
465

<210> SEQ ID NO 69
<211> LENGTH: 568
<212> TYPE: PRT
<213> ORGANISM: Influenza A virus

<400> SEQUENCE: 69

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val

-continued

```
               20                  25                  30
Asp Thr Ile Met Glu Lys Asn Val Thr Val His Ala Gln Asp Ile
            35                  40                  45
Leu Glu Lys Thr His Asn Gly Lys Leu Cys Asp Leu Asp Gly Val Lys
 50                  55                  60
Pro Leu Ile Leu Arg Asp Cys Ser Val Ala Gly Trp Leu Leu Gly Asn
 65                  70                  75                  80
Pro Met Cys Asp Glu Phe Ile Asn Val Pro Glu Trp Ser Tyr Ile Val
                 85                  90                  95
Glu Lys Ala Asn Pro Thr Asn Asp Leu Cys Tyr Pro Gly Ser Phe Asn
                100                 105                 110
Asp Tyr Glu Glu Leu Lys His Leu Leu Ser Arg Ile Asn His Phe Glu
                115                 120                 125
Lys Ile Gln Ile Ile Pro Lys Ser Ser Trp Ser Asp His Glu Ala Ser
            130                 135                 140
Ser Gly Val Ser Ser Ala Cys Pro Tyr Leu Gly Ser Pro Ser Phe Phe
145                 150                 155                 160
Arg Asn Val Val Trp Leu Ile Lys Lys Asn Ser Thr Tyr Pro Thr Ile
                    165                 170                 175
Lys Lys Ser Tyr Asn Asn Thr Asn Gln Glu Asp Leu Leu Val Leu Trp
            180                 185                 190
Gly Ile His His Pro Asn Asp Ala Ala Glu Gln Thr Arg Leu Tyr Gln
            195                 200                 205
Asn Pro Thr Thr Tyr Ile Ser Ile Gly Thr Ser Thr Leu Asn Gln Arg
        210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
                260                 265                 270
Val Lys Lys Gly Asp Ser Ala Ile Met Lys Ser Glu Leu Glu Tyr Gly
            275                 280                 285
Asn Cys Asn Thr Lys Cys Gln Thr Pro Met Gly Ala Ile Asn Ser Ser
        290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Ser Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
            355                 360                 365
Gly Tyr His His Ser Asn Glu Gln Gly Ser Gly Tyr Ala Ala Asp Lys
        370                 375                 380
Glu Ser Thr Gln Lys Ala Met Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
            435                 440                 445
```

```
Glu Asn Glu Arg Thr Leu Asp Phe His Asp Ser Asn Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Ile Arg Asn Gly Thr Cys Asn Tyr Pro Gln Tyr Ser Glu Glu Ala
            500                 505                 510
Arg Leu Lys Arg Glu Glu Ile Ser Gly Val Lys Leu Glu Ser Ile Gly
        515                 520                 525
Thr Tyr Gln Ile Leu Ser Ile Tyr Ser Thr Val Ala Ser Ser Leu Ala
    530                 535                 540
Leu Ala Ile Met Met Ala Gly Leu Ser Leu Trp Met Cys Ser Asn Gly
545                 550                 555                 560
Ser Leu Gln Cys Arg Ile Cys Ile
                565

<210> SEQ ID NO 70
<211> LENGTH: 1701
<212> TYPE: DNA
<213> ORGANISM: Influenza A virus

<400> SEQUENCE: 70
atgaagacta tcattgcttt gagctacatt ctatgtctgg ttttcgctca aaaacttccc      60
ggaaatgaca cagcacggc aacgctgtgc cttgggcacc atgcagtacc aaacggaacg     120
atagtgaaaa caatcacgaa tgaccaaatt gaagttacta tgctactga gctggttcag     180
agttcctcaa caggtggaat atgcgacagt cctcatcaga tccttgatgg agaaaactgc     240
acactaatag atgctctatt gggagaccct cagtgtgatg gcttccaaaa taagaaatgg     300
gacctttttg ttgaacgcag caaagcctac agcaactgtt acccttatga tgtgccggat     360
tatgcctccc ttaggtcact agttgcctca tccggcacac tggagtttaa cgatgaaagc     420
ttcaattgga ctggagtcac tcaaaatgga acaagctctt cttgcaaaag gagatctaat     480
aacagttct ttagtagatt gaattggttg acccacttaa aattcaaata cccagcattg     540
aacgtgacta tgccaaacaa tgaaaaattt gacaaattgt acatttgggg ggttcaccac     600
ccggttacgg acaatgacca atcttcctg tatgctcaag catcaggaag aatcacagtc     660
tctaccaaaa gaagccaaca aactgtaatc ccgaatatcg gatctagacc cagaataagg     720
aatatcccca gcagaataag catctattgg acaatagtaa accgggagc atacttttg     780
attaacagca cagggaatct aattgctcct aggggttact tcaaaatacg aagtgggaaa     840
agctcaataa tgagatcaga tgcacccatt ggcaaatgca attctgaatg catcactcca     900
aatggaagca ttcccaatga caaaccattt caaaatgtaa acaggatcac atatggggcc     960
tgtcccagat atgttaagca aaacactctg aaattggcaa cagggatgcg aaatgtacca    1020
gagaaacaaa ctagaggcat atttggcgca atcgcgggtt tcatagaaaa tggttgggag    1080
ggaatggtgg atggttggta cggtttcagg catcaaaatt ctgagggaat aggacaagca    1140
gcagatctca aaagcactca agcagcaatc aatcaaatca atgggaagct gaataggttg    1200
atcgggaaaa ccaacgagaa attccatcag attgaaaag aattctcaga agtagaaggg    1260
agaattcagg acctcgagaa atatgttgag gacactaaaa tagatctctg gtcatacaac    1320
gcggagcttc ttgttgccct ggagaaccaa catacaattg atctaactga ctcagaaatg    1380
```

```
aacaaactgt tgaaagaac aaagaagcaa ctgagggaaa atgctgagga tatgggcaat    1440
ggttgtttca aaatatacca caaatgtgac aatgcctgca taggatcaat cagaaatgga    1500
acttatgacc atgatgtata cagagatgaa gcattaaaca accggttcca gatcaaaggc    1560
gttgagctga agtcaggata caaagattgg atcctatgga tttcctttgc catatcatgt    1620
tttttgcttt gtgttgcttt gttggggttc atcatgtggg cctgccaaaa aggcaacatt    1680
aggtgcaaca tttgcatttg a                                              1701
```

```
<210> SEQ ID NO 71
<211> LENGTH: 566
<212> TYPE: PRT
<213> ORGANISM: Influenza A virus

<400> SEQUENCE: 71
```

| | | | | | | | | | | | | | | |
|---|---|---|---|---|---|---|---|---|---|---|---|---|---|---|
| Met | Lys | Thr | Ile | Ile | Ala | Leu | Ser | Tyr | Ile | Leu | Cys | Leu | Val | Phe Ala |
| 1 | | | | 5 | | | | | 10 | | | | | 15 |

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
        340                 345                 350

Gly Phe Ile Glu Asn Gly Trp Glu Gly Met Val Asp Gly Trp Tyr Gly
            355                 360                 365

Phe Arg His Gln Asn Ser Glu Gly Ile Gly Gln Ala Ala Asp Leu Lys
        370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
        500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 72
<211> LENGTH: 1828
<212> TYPE: DNA
<213> ORGANISM: Influenza B virus

<400> SEQUENCE: 72
aaaatgaagg caataattgt actactcatg gtagtaacat ccaatgcaga tcgaatctgc      60
actggaataa catcttcaaa ctcacctcat gtggtcaaaa cagccactca aggggaggtc     120
aatgtgactg tgtgatacc actaacaaca acaccaacaa atcttatttt tgcaaatctc     180
aaaggaacaa ggaccagagg gaaactatgc ccagactgtc tcaactgcac agatctggat     240
gtggctttgg gcagaccaat gtgtgtgggg accacacctt cggcgaaagc ttcaatactc     300
cacgaagtca aacctgttac atccgggtgc tttcctataa tgcacgacag aacaaaaatc     360
aggcaactac ccaatcttct cagaggatat gaaaatatca ggctatcaac ccaaaacgtc     420
atcgatgcgg aaaaggcacc aggaggaccc tacagacttg aacctcagg atcttgccct     480 aacgctacca gtaagagcgg atttttcgca acaatggctt gggctgtccc aaaggacaac     540
aacaaaaatg caacgaaccc actaacagta gaagtaccat acatttgtac agaaggggaa     600
gaccaaatca ctgtttgggg gttccattca gatgacaaaa cccaaatgaa gaacctctat     660

```
ggagactcaa atcctcaaaa gttcacctca tctgctaatg gagtaaccac acactatgtt    720
tctcagattg gcagcttccc agatcaaaca gaagacggag gactaccaca aagcggcagg    780
attgttgttg attacatgat gcaaaaacct gggaaaacag gaacaattgt ctaccaaaga    840
ggtgttttgt tgcctcaaaa ggtgtggtgc gcgagtggca ggagcaaagt aataaaaggg    900
tccttgcctt taattggtga agcagattgc cttcatgaaa aatacggtgg attaaacaaa    960
agcaagcctt actacacagg agaacatgca aaagccatag gaaattgccc aatatgggtg   1020
aaaacacctt tgaagcttgc caatggaacc aaatatagac ctcctgcaaa actattaaag   1080 gaaggggtt cttcggagc tattgctggt ttcctagaag gaggatggga aggaatgatt   1140
gcaggctggc acggatacac atctcacgga gcacatggag tggcagtggc ggcggacctt   1200
aagagtacgc aagaagctat aaacaagata acaaaaaatc tcaattcttt gagtgagcta   1260
gaagtaaaga atcttcaaag actaagtggt gccatggatg aactccacaa cgaaatactc   1320
gagctggatg agaaagtgga tgatctcaga gctgacacta aagctcgca aatagaactt   1380 gcagtcttgc tttccaacga aggaataata acagtgaag atgagcatct attggcactt   1440
gagagaaaac taaagaaaat gctgggtccc tctgctgtag agataggaaa tggatgcttc   1500
gaaaccaaac acaagtgcaa ccagacctgc ttagacagga tagctgctgg caccttttaat   1560 gcaggagaat tttctctccc cacttttgat tcactgaaca ttactgctgc atctttaaat   1620
gatgatggat tggataacca tactatactg ctctattact caactgctgc ttctagtttg   1680
gctgtaacat tgatgctagc tatttttatt gtttatatgg tctccagaga caacgtttca   1740
tgctccatct gtctataagg aagattaggc cttgtatttt cctttattgt agtgcttgtt   1800
tgcttgtcat cattacaaag aaacgtta                                        1828

<210> SEQ ID NO 73
<211> LENGTH: 584
<212> TYPE: PRT
<213> ORGANISM: Influenza B virus

<400> SEQUENCE: 73

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Arg Thr
        50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
```

-continued

```
                165                 170                 175
Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
            195                 200                 205

Ser Asp Asp Lys Thr Gln Met Lys Asn Leu Tyr Gly Asp Ser Asn Pro
            210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Asp Tyr Met Met Gln Lys Pro Gly Lys Thr
                260                 265                 270

Gly Thr Ile Val Tyr Gln Arg Gly Val Leu Leu Pro Gln Lys Val Trp
                275                 280                 285

Cys Ala Ser Gly Arg Ser Lys Val Ile Lys Gly Ser Leu Pro Leu Ile
            290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
            370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Asn Glu Ile Leu Glu Leu Asp Glu Lys Val Asp Asp Leu
            435                 440                 445

Arg Ala Asp Thr Ile Ser Ser Gln Ile Glu Leu Ala Val Leu Leu Ser
            450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
                500                 505                 510

Ile Ala Ala Gly Thr Phe Asn Ala Gly Glu Phe Ser Leu Pro Thr Phe
            515                 520                 525

Asp Ser Leu Asn Ile Thr Ala Ala Ser Leu Asn Asp Asp Gly Leu Asp
            530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
                580
```

<210> SEQ ID NO 74
<211> LENGTH: 759
<212> TYPE: DNA
<213> ORGANISM: Influenza A virus

<400> SEQUENCE: 74

```
atgagccttc taaccgaggt cgaaacgtat gttctctcta tcgttccatc aggccccctc     60
aaagccgaga tcgcgcagag acttgaagat gtctttgctg ggaaaaacac agatcttgag    120
gctctcatgg aatggctaaa gacaagacca attctgtcac ctctgactaa ggggattttg    180
gggtttgtgt tcacgctcac cgtgcccagt gagcgaggac tgcagcgtag acgctttgtc    240
caaaatgccc tcaatgggaa tggagatcca ataacatgg acaaagcagt taaactgtat    300
aggaaactta gagggagat aacgttccat ggggccaaag aaatagctct cagttattct    360
gctggtgcac ttgccagttg catgggcctc atatacaata ggatgggggc tgtaaccact    420
gaagtggcat ttggcctggt atgtgcaaca tgtgagcaga ttgctgactc ccagcacagg    480
tctcataggc aaatggtggc aacaaccaat ccattaataa acatgagaaa cagaatggtt    540
ttggccagca ctacagctaa ggctatggag caaatggctg gatcaagtga gcaggcagcg    600
gaggccatgg agattgctag tcaggccagg cagatggtgc aggcaatgag agccattggg    660
actcatccta gttccagtac tggtctaaga gatgatcttc ttgaaaattt gcagacctat    720
cagaaacgaa tggggtgca gatgcaacga ttcaagtga                            759
```

<210> SEQ ID NO 75
<211> LENGTH: 252
<212> TYPE: PRT
<213> ORGANISM: Influenza A virus

<400> SEQUENCE: 75

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
            180                 185                 190
```

Ala Gly Ser Ser Glu Gln Ala Ala Glu Ala Met Glu Ile Ala Ser Gln
            195                 200                 205

Ala Arg Gln Met Val Gln Ala Met Arg Ala Ile Gly Thr His Pro Ser
        210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 76
<211> LENGTH: 747
<212> TYPE: DNA
<213> ORGANISM: Influenza B virus

<400> SEQUENCE: 76
atgtcgctgt ttggagacac aattgcctac ctgctttcat tgacagaaga tggagaaggc     60
aaagcagaac tagcagaaaa attacactgt tggttcggtg ggaaagaatt tgacctagac    120
tctgccttgg aatggataaa aaacaaaaga tgcttaactg acatacagaa agcactaatt    180
ggcgcctcta tctgcttttt aaaacccaaa gaccaggaaa gaaaaagaag attcatcaca    240
gagcccctat caggaatggg gacaacagca acaaaaaaga gggcctgat tctagctgag    300
agaaaaatga agatgtgt gagcttccat gaagcatttg aaatagcaga aggccatgaa    360
agctcagcgt actatattg tctcatggtc atgtacctga atcctggaaa ttattcaatg    420
caagtaaaac taggaacgct ctgtgctttg tgcgaaaaac aagcatcaca ttcacacagg    480
gctcatagca gagcagcgag atcttcagtg cctggagtga cacggaaat gcagatggtc    540
tcagctatga acacagcaaa acaatgaat ggaatgggaa aggagaaga cgttcaaaaa    600
ctggcagaag aactgcaaag caacattgga gtattgagat ctcttggggc aagtcaaaag    660
aatggggaag gaattgcaaa ggatgtaatg gaagtgctaa agcagagctc tatgggaaat    720
tcagctcttg tgaagaaata cctataa                                       747

<210> SEQ ID NO 77
<211> LENGTH: 248
<212> TYPE: PRT
<213> ORGANISM: Influenza B virus

<400> SEQUENCE: 77

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu

```
            130                 135                 140
Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245

<210> SEQ ID NO 78
<211> LENGTH: 585
<212> TYPE: PRT
<213> ORGANISM: Influenza B virus

<400> SEQUENCE: 78

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Val Cys Thr Glu Gly Glu Asp Gln Ile Thr Val Trp Gly Phe His
        195                 200                 205

Ser Asp Asn Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
                245                 250                 255
```

-continued

```
Ser Gly Arg Ile Val Val Asp Tyr Met Val Gln Lys Pro Gly Lys Thr
            260                 265                 270
Gly Thr Ile Val Tyr Gln Arg Gly Val Leu Leu Pro Gln Lys Val Trp
        275                 280                 285
Cys Ala Ser Gly Arg Ser Lys Val Ile Lys Gly Ser Leu Pro Leu Ile
    290                 295                 300
Gly Glu Ala Asp Cys Leu His Glu Lys Tyr Gly Gly Leu Asn Lys Ser
305                 310                 315                 320
Lys Pro Tyr Tyr Thr Gly Glu His Ala Lys Ala Ile Gly Asn Cys Pro
                325                 330                 335
Ile Trp Val Lys Thr Pro Leu Lys Leu Ala Asn Gly Thr Lys Tyr Arg
            340                 345                 350
Pro Pro Ala Lys Leu Leu Lys Glu Arg Gly Phe Phe Gly Ala Ile Ala
        355                 360                 365
Gly Phe Leu Glu Gly Gly Trp Glu Gly Met Ile Ala Gly Trp His Gly
    370                 375                 380
Tyr Thr Ser His Gly Ala His Gly Val Ala Val Ala Ala Asp Leu Lys
385                 390                 395                 400
Ser Thr Gln Glu Ala Ile Asn Lys Ile Thr Lys Asn Leu Asn Ser Leu
                405                 410                 415
Ser Glu Leu Glu Val Lys Asn Leu Gln Arg Leu Ser Gly Ala Met Asp
            420                 425                 430
Glu Leu His Asn Glu Ile Leu Glu Leu Asp Glu Lys Val Asp Asp Leu
        435                 440                 445
Arg Ala Asp Thr Ile Ser Ser Gln Ile Glu Leu Ala Val Leu Leu Ser
    450                 455                 460
Asn Glu Gly Ile Ile Asn Ser Glu Asp Glu His Leu Leu Ala Leu Glu
465                 470                 475                 480
Arg Lys Leu Lys Lys Met Leu Gly Pro Ser Ala Val Asp Ile Gly Asn
                485                 490                 495
Gly Cys Phe Glu Thr Lys His Lys Cys Asn Gln Thr Cys Leu Asp Arg
            500                 505                 510
Ile Ala Ala Gly Thr Phe Asn Ala Gly Glu Phe Ser Leu Pro Thr Phe
        515                 520                 525
Asp Ser Leu Asn Ile Thr Ala Ala Ser Leu Asn Asp Asp Gly Leu Asp
    530                 535                 540
Asn His Thr Gln Ile Leu Ser Ile Tyr Ser Thr Val Ala Ser Ser Leu
545                 550                 555                 560
Ala Leu Ala Ile Met Met Ala Gly Leu Ser Leu Trp Met Cys Ser Asn
                565                 570                 575
Gly Ser Leu Gln Cys Arg Ile Cys Ile
            580                 585

<210> SEQ ID NO 79
<211> LENGTH: 464
<212> TYPE: PRT
<213> ORGANISM: Influenza B virus

<400> SEQUENCE: 79

Met Asn Pro Asn Gln Lys Ile Ile Thr Ile Gly Ser Ile Cys Met Val
1               5                   10                  15
Ile Gly Ile Val Ser Leu Met Leu Gln Ile Gly Asn Met Ile Ser Ser
            20                  25                  30
Asp Ile Leu Leu Lys Phe Ser Thr Glu Ile Thr Ala Pro Thr Met
        35                  40                  45
```

-continued

```
Pro Leu Asp Cys Ala Asn Ala Ser Asn Val Gln Ala Val Asn Arg Ser
 50                  55                  60
Ala Thr Lys Gly Val Thr Leu Leu Pro Glu Pro Glu Trp Thr Tyr
 65                  70                  75                  80
Pro Arg Leu Ser Cys Pro Gly Ser Thr Phe Gln Lys Ala Leu Leu Ile
                 85                  90                  95
Ser Pro His Arg Phe Glu Thr Lys Gly Asn Ser Ala Pro Leu Ile
                100                 105                 110
Ile Arg Glu Pro Phe Ile Ala Cys Gly Pro Lys Glu Cys Lys His Phe
            115                 120                 125
Ala Leu Thr His Tyr Ala Ala Gln Pro Gly Gly Tyr Tyr Asn Gly Thr
        130                 135                 140
Arg Glu Asp Arg Asn Lys Leu Arg His Leu Ile Ser Val Lys Leu Gly
145                 150                 155                 160
Lys Ile Pro Thr Val Glu Asn Ser Ile Phe His Met Ala Ala Trp Ser
                165                 170                 175
Gly Ser Ala Cys His Asp Gly Lys Glu Trp Thr Tyr Ile Gly Val Asp
            180                 185                 190
Gly Pro Asp Ser Asn Ala Leu Leu Lys Ile Lys Tyr Gly Glu Ala Tyr
        195                 200                 205
Thr Asp Thr Tyr His Ser Tyr Ala Asn Asn Ile Leu Arg Thr Gln Glu
210                 215                 220
Ser Ala Cys Asn Cys Ile Gly Gly Asn Cys Tyr Leu Met Ile Thr Asp
225                 230                 235                 240
Gly Ser Ala Ser Gly Ile Ser Glu Cys Arg Phe Leu Lys Ile Arg Glu
                245                 250                 255
Gly Arg Ile Ile Lys Glu Ile Phe Pro Thr Gly Arg Val Lys His Thr
            260                 265                 270
Glu Glu Cys Thr Cys Gly Phe Ala Ser Asn Lys Thr Ile Glu Cys Ala
        275                 280                 285
Cys Arg Asp Asn Ser Tyr Thr Ala Lys Arg Pro Phe Val Lys Leu Asn
    290                 295                 300
Val Glu Thr Asp Thr Ala Glu Ile Arg Leu Met Cys Thr Glu Thr Tyr
305                 310                 315                 320
Leu Asp Thr Pro Arg Pro Asp Asp Gly Ser Ile Thr Gly Pro Cys Glu
                325                 330                 335
Ser Asn Gly Asn Lys Gly Ser Gly Gly Ile Lys Gly Gly Phe Val His
            340                 345                 350
Gln Arg Met Ala Ser Lys Ile Gly Arg Trp Tyr Ser Arg Thr Met Ser
        355                 360                 365
Lys Thr Lys Arg Met Gly Met Gly Leu Tyr Val Lys Tyr Asp Gly Asp
370                 375                 380
Pro Trp Ile Asp Ser Asp Ala Leu Ala Leu Ser Gly Val Met Val Ser
385                 390                 395                 400
Met Glu Glu Pro Gly Trp Tyr Ser Phe Gly Phe Glu Ile Lys Asp Lys
                405                 410                 415
Lys Cys Asp Val Pro Cys Ile Gly Ile Glu Met Val His Asp Gly Gly
            420                 425                 430
Lys Glu Thr Trp His Ser Ala Ala Thr Ala Ile Tyr Cys Leu Met Gly
        435                 440                 445
Ser Gly Gln Leu Leu Trp Asp Thr Val Thr Gly Val Asp Met Ala Leu
    450                 455                 460
```

<210> SEQ ID NO 80
<211> LENGTH: 405
<212> TYPE: PRT
<213> ORGANISM: Artificial Sequence
<220> FEATURE:
<223> OTHER INFORMATION: Chimeric RSV F1 (HA TM/CY) Protein

<400> SEQUENCE: 80

```
Met Glu Gly Glu Val Asn Lys Ile Lys Ser Ala Leu Leu Ser Thr Asn
1               5                   10                  15

Lys Ala Val Val Ser Leu Ser Asn Gly Val Ser Val Leu Thr Ser Lys
            20                  25                  30

Val Leu Asp Leu Lys Asn Tyr Ile Asp Lys Gln Leu Leu Pro Ile Val
        35                  40                  45

Asn Lys Gln Ser Cys Ser Ile Ser Asn Ile Glu Thr Val Ile Glu Phe
    50                  55                  60

Gln Gln Lys Asn Asn Arg Leu Leu Glu Ile Thr Arg Glu Phe Ser Val
65                  70                  75                  80

Asn Ala Gly Val Thr Thr Pro Val Ser Thr Tyr Met Leu Thr Asn Ser
                85                  90                  95

Glu Leu Leu Ser Leu Ile Asn Asp Met Pro Ile Thr Asn Asp Gln Lys
            100                 105                 110

Lys Leu Met Ser Asn Asn Val Gln Ile Val Arg Gln Gln Ser Tyr Ser
        115                 120                 125

Ile Met Ser Ile Ile Lys Glu Glu Val Leu Ala Tyr Val Val Gln Leu
    130                 135                 140

Pro Leu Tyr Gly Val Ile Asp Thr Pro Cys Trp Lys Leu His Thr Ser
145                 150                 155                 160

Pro Leu Cys Thr Thr Asn Thr Lys Glu Gly Ser Asn Ile Cys Leu Thr
                165                 170                 175

Arg Thr Asp Arg Gly Trp Tyr Cys Asp Asn Ala Gly Ser Val Ser Phe
            180                 185                 190

Phe Pro Gln Ala Glu Thr Cys Lys Val Gln Ser Asn Arg Val Phe Cys
        195                 200                 205

Asp Thr Met Asn Ser Leu Thr Leu Pro Ser Glu Ile Asn Leu Cys Asn
    210                 215                 220

Val Asp Ile Phe Asn Pro Lys Tyr Asp Cys Lys Ile Met Thr Ser Lys
225                 230                 235                 240

Thr Asp Val Ser Ser Ser Val Ile Thr Ser Leu Gly Ala Ile Val Ser
                245                 250                 255

Cys Tyr Gly Lys Thr Lys Cys Thr Ala Ser Asn Lys Asn Arg Gly Ile
            260                 265                 270

Ile Lys Thr Phe Ser Asn Gly Cys Asp Tyr Val Ser Asn Lys Gly Met
        275                 280                 285

Asp Thr Val Ser Val Gly Asn Thr Leu Tyr Tyr Val Asn Lys Gln Glu
    290                 295                 300

Gly Lys Ser Leu Tyr Val Lys Gly Glu Pro Ile Ile Asn Phe Tyr Asp
305                 310                 315                 320

Pro Leu Val Phe Pro Ser Asp Glu Phe Asp Ala Ser Ile Ser Gln Val
                325                 330                 335

Asn Glu Lys Ile Asn Gln Ser Leu Ala Phe Ile Arg Lys Ser Asp Glu
            340                 345                 350

Leu Leu His Asn Val Asn Ala Gly Lys Ser Thr Thr Asn Ile Met Gln
        355                 360                 365
```

```
Ile Leu Ser Ile Tyr Ser Thr Val Ala Ser Ser Leu Ala Leu Ala Ile
    370             375             380

Met Met Ala Gly Leu Ser Leu Trp Met Cys Ser Asn Gly Ser Leu Gln
385             390             395             400

Cys Arg Ile Cys Ile
                405
```

HIGHLY EFFICIENT INFLUENZA MATRIX (M1) PROTEINS

CROSS REFERENCE TO RELATED APPLICATIONS

This application is a continuation of Ser. No. 15/287,433, filed Oct. 6, 2016, now U.S. Pat. No. 9,951,317, which is a continuation of Ser. No. 14/628,513, filed Feb. 23, 2015, now U.S. Pat. No. 9,464,276, which is a continuation of Ser. No. 13/280,043, filed Oct. 24, 2011, now U.S. Pat. No. 8,992,939, which is a continuation of Ser. No. 13/032,571, filed Feb. 22, 2011, which is a continuation of Ser. No. 12/832,657, filed Jul. 8, 2010, which is a continuation of Ser. No. 12/558,844, filed Sep. 14, 2009, which claims the benefit to Ser. No. 61/096,561, filed Sep. 12, 2008. Ser. No. 12/558,844 also claims priority as a continuation-in-part to Ser. No. 12/340,186, filed Dec. 19, 2008, now U.S. Pat. No. 8,506,967, which claims benefit to Ser. No. 61/015,440, filed Dec. 20, 2007. Ser. No. 12/558,844 also claims priority, as a continuation-in-part, to Ser. No. 11/582,540, filed Oct. 18, 2006, now U.S. Pat. No. 8,080,255, which claims priority Ser. Nos. 60/727,513, filed Oct. 18, 2005, 60/780,847, filed Mar. 10, 2006, 60/800,006, filed May 15, 2006, 60/831,196, filed Jul. 17, 2006, 60/832,116, filed Jul. 21, 2006, and 60/845,495, filed Sep. 19, 2006, and also claims priority as a continuation-in-part of Ser. No. 10/617,569, filed Jul. 11, 2003, now U.S. Pat. No. 8,592,197; this application is also related to U.S. Non-Provisional patent application Ser. No. 11/372,466, filed Mar. 10, 2006, and International Patent Application Serial No. PCT/US2004/022001, filed Jul. 9, 2004. The disclosure of each of these related applications are incorporated herein by reference in their entireties for all purposes.

GOVERNMENT RIGHTS STATEMENT

A portion of this invention was made with government support under contract RFA-AI-03-016 awarded by the Department of Health and Human Services. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_039_09US_SeqList_ST25.TXT, file size 197 kilobytes).

BACKGROUND OF INVENTION

Influenza virus is a member of Orthomyxoviridae family (for review, see Murphy and Webster, 1996). There are three subtypes of influenza viruses designated A, B, and C. The influenza virion contains a segmented negative-sense RNA genome. The influenza virion includes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2) proteins. The HA, NA, M1, and M2 are membrane associated, whereas NP, PB1, PB2, PA, and NS2 are nucleocapsid associated proteins. The NS1 is the only nonstructural protein not associated with virion particles but specific for influenza-infected cells. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines because they are highly immunogenic.

Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA protein undergoes conformational changes that lead to fusion of viral and host cell membranes followed by virus uncoating and M2-mediated release of M1 proteins from nucleocapsid-associated ribonucleoproteins (RNPs), which migrate into the cell nucleus for viral RNA synthesis. Antibodies to HA molecule can prevent virus infection by neutralizing virus infectivity, whereas antibodies to NA proteins mediate their effect on the early steps of viral replication.

To date, all commercially available influenza vaccines for non-pandemic strains in the United States have been propagated in embryonated hen's eggs. Although influenza virus grows well in hen's eggs, production of vaccine is dependent on the availability of eggs. Supplies of eggs must be organized, and strains for vaccine production selected months in advance of the next flu season, limiting the flexibility of this approach, and often resulting in delays and shortages in production and distribution. Unfortunately, some influenza vaccine strains, do not replicate well in embryonated chicken eggs, and have to be isolated by cell culture in a costly and time consuming procedure.

Systems for producing influenza viruses in cell culture have also been developed in recent years (See, e.g., Furminger. Vaccine Production, in Nicholson et al. (eds) Textbook of Influenza pp. 324-332; Merten et al. (1996) Production of influenza virus in cell cultures for vaccine preparation, in Cohen & Shafferman (eds) Novel Strategies in Design and Production of Vaccines pp. 141-151). Typically, these methods involve the infection of suitable immortalized host cells with a selected strain of virus. While eliminating many of the difficulties related to vaccine production in hen's eggs, not all pathogenic strains of influenza grow well and can be produced according to established tissue culture methods. In addition, many strains with desirable characteristics, e.g., attenuation, temperature sensitivity and cold adaptation, suitable for production of live attenuated vaccines, have not been successfully grown in tissue culture using established methods. In addition, live attenuated viruses have not been accepted by the general public due to fears reversion to a virulent virus.

Inactivated influenza A and B virus vaccines are licensed currently as trivalent vaccines for parenteral administration. These trivalent vaccines are produced as monovalent bulk in the allantoic cavity of embryonated chick eggs, purified by rate zonal centrifugation or column chromatography, inactivated with formalin or β-propiolactone, and formulated as a blend of the two strains of type A and the type B strain of influenza viruses in circulation among the human population for a given year. The available commercial influenza vaccines are whole virus (WV) or subvirion (SV; split or purified surface antigen) virus vaccines. The WV vaccine contains intact, inactivated virions. SV vaccines treated with solvents such as tri-n-butyl phosphate (Flu-Shield, Wyeth-Lederle) contain nearly all of the viral structural proteins and some of the viral envelopes. SV vaccines solubilized with Triton X-100 (Fluzone, Sanofi-Aventis; Fluvirin, Novartis) contain aggregates of HA monomers, NA, and NP principally, although residual amounts of other viral structural proteins are present. A live attenuated cold-adapted virus vaccine (FluMist, MedImmune) was granted marketing approval recently by the FDA for commercial usage as an intranasally delivered vaccine indicated for active immunization and the prevention of disease caused by influenza A and B viruses in healthy children and adolescents, 5-17 years of age and healthy adults 18-49 years of age.

Several recombinant products have been developed as recombinant influenza vaccine candidates. These approaches have focused on the expression, production, and purification of influenza virus type A HA and NA proteins, including expression of these proteins using baculovirus infected insect cells (Crawford et al, 1999; Johansson, 1999; Treanor et al., 1996), viral vectors (Pushko et al., 1997; Berglund et al., 1999), and DNA vaccine constructs (Olsen et al., 1997).

Crawford et al. (1999) demonstrated that influenza HA expressed in baculovirus infected insect cells is capable of preventing lethal influenza disease caused by avian H5 and H7 influenza subtypes. At the same time, another group demonstrated that baculovirus-expressed influenza HA and NA proteins induce immune responses in animals superior to those induced by a conventional vaccine (Johansson et al., 1999). Immunogenicity and efficacy of baculovirus-expressed hemagglutinin of equine influenza virus was compared to a homologous DNA vaccine candidate (Olsen et al., 1997). Taken together, the data demonstrated that a high degree of protection against influenza virus challenge can be induced with recombinant HA or NA proteins, using various experimental approaches and in different animal models.

Lakey et al. (1996) showed that a baculovirus-derived influenza HA vaccine was well-tolerated and immunogenic in human volunteers in a Phase I dose escalation safety study. However, results from Phase II studies conducted at several clinical sites in human volunteers vaccinated with several doses of influenza vaccines comprised of HA and/or NA proteins indicated that the recombinant subunit protein vaccines did not elicit protective immunity [G. Smith, Protein Sciences; M. Perdue, USDA, Personal Communications]. These results indicated that conformational epitopes displayed on the surface of HA and NA peplomers of infectious virions were important in the elicitation of neutralizing antibodies and protective immunity.

Regarding the inclusion of other influenza proteins in recombinant influenza vaccine candidates, a number of studies have been carried out, including the experiments involving influenza nucleoprotein, NP, alone or in combination with M1 protein (Ulmer et al., 1993; Ulmer et al., 1998; Zhou et al., 1995; Tsui et al., 1998). These vaccine candidates, which were composed of quasi-invariant inner virion proteins, elicited a broad spectrum immunity that was primarily cellular (both CD4+ and CD8+ memory T cells). These experiments involved the use of the DNA or viral genetic vectors. Relatively large amounts of injected DNA were needed, as results from experiments with lower doses of DNA indicated little or no protection (Chen et al., 1998). Hence, further preclinical and clinical research may be required to evaluate whether such DNA-based approaches involving influenza NP and M1 are safe, effective, and persistent.

Recently, in an attempt to develop more effective vaccines for influenza, particulate proteins were used as carriers of influenza M2 protein epitopes. The rationale for development of an M2-based vaccine was that in animal studies protective immunity against influenza was elicited by M2 proteins (Slepushkin et al., 1995). Neirynck et al. (1999) used a 23-aa long M2 transmembrane domain as an amino terminal fusion partner with the hepatitis B virus core antigen (HBcAg) to expose the M2 epitope(s) on the surface of HBcAg capsid-like particles. However, in spite of the fact that both full-length M2 protein and M2-HBcAg VLP induced detectable antibodies and protection in mice, it was unlikely that future influenza vaccines would be based exclusively on the M2 protein, as the M2 protein was present at low copy number per virion, was weakly antigenic, was unable to elicit antibodies that bound free influenza virions, and was unable to block virus attachment to cell receptors (i.e. virus neutralization).

Since previous research has shown that the surface influenza glycoproteins, HA and NA, are the primary targets for elicitation of protective immunity against influenza virus and that M1 provides a conserved target for cellular immunity to influenza, a new vaccine candidate may include these viral antigens as a protein macromolecular particle, such as virus-like particles (VLPs). Further, the particle with these influenza antigens may display conformational epitopes that elicit neutralizing antibodies to multiple strains of influenza viruses.

Virus-like particles mimic the overall structure of a virus particle without the requirement of containing infectious material. VLPs lack a viral DNA or RNA genome, but retain the three-dimensional structure of an authentic virus. VLPs have the ability to stimulate B-cell mediated responses, CD4 proliferative responses and cytotoxic T lymphocytes responses (see, Schirmbeck et al. (1996) Eur. J. Immunol., 26, 2812-2822). In addition, virus-like particles induce MHC class I-restricted T-cell responses.

Several studies have demonstrated that recombinant influenza proteins could self-assemble into VLPs in cell culture using mammalian expression plasmids or baculovirus vectors (Gomez-Puertas et al., 1999; Neumann et al., 2000; Latham and Galarza, 2001). Gomez-Puertas et al. (1999) demonstrated that efficient formation of influenza VLP depends on the expression levels of viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing human influenza virus HA, NA, M1, and M2 genes. These studies demonstrated that influenza virion proteins may self-assemble upon co-expression in eukaryotic cells.

However, one problem associated with the use of the M1 protein from human strains of influenza virus is that they are poor proteins for efficient VLP formation. Indeed, the present inventors have found that the use of the M1 protein from human seasonal strains results in low quantities of VLPs that are not sufficient for commercial VLP production. Surprisingly, the present inventors found that M1 proteins derived from avian strains of influenza virus are much more favorable proteins for efficient VLP production. This increased efficiency was found to be mediated in part by a single amino acid difference in the M1 protein (an R to K substitution at position 101 of the M1 protein). This mutation was found almost exclusively in avian M1 proteins. Importantly, the present inventors have found that in order to produce recoverable levels of VLPs sufficient for vaccine production, it is necessary to use M1 proteins, such as avian M1 proteins, harboring the $K^{101}$ amino acid residue. Accordingly, the knowledge that increased formation and recovery of VLPs using M1 proteins containing this amino acid substitution is critical to vaccine development.

SUMMARY OF INVENTION

In a first aspect, the present invention provides virus-like particles (VLPs) comprising an influenza M1 protein comprising a $K^{101}$ residue. In one embodiment, the M1 protein comprises the amino acid residues YKKL (SEQ ID NO: 61) at the amino acids corresponding to positions 100-103 of the protein encoded by SEQ ID NO: 3. In another embodiment, the M1 protein comprises the amino acid residues YKKL at the positions corresponding to positions 100-103 of SEQ ID NO: 49. In another embodiment, the M1 protein is derived from an avian influenza virus strain. In an exemplary embodiment, the avian influenza virus strain is A/Indonesia/5/05.

In various embodiments described herein, the VLPs of the invention may further comprise influenza hemagglutinin (HA) and/or neuraminidase (NA) proteins. In one embodiment, the HA and NA proteins are derived from an avian influenza virus. In one embodiment, the avian influenza virus is H5N1. In another embodiment, the avian influenza virus in H9N2.

In another embodiment, the VLPs of the invention may further comprise HA and/or NA proteins derived from a non-avian influenza virus. In one embodiment, the non-avian influenza protein is a seasonal influenza protein. In one embodiment, the seasonal influenza virus is a type A influenza virus. In another embodiment, the seasonal influenza virus is a type B influenza virus.

In various embodiments described herein, the HA and/or NA may exhibit hemagglutinin and/or neuraminidase activity, respectively.

In additional embodiments, the HA and/or NA may be chimeric proteins. In one embodiment, said chimeric proteins comprise external domains of non-avian influenza HA and/or NA protein sequences fused to the transmembrane and/or cytoplasmic terminal domains of avian or heterologous influenza HA and/or NA. In an exemplary embodiment, the non-avian influenza HA and/or NA are derived from the influenza strain A/Wisconsin/67/2005 and the avian influenza HA and/or NA are derived from influenza strain A/Indonesia/5/05.

In a second aspect, the present invention provides a method of increasing the efficiency of influenza VLP production comprising expressing an influenza M1 protein comprising a $K^{101}$ residue and at least one non-avian influenza protein in a host cell. In one embodiment, the M1 protein comprises the amino acid residues YKKL (SEQ ID NO: 61) at the amino acids corresponding to positions 100-103 of the protein encoded by SEQ ID NO: 3. In another embodiment, the M1 protein comprises the amino acid residues YKKL at the positions corresponding to positions 100-103 of SEQ ID NO: 49. In another embodiment, the M1 protein is derived from an avian influenza virus strain. In an exemplary embodiment, the avian influenza virus strain is A/Indonesia/5/05. In one embodiment, said non-avian influenza protein is a seasonal influenza protein. In another embodiment, said HA or NA have hemagglutinin and neuraminidase activity, respectively. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of avian or heterologous influenza HA and/or NA.

The present invention also comprises a chimeric VLP comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. In one embodiment, the VLP further comprises HA and/or NA proteins derived from a non-avian influenza virus. In one embodiment, the non-avian influenza protein is a seasonal influenza protein. In various embodiments described herein, the HA and/or NA have hemagglutinin and/or neuraminidase activity, respectively. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of avian or heterologous influenza HA and/or NA. In another embodiment, said non-avian influenza protein is from an infectious agent. In another embodiment, said infectious agent is a virus, bacterium, fungus, or parasite. In another embodiment, said non-avian influenza protein is a chimeric protein comprising the transmembrane domain and/or cytoplasmic tail of influenza HA and or influenza NA fused to a protein, or a portion thereof, from an infective agent. In another embodiment, said VLPs comprise more than one protein from an infectious agent. In another embodiment, said infectious agent comprises at least one SARS virus protein. In another embodiment, said SARS virus protein is the S protein. In another embodiment, said S protein is a chimeric protein comprising the transmembrane domain and/or cytoplasmic tail of influenza HA or influenza NA fused to the S protein. In another embodiment, said avian influenza M1 protein comprises a lysine at the second position of the M1 protein L domain. In another embodiment, said L domain comprises the sequence YKKL. In another embodiment, said VLP is expressed from a eukaryotic cell comprising one or more nucleic acids encoding an influenza M1 protein under conditions that permit the formation of VLPs. In another embodiment, said eukaryotic cell is selected from the group consisting of yeast, inset, amphibian, avian and mammalian cells. In another embodiment, said insect cell is Sf9.

The present invention also provides VLPs comprising an influenza M1 protein comprising a lysine at the second position of the M1 protein L domain (e.g. $K^{101}$). In one embodiment, said L domain comprises the sequence YKKL. In another embodiment, the M1 protein exhibits increased VLP formation efficiency as compared to an M1 protein comprising an arginine at the second position of the M1 protein L domain. In another embodiment, the increased VLP formation efficiency is at least a 50% increase in VLP formation with substantially equivalent amounts of M1 protein expression. In another embodiment, the VLP formation efficiency is measured by comparing M1 protein levels in a VLP fraction. In another embodiment, the VLP further comprises an influenza HA and/or NA protein. In another embodiment, the HA and/or NA protein is from an avian, pandemic, and/or seasonal influenza virus. In another embodiment, the VLP further comprises a heterologous protein. In another embodiment, said VLP is expressed from a eukaryotic cell comprising one or more nucleic acids encoding an influenza M1 protein under conditions that permit the formation of VLPs. In another embodiment, said eukaryotic cell is selected from the group consisting of yeast, inset, amphibian, avian and mammalian cells. In another embodiment, said insect cell is Sf9.

The present invention also comprises an antigenic formulation comprising a chimeric VLP comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. In another embodiment, said VLP comprises HA and/or NA from a non-avian influenza virus. In another embodiment, said HA or NA have hemagglutinin and neuraminidase activity, respectively. In another embodiment, said HA and/or NA are chimeric proteins. In another embodiment, chimeric proteins comprise external domains of non-avian influenza HA and/or NA protein sequences fused to the transmembrane and/or cytoplasmic-terminal domains of the avian or heterologous influenza HA and/or NA. In another embodiment, the antigenic formulation comprises a chimeric VLP comprising an influenza M1 protein comprising an lysine at the second position of the M1 protein L domain. In another embodiment, said L domain comprises the sequence YKKL. In another embodiment, said non-avian influenza protein is from an infectious agent. In another embodiment, said infectious agent is from a virus, bacteria, fungus and/or parasite. In another embodiment, said chimeric proteins comprise a fusion between the influenza HA with the protein, or a portion thereof, from an infectious agent. In another embodiment, said non-avian influenza protein is a chimeric protein comprising the transmembrane domain and/or cytoplasmic tail of influenza HA and or influenza NA fused to a protein, or a portion thereof, from an infective agent. In another embodiment, said VLPs comprise more than one protein from an infectious agent.

The present invention also comprises vaccines comprising a chimeric VLP comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. In another embodiment, said VLP comprises HA and/or NA from a non-avian influenza virus. In another embodiment, said HA or NA have hemagglutinin and neuraminidase activity, respectively. In another embodiment, said HA and/or NA are chimeric proteins. In another embodiment, chimeric proteins comprise external domains of non-avian influenza HA and/or NA protein sequences fused to the transmembrane and/or cytoplasmic-terminal domains of the avian or heterologous influenza HA and/or NA. In another embodiment, the antigenic formulation comprises a chimeric VLP comprising an influenza M1 protein comprising an lysine at the second position of the M1 protein L domain. In another embodiment, said L domain comprises the sequence YKKL. In another embodiment, said non-avian influenza protein is derived from an infectious agent. In another embodiment, the infectious agent is a virus, bacterium, fungus or parasite. In another embodiment, said chimeric proteins comprise a fusion between the influenza HA with a protein, or a portion thereof, from an infectious agent. In another embodiment, said non-avian influenza protein is a chimeric protein comprising the transmembrane domain and/or cytoplasmic tail of influenza HA and/or influenza NA fused to a protein, or a portion thereof, from an infectious agent. In another embodiment, said VLPs comprise more than one protein from an infectious agent. In another embodiment, said VLP is formulated with an adjuvant or immune stimulator. In another embodiment, said adjuvant comprises Novasomes®.

The present invention also comprises a method of inducing immunity in a vertebrate comprising administering to said vertebrate a chimeric VLP comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an an influenza M1 protein comprising a $K^{101}$ residue, such as an avian influenza M1 protein, and at least one non-avian influenza protein. In another embodiment, said immune response is a humoral immune response. In another embodiment, said immune response is a cellular immune response. In another embodiment, said method comprises administering to said vertebrate the vaccine orally, intradermally, intranasally, intramuscularly, intraperitoneally, intravenously, or subcutaneously. In another embodiment, at least two effective doses of the vaccine are administered. In another embodiment, said doses are administered at least 2 weeks apart, at least 3 weeks apart, at least 4 weeks apart, at least 5 weeks apart or at least 6 weeks apart.

The present invention also comprises a method of preventing and/or reducing a viral infection or symptom thereof, comprising administering to a vertebrate a chimeric VLP comprising an influenza M1 protein comprising a $K^{101}$ residue, such as an avian influenza M1 protein, and at least one non-avian influenza protein.

The present invention also comprises a method of reducing the severity of influenza in a population, comprising administering the a chimeric VLP comprising an influenza M1 protein comprising a $K^{101}$ residue, such as an avian influenza M1 protein, and at least one non-avian influenza protein to enough individuals in said population in order to prevent or decrease the chance influenza virus transmission to another individual in said population.

The invention also provides for a pharmaceutical pack or kit comprising one or more containers filled with one or more of the ingredients of the vaccine formulations of the invention. In one embodiment, the vaccine formulations of the invention are packaged in a hermetically sealed container such as an ampoule or sachette indicating the quantity of composition.

The present invention provides for a vaccine comprising an influenza VLP, wherein said VLP comprises influenza M1, HA and NA proteins, wherein said vaccine induces substantial immunity to influenza virus infection in an animal susceptible to influenza. In one embodiment, said M1 protein is derived from a different influenza virus strain as compared to the HA and NA proteins. In another embodiment, said HA and/or NA exhibit hemagglutinin activity and/or neuraminidase activity, respectfully. In another embodiment, said influenza VLP comprises seasonal influenza virus HA and NA proteins. In another embodiment, said influenza VLP comprises avian influenza HA and NA proteins. In one embodiment, the influenza M1 protein comprises a $K^{101}$ residue. In a further embodiment, the influenza M1 protein is an avian influenza M1 protein.

The present invention also provides for a method of inducing substantial immunity to influenza virus infection in an animal susceptible to influenza, comprising administering at least one effective dose of the vaccine comprising an influenza VLP. In one embodiment, said method comprises administering to an animal said influenza VLP orally, intradermally, intranasally, intramusclarly, intraperitoneally, intravenously, or subcutaneously.

The present invention also provides for a method of formulating a vaccine that induces substantial immunity to influenza virus infection to an animal susceptible to influenza, comprising adding to said formulation an effective dose of an influenza VLP, wherein said VLP comprises influenza M1, HA and NA proteins, wherein said vaccine induces substantial immunity to influenza virus infection to said animal. In one embodiment, said VLP consists essentially of influenza M1, HA and NA proteins. In another embodiment, said VLP consists of influenza M1, HA and NA proteins. In one embodiment, the influenza M1 protein comprises a $K^{101}$ residue. In a further embodiment, the influenza M1 protein is an avian influenza M1 protein.

The present invention also provides for a virus like particle (VLP) comprising an influenza virus M1 protein and influenza virus H5 and N1 hemagglutinin and neuraminidase proteins. In one embodiment said M1 protein is derived from a different influenza virus strain as compared to the H5 and N1 proteins. In one embodiment, said H5 or N1 are from a H5N1 clade 1 influenza virus. In another embodiment, said H5 and N1 are from a H5N1 clade 2 influenza virus.

The invention also provides a macromolecular protein structure containing (a) a first influenza virus M1 protein and (b) an additional structural protein, which may include a second or more influenza virus M1 protein; a first, second or more influenza virus HA protein; a first, second, or more influenza virus NA protein; and a first, second, or more influenza virus M2 protein. If the additional structural protein is not from a second or more influenza virus M1 protein, then both or all members of the group, e.g., first and second influenza M2 virus proteins are included. As such, there is provided a functional influenza protein structure, including a subviral particle, VLP, or capsomer structure, or a portion thereof, a vaccine, a multivalent vaccine, and mixtures thereof consisting essentially of influenza virus structural proteins produced by the method of the invention. In a particularly preferred embodiment, the influenza macromolecular protein structure includes influenza virus HA, NA, and M1 proteins that are the expression products of influenza virus genes cloned as synthetic fragments from a wild type virus. In one embodiment, the influenza M1 protein comprises a $K^{101}$ residue. In a further embodiment, the influenza M1 protein is an avian influenza M1 protein.

The macromolecular protein structure may also include an additional structural protein, for example, a nucleoprotein (NP), membrane proteins from species other than noninfluenza viruses and a membrane protein from a non-influenza source, which are derived from avian or mammalian origins and different subtypes of influenza virus, including subtype A and B influenza viruses. The invention may include a chimeric macromolecular protein structure, which includes a portion of at least one protein having a moiety not produced by influenza virus.

Prevention of influenza may be accomplished by providing a macromolecular protein structure that may be self-assembled in a host cell from a recombinant construct. The macromolecular protein structure of the invention has the ability to self-assemble into homotypic or heterotypic virus-like particles (VLPs) that display conformational epitopes on HA and NA proteins, which elicit neutralizing antibodies that are protective. The composition may be a vaccine composition, which also contains a carrier or diluent and/or an adjuvant. The functional influenza VLPs elicit neutralizing antibodies against one or more strains or types of influenza virus depending on whether the functional influenza VLPs contain HA and/or NA proteins from one or more viral strains or types. The vaccine may include influenza virus proteins that are wild type influenza virus proteins. Preferably, the structural proteins containing the influenza VLP, or a portion of thereof, may be derived from the various strains of wild type influenza viruses. The influenza vaccines may be administered to humans or animals to elicit protective immunity against one or more strains or types of influenza virus.

The macromolecular protein structures of the invention may exhibit hemagglutinin activity and/or neuraminidase activity.

The invention provides a method for producing a VLP derived from influenza by constructing a recombinant construct that encodes influenza structural genes, including M1, HA, and at least one structural protein derived from influenza virus. In one embodiment, the influenza M1 protein comprises a $K^{101}$ residue. In a further embodiment, the influenza M1 protein is an avian influenza M1 protein. A recombinant construct is used to transfect, infect, or transform a suitable host cell with the recombinant baculovirus. The host cell is cultured under conditions which permit the expression of M1, HA and at least one structural protein derived from influenza virus and the VLP is formed in the host cell. The infected cell media containing a functional influenza VLP is harvested and the VLP is purified. The invention also features an additional step of co-transfecting, co-infecting or co-transforming the host cell with a second recombinant construct which encodes a second influenza protein, thereby incorporating the second influenza protein within the VLP. Such structural proteins may be derived from influenza virus, including NA, M2, and NP, and at least one structural protein is derived from avian or mammalian origins. The structural protein may be a subtype A and B influenza viruses. According to the invention, the host cell may be a eukaryotic cell. In addition, the VLP may be a chimeric VLP.

The invention also features a method of formulating a drug substance containing an influenza VLP by introducing recombinant constructs encoding influenza viral genes into host cells and allowing self-assembly of the recombinant influenza viral proteins into a functional homotypic or heterotypic VLP in cells. The influenza VLP is isolated and purified and a drug substance is formulated containing the influenza VLP. The drug substance may further include an adjuvant. In addition, the invention provides a method for formulating a drug product, by mixing such a drug substance containing an influenza VLP with a lipid vesicle, i.e., a non-ionic lipid vesicle. Thus, functional homotypic or heterotypic VLPs may bud as enveloped particles from the infected cells. The budded influenza VLPs may be isolated and purified by ultracentrifugation or column chromatography as drug substances and formulated alone or with adjuvants such as Novasomes®, a product of Novavax, Inc., as drug products such as vaccines. Novasomes®, which provide an enhanced immunological effect, are further described in U.S. Pat. No. 4,911,928, which is incorporated herein by reference.

The invention provides a method for detecting humoral immunity to influenza virus infection in a vertebrate by providing a test reagent including an effective antibody-detecting amount of influenza virus protein having at least one conformational epitope of an influenza virus macromolecular structure. The test reagent is contacted with a sample of bodily fluid from a vertebrate to be examined for influenza virus infection. Influenza virus specific antibodies contained in the sample are allowed to bind to the conformational epitope of an influenza virus macromolecular structure to form antigen-antibody complexes. The complexes are separated from unbound complexes and contacted with a detectably labeled immunoglobulin-binding agent. The amount of the detectably labeled immunoglobulin-binding agent that is bound to the complexes is determined.

Influenza virus may be detected in a specimen from an animal or human suspected of being infected with the virus by providing antibodies, which have a detectable signal producing label, or are attached to a detectably labeled reagent, having specificity to at least one conformational epitope of the particle of the influenza virus. The specimen is contacted with antibodies and the antibodies are allowed to bind to the influenza virus. The presence of influenza virus in the specimen is determined by means of the detectable label.

The invention provides methods for treatment, prevention, and generating a protective immune response by administering to a vertebrate an effective amount of the composition of the invention.

Alternatively, the influenza VLP drug substance may be formulated as laboratory reagents used for influenza virus structure studies and clinical diagnostic assays. The invention also provides a kit for treating influenza virus by administering an effective amount of a composition of the invention and directions for use.

The invention also provides for a VLP comprising HA, NA and M1 proteins derived from a virus which can cause morbidity or mortality in a vertebrate. In one embodiment, the influenza M1 protein comprises a $K^{101}$ residue. In a further embodiment, the influenza M1 protein is an avian influenza M1 protein. In one embodiment, said HA, NA and M1 proteins are derived from an avian influenza type A virus. In another embodiment the HA is selected from the group consisting of H1, H2, H3, H4, H5, H6, H7, H8, H9, H10, H11, H12, H13, H14, H15 and H16 and the NA is selected from the group consisting of N1, N2, N3, N4, N5, N6, N7, N8 and N9. In a further embodiment, said HA and NA proteins are H5 and N1, respectively. In another embodiment, said HA and NA proteins are H9 and N2, respectively. In another embodiment, said HA and/or NA exhibits hemagglutinin activity and/or neuraminidase activity, respectfully. In one embodiment, the VLP consists essentially of HA, NA and M1 proteins, i.e., these are substantially the only influenza proteins in the VLP.

The invention also provides for a method of producing a VLP, comprising transfecting vectors encoding avian influenza virus proteins into a suitable host cell and expressing said avian influenza virus proteins under condition that allow VLPs to be formed. In one embodiment, this method involves transfecting a host cell with recombinant DNA molecules that encode only the HA, NA and M1 influenza proteins. In one embodiment, the influenza M1 protein comprises a $K^{101}$ residue. In a further embodiment, the influenza M1 protein is an avian influenza M1 protein.

The invention also comprises an antigenic formulation comprising a VLP comprising HA, NA and M1 proteins derived from a virus which can cause morbidity or mortality in a vertebrate. In one embodiment, the influenza M1 protein comprises a $K^{101}$ residue. In a further embodiment, the influenza M1 protein is an avian influenza M1 protein. In another embodiment, the HA is selected from the group consisting of H1, H2, H3, H4, H5, H6, H7, H8, H9, H10, H11, H12, H13, H14, H15 and H16 and the NA is selected from the group consisting of N1, N2, N3, N4, N5, N6, N7, N8 and N9. In a further embodiment, said HA and NA proteins are H5 and N1, respectively. In another embodiment, said HA and NA proteins are H9 and N2, respectively. In a further embodiment, said antigenic formulation is administered to the subject orally, intradermally, intranasally, intramusclarly, intraperitoneally, intravenously, or subcutaneously.

The invention further provides for a method of vaccinating a vertebrate against avian influenza virus comprising administering to said vertebrate a protection-inducing amount of a VLP comprising HA, NA and M1 proteins derived from an avian influenza virus. In one embodiment, the influenza M1 protein comprises a $K^{101}$ residue. In a further embodiment, the influenza M1 protein is an avian influenza M1 protein.

This invention also comprises a method of inducing substantial immunity to influenza virus infection or at least one symptom thereof in a subject, comprising administering at least one effective dose of an influenza VLP. In one embodiment, said VLP consists essentially of HA, NA and M1. In one embodiment, the influenza M1 protein comprises a $K^{101}$ residue. In a further embodiment, the influenza M1 protein is an avian influenza M1 protein. In another embodiment, said VLP comprises influenza proteins, wherein said influenza proteins consist of HA, NA and M1. In another embodiment, said HA and/or NA exhibits hemagglutinin activity and/or neuraminidase activity, respectfully.

This invention also comprises a method of inducing substantial immunity to influenza virus infection or at least one symptom thereof in a subject, comprising administering at least one effective dose of an influenza VLP. In one embodiment, said influenza VLP consists essentially of HA, NA and M1. In another embodiment, said influenza VLP comprises influenza proteins, wherein said influenza proteins consist of HA, NA and M1. In one embodiment, the influenza M1 protein comprises a $K^{101}$ residue. In a further embodiment, the influenza M1 protein is an avian influenza M1 protein.

This invention further comprises a method of inducing substantial immunity to influenza virus infection or at least one symptom thereof in a subject, comprising administering at least one effective dose of a influenza VLP. In one embodiment, said influenza VLP consists essentially of HA, NA and M1. In another embodiment, said influenza VLP comprises influenza proteins, wherein said influenza proteins consist of HA, NA and M1. In one embodiment, the influenza M1 protein comprises a $K^{101}$ residue. In a further embodiment, the influenza M1 protein is an avian influenza M1 protein.

This invention further comprises a method of inducing a substantially protective antibody response to influenza virus infection or at least one symptom thereof in a subject, comprising administering at least one effective dose of an influenza VLP.

This invention comprises a method of inducing a substantially protective cellular immune response to influenza virus infection or at least one symptom thereof in a subject, comprising administering at least one effective dose of an influenza VLP.

This invention further comprises a method of formulating a vaccine that induces substantial immunity to influenza virus infection or at least one symptom thereof to a subject, comprising adding to said formulation an effective dose of an influenza VLP. In one embodiment, said substantial immunity to influenza virus infection or at least one symptom thereof is delivered in one dose. In another embodiment, said substantial immunity to influenza virus infection or at least one symptom thereof is delivered in multiple doses.

This invention further comprises a vaccine comprising an influenza VLP, wherein said vaccine induces substantial immunity to influenza virus infection or at least one symptom thereof when administered to a subject. In one embodiment, said influenza VLP is an avian influenza VLP. In another embodiment, said influenza VLP is a seasonal influenza VLP.

This invention further comprises an antigenic formulation comprising an influenza VLP, wherein said vaccine induces substantial immunity to influenza virus infection or at least one symptom thereof when administered to a subject. In one embodiment, said influenza VLP is an avian influenza VLP. In another embodiment, said influenza VLP is a seasonal influenza VLP.

BRIEF DESCRIPTION OF THE DRAWINGS

FIG. 1 depicts the nucleotide sequence of avian influenza A/Hong Kong/1073/99 (H9N2) virus neuraminidase (NA) gene (SEQ ID NO:1).

FIG. 2 depicts the nucleotide sequence of avian influenza A/Hong Kong/1073/99 (H9N2) virus hemagglutinin (HA) gene (SEQ ID NO:2).

FIG. 3 depicts the nucleotide sequence of avian influenza A/Hong Kong/1073/99 (H9N2) virus matrix protein M1 (M1) gene (SEQ ID NO:3).

FIGS. 4A and 4B depict the transfer vectors for construction of recombinant baculoviruses for expression of avian influenza A/Hong Kong/1073/99 (H9N2) HA, NA, and M1 proteins. FIG. 4A depicts a transfer vector for expression of individual genes and FIG. 4B depicts the transfer vector for multi-expression of the genes.

(FIG. 7A) rabbit anti-H9N2; (FIG. 7B) murine anti-M1 mAb; and (FIG. 7C) murine anti-BACgp64.

FIG. 11 depicts the immunization and bleed schedule for the immunogenicity study of recombinant influenza with purified avian influenza A/Hong Kong/1073/99 (H9N2) VLPs in mice.

FIGS. 12A and 12B depict the results of an immunogenicity study in mice immunized with recombinant influenza H9N2 VLPs. FIG. 12A depicts sera from BALB/c mice immunized with recombinant VLPs comprised of HA, NA, and M1 proteins from avian influenza virus type A/H9N2/Hong Kong/1073/99. FIG. 12B depicts sera from New Zealand white rabbits immunized with inactivated avian influenza virus type A H9N2 were reacted with Western blots containing inactivated avian influenza virus type A H9N2 (lanes 1 and 3) or cold-adapted avian influenza virus type A H9N2 (lanes 2 and 4).

FIG. 16 depicts lung virus titers at 3 and 5 days post challenge with H9N2.

FIGS. 17A, 17B and 17C depict mice antibody response to A/Fujian/411/2002 when immunized with H3N2 VLP.

FIGS. 18A and 18B depict mice IgG antibody isotypes

FIG. 22 depicts serum hemagglutinin inhibition (HI) responses in ferrets.

FIG. 23 depicts serum hemagglutinin inhibition (HI) responses from serum pulled on days 21 and 42 from ferrets after administration of different strains of H3N2 VLPs.

FIG. 29 depicts virus shedding in nasal washes of ferret inoculated with H9N2 VLP vaccine and subsequently challenged intranasally with H9N2 virus.

FIG. 30A, 30B, 30C, 30D, 30E, 30F, 30G, 30H depicts hemagglutinin inhibition (HI) antibody responses in mice after inoculation with different doses of A/Fujian/411/2002 (H3N2) VLPs intramuscularly or intranasally tested against different H3N2 strains of influenza viruses.

FIG. 35 depicts the amino acids sequence of SARS S protein with Indonesia H5N1 HA transmembrane and carboxyl terminal domain (underlined) (SEQ ID NO: 62).

FIG. 36 depicts the amino acids sequence of Indonesia H5N1 M1 protein.

FIG. 39A) Coomassie blue stain; FIG. 39B) Western blot, top panel: anti SARS S; bottom panel: anti SARS M.

FIG. 41A) EM image for buffer control; FIG. 41B) Selected EM images for VLPs; FIG. 41C) Selected EM images for VLPs at higher magnification.

FIGS. 52A and 52B depict purified H3N1 VLPs, by coomassie staining (FIG. 52A) and transmission electron microscopy (FIG. 52B). Lane 1 (FIG. 52A), panel 1 (FIG. 52B), native VLPs containing M1 derived from A/Brisbane/10/07 (H3N2) and generated in Sf9 cells infected with rBV 528 (FIG. 50). Lane 2 (FIG. 52A), panel 2 (FIG. 52B), reassortant VLPs containing M1 derived from A/Indonesia.5/05 (H5N1) and generated using rBV 520. Lane 3 (FIG. 52A), panel 3 (FIG. 52B), reassortant VLPs containing M1 derived from A/PR/8/34 (H1N1) and generated using rBV 521. Lane 4 (FIG. 52A), panel 4 (FIG. 52B), M1-deficient VLPs generated using rBV 547 (FIG. 50). Protein molecular weights and location of influenza proteins are indicated. For electron microscopy, VLPs were stained with 1% phosphotungstic acid. Direct magnification 120 000×. Bar, 100 nm.

(FIG. 53A) Mutagenesis of residues $R^{101}$, $S^{207}$, $S^{224}$, and $T^{227}$ of A/Fujian/411/02 M1 protein to $K^{101}$, $N^{207}$, $N^{224}$, or $A^{227}$ of A/Indonesia/5/05 M1 protein. Expression of M1 in infected Sf9 cells (lanes 1-7) and media (lanes 8-14), by coomassie staining and western blot using antibody to M1. Lanes 1, 8, $T^{227}A$; lanes 2, 9, double mutant $S^{224}N$, $T^{227}A$; lanes 3, 10, $R^{101}K$, lanes 4, 11, $S^{207}N$; lanes 5, 12, $S^{224}N$; lanes 6, 13, triple mutant $S^{207}N$, $S^{224}N$, $T^{227}A$; lanes 7, 14, quadruple mutant $R^{101}K$, $S^{207}N$, $S^{224}N$, $T^{227}A$. (FIG. 53B) Mutagenesis of M1 from A/Indonesia/5/05 and A/Udorn/72. Expression of M1 proteins in infected Sf9 cells (lanes 1-4) and media (lanes 5-8), by coomassie staining and western blot using antibody to M1. Lanes 1, 5, wild type M1 protein derived from A/Indonesia/5/05 (H5N1); lanes 2, 6, mutant M1-$R^{101}$ protein derived from A/Indonesia/5/05 (H5N1); lanes 3,7, wild type M1 protein derived from A/Udorn/72 (H3N2); lanes 4, 8, mutant M1-$K^{101}$ protein derived from A/Udorn/72 (H3N2).

(FIG. 54A) Three-dimensional structure of two M1 monomers, as seen on Cn3D image of PDB ID 1EA3 determined by X-ray crystallography (Arzt et al., 2001). The location of R/$K^{101}$ residue within α-helix 6 is highlighted in yellow. (FIG. 54B) Alignment of M1 protein fragment 91-105 containing $K^{101}$ residue. NNMDKAVKLYRKLKR (residues 91-105 of SEQ ID NO: 75).

(FIG. 55A) Constructs for expression of influenza A/Fujian/411/02

(H3N2) VLPs. The constructs include a tandem for co-expression of HA and NA genes, as well as the wild type and mutant M1 containing $R^{101}$ and $K^{101}$, respectively. As a control, M1 derived from A/Indonesia/5/05 (H5N1) containing $K^{101}$ was used. (FIG. 55B) Expression of M1 alone and within VLPs in the infected Sf9 cells (lanes 1-6) and medium (lanes 7-12), by coomassie staining and western blot. Lanes 1, 7, wild type M1-K101 protein derived from A/Indonesia/5/05 (H5N1); lanes 2, 8, wild type $R^{101}$ protein derived from A/Fujian/411/02 (H3N2); mutant M1-$K^{101}$ protein derived from A/Fujian/411/02 (H3N2).

DETAILED DESCRIPTION OF THE INVENTION

Definitions

Figure 5B:
FIGS. 5A and 5B depict depicts the expression of avian influenza A/Hong Kong/1073/99 (H9N2) virus HA, NA, and M1 proteins in Sf-9S cells.

As used herein, the term "baculovirus," also known as baculoviridae, refers to a family of enveloped DNA viruses of arthropods, members of which may be used as expression vectors for producing recombinant proteins in insert cell cultures. The virion contains one or more rod-shaped nucleocapsids containing a molecule of circular supercoiled double-stranded DNA (Mr $54 \times 10^6$-$154 \times 10^6$). The virus used as a vector is generally *Autographa californica* nuclear polyhedrosis virus (NVP). Expression of introduced genes is under the control of the strong promoter that normally regulates expression of the polyhedron protein component of the large nuclear inclusion in which the viruses are embedded in the infected cells.

As used herein, the term "derived from" refers to the origin or source, and may include naturally occurring, recombinant, unpurified, or purified molecules. The proteins and molecules of the present invention may be derived from influenza or non-influenza molecules.

As used herein, the term "chimeric protein" refers a constructs that links at least two heterologous proteins into a single macromolecule (fusion protein).

As used herein, the term "chimeric VLP" refers to a virus-like particle that comprises an M1 protein derived from a first source and at least one protein, or portion thereof, that is not derived from said first source.

As used herein the term "first" influenza virus protein, i.e., a first influenza virus M1 protein, refers to a protein, such as M1, HA, NA, and M2, that is derived from a particular strain of influenza virus. The strain or type of the first influenza virus differs from the strain or type of the second influenza virus protein. Thus, "second" influenza virus protein, i.e., the second influenza virus M1 protein, refers to a protein, such as M1, HA, NA, and M2, that is derived from a second strain of influenza virus, which is a different strain or type than the first influenza virus protein.

As used herein, the term "hemagglutinin activity" refers to the ability of HA-containing proteins, VLPs, or portions thereof to bind and agglutinate red blood cells (erythrocytes).

As used herein, the term "neuraminidase activity" refers to the enzymatic activity of NA-containing proteins, VLPs, or portions thereof to cleave sialic acid residues from substrates including proteins such as fetuin.

As used herein, the term "heterotypic" refers to one or more different types or strains of virus.

As used herein, the term "homotypic" refers to one type or strain of virus.

As used herein, the term "macromolecular protein structure" refers to the construction or arrangement of one or more proteins.

As used herein, the term "multivalent" vaccine refers to a vaccine against multiple types or strains of influenza virus.

As used herein, the term "non-influenza" refers to a protein or molecule that is not derived from influenza virus.

As used herein, the term "vaccine" refers to a preparation of dead or weakened pathogens, or of derived antigenic determinants, that is used to induce formation of antibodies or immunity against the pathogen. A vaccine is given to provide immunity to the disease, for example, influenza, which is caused by influenza viruses. The present invention provides vaccine compositions that are immunogenic and provide protection. In addition, the term "vaccine" also refers to a suspension or solution of an immunogen (e.g. VLP) that is administered to a vertebrate to produce protective immunity, i.e., immunity that reduces the severity of disease associated with infection.

As used herein the term "substantial immunity" refers to an immune response in which when VLPs of the invention are administered to a vertebrate there is an induction of the immune system in said vertebrate which results in the prevention of influenza infection, amelioration of influenza infection or reduction of at least one symptom related to influenza virus infection in said vertebrate. Substantial immunity may also refer to a haemagglutination inhibition (HI) titer of 40 in a mammal wherein the VLPs of the invention have been administered and have induced an immune response.

As used herein the term "adjuvant" refers to a compound that, when used in combination with a specific immunogen (e.g. a VLP) in a formulation, augments or otherwise alters or modifies the resultant immune response. Modification of the immune response includes intensification or broadening the specificity of either or both antibody and cellular immune responses. Modification of the immune response can also mean decreasing or suppressing certain antigen-specific immune responses.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as the influenza VLPs, or can be administered separately. Either the protein or an expression vector encoding the protein can be administered to produce an immunostimulatory effect.

As used herein an "effective dose" generally refers to that amount of the VLP of the invention sufficient to induce immunity, to prevent and/or ameliorate influenza virus infection or to reduce at least one symptom of influenza infection and/or to enhance the efficacy of another dose of a VLP. An effective dose may refer to the amount of the VLP sufficient to delay or minimize the onset of an influenza infection. An effective dose may also refer to the amount of the VLP that provides a therapeutic benefit in the treatment or management of influenza infection. Further, an effective dose is the amount with respect to the VLPs of the invention alone, or in combination with other therapies, that provides a therapeutic benefit in the treatment or management of an influenza viral infection. An effective dose may also be the amount sufficient to enhance a subject's (e.g., a human's) own immune response against a subsequent exposure to influenza virus. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease or reduces the severity of symptoms.

As used herein, the term "external domain" when referring to membrane associated proteins refer to the domain(s) of the protein that are external to the cell and/or cytosol and/or a lumen. The external domain of a protein is also known as an ectodomain.

As used herein the term "avian influenza virus" refers to influenza viruses found chiefly in birds but that can also infect humans or other animals. In some instances, avian influenza viruses may be transmitted or spread from one human to another. An avian influenza virus that infects humans has the potential to cause an influenza pandemic, i.e., morbidity and/or mortality in humans. A pandemic occurs when a new strain of influenza virus (a virus in which human have no natural immunity) emerges, spreading beyond individual localities, possibly around the globe, and infecting many humans at once.

As used herein the term "non-avian influenza protein" refers to a protein that is heterologous to an avian influenza virus. Said non-avian influenza protein may be recombinantly expressed from an expression vector and may be heterologous to the expression vector.

As used herein the term "seasonal influenza virus" refers to the influenza viral strains that have been determined to be passing within the human population for a given influenza season based on epidemiological surveys conducted by National Influenza Centers worldwide. These epidemiological studies, and some isolated influenza viruses, are sent to one of four World Health Organization (WHO) reference laboratories, one of which is at the Centers for Disease Control and Prevention (CDC) in Atlanta for detailed testing. These laboratories test how well antibodies made to the current vaccine react to the circulating virus and new flu viruses. This information, along with information about flu activity, is summarized and presented to an advisory committee of the U.S. Food and Drug Administration (FDA) and at a WHO meeting. These meetings result in the selection of three viruses (two subtypes of influenza A viruses and one influenza B virus) to go into flu vaccines for the following fall and winter. The selection occurs in February for the northern hemisphere and in September for the southern hemisphere. Usually, one or two of the three virus strains in the vaccine changes each year.

As used herein, the term "influenza VLP" refers to a VLP comprising at least one influenza protein. Said VLPs can comprise additional influenza and/or non-influenza proteins.

As use herein, the term "infectious agent" refers to microorganisms that cause an infection in a vertebrate. Usually, the organisms are viruses, bacteria, parasites and/or fungi. The term also refers to different antigenic variations of the same infectious agent.

As used herein the term "substantially protective antibody response" refers to an immune response mediated by antibodies against an influenza virus, which is exhibited by a vertebrate (e.g., a human), that prevents or ameliorates influenza infection or reduces at least one symptom thereof. VLPs of the invention can stimulate the production of antibodies that, for example, neutralizing antibodies that block influenza viruses from entering cells, blocks replication of said influenza virus by binding to the virus, and/or protect host cells from infection and destruction.

As used herein the term "substantially protective cellular response" refers to an immune response that is mediated by T-lymphocytes and/or other white blood cells against influenza virus, exhibited by a vertebrate (e.g., a human), that prevents or ameliorates influenza infection or reduces at least one symptom thereof. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

As used herein the term "immunity" refers to induction of the immune system of a vertebrate wherein said induction results in the prevention, amelioration, and/or reduction of at least one symptom of an infection in said vertebrate. Immunity may also refer to a hemagglutination inhibition (HI) titer of 40 when VLPs of the invention have been administered to a vertebrate and said VLPs have induced an immune response against a HA of an influenza virus.

As used herein the term "substantial immunity in a population-wide basis" refers to immunity as a result of VLPs of the invention administered to individuals in a population. The immunity in said individual in said population results in the prevention, amelioration of influenza infection, or reduction of at least one symptom related to influenza virus infection in said individual, and prevents the spread of said influenza virus to others in the population. The term population is defined as group of individuals (e.g. schoolchildren, elderly, healthy individuals etc.) and may comprise a geographic area (e.g. specific cities, schools, neighborhoods, workplace, country, state, etc.).

As use herein, the term "antigenic formulation" or "antigenic composition" refers to a preparation which, when administered to a vertebrate, especially a bird or a mammal, will induce an immune response.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered.

As used herein, the term "virus-like particle" (VLP) refers to a structure that in at least one attribute resembles a virus but which has not been demonstrated to be infectious. Virus-like particle in accordance with the invention do not carry genetic information encoding for the proteins of virus-like particles. In general, virus-like particles lack a viral genome and, therefore, are noninfectious. In addition, virus-like particles can often be produced in large quantities by heterologous expression and can be easily purified.

Influenza Virus Vaccines

Influenza remains a pervasive public health concern despite the availability of specific inactivated virus vaccines that are 60-80% effective under optimal conditions. When these vaccines are effective, illness is usually averted by preventing viral infection. Vaccine failure can occur as a result of accumulated antigenic differences (antigenic shift and antigenic drift). For example, avian influenza virus type A H9N2 co-circulated with human influenza virus type A Sydney/97 (H3N2) in pigs and led to genetic reassortment and emergence of new strains of human influenza virus with pandemic potential (Peiris et al., 2001). In the event of such antigenic shift, it is unlikely that current vaccines would provide adequate protection.

Another reason for the paucity of influenza vaccine programs is the relatively short persistence of immunity elicited by the current vaccines. Further inadequacy of influenza control measures reflects restricted use of current vaccines because of vaccine reactogenicity and side effects in young children, elderly, and people with allergies to components of eggs, which are used in manufacturing of commercially licensed inactivated virus influenza vaccines.

Additionally, inactivated influenza virus vaccines often lack or contain altered HA and NA conformational epitopes, which elicit neutralizing antibodies and play a major role in protection against disease. Thus, inactivated viral vaccines, as well as some recombinant monomeric influenza subunit protein vaccines, deliver inadequate protection. On the other hand, macromolecular protein structures, such as capsomers, subviral particles, and/or VLPs, include multiple copies of native proteins exhibiting conformational epitopes, which are advantageous for optimal vaccine immunogenicity.

The present invention describes the cloning of avian influenza A/Hong Kong/1073/99 (H9N2) virus HA, NA, and M1 genes into a single baculovirus expression vector alone or in tandem and production of influenza vaccine candidates or reagents comprised of recombinant influenza structural proteins that self-assemble into functional and immunogenic homotypic macromolecular protein structures, including subviral influenza particles and influenza VLP, in baculovirus-infected insect cells.

The present invention describes the cloning of human influenza A/Sydney/5/97 and A/Fujian/411/2002 (H3N2) virus HA, NA, M1, M2, and NP genes into baculovirus expression vectors and production influenza vaccine candidates or reagents comprised of influenza structural proteins that self-assemble into functional and immunogenic homotypic macromolecular protein structures, including subviral influenza particles and influenza VLP, in baculovirus-infected insect cells.

In addition, the instant invention describes the cloning of the HA gene of human influenza A/Sydney/5/97 and A/Fujian/411/2002 (H3N2) virus and the HA, NA, and M1 genes of avian influenza A/Hong Kong/1073/99 (H9N2) into a single baculovirus expression vector in tandem and production influenza vaccine candidates or reagents comprised of influenza structural proteins that self-assemble into functional and immunogenic heterotypic macromolecular protein structures, including subviral influenza particles and influenza VLP, in baculovirus-infected insect cells.

VLPs of the Invention and Methods of Making VLPs

In general, virus-like particles (VLPs) lack a viral genome and, therefore, are non-infectious. In addition, virus-like particles can often be produced by heterologous expression and can be easily purified. Most VLPs comprise at least a viral core protein. This core protein usually drives budding and release of particles from a host cell. Examples of such proteins comprise RSV M, influenza M1, HIV gag and vesicular *stomatis* virus (VSV) M protein. In general, VLPs are useful for preparing antigenic formulation and/or vaccines against infectious agents, e.g. influenza.

However, VLP production has not been particularly efficient. One goal of VLP production is the optimization of culture conditions to obtain the greatest possible productivity. Even incremental increases in productivity can be economically significant and can save lives. The inventors of the present invention have unexpectedly discovered that expressing expressing an influenza M1 protein comprising a $K^{101}$ residue, such as avian M1 protein, in a host cell significantly enhances production of VLPs from host cells.

Thus, the invention described herein comprises VLPs comprising an influenza M1 protein comprising a $K^{101}$ residue, such as an avian influenza M1 protein, and at least one non-avian influenza protein (e.g. a protein from an infectious agent). In one embodiment, said non-avian influenza protein is HA and/or NA from a non-avian influenza virus. In another embodiment, said non-avian influenza protein is a seasonal influenza protein. In another embodiment, said HA or NA seasonal influenza are A/Wisconsin/67/2005 and/or A/Fujian/411/02. In another embodiment, said HA or NA has hemagglutinin or neuraminidase activity, respectively. In another embodiment, said non-avian influenza protein is from a virus, bacterium, fungus and/or parasite.

In another embodiment, the invention comprises a VLP consisting essentially of an influenza M1 protein comprising a $K^{101}$ residue, such as avian M1 protein, and at least one non-avian influenza protein (e.g. a protein from an infectious agent). These VLPs may comprise additional influenza proteins and/or protein contaminates in negligible concentrations. For example, these VLPs contain an influenza M1 protein comprising a $K^{101}$ residue, such as avian M1 protein, and at least one non-avian influenza protein and may contain additional cellular constituents such as cellular proteins, baculovirus proteins, lipids, carbohydrates etc., but do not contain additional influenza proteins (other than fragments of M1 and the non-avian influenza protein). In another embodiment, said VLP consists of an influenza M1 protein comprising a $K^{101}$ residue, such as avian M1 protein, and at least one non-avian influenza protein.

Chimeric VLPs of the invention are useful for preparing vaccines and immunogenic compositions. One important feature of said chimeric VLPs is the ability to express proteins on the surface of said VLPs so that the immune system of a vertebrate can induce an immune response against said protein. However, not all proteins can be expressed on the surface of VLPs. There may be many reasons why certain proteins are not expressed, or poorly expressed, on the surface of VLPs. One reason is that said protein is not directed to the membrane of a host cell or that said protein does not have a transmembrane domain. Sequences near the carboxyl terminus of influenza hemagglutinin may be important for incorporation of HA into the lipid bilayer of the mature influenza enveloped nucleocapsids and for the assembly of HA trimer interaction with the influenza core protein M1 (Ali, et al., (2000) J. Virol. 74, 8709-19). Thus, one method of overcoming the inability of expressing non-avian influenza proteins on the surface of VLPs, and/or increasing the expression of said proteins, is to fuse the cytoplasmic and/or the transmembrane domains of influenza HA and/or NA to a non-avian influenza protein thus creating a chimeric protein.

Thus, in one embodiment of the invention, said chimeric VLPs of the invention comprise at least one chimeric protein. In another embodiment, said chimeric protein comprise at least one external domain (ectodomain) of non-avian influenza HA and/or NA protein sequences fused to the transmembrane and/or cytoplasmic-terminal domains of a heterologous HA and/or NA. In another embodiment, said heterologous transmembrane and/or cytoplasmic-terminal domains HA and/or NA is from a pandemic, seasonal and/or avian influenza virus. There are 16 different hemagglutinin (HA) and 9 different neuraminidase (NA) all of which have been found among wild birds. Wild birds are the primary natural reservoir for all types of influenza A viruses and are thought to be the source of all types of influenza A viruses in all other vertebrates. These subtypes differ because of changes in the hemagglutinin (HA) and neuraminidase (NA) on their surface. Many different combinations of HA and NA proteins are possible. Each combination represents a different type of influenza A virus. In addition, each type can be further classified into strains based on different mutations found in each of its 8 genes. Thus, in another embodiment, said heterologous transmembrane and/or cytoplasmic-terminal domains HA and/or NA is from a pandemic, seasonal and/or avian influenza virus and a NA from a pandemic, seasonal and/or avian influenza virus, wherein said HA is selected from the group consisting of H1, H2, H3, H4, H5, H6, H,7 H8, H9, H10, H11, H12, H13, H14, H15 and H16 and said NA is selected from the group consisting of N1, N2, N3, N4, N5, N6, N7, N8 and N9. In another embodiment, said non-avian influenza HA and/or NA are from a seasonal influenza strain A/Wisconsin/67/2005 and HA and/or NA transmembrane and/or cytoplasmic-terminal domains are from an avian influenza strain. In another embodiment, said non-avian influenza HA and/or NA are from influenza strain A/Fujian/411/02 and HA and/or NA transmembrane and/or cytoplasmic-terminal domains are from an avian influenza strain. Said HA and/or NA transmembrane and/or cytoplasmic-terminal domains from avian influenza can be derived from the group consisting of influenza virus H9N2 and influenza virus H5N1.

Said HA and/or NA from H9N2 influenza strain can be isolated from any one of the influenza virus from the group consisting of A/quail/Hong Kong/G1/97, A/Hong Kong/1073/99, A/Hong Kong/2108/03, Duck/HK/Y280/97, CK/HK/G9/97, Gf/HK/SSP607/03, Ph/HK/CSW1323/03, WDk/ST/4808/01, CK/HK/NT142/03, CK/HK/WF126/03, SCk/HK/WF285/03, CK/HK/YU463/03, CK/HK/YU577/03, SCk/HK/YU663/03, Ck/HK/CSW161/03, and GF/HK/NT101/03. In one embodiment, said H9N2 influenza strain is A/Hong Kong/1073/99. In another embodiment, said HA and/or NA from influenza strain H5N1 can be from clade 1 and/or clade 2. In another embodiment, said H5N1 is from clade 1. In another embodiment, said H5N1 is from clade 2. In another embodiment, said H5N1 is selected from the group consisting of A/Vietnam/1194/04, A/Vietnam/1203/04, A/Hongkong/213/03, A/Indonesia/2/2005, A/Bar headed goose/Quinghai/1A/2005, A/Anhui/1/2005, and A/Indonesia/5/05. In another embodiment, said H5N1 strain is A/Indonesia/5/05.

Chimeric VLPs of the invention may comprise an avian influenza M1 protein. Said M1 protein can be derived from influenza strain H9N2 or H5N1. Said H9N2 influenza M1 can be isolated from any one of the influenza virus from the group consisting of A/quail/Hong Kong/G1/97, A/Hong Kong/1073/99, A/Hong Kong/2108/03, Duck/HK/Y280/97, CK/HK/G9/97, Gf/HK/SSP607/03, Ph/HK/CSW1323/03, WDk/ST/4808/01, CK/HK/NT142/03, CK/HK/WF126/03, SCk/HK/WF285/03, CK/HK/YU463/03, CK/HK/YU577/03, SCk/HK/YU663/03, Ck/HK/CSW161/03, and GF/HK/NT101/03. In one embodiment, said H9N2 influenza strain is A/Hong Kong/1073/99. In another embodiment, said M1 can be from influenza strain H5N1. In another embodiment, said H5N1 is selected from the group consisting of A/Vietnam/1194/04, A/Vietnam/1203/04, A/Hongkong/213/03, A/Indonesia/2/2005, A/Bar headed goose/Quinghai/1A/2005, A/Anhui/1/2005, and A/Indonesia/5/05. In another embodiment, said H5N1 strain is A/Indonesia/5/05.

In another embodiment of the invention, said chimeric VLPs of the invention comprise chimeric proteins from influenza B viruses. In one embodiment, said chimeric proteins comprise external domains of influenza B HA and/or NA protein sequences fused to the transmembrane and/or cytoplasmic-terminal domains of a heterologous HA and/or NA cytoplasmic and/or transmembrane region. In another embodiment, said heterologous HA and/or NA is from seasonal influenza A/Wisconsin/67/2005 and/or A/Fujian/411/02 and/or avian influenza A/Indonesia/5/05. In another embodiment, said influenza B viruses are from B/Shanghai/361/2002 and/or B/Hong Kong/330/2001.

In another embodiment of the invention, chimeric VLPs of the invention comprise an influenza M1 protein comprising a $K^{101}$ residue, such as avian M1 protein, and at least one protein from another infectious agent (non-avian influenza protein). Said protein from another infectious agent can be a type I and/or a type II protein. A type I protein has a C-terminus located in the cytosol (the transmembrane domain is located near the C-terminus), whereas a type II protein has an N-terminus that is located in the cytosol (the transmembrane domain is located near the N-terminus). In another embodiment, said protein may comprise epitopes that can induce an immune response against said protein when administered to a vertebrate. In another embodiment, said protein can associate with an influenza M1 protein comprising a $K^{101}$ residue, such as avian M1 protein, directly or indirectly. In another embodiment, said protein is expressed on the surface of the VLP. In another embodiment, said protein, or portion thereof, can be fused to a heterologous protein creating a chimeric protein. For example, the external domains of proteins from infective agents, such as non-avian influenza virus, coronavirus, VZV, dengue, or yellow fever and/or other agents can be used to generate chimeric proteins by fusing said proteins from infective agents with a protein that associates with an influenza M1 protein comprising a $K^{101}$ residue, such as avian M1 protein. In one embodiment, said protein that associates with an influenza M1 protein comprising a $K^{101}$ residue is an influenza protein. In another embodiment, said protein that associates with the influenza M1 is a HA and/or NA from influenza. In another embodiment, said HA and/or NA is from a seasonal influenza virus. In another embodiment, said HA and/or NA is from an avian influenza virus. In another embodiment, said avian influenza virus is H5N1. In another embodiment, said H5N1 strain is A/Indonesia/5/05. In another embodiment, said infectious agent comprises at least one SARS virus protein. In another embodiment, said SARS virus protein is SARS coronavirus (SARS-CoV) Urbani strain spike (S) protein (NCBI access number AAP13441, SEQ ID NO: 63).

In another embodiment, the invention comprises a VLP comprising a chimeric protein comprising the transmembrane domain and/or cytoplasmic tail of influenza HA and/or influenza NA fused to a protein from an infective agent. In another embodiment, the transmembrane domain and/or cytoplasmic tail of the HA and/or NA protein extends from the N or C-terminus to approximately 0, 1, 2, 3 4, 5, 6, 7, 8, 9, 10, 11, 12, 13, 14, 15, 16, 17, 18, 19, 20 to about 50 amino acids past the transmembrane domain and is fused to said protein from another infectious agent. In another embodiment, the portion of the protein from another infectious agent that comprises the cytoplasmic and the transmembrane domain is replaced with a cytoplasmic and/or transmembrane domain from an influenza protein (i.e. avian and/or seasonal influenza NA and/or HA). In another embodiment, said seasonal influenza HA and/or NA are from influenza strain A/Wisconsin/67/2005 and/or A/Fujian/411/02 and/or avian influenza A/Indonesia/5/05. In another embodiment, said M1 is from an avian influenza strain H5N1. In another embodiment, said M1 is from influenza strain A/Indonesia/5/05. In another embodiment, said M1 is from influenza strain H9N2. In another embodiment, said M1 is from influenza strain A/Hong Kong/1073/99. In another embodiment, the transmembrane domain and/or cytoplasmic tail of A/Wisconsin/67/2005 HA and/or NA is fused to a protein from an infectious agent. In another embodiment, the transmembrane domain and/or cytoplasmic tail of A/Fujian/411/02 HA and/or NA is fused to a protein from an infectious agent. In another embodiment, the transmembrane domain and/or cytoplasmic tail of A/Indonesia/5/05 HA and/or NA is fused to a protein from an infectious agent.

In another embodiment, the transmembrane domain and/or cytoplasmic tail of influenza HA and/or influenza NA fused to a protein from an infective agent comprises a spacer sequence between the protein segments. Said space sequences can be any amino acid not in the protein. This spacer sequence may be important for expressing said protein from an infective agent on the surface of the VLP. Examples of spacer sequences include a poly-G amino acids. Said spacer can be from 1 to about 100 amino acids long.

In another embodiment of the invention, said VLPs comprise more than one protein from an infectious agent. In this embodiment, said VLPs are multivariant VLPs capable of inducing an immune response to several proteins from infectious agents. In another embodiment said VLPs comprise proteins from at least two different influenza viruses. For example said multivariant VLPs can comprise a HA and/or NA from a seasonal influenza virus A and/or B and/or from an avian influenza virus. This embodiment also comprises the presentation of HA and/or NA of the three influenza viruses (two subtypes of influenza A viruses and one influenza B virus) that are chosen by WHO and the CDC (see above) to be in the flu vaccines for the fall and winter in a single VLP. In another embodiment, said multivariant VLPs comprise proteins from several viruses, bacteria and/or parasites. For example, said VLPs comprise proteins from influenza and RSV, influenza, RSV and parainfluenza. In another embodiment, said proteins are chimeric proteins wherein each protein comprises the HA and/or NA from an influenza virus. In another embodiment, said multivalent VLPs comprise an influenza M1 protein comprising a $K^{101}$ residue. In one embodiment, the influenza M1 protein comprising a $K^{101}$ residue is derived from an avian influenza virus strain. In another embodiment, said avian influenza virus strain is A/Indonesia/5/05.

In another embodiment, said chimeric proteins comprise a fusion between the influenza HA with the protein, or a portion thereof, from an infectious agent. In another embodiment, said chimeric proteins comprise a fusion between the proteins, or a portion thereof, of two infectious agents or antigenic variations of the same agent. Said fusion protein will comprise antigenic agents from each protein from said infectious agent. In another embodiment, said chimeric protein comprises an amino acid linker between the proteins. An example of this embodiment is a fusion between the influenza HA and the RSV F protein. An example of this embodiment is a fusion between the influenza HA and the RSV F1 protein (e.g. SEQ ID NO: 64). In another embodiment, said chimeric protein comprises the HA and/or NA transmembrane and/or cytoplasmic domain from an avian influenza virus. In another embodiment, said multivalent VLPs comprise an avian influenza M1 protein. In another embodiment, said avian influenza is A/Indonesia/5/05.

In another embodiment of the invention, the chimeric genes encoding the chimeric proteins (as described above), which may be codon optimized, are synthesized and cloned through a series of steps into a bacmid construct followed by rescue of recombinant baculovirus by plaque isolation and expression analyses. The VLPs for each of these targets can then be rescued by co-infection with the use of two recombinant baculoviruses (1) expressing the M1, and (2) expressing the chimeric protein from an infectious agent (e.g. VZV, RSV, dengue, yellow fever) with cytoplasmic and/or transmembrane domain from HA and/or NA from a seasonal and/or avian influenza virus. In another embodiment, the VLPs of the invention can be rescued by infection with the use of a recombinant baculovirus expressing the M1 and the chimeric protein from an infectious agent (e.g. VZV, RSV, dengue, yellow fever) with cytoplasmic and transmembrane domain from influenza HA and/or NA. In one embodiment, the influenza M1 protein comprises a $K^{101}$ residue. In another embodiment, the influenza M1 protein is derived from an avian influenza virus strain. In another embodiment, said avian influenza virus strain is A/Indonesia/5/05.

Infectious agents can be viruses, bacteria, fungi and/or parasites. A protein that may be expressed on the surface of chimeric VLPs of the invention can be derived from viruses, bacteria, fungi and/or parasites. In other embodiments, the proteins expressed on the surface of said chimeric VLPs may be tumor or cancer antigens. The proteins derived from viruses, bacteria, fungi and/or parasites can induce an immune response (cellular and/or humoral) in a vertebrate that which will prevent, treat, manage and/or ameliorate an infectious disease in said vertebrate.

Non-limiting examples of viruses from which said infectious agent proteins can be derived from are the following: coronavirus (e.g. the agent that causes SARS), hepatitis viruses A, B, C, D & E3, human immunodeficiency virus (HIV), herpes viruses 1, 2, 6 & 7, cytomegalovirus, varicella zoster, papilloma virus, Epstein Barr virus, parainfluenza viruses, respiratory syncytial virus (RSV), human metapneumovirus, adenoviruses, bunya viruses (e.g. hanta virus), coxsakie viruses, picoma viruses, rotaviruses, rhinoviruses, rubella virus, mumps virus, measles virus, Rubella virus, polio virus (multiple types), adeno virus (multiple types), parainfluenza virus (multiple types), avian influenza (various types), shipping fever virus, Western and Eastern equine encephalomyelitis, Japanese encephalomyelitis, fowl pox, rabies virus, slow brain viruses, rous sarcoma virus, Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), Togaviridae (e.g., Rubivirus), Newcastle disease virus, West Nile fever virus, Tick borne encephalitis, yellow fever, chikungunya virus, and dengue virus (all serotypes).

In another embodiment, the specific proteins from viruses may comprise: HA and/or NA from influenza virus (including avian), S protein from coronavirus, gp160, gp140 and/or gp41 from HIV, gp I to IV and Vp from varicella zoster, E and preM/M from yellow fever virus, dengue (all serotypes) or any flavivirus. Also included are any proteins from a virus that can induce an immune response (cellular and/or humoral) in a vertebrate that can prevent, treat, manage and/or ameliorate an infectious disease in said vertebrate.

Non-limiting examples of bacteria from which said infectious agent proteins can be derived from are the following: *B. pertussis, Leptospira pomona, S. paratyphi A and B, C. diphtheriae, C. tetani, C. botulinum, C. perfringens, C. feseri* and other gas gangrene bacteria, *B. anthraces, P. pestis, P. multocida, Neisseria meningitidis, N. gonorrheae, Hemophilus influenzae, Actinomyces* (e.g., *Norcardia*), *Acinetobacter*, Bacillaceae (e.g., *Bacillus anthraces*), Bacteroides (e.g., *Bacteroides fragilis*), Blastomycosis, Bordetella, Borrelia (e.g., *Borrelia burgdorferi*), Brucella, Campylobacter, Chlamydia, Coccidioides, Corynebacterium (e.g., *Corynebacterium diptheriae*), *E. coli* (e.g., Enterotoxigenic *E. coli* and Enterohemorrhagic *E. coli*), Enterobacter (e.g. *Enterobacter aerogenes*), Enterobacteriaceae (*Klebsiella, Salmonella* (e.g., *Salmonella typhi, Salmonella enteritidis, Serratia, Yersinia, Shigella*), *Erysipelothrix, Haemophilus* (e.g., *Haemophilus* influenza type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Pasteurellacea, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., *Meningiococcus, Pneumococcus* and *Streptococcus* (e.g., *Streptococcus pneumoniae* and Groups A, B, and C Streptococci), *Ureaplasmas. Treponema pollidum, Staphylococcus aureus, Pasteurella haemolytica, Corynebacterium diptheriae* toxoid, Meningococcal polysaccharide, *Bordetella pertusis, Streptococcus pneumoniae, Clostridium tetani* toxoid, and *Mycobacterium bovis*.

Non-limiting examples of parasites from which said infectious agent proteins can be derived from are the following: leishmaniasis (*Leishmania tropica mexicana, Leishmania tropica, Leishmania major, Leishmania aethiopica, Leishmania braziliensis, Leishmania donovani, Leishmania infantum, Leishmania chagasi*), trypanosomiasis (*Trypanosoma brucei gambiense, Trypanosoma brucei rhodesiense*), toxoplasmosis (*Toxoplasma gondii*), schistosomiasis (*Schistosoma haematobium, Schistosoma japonicum, Schistosoma mansoni, Schistosoma mekongi, Schistosoma intercalatum*), malaria (*Plasmodium virax, Plasmodium falciparium, Plasmodium malariae* and *Plasmodium ovale*) Amebiasis (*Entamoeba histolytica*), Babesiosis (*Babesiosis micron*), Cryptosporidiosis (*Cryptosporidium parvum*), Dientamoebiasis (*Dientamoeba fragilis*), Giardiasis (*Giardia lamblia*), Helminthiasis and *Trichomonas* (*Trichomonas vaginalis*).

Non-limiting examples of fungi from which said glycoproteins can be derived are from the following: *Absidia* (e.g. *Absidia corymbifera*), *Ajellomyces* (e.g. *Ajellomyces capsulatus, Ajellomyces dermatitidis*), *Arthroderma* (e.g. *Arthroderma benhamiae, Arthroderma fulvum, Arthroderma gypseum, Arthroderma incurvatum, Arthroderma otae, Arthroderma vanbreuseghemii*), *Aspergillus* (e.g. *Aspergillus fumigatus, Aspergillus niger*), *Candida* (e.g. *Candida albicans, Candida albicans* var. *stellatoidea, Candida dublinensis, Candida glabrata, Candida guilliermondii* (*Pichia guilliermondii*), *Candida krusei* (*Issatschenkia orientalis*), *Candida parapsilosis, Candida pelliculosa* (*Pichia anomala*), *Candida tropicalis, Coccidioides* (e.g. *Coccidioides immitis*), *Cryptococcus* (e.g. *Cryptococcus neoformans* (*Filobasidiella neoformans*), *Histoplasma* (e.g. *Histoplasma capsulatum* (*Ajellomyces capsulatus*), *Microsporum* (e.g. *Microsporum canis* (*Arthroderma otae*), *Microsporum fulvum* (*Arthroderma fulvum*), *Microsporum gypseum*, Genus *Pichia* (e.g. *Pichia anomala, Pichia guilliermondii*), *Pneumocystis* (e.g. *Pneumocystis jirovecii*), *Cryptosporidium, Malassezia furfur, Paracoccidioides*.

The above lists are meant to be illustrative and by no means are meant to limit the invention to those particular bacterial, viral or parasitic organisms.

The inventors discovered that the use of influenza M1 proteins comprising a $K^{101}$ residue in the putative L-domain sequence (YXXL at amino acid positions 100-103) results in highly efficient VLP production. Moreover, the present inventors have discovered this $K^{101}$ residue as part of the putative L-domain is found almost exclusively in avian M1 proteins. Thus, in one aspect, the present invention provides VLPs comprising an influenza M1 protein which comprises a lysine at the second position (e.g. position 101) of the M1 protein L-domain. In one embodiment, the L-domain comprises the sequence of YKKL. In another embodiment, the M1 protein comprising a lysine at the second position of the M1 protein L domain (e.g. YKKL) exhibits increased VLP formation efficiency as compared to an M1 protein comprising an arginine at the second position of the M1 protein L domain (e.g. YRKL). In another embodiment, the increased VLP formation efficiency using an M1 protein comprising a $K^{101}$ residue in the putative L-domain sequence is at least an about 10%, about 20%, about 30%, about 40%, about 50%, about 60%, about 70%, about 80%, about 90%, about 100%, about 120%, about 140%, about 160%, about 180%, about 200%, about 500%, or about 1000% more than a corresponding M1 protein without the $K^{101}$ residue substitution. In one embodiment, the VLP comprising an influenza M1 with a $K^{101}$ residue in the putative L-domain sequence further comprises an influenza HA and/or NA protein. In another embodiment, said HA and/or NA protein is from a pandemic, seasonal, or avian influenza virus. In another embodiment, the VLP comprising an influenza M1 with a $K^{101}$ residue in the putative L-domain sequence further comprises a heterologous protein (e.g., a non-avian influenza protein as described above).

The invention also encompasses variants of the said proteins expressed on or in the chimeric VLPs of the invention. The variants may contain alterations in the amino acid sequences of the constituent proteins. The term "variant" with respect to a protein refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to mutations in the proteins. These mutations may lead to antigenic variability within individual groups of infectious agents, for example influenza. Thus, a person infected with an influenza strain develops antibody against that virus, as newer virus strains appear, the antibodies against the older strains no longer recognize the newer virus and reinfection can occur. The invention encompasses all antigenic and genetic variability of proteins from infectious agents for making chimeric VLPs.

General texts which describe molecular biological techniques, which are applicable to the present invention, such as cloning, mutation, cell culture and the like, include Berger and Kimmel, Guide to Molecular Cloning Techniques, Methods in Enzymology, Vol. 152 Academic Press, Inc., San Diego, Calif. ("Berger"); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating HA, NA and/or proteins from infectious agents, etc. Thus, the invention also encompasses using known methods of protein engineering and recombinant DNA technology to improve or alter the characteristics of the proteins expressed on or in the VLPs of the invention. Various types of mutagenesis can be used to produce and/or isolate variant nucleic acids that encode for protein molecules and/or to further modify/mutate the proteins in or on the VLPs of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The invention further comprises protein variants which show substantial biological activity, e.g., able to elicit an effective antibody response when expressed on or in VLPs of the invention. Such variants include deletions, insertions, inversions, repeats, and substitutions selected according to general rules known in the art so as have little effect on activity.

Methods of cloning said proteins are known in the art. For example, the gene encoding a specific virus protein can be isolated by RT-PCR from polyadenylated mRNA extracted from cells which had been infected with a virus (DNA or RNA virus) or PCR from cells which had been infected with a DNA virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, said nucleotides that encode for HA from an avian, pandemic and/or seasonal influenza virus is selected from the group consisting of H1, H2, H3, H4, H5, H6, H7, H8, H9, H10, H11, H12, H13, H14, H15 and H16. In another embodiment, said nucleotides that encode for NA from an avian, pandemic and/or seasonal influenza virus, is selected from the group consisting of N1, N2, N3, N4, N5, N6, N7, N8 and N9. In another embodiment, said vector comprises nucleotides that encode the HA, NA and/or M1 influenza protein. In another embodiment, said vector consists of nucleotides that encodes the HA, NA and M1 influenza protein. A preferred expression vector is a baculovirus vector. After the nucleotides encoding said influenza proteins have been cloned said nucleotides can be further manipulated. For example, a person with skill in the art can mutate specific bases in the coding region to produce variants. The variants may contain alterations in the coding regions, non-coding regions, or both. Such variants may increase the immunogenticity of an influenza protein or remove a splice site from a protein or RNA. For example, in one embodiment, the donor and acceptor splicing sites on the influenza M protein (full length) are mutated to prevent splicing of the M mRNA into M1 and M2 transcripts. In another embodiment the HA is engineered to remove or mutate the cleavage site. For example, wild type H5 HA has a cleavage site that contains multiple basic amino acids (RRRKR, SEQ ID NO: 59). This wild type sequence makes the HA more susceptible to multiple ubiquitous proteases that may be present in host or system expression these HAs. In one embodiment, removing these amino acids can reduce the susceptibility of the HA to various proteases. In another embodiment, the cleavage site can be mutated to remove the cleavage site (e.g. mutate to RESR SEQ ID NO: 60).

In one embodiment, said nucleotides encode for a non-avian influenza protein and/or chimeric protein (as discussed above). In another embodiment, the expression vector comprises nucleotides that encode for a non-avian influenza protein and/or chimeric protein and an influenza M1 protein comprising a $K^{101}$ residue, such as an avian influenza M1 protein. In another embodiment, said vector comprises nucleotides that encode a chimeric protein comprising the cytoplasmic and/or the transmembrane domain of HA and/or NA from avian and/or seasonal influenza protein. In another embodiment, said seasonal influenza HA and/or NA are from influenza strain A/Wisconsin/67/2005 and said avian influenza HA and/or NA are from influenza strain A/Indonesia/5/05. In another embodiment, said vector comprises nucleotides that encode M1 from influenza strain A/Indonesia/5/05 and a chimeric protein comprising the A/Wisconsin/67/2005 (seasonal influenza) cytoplasmic and/or the transmembrane from HA and/or NA. In another embodiment, said vector comprises nucleotides that encode M1 from influenza strain A/Indonesia/5/05 and a chimeric protein comprising the A/Indonesia/5/05 (avian influenza) cytoplasmic and/or the transmembrane from HA and/or NA. In another embodiment, an influenza NA nucleic acid or protein is at least 85%, 90%, 95%, 96%, 97%, 98% or 99% identical to SEQ ID NOs. 1, 11, 38, 39, 46, 47, 54, 55, 65, 66, 67, 68, or 79. In another embodiment, an influenza HA nucleic acid or protein is at least 85%, 90%, 95%, 96%, 97%, 98% or 99% identical to SEQ ID NOs. 2, 10, 27, 28, 29, 30, 33, 34, 35, 36, 37, 42, 43, 44, 45, 50, 51, 52, 53, 69, 70, 71, 72, 73, or 78. In another embodiment, an influenza M1 nucleic acid or protein is at least 85%, 90%, 95%, 96%, 97%, 98% or 99% identical to SEQ ID NOs. 3, 12, 40, 41, 48, 49, 74, 75, 76, or 77. In another embodiment, a S nucleic acid or protein is at least about 85%, 90%, 95%, 96%, 97%, 98% or 99% identical to SEQ ID NOs. 62 or 63.

In some embodiments, said proteins may comprise, mutations containing alterations that produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells). See U.S. patent publication 2005/0118191, herein incorporated by reference in its entirety for all purposes. Examples of optimized codon sequences of the invention are disclosed below (e.g. SEQ ID 42, 44, 46, 48, 50, 52, and 54).

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the influenza proteins (including chimeric proteins) can be cloned. A person with skill in the art understands that additional methods are available and are possible.

The invention also provides for constructs and/or vectors that comprise nucleotides that encode for an influenza M1 protein comprising a $K^{101}$ residue, such as an avian influenza M1 proteins, and non-avian influenza proteins and/or chimeric proteins (as described above). The constructs and/or vectors that comprise avian M1 and non-avian influenza proteins and/or chimeric proteins, should be operatively linked to an appropriate promoter, such as the AcMNPV polyhedrin promoter (or other baculovirus), phage lambda PL promoter, the E. coli lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418, or neomycin resistance for eukaryotic cell culture and tetracycline, kanamycin, or ampicillin resistance genes for culturing in E. coli and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1, and pSG, pSVK3, pBPV, pMSG, and pSVL. Other suitable vectors will be readily apparent to the skilled artisan.

Next, the recombinant constructs mentioned above could be used to transfect, infect, or transform and can express avian M1 and a non-avian influenza protein and/or chimeric proteins, into eukaryotic cells and/or prokaryotic cells. Thus, the invention provides for host cells that comprise a vector (or vectors) that contain nucleic acids which code for avian M1 and chimeric proteins, and permit the expression of said constructs in said host cell under conditions which allow the formation of VLPs.

Among eukaryotic host cells are yeast, insect, avian, plant, C. elegans (or nematode), and mammalian host cells. Non limiting examples of insect cells are, Spodoptera frugiperda (Sf) cells, e.g. Sf9, Sf21, Trichoplusia ni cells, e.g. High Five cells, and Drosophila S2 cells. Examples of fungi (including yeast) host cells are S. cerevisiae, Kluyveromyces lactis (K. lactis), species of Candida including C. albicans and C. glabrata, Aspergillus nidulans, Schizosaccharomyces pombe (S. pombe), Pichia pastoris, and Yarrowia lipolytica. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero, and Hep-2 cells. Xenopus laevis oocytes, or other cells of amphibian origin, may also be used. Prokaryotic host cells include bacterial cells, for example, E. coli, B. subtilis, and mycobacteria.

Vectors, e.g., vectors comprising polynucleotides of avian M1 and non-avian influenza proteins and/or chimeric proteins, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, said vector is a recombinant baculovirus. In another embodiment, said recombinant baculovirus is transfected into a eukaryotic cell. In a preferred embodiment, said cell is an insect cell. In another embodiment, said insect cell is a Sf9 cell.

In another embodiment, said vector and/or host cell comprise nucleotides that encode an influenza M1 protein comprising a $K^{101}$ residue, such as an avian influenza M1 proteins, and non-avian influenza proteins and/or chimeric proteins. In another embodiment, said vector and/or host cell consists essentially of an influenza M1 protein comprising a $K^{101}$ residue, such as an avian influenza M1 proteins, and non-avian influenza proteins and/or chimeric proteins. In a further embodiment, said vector and/or host cell consists of an influenza M1 protein comprising a $K^{101}$ residue, such as an avian influenza M1 proteins, and non-avian influenza proteins and/or chimeric proteins. These vector and/or host cell contain an influenza M1 protein comprising a $K^{101}$ residue, such as an avian influenza M1 proteins, and non-avian influenza proteins and/or chimeric proteins, and may contain additional markers, such as an origin of replication, selection markers, etc.

The invention also provides for constructs and methods that will further increase the efficiency of VLP production. For example, the addition of leader sequences to the influenza M1 protein comprising a $K^{101}$ residue, such as an avian influenza M1 protein, and non-avian influenza proteins and/or chimeric proteins, can improve the efficiency of protein transporting within the cell. For example, a heterologous signal sequence can be fused to the M1 protein and non-avian influenza proteins and/or chimeric proteins. In one embodiment, the signal sequence can be derived from the gene of an insect preprotein and fused to the M1 and non-avian influenza proteins and/or chimeric proteins. In another embodiment, the signal peptide is the chitinase signal sequence, which works efficiently in baculovirus expression systems.

Influenza VLPs of the invention are useful for preparing vaccines against influenza viruses. One important feature of this system is the ability to replace the surface glycoproteins with different subtypes of HA and/or NA or other viral proteins, thus, allowing updating of new influenza antigenic variants every year or to prepare for an influenza pandemic. As antigenic variants of these glycoproteins are identified, the VLPs can be updated to include these new variants (e.g. for seasonal influenza vaccines). In addition, surface glycoproteins from potentially pandemic viruses, such as H5N1, or other HA, NA combinations with pandemic potential could be incorporated into VLPs without concern of releasing genes that had not circulated in humans for several decades. This is because the VLPs are not infectious, do not replicate and cannot cause disease. Thus, this system allows for creating a new candidate influenza vaccine every year and/or an influenza pandemic vaccine whenever it is necessary.

There are 16 different hemagglutinin (HA) and 9 different neuraminidase (NA) all of which have been found among wild birds. Wild birds are the primary natural reservoir for all types of influenza A viruses and are thought to be the source of all types of influenza A viruses in all other vertebrates. These subtypes differ because of changes in the hemagglutinin (HA) and neuraminidase (NA) on their surface. Many different combinations of HA and NA proteins are possible. Each combination represents a different type of influenza A virus. In addition, each type can be further classified into strains based on different mutations found in each of its 8 genes.

All known types of influenza A viruses can be found in birds. Usually avian influenza viruses do not infect humans. However, some avian influenza viruses develop genetic variations associated with the capability of crossing the species barrier. Such a virus is capable of causing a pandemic because humans have no natural immunity to the virus and can easily spread from person to person. In 1997, avian influenza virus jumped from a bird to a human in Hong Kong during an outbreak of bird flu in poultry. This virus was identified as influenza virus H5N1. The virus caused severe respiratory illness in 18 people, six of whom died. Since that time, many more cases of known H5N1 infections have occurred among humans worldwide; approximately half of those people have died.

Thus, the present invention encompasses the cloning of HA, NA and M1 nucleotides from avian influenza viruses, influenza viruses with pandemic potential and/or seasonal influenza viruses into expression vectors. The present invention also describes the production of influenza vaccine candidates or reagents comprised of influenza proteins that self-assemble into functional VLPs. All combinations of viral proteins must be co-expressed with a M1 nucleotide.

VLPs of the invention consist or comprise influenza HA, NA and M1 proteins. In one embodiment, said VLP comprises a HA from an avian, pandemic and/or seasonal influenza virus and a NA from an avian, pandemic and/or seasonal influenza virus, wherein said HA is selected from the group consisting of H1, H2, H3, H4, H5, H6, H,7 H8, H9, H10, H11, H12, H13, H14, H15 and H16 and said NA is selected from the group consisting of N1, N2, N3, N4, N5, N6, N7, N8 and N9. In another embodiment, the invention comprises a VLP that consists essentially of HA, NA and M1. Said HA and NA can be from the above list of HA and NA. These VLPs may comprise additional influenza proteins and/or protein contaminates in negligible concentrations. In another embodiment, said influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, the HA and/or the NA may exhibit hemagglutinin activity and/or neuraminidase activity, respectively, when expressed on the surface of VLPs.

In another embodiment, said VLP comprises HA and NA of the H5N1 virus and a M1 protein (the M1 protein may or may not be from the same viral strain). In another embodiment, said VLP consists essentially of HA, NA of the H5N1 virus and a M1 protein. These VLPs may comprise additional influenza proteins and/or protein contaminates in negligible concentrations. In a further embodiment, said VLP consists of HA, NA of the H5N1 virus and a M1 protein. In another embodiment, said influenza VLP comprises influenza proteins, wherein said influenza proteins consist of H5, N1 and M1 proteins. These VLPs contain H5, N9 and M1 and may contain additional cellular constituents such as cellular proteins, baculovirus proteins, lipids, carbohydrates etc., but do not contain additional influenza proteins (other than fragments of M1, H5 and/or N1). In another embodiment, the H5 and/or the N1 may exhibit hemagglutinin activity and/or neuraminidase activity, respectively, when expressed on the surface of VLPs.

In another embodiment, said VLP comprises the HA and NA of the H9N2 virus, and a M1 protein. In another embodiment, said VLP consists essentially of the HA and NA of the H9N2 virus, and a M1 protein. These VLPs may comprise additional influenza proteins and/or protein contaminates in negligible concentrations. In another embodiment, said VLP consists of the HA and NA of the H9N2 virus, and a M1 protein. In another embodiment, said influenza VLP comprises influenza proteins, wherein said influenza proteins consist of H9, N2 and M1 proteins. These VLPs contain H9, N2 and M1 and may contain additional cellular constituents such as cellular proteins, baculovirus proteins, lipids, carbohydrates etc., but do not contain additional influenza proteins (other than fragments of M1, H9 and/or N2). In another embodiment, the H9 and/or the N2 may exhibit hemagglutinin activity and/or neuraminidase activity, respectively, when expressed on the surface of VLPs.

In another embodiment, said VLP comprises the HA and NA from an influenza B virus, and a M1 protein. Influenza B viruses are usually found only in humans. Unlike influenza A viruses, these viruses are not classified according to subtype. Influenza B viruses can cause morbidity and mortality among humans, but in general are associated with less severe epidemics than influenza A viruses. In another embodiment, said VLP consists essentially of the HA and NA of the influenza B virus, and a M1 protein. These VLPs may comprise additional influenza proteins and/or protein contaminates in negligible concentrations. In another embodiment, said influenza VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, said VLP consists of the HA and NA of the influenza B virus, and a M1 protein. In another embodiment, the HA and/or the NA may exhibit hemagglutinin activity and/or neuraminidase activity, respectively, when expressed on the surface of VLPs.

The invention also encompasses variants of the said influenza proteins expressed on or in the VLPs of the invention. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to antigenic drifts. Antigenic drifts are small changes in the viral proteins that happen continually over time. Thus, a person infected with a particular flu virus strain develops antibody against that virus, as newer virus strains appear, the antibodies against the older strains no longer recognize the newer virus and reinfection can occur. This is why there is a new vaccine for influenza each season. In addition, some changes in an influenza virus can cause influenza virus to cross species. For example, some avian influenza viruses developed genetic variations associated with the capability of crossing the species barrier. Such a virus is capable of causing a pandemic because people have no natural immunity to the virus and the virus can easily spread from person to person. These naturally occurring variations of the influenza proteins are an embodiment of the invention.

The invention also utilizes nucleic acid and polypeptides which encode NA, HA and M1. In one embodiment, an influenza NA nucleic acid or protein is at least 85%, 90%, 95%, 96%, 97%, 98% or 99% identical to SEQ ID NOs 1, 11, 31, 32, 38, 39, 46, 47, 54, 55, 65, 66, 67, or 68. In another embodiment, an influenza HA nucleic acid or protein is at least 85%, 90%, 95%, 96%, 97%, 98% or 99% identical to SEQ ID NOs 2, 10, 27, 28, 29, 30, 33, 34, 35, 36, 37, 42, 43, 44, 45, 50, 51, 52, 53, 56, 57, 58, 69, 70, 71, 72, or 73. In another embodiment, an influenza M1 nucleic acid or protein is at least 85%, 90%, 95%, 96%, 97%, 98% or 99% identical to SEQ ID NOs 3, 12, 40, 41, 48, 49, 74, 75, 76, or 77.

In one embodiment, the vectors and/or host cells of the invention comprise nucleotides which encode an avian, pandemic and/or seasonal influenza virus HA protein selected from the group consisting of H1, H2, H3, H4, H5, H6, H7, H8, H9, H10, H11, H12, H13, H14, H15 and H16. In another embodiment, said vector and/or host cells comprise nucleotides which encode an NA protein which is selected from the group consisting of N1, N2, N3, N4, N5, N6, N7, N8 and N9. In another embodiment, said vector and/or host cell comprises influenza HA, M1 and/or NA. In another embodiment, said vector and/or host cell consists essentially of HA, M1 and/or NA. In a further embodiment, said vector and/or host cell consists of influenza protein comprising HA, M1 and NA. These vector and/or host cell contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, said nucleotides encode for an HA and/or the NA that exhibits hemagglutinin activity and/or neuraminidase activity, respectively, when expressed on the surface of VLPs.

This invention also provides for constructs and methods that will increase the efficiency of VLPs production. For example, removing cleavage sites from proteins in order to increase protein expression (see above). Other method comprises the addition of leader sequences to the HA, NA and/or M1 protein for more efficient transporting. For example, a heterologous signal sequence can be fused to the HA, NA and/or M1 influenza protein. In one embodiment, the signal sequence can be derived from the gene of an insect cell and fused to the influenza HA protein (for expression in insect cells). In another embodiment, the signal peptide is the chitinase signal sequence, which works efficiently in baculovirus expression systems. In other embodiment, interchanging leader sequences between influenza proteins can provide better protein transport. For example, it has been shown that H5 hemagglutinin is less efficient at being transported to the surface of particles. H9 hemagglutinins, however, targets the surface and is integrated into the surface more efficiently. Thus, in one embodiment, the H9 leader sequence is fused to the H5 protein.

Another method to increase efficiency of VLP production is to codon optimize the nucleotides that encode HA, NA and/or M1 proteins for a specific cell type. For example, codon optimizing nucleic acids for expression in Sf9 cell (see U.S. patent publication 2005/0118191, herein incorporated by reference in its entirety for all purposes). Examples of optimized codon sequences for Sf9 cells are disclosed below (e.g. SEQ ID 42, 44, 46, 48, 50, 52, and 54). In one embodiment, the nucleic acid sequence of codon optimized influenza protein is at least 85%, 90%, 95%, 96, 97, 98, or 99% to any one of SEQ ID Nos. 42, 44, 46, 48, 50, 52, and 54.

The invention also comprises a method of increasing the efficiency of producing chimeric VLPs comprising expressing an influenza M1 protein comprising a $K^{101}$ residue, such as an avian influenza M1 protein, and at least one non-avian influenza protein in a host cell. In one embodiment, said VLP comprises HA and/or NA from a non-avian influenza virus. In another embodiment, said non-avian influenza protein is a seasonal influenza protein. In another embodiment, said HA or NA have hemagglutinin and neuraminidase activity, respectively. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005. In another embodiment, said avian M1 comprises a lysine at the second position of the M1 protein L domain. In another embodiment, the putative L-domain comprises the sequence YKKL.

In another embodiment of the invention, the increase in VLP production, for chimeric or non-chimeric VLPs, is about 2-fold, about 4-fold, about 8-fold, about 16-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, or more when compared to VLP production using an M1 protein that does not harbor the putative L-domain sequence YKKL under similar conditions, for instance a human seasonal influenza M1. In one embodiment, the efficiency of producing influenza VLPs is increase by about 10%, about 20% about 30%, about 40%, about 50% about 60%, about 70% about 80%, about 90%, about 100%, about 150%, about 200%, about 250%, about 300%, about 350%, about 400%, about 450%, about 500%, about 550%, about 600%, about 650%, about 700%, about 750%, about 800%, about 850%, about 900%, about 950%, about 1000%, or more when compared to VLP production using an M1 protein that does not harbor the putative L-domain sequence YKKL under similar conditions. In a preferred embodiment, the M1 is from the avian influenza virus strain A/Indonesia/5/05 (SEQ ID NO: 49).

The invention also provides for methods of producing VLPs of the invention, said methods comprising expressing an influenza M1 protein comprising a $K^{101}$ residue, such as an avian influenza M1 protein, and a non-avian influenza protein (e.g. seasonal HA and/or NA) under conditions that allow the formation of VLPs. Depending on the expression system and host cell selected, VLPs are produced by growing host cells transformed by an expression vector under conditions whereby the recombinant proteins (e.g. an influenza M1 protein comprising a $K^{101}$ residue, such as an avian influenza M1 protein, and a non-avian influenza protein) are expressed and VLPs are formed. The selection of the appropriate growth conditions is within the skill or a person with skill of one of ordinary skill in the art.

Methods to grow cells engineered to produce VLPs of the invention include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, said bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L.

VLPs are then isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. Usually VLPs are produced from recombinant cell lines engineered to create a VLP when said cells are grown in cell culture (see above). A person of skill in the art would understand that there are additional methods that can be utilized to make and purify VLPs of the invention, thus the invention is not limited to the method described.

Production of VLPs of the invention can start by seeding Sf9 cells (non-infected) into shaker flasks, allowing the cells to expand and scaling up as the cells grow and multiply (for example from a 125 ml flask to a 50 L Wave bag). The medium used to grow the cell is formulated for the appropriate cell line (preferably serum free media, e.g. insect medium ExCell-420, JRH). Next, said cells are infected with recombinant baculovirus at the most efficient multiplicity of infection (e.g. from about 1 to about 3 plaque forming units per cell). Once infection has occurred, the influenza M1 protein comprising a $K^{101}$ residue, such as an avian influenza M1 protein, and at least one avian influenza heterologous protein are expressed from the virus genome, self assemble into VLPs and are secreted from the cells approximately 24 to 72 hours post infection. Usually, infection is most efficient when the cells are in mid-log phase of growth ($4\text{-}8\times10^6$ cells/ml) and are at least about 90% viable.

VLPs of the invention can be harvested approximately 48 to 96 hours post infection, when the levels of VLPs in the cell culture medium are near the maximum but before extensive cell lysis. The Sf9 cell density and viability at the time of harvest can be about $0.5\times10^6$ cells/ml to about $1.5\times10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 µm filter cartridge or a similar device.

Next, VLPs in the clarified culture medium can be concentrated by ultrafiltration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be further purified on a 20% to 60% discontinuous sucrose gradient in pH 7.2 PBS buffer with 0.5 M NaCl by centrifugation at 6,500×g for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluted via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propyllactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

Expansion and production of baculovirus expression vectors and infection of cells with recombinant baculovirus to produce recombinant influenza VLPs can be accomplished in insect cells, for example Sf9 insect cells as previously described. In a preferred embodiment, the cells are Sf9 infected with recombinant baculovirus engineered to produce VLPs of the invention.

Pharmaceutical or Vaccine Formulations and Administration

The invention comprises an antigenic formulation comprising a chimeric VLP comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. In another embodiment, said VLP comprises HA and/or NA from a non-avian influenza virus. In another embodiment, said HA or NA have hemagglutinin and neuraminidase activity, respectively. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005. In another embodiment, said non-avian influenza protein is from a virus, bacteria, fungus and/or parasite. For example, the non-avian influenza protein is a SARS virus S protein. In another embodiment, said non-avian protein is a chimeric protein comprising the transmembrane domain and/or cytoplasmic tail of influenza HA and/or influenza NA fused to a protein from an infective agent, wherein said HA and NA proteins are described above. In another embodiment, the antigenic formulation comprises a chimeric VLP comprising an influenza M1 protein comprising an Lysine at the second position of the M1 protein L domain. In another embodiment, said L domain comprises the sequence YKKL. In another embodiment of the invention, said VLPs comprise more than one protein from an infectious agent. In another embodiment, said chimeric proteins comprise a fusion between the influenza HA with the protein, or a portion thereof, from an infectious agent. In another embodiment, said infectious agent is from a virus, bacteria, fungus and/or parasite. In another embodiment, said non-avian influenza protein is a chimeric protein comprising the transmembrane domain and/or cytoplasmic tail of influenza HA and or influenza NA fused to a protein from an infective agent. In another embodiment, said VLPs comprise more than one protein from an infectious agent. In another embodiment, said chimeric proteins comprise a fusion between the influenza HA with the protein, or a portion thereof, from an infectious agent.

Said formulations of the invention comprise a formulation comprising VLPs comprising an influenza M1 protein comprising a $K^{101}$ residue, such as an avian influenza M1 protein, and at least one protein from a non-avian influenza protein (e.g. a protein from an infectious agent described above) and a pharmaceutically acceptable carrier or excipient. Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In another embodiment, the formulation is suitable for administration to humans, preferably is sterile, non-particulate, and/or non-pyrogenic.

The formulation, if desired, can also contain minor amounts of wetting or emulsifying agents, or pH buffering agents. The formulation can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The pharmaceutical formulation useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of the invention. As used herein, the term "pharmaceutically acceptable" means being approved by a regulatory agency of the Federal or a state government or listed in the U.S. Pharmacopia, European Pharmacopia, or other generally recognized pharmacopia for use in mammals, and more particularly in humans. These compositions can be useful as a vaccine and/or antigenic compositions for inducing a protective immune response in a vertebrate.

The invention comprises a vaccine comprising a chimeric VLP comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. In another embodiment, said VLP comprises HA and/or NA from a non-avian influenza virus. In another embodiment, said HA or NA have hemagglutinin and neuraminidase activity, respectively. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005. In another embodiment, said non-avian influenza protein is from a virus, bacteria, fungus and/or parasite. For example, the non-avian influenza protein is a SARS virus S protein. In another embodiment, said non-avian protein is a chimeric protein comprising the transmembrane domain and/or cytoplasmic tail of influenza HA and/or influenza NA fused to a protein from an infective agent, wherein said HA and NA proteins are described above. In another embodiment, the antigenic formulation comprises a chimeric VLP comprising an influenza M1 protein comprising an Lysine at the second position of the M1 protein L domain. In another embodiment, said L domain comprises the sequence YKKL. In another embodiment of the invention, said VLPs comprise more than one protein from an infectious agent. In another embodiment, said chimeric proteins comprise a fusion between the influenza HA with the protein, or a portion thereof, from an infectious agent. In another embodiment, said infectious agent is from a virus, bacteria, fungus and/or parasite. In another embodiment, said non-avian influenza protein is a chimeric protein comprising the transmembrane domain and/or cytoplasmic tail of influenza HA and or influenza NA fused to a protein, or a portion thereof, from an infective agent. In another embodiment, said VLPs comprise more than one protein from an infectious agent.

The invention also provides for a pharmaceutical pack or kit comprising one or more containers filled with one or more of the ingredients of the vaccine formulations of the invention. In one embodiment, the kit comprises two containers, one containing VLPs and the other containing an adjuvant. In another embodiment, the kit comprises two containers, one containing freeze dried VLPs and the other containing a solution to resuspend said VLPs. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the VLP formulation be packaged in a hermetically sealed container such as an ampoule or sachette indicating the quantity of composition. In one embodiment, the VLP composition is supplied as a liquid, in another embodiment, as a dry sterilized lyophilized powder or water free concentrate in a hermetically sealed container and can be reconstituted, e.g., with water or saline, to the appropriate concentration for administration to a subject. In one embodiment, said container comprises at least about 50 µg/ml, more preferably at least about 100 µg/ml, at least about 200 µg/ml, at least 500 µg/ml, or at least 1 mg/ml of an antigen associated with VLPs of the invention. These doses may be measured as total VLPs or as µg of HA. The VLP composition should be administered within about 12 hours, preferably within about 6 hours, within about 5 hours, within about 3 hours, or within about 1 hour after being reconstituted from the lyophilized powder.

In an alternative embodiment, the VLP composition is supplied in liquid form in a hermetically sealed container indicating the quantity and concentration of the VLP composition. The liquid form of the VLP composition is supplied in a hermetically sealed container at least about 50 µg/ml, more preferably at least about 100 µg/ml, at least about 200 µg/ml, at least 500 µg/ml, or at least 1 mg/ml of an antigen associated with VLPs of the invention.

Generally, VLPs of the invention are administered in an effective amount or quantity (as defined above) sufficient to stimulate an immune response against one or more infectious agents. Preferably, administration of the VLP of the invention elicits immunity against an infectious agent. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in an immune response, intranasal administration confers the added benefit of eliciting mucosal immunity at the site of entry of many viruses, including RSV and influenza.

Thus, the invention also comprises a method of formulating a vaccine or antigenic composition that induces immunity to an infection or at least one symptom thereof to a mammal, comprising adding to said formulation an effective dose of VLPs of the invention.

Methods of administering a composition comprising VLPs (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising VLPs of the invention may induce an antibody or other immune response that is substantially higher than other routes of administration. In another embodiment, intranasal or other mucosal routes of administration of a composition comprising VLPs of the invention may induce an antibody or other immune response that will induce cross protection against other strains or organisms that cause infection. For example, a VLP comprising influenza protein, when administered to a vertebrate, can induce cross protection against several influenza strains. Administration can be systemic or local.

In yet another embodiment, the vaccine and/or antigenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or antigenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, said VLPs of the invention can be administered as part of a combination therapy. For example, VLPs of the invention can be formulated with other immunogenic compositions, antivirals (e.g. amantadine, rimantidine, zanamivir, and osteltamivir) and/or antibiotics.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat. Most animals are not natural hosts to infectious agents but can still serve in studies of various aspects of the disease. For example, any of the above animals can be dosed with a vaccine candidate, e.g. VLPs of the invention, to partially characterize the immune response induced, and/or to determine if any neutralizing antibodies have been produced. For example, many studies have been conducted in the mouse model because mice are small size and their low cost allows researchers to conduct studies on a larger scale. Nevertheless, the mouse's small size also increases the difficulty of readily observing any clinical signs of disease and the mouse is not a predictive model for disease in humans.

There has been extensive use of ferrets for studying various aspects of human influenza viral infection and its course of action. The development of many of the contemporary concepts of immunity to the influenza virus would have been impossible without the use of the ferret (Maher et al. 2004). Ferrets have proven to be a good model for studying influenza for several reasons: influenza infection in the ferret closely resembles that in humans with respect to clinical signs, pathogenesis, and immunity; types A and B of human influenza virus naturally infect the ferret, thus providing an opportunity to study a completely controlled population in which to observe the interplay of transmission of infection, illness, and sequence variation of amino acids in the glycoproteins of the influenza virus; and ferrets have other physical characteristics that make it an ideal model for deciphering the manifestations of the disease. For example, ferrets and humans show very similar clinical signs of influenza infection that seem to depend on the age of the host, the strain of the virus, environmental conditions, the degree of secondary bacterial infection, and many other variables. Thus, one skilled in the art can more easily correlate the efficacy of an influenza vaccine and dosage regiments from a ferret model to humans as compared to a mouse or any other model described above.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients ($2^{nd}$ Edition)," herein incorporated by reference in its entirety for all purposes, is envisioned within the scope of this invention.

Exemplary, adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In one embodiment of the invention, the adjuvant is a paucilamellar lipid vesicle having about two to ten bilayers arranged in the form of substantially spherical shells separated by aqueous layers surrounding a large amorphous central cavity free of lipid bilayers. Paucilamellar lipid vesicles may act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the preformed vesicles such that the antigen remains extracellular to the vesicles. By encapsulating an antigen within the central cavity of the vesicle, the vesicle acts both as an immune stimulator and as a carrier for the antigen. In another embodiment, the vesicles are primarily made of nonphospholipid vesicles. In another embodiment, the vesicles are Novasomes®. Novasomes® are paucilamellar nonphospholipid vesicles ranging from about 100 nm to about 500 nm. They comprise Brij 72, cholesterol, oleic acid and squalene. Novasomes® have been shown to be an effective adjuvant for influenza antigens (see, U.S. Pat. Nos. 5,629,021, 6,387,373, and 4,911,928, herein incorporated by reference in their entireties for all purposes).

In one aspect, an adjuvant effect is achieved by use of an agent, such as alum, used in about 0.05 to about 0.1% solution in phosphate buffered saline. Alternatively, the VLPs can be made as an admixture with synthetic polymers of sugars (Carbopol®) used as an about 0.25% solution. Some adjuvants, for example, certain organic molecules obtained from bacteria; act on the host rather than on the antigen. An example is muramyl dipeptide (N-acetylmuramyl-L-alanyl-D-isoglutamine [MDP]), a bacterial peptidoglycan. In other embodiments, hemocyanins and hemoerythrins may also be used with VLPs of the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin. In another embodiment, a lipophilic disaccharide-tripeptide derivative of muramyl dipeptide which is described for use in artificial liposomes formed from phosphatidyl choline and phosphatidyl glycerol.

Amphipathic and surface active agents, e.g., saponin and derivatives such as QS21 (Cambridge Biotech), form yet another group of adjuvants for use with the VLPs of the invention. Nonionic block copolymer surfactants (Rabinovich et al., 1994) may also be employed. Oligonucleotides are another useful group of adjuvants (Yamamoto et al., 1988). Quil A and lentinen are other adjuvants that may be used in certain embodiments of the present invention.

Another group of adjuvants are the detoxified endotoxins, such as the refined detoxified endotoxin of U.S. Pat. No. 4,866,034. These refined detoxified endotoxins are effective in producing adjuvant responses in vertebrates. Of course, the detoxified endotoxins may be combined with other adjuvants to prepare multi-adjuvant formulation. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

Those of skill in the art will know the different kinds of adjuvants that can be conjugated to vaccines in accordance with this invention and these include alkyl lysophosphilipids (ALP); BCG; and biotin (including biotinylated derivatives) among others. Certain adjuvants particularly contemplated for use are the teichoic acids from Gram-cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Various adjuvants, even those that are not commonly used in humans, may still be employed in other vertebrates, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

Another method of inducing an immune response can be accomplished by formulating the VLPs of the invention with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the RSV VLPs, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

Thus, one embodiment of the invention comprises a formulation comprising a chimeric VLP comprising an influenza M1 protein comprising a $K^{101}$ residue, such as an avian influenza M1 protein, and at least one non-avian influenza protein (or at least one protein from an infectious agent) and adjuvant and/or an immune stimulator. In another embodiment, said adjuvant are Novasomes®. In another embodiment, said formulation is suitable for human administration. In another embodiment, the formulation is administered to a vertebrate orally, intradermally, intranasally, intramuscularly, intraperitoneally, intravenously or subcutaneously. In another embodiment, different chimeric VLPs are blended together to create a multivalent formulation. These VLPs may comprise VLPs HA and/or NA from different strains of influenza virus (e.g. influenza A and/or influenza B) or protein from different infectious agents (e.g. RSV, coronavirus, HIV).

While stimulation of immunity with a single dose is preferred, additional dosages can be administered by the same or different route to achieve the desired effect. In neonates and infants, for example, multiple administrations may be required to elicit sufficient levels of immunity. Administration can continue at intervals throughout childhood, as necessary to maintain sufficient levels of protection against infections. Similarly, adults who are particularly susceptible to repeated or serious infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection. In one embodiment, doses are administered at least 2 weeks apart, at least 3 weeks apart, at least 4 weeks apart, at least 5 weeks apart or at least 6 weeks apart.

Methods of Stimulating an Immune Response

As mentioned above, the VLPs of the invention are useful for preparing compositions that stimulate an immune response that confers immunity to infectious agents. Both mucosal and cellular immunity may contribute to immunity to infectious agents and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. The immune response induced by an infection protects against reinfection with the same virus or an antigenically similar viral strain. For example, influenza undergoes frequent and unpredictable changes; therefore, after natural infection, the effective period of protection provided by the host's immunity may only be a few years against the new strains of virus circulating in the community.

VLPs of the invention can induce immune responses in a vertebrate (e.g. a human) when administered to said vertebrate. The immunity results from an immune response against VLPs of the invention that protects or ameliorates infection or at least reduces a symptom of infection in said vertebrate. In some instances, if the said vertebrate is infected, said infection will be asymptomatic. The response may be not a fully protective response. In this case, if said vertebrate is infected with an infectious agent, the vertebrate will experience reduced symptoms or a shorter duration of symptoms compared to a non-immunized vertebrate.

The invention comprises methods of inducing immune response in a vertebrate comprising administering to said vertebrate the VLP of the present invention comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said immune response is a humoral immune response. In another embodiment, said immune response is a cellular immune response. In another embodiment, said non-avian influenza protein is HA and/or NA from a non-avian influenza virus. In another embodiment, said non-avian influenza protein is a seasonal influenza protein. In another embodiment, said HA or NA has hemagglutinin or neuraminidase activity, respectively. In one embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA transmembrane and/or cytoplasmic-terminal domains are from influenza strain A/Indonesia/5/05. In another embodiment, said M1 is from influenza strain A/Indonesia/5/05. In another embodiment, said HA and/or NA is from influenza strain A/Wisconsin/67/2005. In another embodiment, the chimeric VLP comprises an influenza M1 protein comprising an lysine at the second position of the M1 protein putative L-domain. In another embodiment, said putative L-domain comprises the sequence YKKL. In another embodiment, said VLPs comprise more than one protein from an infectious agent. In another embodiment, said chimeric proteins comprise a fusion between the influenza HA with the protein, or a portion thereof, from an infectious agent. The VLPs may comprise additional proteins and/or protein contaminates in negligible concentrations. In another embodiment, the VLP comprises a M1 protein and at least one chimeric protein, wherein said VLP contains a M1 protein and at least one chimeric protein and may contain additional cellular constituents such as cellular proteins, baculovirus proteins, lipids, carbohydrates etc., but do not contain additional fragments of the M1 protein and the chimeric protein. In one embodiment, said method comprises administering to said vertebrate the VLP orally, intradermally, intranasally, intramuscularly, intraperitoneally, intravenously, or subcutaneously. In one embodiment, at least two effective doses of the vaccine are administered. In another embodiment, the doses are administered at least 2 weeks apart, at least 3 weeks apart, at least 4 weeks apart, at least 5 weeks apart or at least 6 weeks apart. In another embodiment, said vaccine further comprises an adjuvant or immune stimulator.

In another embodiment, said non-avian influenza protein is from a virus, bacteria, fungus and/or parasite. For example, the non-avian influenza protein is a SARS virus S protein. In another embodiment, said non-avian protein is a chimeric protein comprising the transmembrane domain and/or cytoplasmic tail of influenza HA and/or influenza NA fused to a protein, or a portion thereof, from an infective agent. In another embodiment, said chimeric protein comprise at least one external domain (ectodomain) of influenza HA and/or NA protein sequences fused to the transmembrane and/or cytoplasmic-terminal domains of a heterologous HA and/or NA. In another embodiment, said heterologous transmembrane and/or cytoplasmic-terminal domains HA and/or NA is from a pandemic, seasonal and/or avian influenza virus. In another embodiment, said heterologous transmembrane and/or cytoplasmic-terminal domains HA and/or NA is from a pandemic, seasonal and/or avian influenza virus and a NA from a pandemic, seasonal and/or avian influenza virus, wherein said HA is selected from the group consisting of H1, H2, H3, H4, H5, H6, H,7 H8, H9, H10, H11, H12, H13, H14, H15 and H16 and said NA is selected from the group consisting of N1, N2, N3, N4, N5, N6, N7, N8 and N9. In another embodiment, said influenza HA and/or NA are from a seasonal influenza strain A/Wisconsin/67/2005 and HA and/or NA transmembrane and/or cytoplasmic-terminal domains are from an avian influenza strain. In another embodiment, said non-avian influenza HA and/or NA are from influenza strain A/Fujian/411/02 and HA and/or NA transmembrane and/or cytoplasmic-terminal domains are from an avian influenza strain. Said HA and/or NA transmembrane and/or cytoplasmic-terminal domains from avian influenza can be derived from the group consisting of influenza virus H9N2 and influenza virus H5N1.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as γ, α, δ, or ε, which in turn define the immunoglobulin classes, IgG, IgM, IgA, IgD, and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Antibodies exist as intact immunoglobulins or as a number of well-characterized fragments produced by digestion with various peptidases.

In another embodiment, the invention comprises a method of inducing a protective cellular response to an infection or at least one symptom thereof in a subject, comprising administering at least one effective dose of VLPs of the invention, wherein said VLPs comprise an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. Cell-mediated immunity also plays a role in recovery from infection and may prevent additional complication and contribute to long term immunity.

As mentioned above, the VLPs of the invention can prevent or reduce at least one symptom of an infection in a subject when administered to said subject. Most symptoms of most infections are well known in the art. Thus, the method of the invention comprises the prevention or reduction of at least one symptom associated with an infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of an infection or additional symptoms, reduced severity of symptoms, or suitable assays (e.g. antibody titer and/or T-cell activation assay). The objective assessment comprises both animal and human assessments.

The invention comprises a method of preventing and/or reducing an infection or symptom thereof, comprising administering to said vertebrate a chimeric VLP comprising an influenza M1 protein comprising a $K^{101}$ residue, such as an avian influenza M1 protein, and at least one non-avian influenza protein. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. In another embodiment said infection is a viral infection. In another embodiment, said viral infection is an influenza infection.

A strategy for the control of infectious diseases during an outbreak, e.g. influenza, is the universal vaccination of healthy individuals, including children. For example, vaccination with current influenza vaccines of approximately 80% of schoolchildren in a community has decreased respiratory illnesses in adults and excess deaths in the elderly (Reichert et al., 2001). This concept is known as community immunity or "herd immunity" and is thought to play an important part of protecting the community against diseases. Because vaccinated people have antibodies that neutralize and infectious agent, e.g. influenza virus, they are much less likely to transmit said agent to other people. Thus, even people who have not been vaccinated (and those whose vaccinations have become weakened or whose vaccines are not fully effective) often can be shielded by the herd immunity because vaccinated people around them are not getting sick. Herd immunity is more effective as the percentage of people vaccinated increases. It is thought that approximately 95% of the people in the community must be protected by a vaccine to achieve herd immunity. People who are not immunized increase the chance that they and others will get the disease.

Thus, the invention also comprises a method of reducing the severity of an infectious disease in a population, comprising administering a VLP comprising an influenza M1 protein comprising a $K^{101}$ residue, such as an avian influenza M1 protein, and at least one non-avian influenza protein to enough individuals in said population in order to prevent or decrease the chance of transmission to another individual in said population. In one embodiment, said VLP consists essentially of an influenza M1 protein comprising a $K^{101}$ residue, such as an avian influenza M1 protein, and at least one non-avian influenza protein. In another embodiment, said VLP consists of an influenza M1 protein comprising a $K^{101}$ residue, such as an avian influenza M1 protein, and at least one non-avian influenza protein. In another embodiment, said infectious disease is caused by influenza virus. The invention also encompasses a method of inducing immunity to an infectious agent to a population or a community in order to reduce the incidence of infections among immunocompromised individuals or non-vaccinated individual buy administering VLPs of the invention to a population in a community. In one embodiment, most school-aged children are immunized by administering the VLPs of the invention. In another embodiment, most healthy individuals in a community to are immunized by administering the VLPs of the invention. In another embodiment, VLPs of the invention are part of a "dynamic vaccination" strategy. Dynamic vaccination is the steady production of a low-efficacy vaccine that is related to an emerging pandemic strain, but due to an antigenic drift may not provide complete protection in a mammal (see Germann et al., 2006).

Method of Stimulating an Anti-Influenza Immune Response

In one embodiment, the invention comprises a method of inducing substantial immunity to influenza virus infection or at least one symptom thereof in a subject, comprising administering at least one effective dose of an influenza VLP. In another embodiment, said induction of substantial immunity reduces duration of influenza symptoms. In another embodiment, a method to induce substantial immunity to influenza virus infection or at least one symptom thereof in a subject, comprises administering at least one effective dose of an influenza VLP, wherein said VLP comprises influenza HA, NA and M1 proteins. In one embodiment, said influenza M1 protein comprises a $K^{101}$ residue. In one embodiment, said influenza M1 protein is an avian influenza M1 protein. In another embodiment, said influenza VLP comprises influenza proteins, wherein said influenza proteins consist of HA, NA and M1 proteins. In one embodiment, said influenza M1 protein comprises a $K^{101}$ residue. In one embodiment, said influenza M1 protein is an avian influenza M1 protein. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, a method of inducing substantial immunity to influenza virus infection or at least one symptom thereof in a subject, comprises administering at least one effective dose of an influenza VLP, wherein said VLP consists essentially of influenza HA, NA and M1. In one embodiment, said influenza M1 protein comprises a $K^{101}$ residue. In one embodiment, said influenza M1 protein is an avian influenza M1 protein. Said VLPs may comprise additional influenza proteins and/or protein contaminates in negligible concentrations. In another embodiment, a method of inducing substantial immunity to influenza virus infection or at least one symptom thereof in a subject, comprises administering at least one effective dose of an influenza VLP, wherein said VLP consists of influenza HA, NA and M1. In one embodiment, said influenza M1 protein comprises a $K^{101}$ residue. In one embodiment, said influenza M1 protein is an avian influenza M1 protein. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

Recently there has been a concerted effort to create a vaccine against avian influenza virus that has the potential to create a pandemic. That is because a number of avian influenza viruses have crossed the species barrier and directly infected humans resulting in illness and, in some cases, death. These viruses were H5N1, H9N2 and H7N7 (Cox et al., 2004). A recent study examined the potential of using inactivated H5N1 influenza virus as a vaccine. The formulation of the vaccine was similar to the licensed inactivated vaccines currently licensed for marketing. The study concluded that using inactivated H5N1 virus did induce an immune response in humans, however the dose given was very high (90 µg of avian influenza compared to 15 µg of the licensed vaccine) (Treanor et al., 2006). This high amount of avian influenza antigen is impractical for a worldwide vaccination campaign. As illustrated below, the VLPs of the invention induces an immune response in a vertebrate when administered to said vertebrate.

Thus, the invention encompasses a method of inducing substantial immunity to influenza virus infection or at least one symptom thereof in a subject, comprising administering at least one effective dose of an avian influenza VLP. In another embodiment, said induction of substantial immunity reduces duration of influenza symptoms. In another embodiment, said induction of immunity is from administering at least 0.2 µg of avian HA in VLPs of the invention. In another embodiment, said induction of immunity is from administering about 0.2 µg of avian HA to about 15 µg of avian HA in VLPs of the invention. In another embodiment, said induction of immunity is from administering about 15 µg of avian HA to about 45 µg of avian HA in VLPs of the invention. In another embodiment, said induction of immunity is from administering about 45 µg of avian HA to about 135 µg of avian HA in VLPs of the invention. In another embodiment, said induction of immunity is from administering about 10 µg, about 20 µg, about 30 µg, about 40 µg, about 45 µg, about 50 µg, about 60 µg, about 70 µg, about 80 µg, about 90 µg, about 100 µg, about 110 µg, about 120 µg, about 130 µg, about 140 µg, about 150 µg or higher. Administration may be in one or more doses, but may be advantageously in a single dose. In another embodiment, said VLP avian HA is derived from avian influenza H5N1. In one embodiment, said influenza M1 protein comprises a $K^{101}$ residue. In another embodiment, said influenza M1 protein is an avian influenza M1 protein.

In another embodiment, the invention comprises a method of inducing substantial immunity to avian influenza virus infection or at least one symptom thereof in a subject comprising administering at least one effective dose of an avian influenza VLP, wherein said VLP comprises an avian influenza HA, NA and M1. In another embodiment, said avian influenza VLP comprises avian influenza proteins, wherein said avian influenza proteins consist of HA, NA and M1 proteins. In one embodiment, said avian influenza M1 protein comprises a $K^{101}$ residue.

These VLPs contain HA, NA and M1 and may contain additional cellular constituents such as cellular proteins, baculovirus proteins, lipids, carbohydrates etc. but do not contain additional influenza proteins (other than fragments of M1, HA and/or NA). In another embodiment, said method of inducing substantial immunity to avian influenza virus infection or at least one symptom thereof in a subject comprises administering at least one effective dose of an avian influenza VLP, wherein said VLP consists essentially of avian influenza HA, NA and M1. In one embodiment, said avian influenza M1 protein comprises a $K^{101}$ residue.

Said VLPs may comprise additional influenza proteins and/or protein contaminates in negligible concentrations. In another embodiment, a method to induce substantial immunity to influenza virus infection or at least one symptom thereof in a subject, comprises administering at least one effective dose of an influenza VLP, wherein said VLP consists of avian influenza HA, NA and M1. In one embodiment, said influenza M1 protein comprises a $K^{101}$ residue.

In another embodiment, said avian influenza HA and NA are H5N1, respectively. In another embodiment, said avian influenza HA and NA are H9N2, respectively. In another embodiment, said avian influenza HA and NA are H7N7, respectively. In another embodiment, said avian influenza HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

In another embodiment, said avian influenza VLPs will induce an immune response in a vertebrate that is about 2 fold, about 4 fold, about 8 fold, about 16 fold, about 32 fold about 64 fold, about 128 fold increase (or higher) more potent than a similar avian influenza antigens formulated similarly to the licensed inactivated vaccines currently licensed for marketing. Current formulations comprise whole inactivated virus (e.g. formaldehyde treated), split virus (chemically disrupted), and subunit (purified glycoprotein) vaccines. Methods for determining potency for a vaccine are known and routine in the art. For example, microneutralization assays and hemagglutination inhibition assays can be performed to determine potency of an avian VLP vaccine compared to avian influenza antigens formulated similar to the licensed inactivated vaccines currently licensed for marketing. In one embodiment, said increase in potency is realized when about 0.2 µg, about 0.4 µg, about 0.6 µg about 0.8 µg, about 1 µg, about 2 µg, about 3 µg, about 4 µg, about 5 µg, about 6 µg, about 7 µg, about 9 µg, about 10 µg, about 15 µg, about 20 µg, about 25 µg, about 30 µg, about 35 µg, 40 µg, about 45 µg, about 50 µg, about 60 µg, about 70 µg, about 80 µg, about 90 µg, about 100 µg, about 110 µg, about 120 µg, about 130 µg, about 140 µg, about 150 µg or higher of VLPs and the antigen formulated similarly to the inactivated vaccines currently licensed for marketing is administered to a vertebrate (i.e. equivalent amounts of HA and/or NA in a VLP with equivalent amounts of HA and/or NA formulated in similarly to the licensed inactivated vaccines and/or any other antigen) Amounts can be measured according to HA content. For example, 1 µg of a VLP of the invention is about 1 µg of HA in a solution of VLPs comprising HA or may be measured by weight of VLPs.

Seasonal influenza vaccines are administered to humans every year to reduce the incidence of influenza cases every year. At present, there are two subtypes of influenza A and influenza B circulating in the United States. Current vaccines are, therefore, trivalent to provide protection against the strains currently circulating. Each year a different stain or variation of an influenza viral changes. Thus, for most years a new vaccine composition is manufactured and administered. Inactivated vaccines are produced by propagation of the virus in embryonated hens' eggs. The allantoic fluid is harvested, and the virus is concentrated and purified, then inactivated. Thus, the current licensed influenza virus vaccines may contain trace amounts of residual egg proteins and, therefore, should not be administered to persons who have anaphylactic hypersesitiviety to eggs. In addition, supplies of eggs must be organized and strains for vaccine production must be selected months in advance of the next influenza season, thus limiting the flexibility of this approach and often resulting in delays and shortages in production and distribution. In addition, some influenza strains do not replicate well in embryonated chicken eggs which may limit the influenza strains which can be grown and formulated into vaccines.

As mentioned above, VLP of the invention do not require eggs for production. These VLPs are made via a cell culture system. Thus, the invention encompasses a method of inducing substantial immunity to influenza virus infection or at least one symptom thereof in a subject, comprising administering at least one effective dose of a seasonal influenza VLP. A discussed above, seasonal influenza virus refers to the influenza viral strains that has been determined to be passing within the human population for a given influenza season based on the epidemiological surveys by National Influenza Centers worldwide. Said studies and some isolated influenza viruses are sent to one of four World Health Organization (WHO) reference laboratories, one of which is located at the Centers for Disease Control and Prevention (CDC) in Atlanta, for detailed testing. These laboratories test how well antibodies made to the current vaccine react to the circulating virus and new flu viruses. This information, along with information about flu activity, is summarized and presented to an advisory committee of the U.S. Food and Drug Administration (FDA) and at a WHO meeting. These meetings result in the selection of three viruses (two subtypes of influenza A viruses and one influenza B virus) to go into flu vaccines for the following fall and winter. The selection occurs in February for the northern hemisphere and in September for the southern hemisphere. Usually, one or two of the three virus strains in the vaccine changes each year. In another embodiment, said induction of substantial immunity reduces duration of influenza symptoms.

In another embodiment, the invention comprises a method of inducing substantial immunity to a seasonal influenza virus infection or at least one symptom thereof in a subject comprising administering at least one effective dose of a seasonal influenza VLP, wherein said VLP comprises a seasonal influenza HA, NA and M1. In one embodiment, said seasonal influenza M1 protein has been mutated to comprise a $K^{101}$ residue.

In another embodiment, said seasonal influenza VLP comprises seasonal influenza proteins, wherein said influenza proteins consist of HA, NA and M1 proteins. In one embodiment, said seasonal influenza M1 protein has been mutated to comprise a $K^{101}$ residue. These VLPs contain HA, NA and M1 and may contain additional cellular constituents such as cellular proteins, baculovirus proteins, lipids, carbohydrates etc. but do not contain additional influenza proteins (other than fragments of M1, HA and/or NA). In another embodiment, said method of inducing substantial immunity to seasonal influenza virus infection or at least one symptom thereof in a subject comprises administering at least one effective dose of a seasonal influenza VLP, wherein said VLP consists essentially of seasonal influenza HA, NA and M1. In one embodiment, said seasonal influenza M1 protein has been mutated to comprise a $K^{101}$ residue. Said VLPs may comprise additional influenza proteins and/or protein contaminates in negligible concentrations. In another embodiment, a method to induce substantial immunity to influenza virus infection or at least one symptom thereof in a subject, comprises administering at least one effective dose of an influenza VLP, wherein said VLP consists of seasonal influenza HA, NA and M1. In one embodiment, said seasonal influenza M1 protein has been mutated to comprise a $K^{101}$ residue. In another embodiment, said avian influenza HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

Generally, seasonal influenza VLPs of the invention are administered in a quantity sufficient to stimulate substantial immunity for one or more strains of seasonal influenza virus. In one embodiment, the VLPs are blended together with other VLPs comprising different influenza subtypes proteins (as listed above). In another embodiment, the formulation is a trivalent formulation which comprises a mixture of VLPs with seasonal influenza HA and/or NA proteins from at least two influenza A and/or one at least one B subtype. In another embodiment, said B subtype is produced by the same method as described above. In another embodiment, a multivalent formulation comprises one or more of the VLP of the invention as described above.

In another embodiment, VLPs of the invention (avian or seasonal VLPs) may elicit an immune response that will provide protection against more than one strain of influenza virus. This cross-protection of a vertebrate with an influenza VLP constructed from a particular strain, of a particular subgroup, may induce cross-protection against influenza virus of different strains and/or subgroups. The examples below show that VLPs of the invention are capable of inducing cross reactivity with different strains and/or subgroups.

The humoral immune system produces antibodies against different influenza antigens, of which the HA-specific antibody is the most important for neutralization of the virus and thus prevention of illness. The NA-specific antibodies are less effective in preventing infection, but they lessen the release of virus from infected cells. The mucosal tissues are the main portal entry of many pathogens, including influenza, and the mucosal immune system provides the first line of defense against infection apart from innate immunity. SIgA and, to some extent, IgM are the major neutralizing antibodies directed against mucosal pathogens preventing pathogen entry and can function intracellularly to inhibit replication of virus. Nasal secretions contain neutralizing antibodies particularly to influenza HA and NA, which are primarily of the IgA isotype and are produced locally. During primary infection, all three major Ig classes (IgG, IgA and IgM) specific to HA can be detected by enzyme-linked immunosorbent assay in nasal washings, although IgA and IgM are more frequently detected than IgG. Both IgA and, to some extent, IgM are actively secreted locally, whereas IgG is derived as a serum secretion. In subjects who have a local IgA response, a serum IgA response also is observed. The local IgA response stimulated by natural infection lasts for at least 3-5 months, and influenza-specific, IgA-committed memory cells can be detected locally. IgA also is the predominant Ig isotype in local secretions after secondary infection, and an IgA response is detected in the serum upon subsequent infection. The presence of locally produced neutralizing antibodies induced by live virus vaccine correlates with resistance to infection and illness after challenge with wild-type virus.

Resistance to influenza infection or illness is correlated with the level of local and/or serum antibody to HA and NA. Serum anti-HA antibodies are the most commonly measured correlate of protection against influenza (Cox et al., 1999). A protective serum antibody (haemagglutination inhibition (HI) titer ≥40) response can be detected in approximately 80% of subjects after natural influenza infection. B cells producing all three major Ig classes are present in the peripheral blood in normal subjects (Cox et al., 1994) and individuals undergoing influenza infection. In humans, serum antibodies play a role in both resistance to and recovery from influenza infection. The level of serum antibody to HA and NA in humans can be correlated with resistance to illness following experimental infection and natural infection. During primary infection, the three major Ig classes can be detected within 10-14 days. IgA and IgM levels peak after 2 weeks and then begin to decline, whereas the level of IgG peaks at 4-6 weeks. Whereas IgG and IgM are dominant in the primary response, IgG and IgA predominate in the secondary immune response.

Thus, the invention encompasses a method of inducing a substantially protective antibody response to influenza virus infection or at least one symptom thereof in a subject, comprising administering at least one effective dose of an influenza VLP. In another embodiment, said induction of substantially protective antibody response reduces duration of influenza symptoms. In another embodiment, a method to induce substantially protective antibody response to influenza virus infection or at least one symptom thereof in a subject, comprises administering at least one effective dose of an influenza VLP, wherein said VLP comprises influenza HA, NA and M1 proteins. In one embodiment, said influenza M1 protein comprises a $K^{101}$ residue. In another embodiment, said influenza M1 protein is an avian influenza M1 protein.

In another embodiment, the invention comprises a method of inducing substantially protective antibody response to influenza virus infection or at least one symptom thereof in a subject, comprises administering at least one effective dose of an influenza VLP, wherein said VLP consists essentially of influenza HA, NA and M1. In one embodiment, said influenza M1 protein comprises a $K^{101}$ residue. In another embodiment, said influenza M1 protein is an avian influenza M1 protein. Said VLPs may comprise additional influenza proteins and/or protein contaminates in negligible concentrations. In another embodiment, said influenza VLP comprises influenza proteins, wherein said influenza proteins consist of HA, NA and M1 proteins. In one embodiment, said influenza M1 protein comprises a $K^{101}$ residue. In another embodiment, said influenza M1 protein is an avian influenza M1 protein. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In another embodiment, a method of inducing substantial immunity to influenza virus infection or at least one symptom thereof in a subject, comprises administering at least one effective dose of an influenza VLP, wherein said VLP consists of influenza HA, NA and M1. In one embodiment, said influenza M1 protein comprises a $K^{101}$ residue. In another embodiment, said influenza M1 protein is an avian influenza M1 protein. In another embodiment, said influenza HA, NA and M1 is derived from seasonal influenza and/or avian influenza. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Antibodies exist as intact immunoglobulins or as a number of well-characterized fragments produced by digestion with various peptidases.

Cell-mediated immunity also plays a role in recovery from influenza infection and may prevent influenza-associated complications. Influenza-specific cellular lymphocytes have been detected in the blood and the lower respiratory tract secretions of infected subjects. Cytolysis of influenza-infected cells is mediated by CTLs in concert with influenza-specific antibodies and complement. The primary cytotoxic response is detectable in blood after 6-14 days and disappears by day 21 in infected or vaccinated individuals (Ennis et al., 1981). Influenza-specific CTLs exhibit cross-reactive specificities in in vitro cultures; thus, they lyse cells infected with the same type of influenza but not with other types (e.g. influenza A but not influenza B virus). CTLs that recognize the internal nonglycosylated proteins, M, NP and PB2 have been isolated (Fleischer et al., 1985). The CTL response is cross-reactive between influenza A strains (Gerhard et al., 2001) and is important in minimizing viral spread in combination with antibody (Nguyen et al., 2001).

Cell-mediated immunity also plays a role in recovery from influenza infection and may prevent influenza-associated complications. Influenza-specific cellular lymphocytes have been detected in the blood and the lower respiratory tract secretions of infected subjects. Cytolysis of influenza-infected cells is mediated by CTLs in concert with influenza-specific antibodies and complement. The primary cytotoxic response is detectable in blood after 6-14 days and disappears by day 21 in infected or vaccinated individuals (Ennis et al., 1981). Influenza-specific CTLs exhibit cross-reactive specificities in in vitro cultures; thus, they lyse cells infected with the same type of influenza but not with other types (e.g. influenza A but not influenza B virus). CTLs that recognize the internal nonglycosylated proteins, M, NP and PB2 have been isolated (Fleischer et al., (1985). The CTL response is cross-reactive between influenza A strains (Gerhard et al., 2001) and is important in minimizing viral spread in combination with antibody (Nguyen et al., 2001).

Thus, the invention encompasses a method of inducing a substantially protective cellular immune response to influenza virus infection or at least one symptom thereof in a subject, comprising administering at least one effective dose of an influenza VLP. In another embodiment, a method of inducing substantial immunity to influenza virus infection or at least one symptom thereof in a subject, comprises administering at least one effective dose of an influenza VLP, wherein said VLP consists of influenza HA, NA and M1. In one embodiment, said influenza M1 protein comprises a $K^{101}$ residue. In another embodiment, said influenza M1 protein is an avian influenza M1 protein. In another embodiment, said influenza VLP comprises influenza proteins, wherein said influenza proteins consist of HA, NA and M1 proteins. In one embodiment, said influenza M1 protein comprises a $K^{101}$ residue. In another embodiment, said influenza M1 protein is an avian influenza M1 protein. These VLPs contain HA, NA and M1 and may contain additional cellular constituents such as cellular proteins, baculovirus proteins, lipids, carbohydrates etc. but do not contain additional influenza proteins (other than fragments of M1, HA and/or NA). In another embodiment wherein said influenza HA, NA and M1 is derived from seasonal influenza and/or avian influenza virus. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator.

As mentioned above, the VLPs of the invention (e.g. avian and/or seasonal influenza VLPs) prevent or reduce at least one symptom of influenza infection in a subject. Symptoms of influenza are well known in the art. They include fever, myalgia, headache, severe malaise, nonproductive cough, sore throat, weight loss and rhinitis. Thus, the method of the invention comprises the prevention or reduction of at least one symptom associated with influenza viral infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of an influenza infection or additional symptoms, a reduced severity of a influenza symptoms or a suitable assays (e.g. antibody titer and/or T-cell activation assay). The objective assessment comprises both animal and human assessments.

The principal strategy advocated by the Advisory Committee on Immunization Practices (ACIP) for control of influenza has been the vaccination of persons at risk for serious complications from influenza, in particular, people ≥65 years old. Yearly influenza epidemics, however, continue unabated and are responsible for significant health and financial burden to our society (Glaser et al., 1996). In the last 20 years (1976-1999), a significant increase has occurred in influenza-associated all cause excess deaths. From 1990 to 1999, the annual number of influenza-associated all cause deaths exceeded 50,000 (Thompson et al., 2003). Despite the increase in vaccine coverage of people ≥65 years to 65% during the last decade, a corresponding reduction in influenza-associated all cause excess deaths has not been observed.

Thus, another strategy for the prevention and control of influenza is universal vaccination of healthy children and individuals. Children have high rates of infection, medically attended illness and hospitalization from influenza (Neuzil et al., 2000). Children play an important role in the transmission of influenza within schools, families and communities. Vaccination with current influenza vaccines of approximately 80% of schoolchildren in a community has decreased respiratory illnesses in adults and excess deaths in the elderly (Reichert et al., 2001). This concept is known as community immunity or "herd immunity" and is thought to play an important part of protecting the community against disease. Because vaccinated people have antibodies that neutralize influenza virus, they are much less likely to transmit influenza virus to other people. Thus, even people who have not been vaccinated (and those whose vaccinations have become weakened or whose vaccines are not fully effective) often can be shielded by the herd immunity because vaccinated people around them are not getting sick. Herd immunity is more effective as the percentage of people vaccinated increases. It is thought that approximately 95% of the people in the community must be protected by a vaccine to achieve herd immunity. People who are not immunized increase the chance that they and others will get the disease.

Thus, the invention encompasses a method of inducing a substantially protective immunity to influenza virus infection to a population or a community in order to reduce the incidence of influenza virus infections among immunocompromised individuals or non-vaccinated individual buy administering VLPs of the invention to a population in a community. In one embodiment, most school-aged children are immunized against influenza virus by administering the VLPs of the invention. In another embodiment, most healthy individuals in a community to are immunized against influenza virus by administering the VLPs of the invention. In another embodiment VLPs of the invention are part of a "dynamic vaccination" strategy. Dynamic vaccination is the steady production of a low-efficacy vaccine that is related to an emerging pandemic strain, but due to an antigentic drift may not provide complete protection in a mammal (see Germann et al., 2006). Because of the uncertainty about the future identity of a pandemic strain, it is almost impossible to stockpile a well matched pandemic strain. However, vaccination with a poorly matched but potentially efficacious vaccine may slow the spread of the pandemic virus and/or reduce the severity of symptoms of a pandemic strain of influenza virus.

The invention also encompasses a vaccine comprising an influenza VLP, wherein said vaccine induces substantial immunity to influenza virus infection or at least one symptom thereof when administered to a subject. In another embodiment, said induction of substantial immunity reduces duration of influenza symptoms. In another embodiment, a said vaccine induces substantial immunity to influenza virus infection or at least one symptom thereof in a subject, comprises a VLP which comprises influenza HA, NA and M1 proteins. In one embodiment, said influenza M1 protein comprises a $K^{101}$ residue. In another embodiment, said influenza M1 protein is an avian influenza M1 protein. In another embodiment, a said vaccine induces substantial immunity to influenza virus infection or at least one symptom thereof in a subject, comprises a VLP which consists essentially of influenza HA, NA and M1 proteins. In one embodiment, said influenza M1 protein comprises a $K^{101}$ residue. In another embodiment, said influenza M1 protein is an avian influenza M1 protein. Said VLPs may comprise additional influenza proteins and/or protein contaminates in negligible concentrations. In another embodiment, a said vaccine induces substantial immunity to influenza virus infection or at least one symptom thereof in a subject, comprises a VLP which consists of influenza HA, NA and M1 proteins. In one embodiment, said influenza M1 protein comprises a $K^{101}$ residue. In another embodiment, said influenza M1 protein is an avian influenza M1 protein. In another embodiment, a said vaccine induces substantial immunity to influenza virus infection or at least one symptom thereof in a subject, comprises a VLP comprises influenza proteins, wherein said influenza proteins consist of HA, NA and M1 proteins. These VLPs contain HA, NA and M1 and may contain additional cellular constituents such as cellular proteins, baculovirus proteins, lipids, carbohydrates etc., but do not contain additional influenza proteins (other than fragments of M1, HA and/or NA). In one embodiment, said influenza M1 protein comprises a $K^{101}$ residue. In another embodiment, said influenza M1 protein is an avian influenza M1 protein. In another embodiment, said influenza HA, NA and M1 proteins are derived from an avian and/or seasonal influenza virus. In another embodiment, said HA and/or NA exhibits hemagglutinin activity and/or neuraminidase activity, respectfully. In another embodiment, said subject is a mammal. In another embodiment, said mammal is a human. In a further embodiment, said VLP is formulated with an adjuvant or immune stimulator. In another embodiment, where said vaccine is administered to a mammal. In a further embodiment, said mammal is a human.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Materials and Methods

Figure 2:
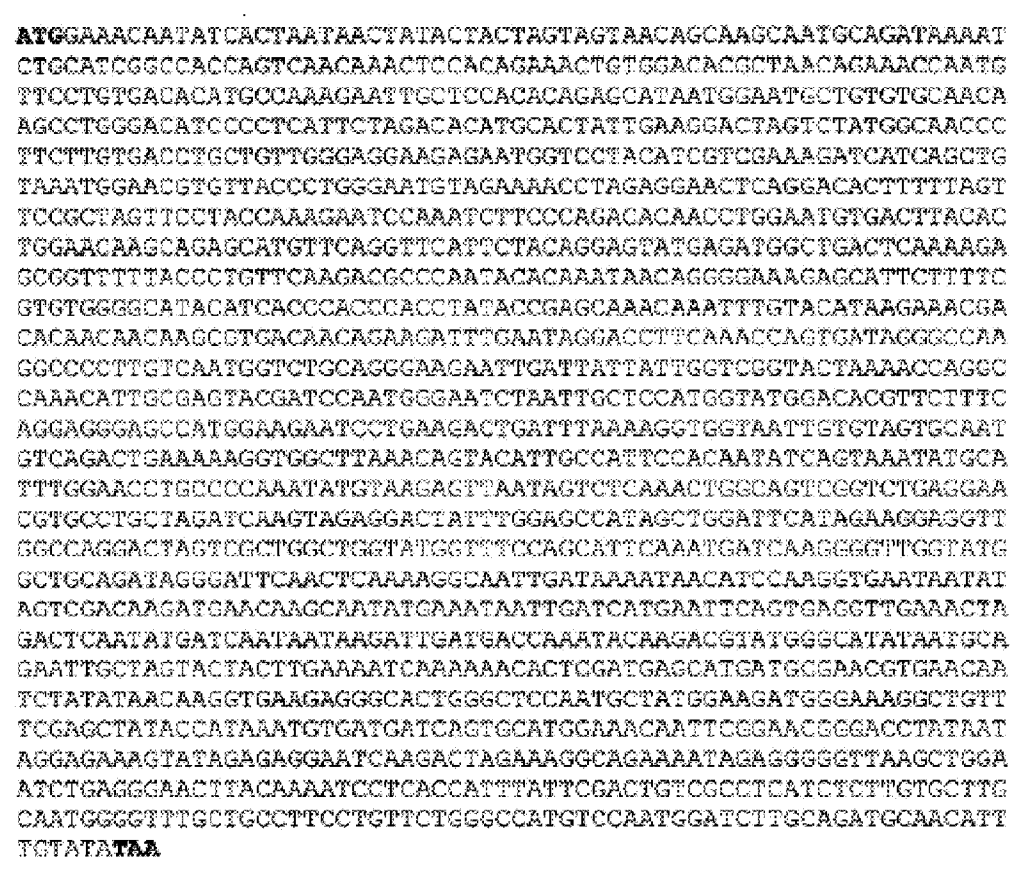

Avian influenza A/Hong Kong/1073/99 (H9N2) virus HA, NA, and M1 genes were expressed in *Spodoptera frugiperda* cells (Sf-9S cell line; ATCC PTA-4047) using the baculovirus bacmid expression system. The HA, NA, and M1 genes were synthesized by the reverse transcription and polymerase chain reaction (PCR) using RNA isolated from avian influenza A/Hong Kong/1073/99 (H9N2) virus (FIGS. 1, 2, and 3). For reverse transcription and PCR, oligonucleotide primers specific for avian influenza A/Hong Kong/1073/99 (H9N2) virus HA, NA, and M1 genes were used (Table 1). The cDNA copies of these genes were cloned initially into the bacterial subcloning vector, pCR2.1TOPO. From the resulting three pCR2.1TOPO-based plasmids, the HA, NA, and M1 genes were inserted downstream of the AcMNPV polyhedrin promoters in the baculovirus transfer vector, pFastBac1 (InVitrogen), resulting in three pFastBac1-based plasmids: pHA, pNA, and pM1 expressing these influenza virus genes, respectively. Then, a single pFastBac1-based plasmid pHAM was constructed encoding both the HA and M1 genes, each downstream from a separate polyhedrin promoter (FIG. 4). The nucleotide sequence of the NA gene with the adjacent 5'- and 3'-regions within the pNA plasmid was determined (SEQ ID NO:1) (FIG. 1). At the same time, the nucleotide sequences of the HA and M1 genes with the adjacent regions were also determined using the pHAM plasmid (SEQ ID NOs: 2 and 3) (FIGS. 2 and 3).

Finally, a restriction DNA fragment from the pHAM plasmid that encoded both the HA and M1 expression cassettes was cloned into the pNA plasmid. This resulted in the plasmid pNAHAM encoding avian influenza A/Hong Kong/1073/99 (H9N2) virus HA, NA, and M1 genes (FIG. 4).

Plasmid pNAHAM was used to construct a recombinant baculovirus containing influenza virus NA, HA, and M1 genes integrated into the genome, each downstream from a separate baculovirus polyhedrin promoter. Infection of permissive Sf-9S insect cells with the resulting recombinant baculovirus resulted in co-expression of these three influenza genes in each Sf-9S cell infected with such recombinant baculovirus.

Figure 5A:
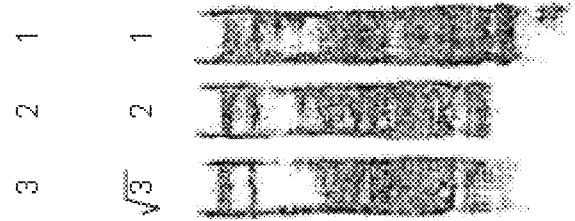

The expression products in infected Sf-9S cells were characterized at 72 hr postinfection (p.i. by SDS-PAGE analysis, Coomassie blue protein staining, and Western immunoblot analysis using HA- and M1-specific antibodies (FIG. 5). Western immunoblot analysis was carried out using rabbit antibody raised against influenza virus type A/Hong Kong/1073/99 (H9N2) (CDC, Atlanta, Ga., USA), or mouse monoclonal antibody to influenza M1 protein (Serotec, UK). The HA, NA, and M1 proteins of the expected molecular weights (64 kd, 60 kd, and 31 kd, respectively) were detected by Western immunoblot analysis. Compared to the amount of HA protein detected in this assay, the NA protein showed lower reactivity with rabbit serum to influenza A/Hong Kong/1073/99 (H9N2) virus. Explanations for the amount of detectable NA protein included lower expression levels of the NA protein from Sf-9S cells infected with recombinant baculovirus as compared to the HA protein, lower reactivity of the NA with this serum under denaturing conditions in the Western immunoblot assay (due to the elimination of important NA epitopes during gel electrophoresis of membrane binding), lower NA-antibody avidity as compared to HA-antibody, or a lower abundance of NA-antibodies in the serum.

The culture medium from the Sf-9S cells infected with recombinant baculovirus expressing A/Hong Kong/1073/99 (H9N2) HA, NA, and M1 proteins was also probed for influenza proteins. The clarified culture supernatants were subjected to ultracentrifugation at 27,000 rpm in order to concentrate high-molecular protein complexes of influenza virus, such as subviral particles, VLP, complexes of VLP, and possibly, other self-assembled particulates comprised of influenza HA, NA, and M1 proteins. Pelleted protein products were resuspended in phosphate-buffered saline (PBS, pH 7.2) and further purified by ultracentrifugation on discontinuous 20-60% sucrose step gradients. Fractions from the sucrose gradients were collected and analyzed by SDS-PAGE analysis, Western immunoblot analysis, and electron microscopy.

Figure 6:
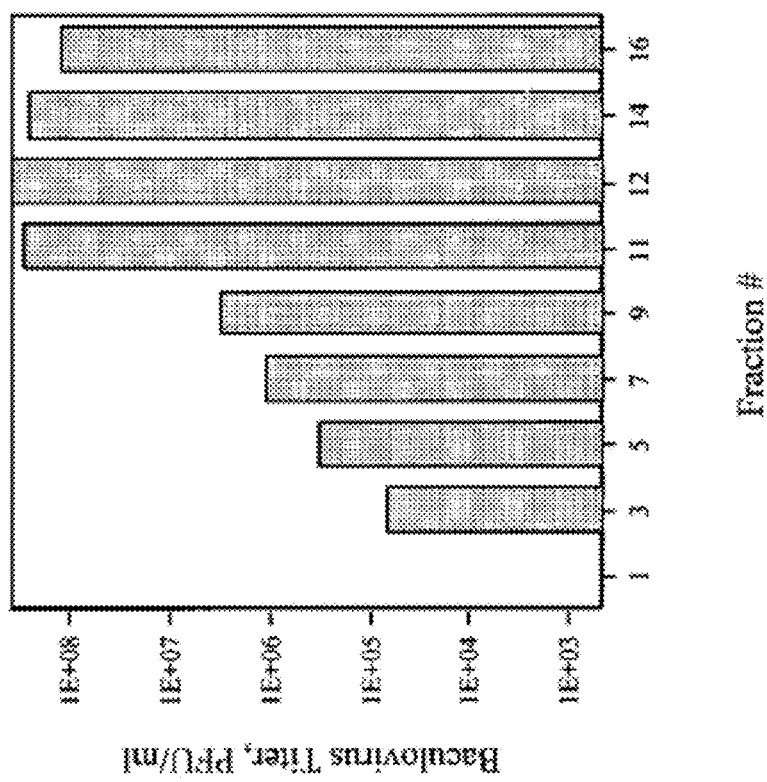
FIG. 6 depicts the purification of avian influenza A/Hong Kong/1073/99 (H9N2) VLPs by the sucrose density gradient method.
Figure 10:
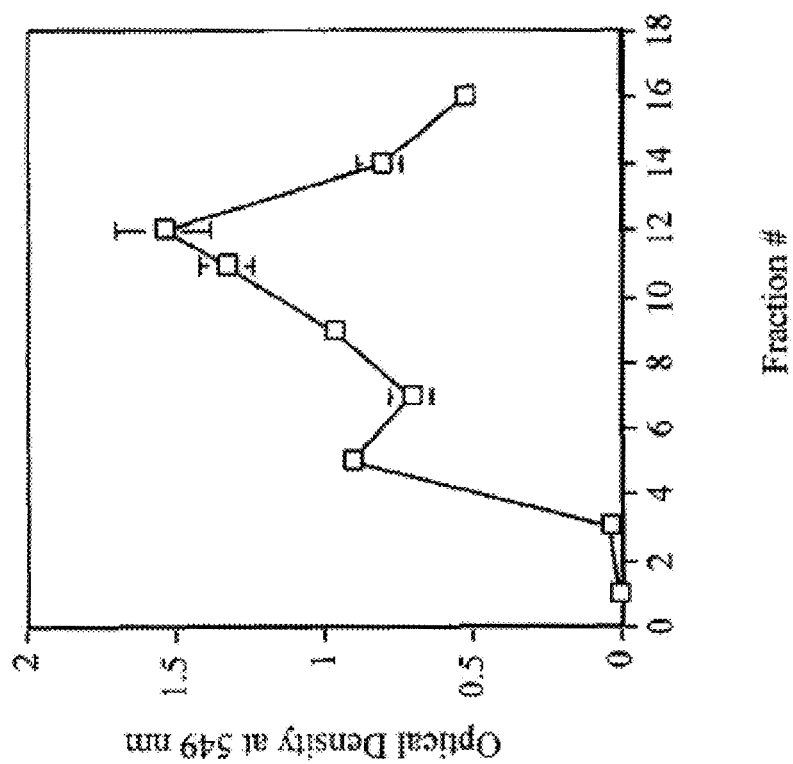
FIG. 10 depicts the neuraminidase activity of purified avian influenza A/Hong Kong/1073/99 (H9N2) VLPs.

Influenza HA and M1 proteins of the expected molecular weights were detected in multiple sucrose density gradient fractions by Coomassie blue staining and Western immunoblot analysis (FIG. 6, Table 1). This suggested that influenza viral proteins from infected Sf-9S cells are aggregated in complexes of high-molecular weight, such as capsomers, subviral particles, VLP, and/or VLP complexes. The NA proteins, although inconsistently detected by Coomassie blue staining and Western immunoblot analysis, which was likely due to the inability of the rabbit anti-influenza serum to recognize denatured NA protein in the Western immunoblot assay, were consistently detected in neuraminidase enzyme activity assay (FIG. 10).

TABLE 1

| Fraction#* | Titer |
|---|---|
| 1 | <1:5001 |
| 3 | <1:500 |
| 5 | 1:500 |
| 7 | 1:1000 |
| 9 | 1:2000 |
| 11 | 1:2000 |

TABLE 1-continued

| | |
|---|---|
| 12 | 1:4000 |
| 14 | 1:500 |
| 16 | <1:500 |
| PBS** | <1:500 |
| A/Shangdong/9/93 | <1:1000 |

| Virus Strain | Gene | RT-PCR Primer | | SEQ ID NO |
|---|---|---|---|---|
| Type A (H3N2) Sydney/5/97 | Hemagglutinin (HA) | Forward | 5'-A <u>GGATCC</u>ATG AAGACTATCATTGCTTTGAG-3' | 13 |
| | | Reverse | 5'-A <u>GGTACC</u> TCAAATGCAAATGTTGCACCTAATG-3' | 14 |
| | Neuraminidase (NA) | Forward | 5'-GGGGACAAGTTTGTACAAAAAAGCAGGCTTAGAAG GAGATAGAACC ATG AATCCAAATCAAAAGATAATAAC-3' | 15 |
| | | Reverse | 5'-GGGGACCACTTTGTACAAGAAAGCTGGGTCCTATAT AGGCATGAGATTGATGTCCGC-3' | 16 |
| | Matrix (M1) | Forward | 5'-AAA <u>GAATTC</u> ATG AGTCTTCTAACCGAGGTCGAAACGTA-3' | 17 |
| | | Reverse | 5'-AAA <u>TTCGAA</u> TTACTCCAGCTCTATGCTGACAAAATGAC-3' | 18 |
| | M2 | Forward | 5'-A <u>GAATC</u> ATG AGTCTTCTAACCGAGGTCGAAACGCCT ATCAGAAACGAATGGGGGTGC-3' | 19 |
| | | Reverse | 5'-AAA <u>TTCGAA</u> TTACTCCAGCTCTATGCTGACAAAATGAC-3' | 20 |
| | Nucleoprotein (NP) | Forward | 5'-A <u>GAATTC</u> ATG GCGTCCCAAGGCACCAAACG-3' | 21 |
| | | Reverse | 5'-A <u>GCGGCCGC</u>TTAATTGTCGTACTCCTCTGCATTGTCTCCGAA GAAATAAG-3' | 22 |
| Type B Harbin | Hemagglutinin (HA) | Forward | 5'-A <u>GAATTC</u> ATG AAGGCAATAATTGTACTACTCATGG-3' | 23 |
| | | Reverse | 5'-A <u>GCGGCCGC</u>TTATAGACAGATGGAGCAAGAAACATTGTC TCTGGAGA-3' | 24 |
| | Neuraminidase (NA) | Forward | 5'-A <u>GAATT</u> CATG CTACCTTCAACTATACAAACG-3' | 25 |
| | | Reverse | 5'-A GCGGCCGCTTACAGAGCCATATCAACACCTGTGACAGTG-3' | 26 |

*Fraction from 20-60% sucrose gradient
**Negative Control
***Positive Control

Figure 7A:
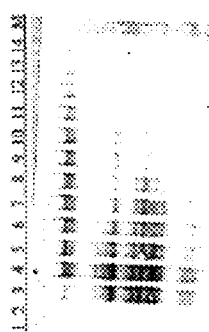
FIGS. 7A, 7B, and 7C depict the detection of influenza virus protein by gel filtration chromatography. The antibodies used in the Western blot analyses are as follows.
Figure 7B:
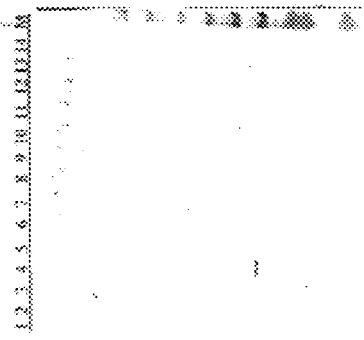
Figure 7C:
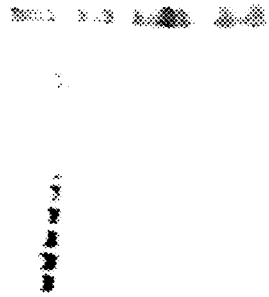

The presence of high-molecular VLPs was confirmed by gel filtration chromatography. An aliquot from sucrose density gradient fractions containing influenza viral proteins was loaded onto a Sepharose CL-4B column for fractionation based on mass. The column was calibrated with dextran blue 2000, dextran yellow, and vitamin B12 (Amersham Pharmacia) with apparent molecular weights of 2,000,000; 20,000; and 1,357 daltons, respectively, and the void volume of the column was determined. As expected, high-molecular influenza viral proteins migrated in the void volume of the column, which was characteristic of macromolecular proteins, such as virus particles. Fractions were analyzed by Western immunoblot analysis to detect influenza and baculovirus proteins. For example, M1 proteins were detected in the void volume fractions, which also contained baculovirus proteins (FIG. 7).

Figure 8:
FIG. 8 depicts the detection of avian influenza A/Hong Kong/1073/99 (H9N2) proteins including subviral particles, VLP, and VLP complexes, by electron microscopy.

The morphology of influenza VLPs and proteins in sucrose gradient fractions was elucidated by electron microscopy. For negative-staining electron microscopy, influenza proteins from two sucrose density gradient fractions were fixed with 2% glutaraldehyde in PBS, pH 7.2. Electron microscopic examination of negatively-stained samples revealed the presence of macromolecular protein complexes or VLPs in both fractions. These VLPs displayed different sizes including diameters of approximately 60 and 80 nm and morphologies (spheres). Larger complexes of both types of particles were also detected, as well as rod-shaped particles (FIG. 8). All observed macromolecular structures had spikes (peplomers) on their surfaces, which is characteristic of influenza viruses. Since the size and appearance of 80 nm particles was similar to particles of wild type influenza virus, these structures likely represented VLPs, which have distinct similarities to wild type influenza virions, including similar particle geometry, architecture, triangulation number, symmetry, and other characteristics. The smaller particles of approximately 60 nm may represent subviral particles that differ from VLPs both morphologically and structurally. Similar phenomenon of recombinant macromolecular proteins of different sizes and morphologies was also reported for other viruses. For example, recombinant core antigen (HBcAg) of hepatitis B virus forms particles of different sizes, which have different architecture and triangulation number T=4 and T=3, respectively (Crowther et al., 1994).

Figure 9:
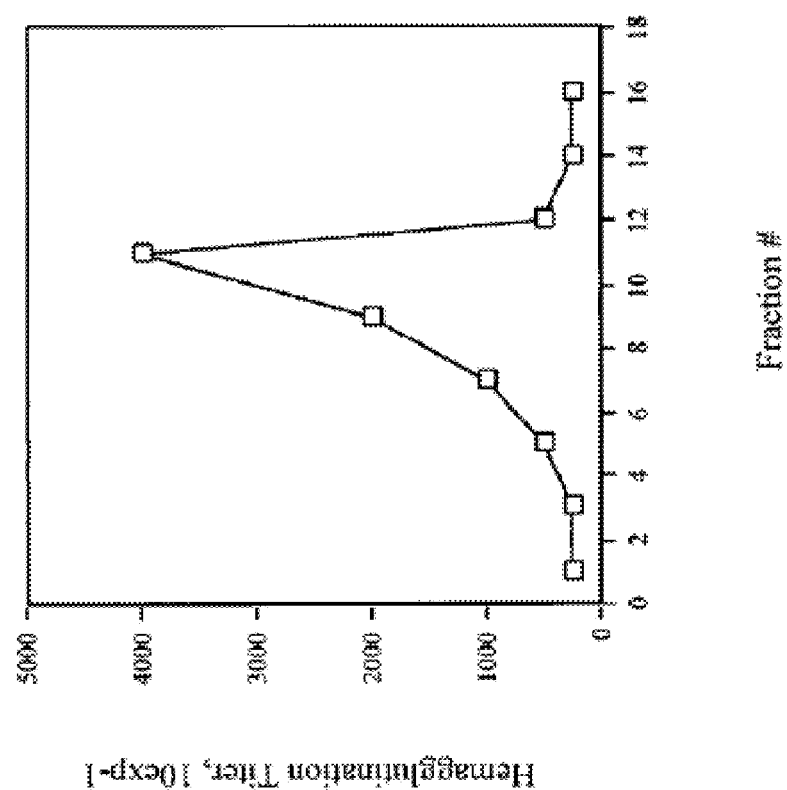
FIG. 9 depicts the hemagglutination activity of purified avian influenza A/Hong Kong/1073/99 (H9N2) VLPs.

To characterize the functional properties of the purified influenza A/Hong Kong/1073/99 (H9N2) VLPs, samples were tested in a hemagglutination assay (FIG. 9) and a neuraminidase enzyme assay (FIG. 10). For the hemagglutination assay, 2-fold dilutions of purified influenza VLPs were mixed with 0.6% guinea pig red blood cells and incubated at 4° C. for 1 hr or 16 hr. The extent of hemagglutination was inspected visually and the highest dilution of recombinant influenza proteins capable of agglutinating red blood cells was determined and recorded (FIG. 9). Again, many fractions from the sucrose density gradient exhibited hemagglutination activity, suggesting that multiple macromolecular and monomeric forms of influenza proteins were present. The highest titer detected was 1:4000. In a control experiment, wild-type influenza A/Shangdong virus demonstrated a titer of 1:2000. The hemagglutination assay revealed that the recombinant VLPs consisting of influenza A/Hong Kong/1073/99 (H9N2) virus HA, NA, and M1 proteins were functionally active. This suggested that the assembly, conformation, and folding of the HA subunit proteins within the VLPs were similar or identical to that of the wild type influenza virus.

Additionally, a neuraminidase enzyme assay was performed on samples of purified H9N2 VLPs. The amount of neuraminidase activity in sucrose density gradient fractions was determined using fetuin as a substrate. In the neuraminidase assay, the neuraminidase cleaved sialic acid from substrate molecules to release sialic acid for measurement. Arsenite reagent was added to stop enzyme activity. The amount of sialic acid liberated was determined chemically with thiobarbituric acid that produces a pink color that was proportional to the amount of free sialic acid. The amount of color (chromophor) was measured spectrophotometrically at wavelength 549 nm. Using this method, neuraminidase activity was demonstrated in sucrose gradient fractions containing influenza VLPs (FIG. 10). As expected, the activity was observed in several fractions, with two peak fractions. As a positive control, wild type influenza virus was used. The wild type influenza virus exhibited neuraminidase enzyme activity comparable to that of purified influenza VLPs. These findings corroborated the HA results with regard to protein conformation and suggested that purified VLPs of influenza A/Hong Kong/1073/99 (H9N2) virus were functionally similar to wild type influenza virus.

The results from the above analyses and assays indicated that expression of influenza A/Hong Kong/1073/99 (H9N2) HA, NA, and M1 proteins was sufficient for the self-assembly and transport of functional VLPs from baculovirus-infected insect cells. Since these influenza VLPs represented self-assembled influenza structural proteins and demonstrated functional and biochemical properties similar to those of wild type influenza virus, these influenza VLPs conserved important structural conformations including surface epitopes necessary for effective influenza vaccines.

Example 2

RT-PCR Cloning of Avian Influenza A/Hong Kong/1073/99 Viral Genes

It is an object of the present invention to provide synthetic nucleic acid sequences capable of directing production of recombinant influenza virus proteins. Such synthetic nucleic acid sequences were obtained by reverse transcription and polymerase chain reaction (PCR) methods using influenza virus natural genomic RNA isolated from the virus. For the purpose of this application, nucleic acid sequence refers to RNA, DNA, cDNA or any synthetic variant thereof which encodes the protein.

Avian influenza A/Hong Kong/1073/99 (H9N2) virus was provided by Dr. K. Subbarao (Centers for Disease Control, Atlanta, Ga., USA). Viral genomic RNA was isolated by the acid phenol RNA extraction method under Biosafety Level 3 (BSL3) containment conditions at CDC using Trizol LS reagent (Invitrogen, Carlsbad, Calif. USA). cDNA molecules of the viral RNAs were obtained by reverse transcription using MuLV reverse transcriptase (InVitrogen) and PCR using oligonucleotide primers specific for HA, NA, and M1 proteins and Taq I DNA polymerase (InVitrogen) (Table 1). The PCR fragments were cloned into the bacterial subcloning vector, pCR2.1TOPO (InVitrogen), between Eco RI sites that resulted in three recombinant plasmids, containing the HA, NA, and M1 cDNA clones.

Example 3

RT-PCR Cloning of Human Influenza A/Sydney/5/94 (H3N2) Viral Genes

Influenza A/Sydney/5/97 (H3N2) Virus was obtained from Dr. M. Massare (Novavax, Inc., Rockville, Md.). Viral genomic RNA was isolated by the RNA acid phenol extraction method under BSL2 containment conditions at Novavax, Inc. using Trizol LS reagent (Invitrogen). cDNA molecules of the viral RNAs were obtained by reverse transcription and PCR using oligonucleotide primers specific for HA, NA, M1, M2, and NP proteins (Table 1). The PCR fragments were cloned into the bacterial subcloning vector, pCR2.1TOPO, between Eco RI sites that resulted in five recombinant plasmids, containing the HA, NA, M1, M2, and NP cDNA clones.

Example 4

Cloning of Avian Influenza A/Hong Kong/1073/99 Viral cDNAs into Baculovirus Transfer Vectors From the pCR2.1TOPO-based plasmids, the HA, NA, or M1 genes were subcloned into pFastBac1 baculovirus transfer vector (InVitrogen) within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-HA was inserted into BamHI-KpnI digested pFastBac1 plasmid DNA. For the NA gene, an EcoRI DNA fragment from pCR2.1TOPO-NA was inserted into EcoRI digested pFastBac1 plasmid DNA. For the M1 gene, an Eco RI DNA fragment from pCR2.1TOPO-M1 was inserted into Eco RI digested pFastBac1 plasmid DNA. Competent *E. coli* DH5a bacteria (InVitrogen) were transformed with these DNA ligation reactions, transformed colonies resulted, and bacterial clones isolated. The resulting pFastBac1-based plasmids, pFastBac1-HA, pFastBac1-NA, and pFastBac1-M1 were characterized by restriction enzyme mapping on agarose gels (FIG. 4A). The nucleotide sequences as shown on FIGS. 1-3 of the cloned genes were determined by automated DNA sequencing. DNA sequence analysis showed that the cloned influenza HA, NA, and M1 genes were identical to the nucleotide sequences for these genes as published previously [NA, HA, and M1 genes of influenza A/Hong Kong/1073/99 (H9N2) (GenBank accession numbers AJ404629, AJ404626, and AJ278646, respectively)].

Example 5

Cloning of Human Influenza A/Sydney/5/97 Viral cDNAs into Baculovirus Transfer Vectors From the pCR2.1TOPO-based plasmids, the HA, NA, M1, M2, and NP genes were subcloned into pFastBac1 baculovirus transfer vector within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-hHA3 was inserted into BamHI-KpnI digested pFastBac1 plasmid DNA. For the NA gene, an Eco RI DNA fragment from pCR2.1TOPO-hNA was inserted into EcoRI digested pFastBac1 plasmid DNA. For the M1 gene, an Eco RI DNA fragment from pCR2.1TOPO-hM1 was inserted into EcoRI digested pFastBac1 plasmid DNA. For the M2 gene, an EcoRI DNA fragment from pCR2.1TOPO-hM2 was inserted into EcoRI digested pFastBac1 plasmid DNA. For the NP gene, an EcoRI DNA fragment from pCR2.1TOPO-hNP was inserted into EcoRI digested pFastBac1 plasmid DNA. Competent *E. coli* DH5a bacteria were transformed with these DNA ligation reactions, transformed colonies resulted, and bacterial clones isolated. The resulting pFastBac 1-based plasmids, pFastBac1-hHA3, pFastBac1-hNA2, pFastBac1-hM1, pFAST- BAC1-hM2, and pFASTBAC1-hNP were characterized by restriction enzyme mapping on agarose gels. The nucleotide sequences of the cloned genes were determined by automated DNA sequencing. DNA sequence analysis showed that the cloned influenza HA, NA, M1, M2, and NP genes were identical to the nucleotide sequences for these genes as published previously.

Example 6

Construction of Multigenic Baculovirus Transfer Vectors Encoding Multiple Avian Influenza A/Hong Kong/1073/99 Viral Genes In order to construct pFastBac1-based bacmid transfer vectors expressing multiple influenza A/Hong Kong/1073/99 (H9N2) virus genes, initially a Sna BI-Hpa I DNA fragment from pFastBac1-M1 plasmid containing the M1 gene was cloned into Hpa I site of pFastBac1-HA. This resulted in pFastBac1-HAM plasmid encoding both HA and M1 genes within independent expression cassettes and expressed under the control of separate polyhedrin promoters.

Finally, a SnaBI-AvrII DNA fragment from pFastBac1-HAM containing the HA and M1 expression cassettes, was transferred into Hpa I-Avr II digested pFastBac1-NA plasmid DNA. This resulted in the plasmid pFastBac1-NAHAM encoding three independent expression cassettes for expression of influenza HA, NA, and M1 genes and expressed under the control of separate polyhedrin promoters (FIG. 4B).

In another example, the H3 gene from pFASTBAC1-hHA3 (see Example 5) was cloned into pFASTBAC1-NAHAM as a fourth influenza viral gene for the expression and production of heterotypic influenza VLPs.

Example 7

Generation of Multigenic Recombinant Baculovirus Encoding NA, HA, and M1 Genes of Avian Influenza A/Hong Kong/1073/99 Virus in Insect Cells The resulting multigenic bacmid transfer vector pFastBac1-NAHAM was used to generate a multigenic recombinant baculovirus encoding avian influenza A/Hong Kong/1073/99 (H9N2) HA, NA, and M1 genes for expression in insect cells. Recombinant bacmid DNAs were produced by site-specific recombination at polyhedrin and Tn7 att DNA sequences between pFastBac1-NAHAM DNA and the AcMNPC baculovirus genome harbored in competent *E. coli* DH10BAC cells (InVitrogen) (FIG. 4B). Recombinant bacmid DNA was isolated by the mini-prep plasmid DNA method and transfected into Sf-9s cells using the cationic lipid CELLFECTIN (InVitrogen). Following transfection, recombinant baculoviruses were isolated, plaque purified, and amplified in Sf-9S insect cells. Virus stocks were prepared in Sf-9S insect cells and characterized for expression of avian influenza viral HA, NA, and M1 gene products. The resulting recombinant baculovirus was designated bNAHAM-H9N2.

Example 8

Expression of Recombinant Avian Influenza A/Hong Kong/1073/99 Proteins in Insect Cells Sf-9S insect cells maintained as suspension cultures in shaker flasks at 28° C. in serum-free medium (HyQ SFM, HyClone, Ogden, Utah) were infected at a cell density of $2\times10^6$ cells/ml with the recombinant baculovirus, bNAHAM-H9N2, at a multiplicity of infection (MOI) of 3 pfu/cell. The virus infection proceeded for 72 hrs. to allow expression of influenza proteins. Expression of avian influenza A/Hong Kong/1073/99 (H9N2) HA and M1 proteins in infected insect cells was confirmed by SDS-PAGE and Western immunoblot analyses. SDS-PAGE analysis was performed on 4-12% linear gradient NuPAGE gels (Invitrogen) under reduced and denaturing conditions. Primary antibodies in Western immunoblot analysis were polyclonal rabbit antiserum raised against avian influenza A/Hong Kong/1073/99 (H9N2) obtained from CDC and monoclonal murine antiserum to influenza M1 protein (Serotec, UK). Secondary antibodies for Western immunoblot analysis were alkaline phosphatase conjugated goat IgG antisera raised against rabbit or mouse IgG (H+L) (Kirkegaard and Perry Laboratories, Gaithersburg, Md., USA). Results of these analyses (FIG. 5) indicated that the HA and M1 proteins were expressed in the baculovirus-infected insect cells.

Example 9

Purification of Recombinant Avian Influenza H9N2 Virus-Like Particles and Macromolecular Protein Complexes Culture supernatants (200 ml) from Sf-9S insect cells infected with the recombinant baculovirus bNAHAM-H9N2 that expressed avian influenza A/Hong Kong/1073/99 (H9N2) HA, NA, and M1 gene products were harvested by low speed centrifugation. Culture supernatants were clarified by centrifugation in a Sorval RC-5B superspeed centrifuge for 1 hr at 10,000×g and 4° C. using a GS-3 rotor. Virus and VLPs were isolated from clarified culture supernatants by centrifugation in a Sorval OTD-65 ultracentrifuge for 3 hr at 27,000 rpm and 4° C. using a Sorval TH-641 swinging bucket rotor. The virus pellet was resuspended in 1 ml of PBS (pH 7.2), loaded onto a 20-60% (w/v) discontinuous sucrose step gradient, and resolved by centrifugation in a Sorval OTD-65 ultracentrifuge for 16 hr at 27,000 rpm and 4° C. using a Sorval TH-641 rotor. Fractions (0.5 ml) were collected from the top of the sucrose gradient.

Influenza proteins in the sucrose gradient fractions were analyzed by SDS-PAGE and Western immunoblot analyses as described above in Example 6. The HA and M1 proteins were found in the same sucrose gradient fractions (FIG. 6) as shown by Western blot analysis and suggested that the HA and M1 proteins were associated as macromolecular protein complexes. Also the HA and M1 proteins were found in fractions throughout the sucrose gradient suggesting that these recombinant viral proteins were associated with macromolecular protein complexes of different densities and compositions.

Example 10

Analysis of Recombinant Avian Influenza H9N2 VLPs and Proteins by Gel Filtration Chromatography Protein macromolecules such as VLPs and monomeric proteins migrate differently on gel filtration or size exclusion chromatographic columns based on their mass size and shape. To determine whether the recombinant influenza proteins from sucrose gradient fractions were monomeric proteins or macromolecular protein complexes such as VLPs, a chromatography column (7 mm×140 mm) with a resin bed volume of 14 ml of Sepharose CL-4B (Amersham) was prepared. The size exclusion column was equilibrated with PBS and calibrated with Dextran Blue 2000, Dextran Yellow, and Vitamin B12 (Amersham Pharmacia) with apparent molecular weights of 2,000,000; 20,000; and 1,357, respectively, to ascertain the column void volume. Dextran Blue 2000 eluted from the column in the void volume (6 ml fraction) also. As expected, the recombinant influenza protein complexes eluted from the column in the void volume (6 ml fraction). This result was characteristic of a high molecular weight macromolecular protein complex such as VLPs. Viral proteins in the column fractions were detected by Western immunoblot analysis as described above in Example 6. The M1 proteins were detected in the void volume fractions (FIG. 7). As expected baculovirus proteins were also in the void volume.

Example 11

Electron Microscopy of Recombinant Influenza VLPs

To determine whether the macromolecular protein complexes isolated on sucrose gradients and containing recombinant avian influenza proteins had morphologies similar to influenza virions, electron microscopic examination of negatively stained samples was performed. Recombinant avian influenza A/Hong Kong/1073/99 (H9N2) protein complexes were concentrated and purified from culture supernatants by ultracentrifugation on discontinuous sucrose gradients as described in Example 7. Aliquots of the sucrose gradient fractions were treated with a 2% glutaraldehyde in PBS, pH7.2, absorbed onto fresh discharged plastic/carbon-coated grids, and washed with distilled water. The samples were stained with 2% sodium phosphotungstate, pH 6.5, and observed using a transmission electron microscope (Philips). Electron micrographs of negatively-stained samples of recombinant avian influenza H9N2 protein complexes from two sucrose gradient fractions showed spherical and rod-shaped particles (FIG. 8) from two sucrose gradient fractions. The particles had different sizes (60 and 80 nm) and morphologies. Larger complexes of both types of particles were also detected, as well as rod-shaped particles (FIG. 8). All observed protein complex structures exhibited spike like surface projections resembling influenza virus HA and NA peplomers. Since the size and appearance of the 80 nm particles was similar to that of wild type influenza virus particles, these structures likely represented enveloped influenza VLPs. The smaller particles of approximately 60 nm probably represented subviral particles that differed from the above VLPs both morphologically and structurally.

Example 12

Analysis of Functional Characteristics of Influenza Proteins by Hemagglutination Assay To determine whether the purified influenza VLPs and proteins possessed functional activities, such as hemagglutination and neuraminidase activity, which were characteristic for influenza virus, the purified influenza VLPs and proteins were tested in hemagglutination and neuraminidase assays.

For the hemagglutination assay, a series of 2-fold dilutions of sucrose gradient fractions containing influenza VLPs or positive control wild type influenza virus type A were prepared. Then they were mixed with 0.6% guinea pig red blood cells in PBS (pH 7.2) and incubated at 4° C. for 1 to 16 hr. As a negative control, PBS was used. The extent of hemagglutination was determined visually, and the highest dilution of fraction capable of agglutinating guinea pig red blood cells was determined (FIG. 9). The highest hemagglutination titer observed for the purified influenza VLPs and proteins was 1:4000, which was higher than the titer shown by the wild type influenza control, which was 1:2000.

Example 13

Analysis of Functional Characteristics of Influenza Proteins by Neuraminidase Assay The amount of neuraminidase activity in influenza VLP-containing sucrose gradient fractions was determined by the neuraminidase assay. In this assay the NA (an enzyme) acted on the substrate (fetuin) and released sialic acid. Arsenite reagent was added to stop enzyme activity. The amount of sialic acid liberated was determined chemically with the thiobarbituric acid that produced a pink color in proportion to free sialic acid. The amount of color (chromophor) was measured in a spectrophotometer at wavelength 594 nm. The data, as depicted in FIG. 8, showed that a significant amount of sialic acid was produced by VLP-containing fractions of the sucrose gradients and that these fractions corresponded to those fractions exhibiting hemagglutination activity.

Example 14

Immunization of BALB/c Mice with Functional Homotypic Recombinant Influenza H9N2 VLPs The immunogenicity of the recombinant influenza VLPs was ascertained by immunization of mice followed by Western blot analysis of immune sera. Recombinant VLPs (1 μg/injection) comprised of viral HA, NA, and M1 proteins from avian influenza virus type A/Honk Kong/1073/99 and purified on sucrose gradients were inoculated subcutaneously into the deltoid region of ten (10) female BALB/c mice at day 0 and day 28 (FIG. 11). PBS (pH 7.2) was administered similarly as a negative control into five (5) mice. The mice were bled from the supraorbital cavity at day-1 (pre-bleed), day 27 (primary bleed), and day 54 (secondary bleed). Sera were collected from blood samples following overnight clotting and centrifugation.

For Western blot analysis, 200 ng of inactivated avian influenza virus type A H9N2 or cold-adapted avian influenza virus type A H9N2, as well as See Blue Plus 2 pre-stained protein standards (InVitrogen), was denatured (95° C., 5 minutes) and subjected to electrophoresis under reduced conditions (10 mM β-mercaptoethanol) on 4-12% polyacrylamide gradient NuPAGE gels (InVitrogen) in MES buffer at 172 volts until the bromophenol blue tracking dye disappeared. For protein gels, the electrophoreses proteins were visualized by staining with Colloidal Coomassie Blue reagent (InVitrogen). Proteins were transferred from the gel to nitrocellulose membranes in methanol by the standard Western blot procedure. Sera from VLP-immunized mice and rabbits immunized with inactivated avian influenza virus H9N2 (positive control sera) were diluted 1:25 and 1:100, respectively, in PBS solution (pH 7.2) and used as primary antibody. Protein bound membranes, which were blocked with 5% casein, were reacted with primary antisera for 60 minutes at room temperature with constant shaking. Following washing of primary antibody membranes with phosphate buffered saline solution containing Tween 20, secondary antisera [goat anti-murine IgG—alkaline phosphatase conjugate (1:10,000) or goat anti-rabbit IgG—alkaline phosphatase conjugate (1:10,000)] were reacted 60 minutes with the membrane. Following washing of secondary antibody membranes with phosphate buffered saline solution containing Tween 20, antibody-binding proteins on the membranes were visualized by development with the chromogenic substrate such as NBT/BCIP (InVitrogen).

The results of Western blot analysis (FIG. 12) were that proteins with molecular weights similar to viral HA and M1 proteins (75 and 30 kd, respectively) bound to positive control sera (FIG. 12B) and sera from mice immunized with the recombinant influenza H9N2 VLPs (FIG. 12A). These results indicated that the recombinant influenza H9N2 VLPs alone were immunogenic in mice by this route of administration.

Example 15

Kong/1073/99 (H9N2) VLP Immunogenicity And Challenge Study In BALB/c Mice

BALB/C mice were immunized with H9N2 VLPs (1 µg HA or 10 µg HA/dose), with or without 100 µg Novasome adjuvant, on day 0 and day 21 and challenged with homologous infectious virus IN on day 57. Mice were bled on days 0, 27 and 57 with the serum assayed for anti-HA antibodies by the hemagglutination inhibition assay (HI) using turkey RBCs, and influenza by ELISA. Results of this study are shown in FIG. 13 through FIG. 16.

Figure 13:
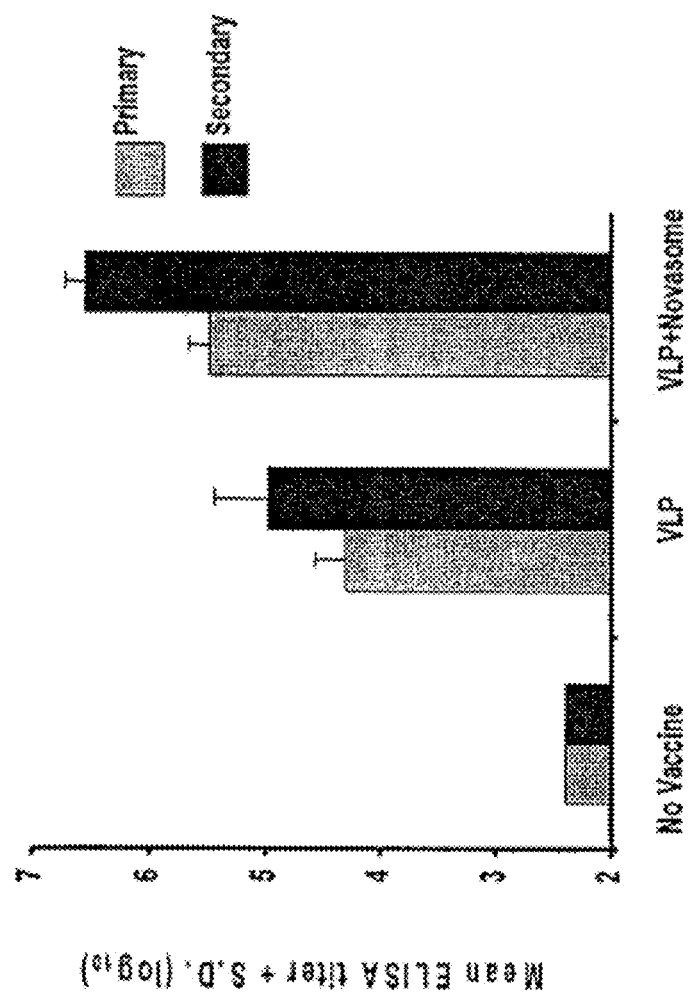
FIG. 13 depicts the geometric mean antibody responses in BALB/c mice after a primary and secondary immunization.

High titers of H9N2 antibodies were induced after a single immunization (primary) with H9N2 VLP vaccine without or with Novasomes and a dose of 10 µg VLPs containing 1 µg HA (FIG. 13). Specific antibody titers were increased about half to one log following a booster immunization.

Figure 14:
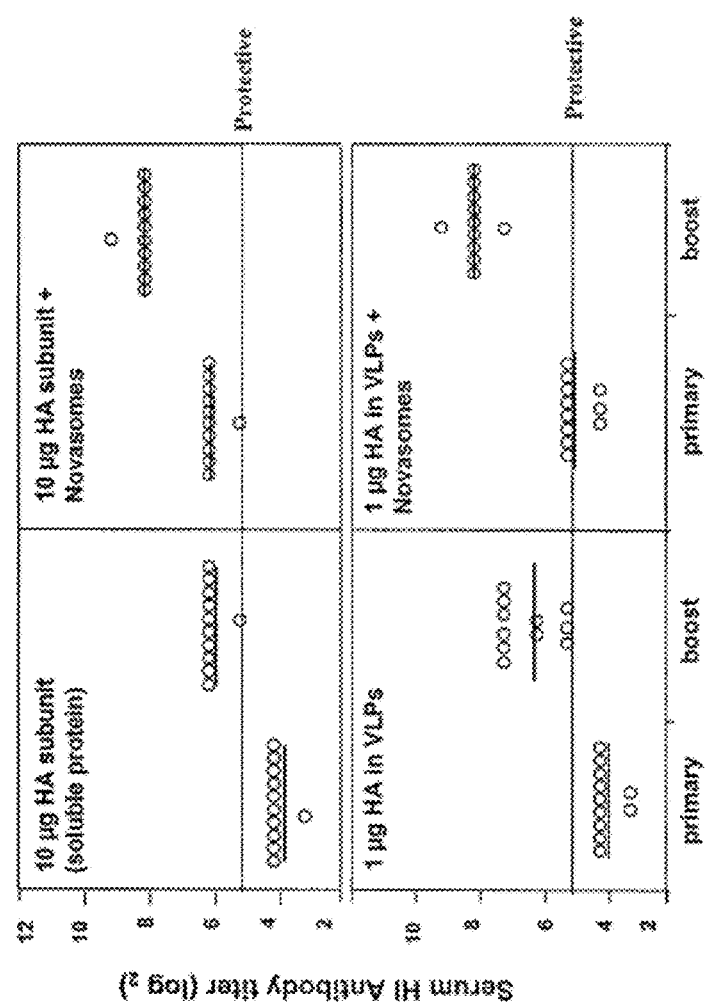
FIG. 14 depicts serum hemagglutinin inhibition (HI) responses in BALB/c mice.

After immunization and a boost with 1 µg of HA in the form of H9N2 VLPs the serum HI levels were at or above the level generally considered protective (log 2=5) in all animals (FIG. 14, lower left panel). H9N2 VLPs formulated with Novasome adjuvant increased HI responses about 2 fold following primary immunization and about 4 fold after the booster (FIG. 14, lower right panel). Purified subunit H9N2 hemagglutinin also induced protective levels of HI antibodies after boosting and Novasomes again increased HI antibody responses by about 2 fold after the primary and 4 fold after the booster immunizations (FIG. 14, upper panels). The level of HI antibody induced with 10 µg of HA given as a subunit vaccine was equivalent to 1 µg of HA presented in the form of a VLP.

Figure 15:
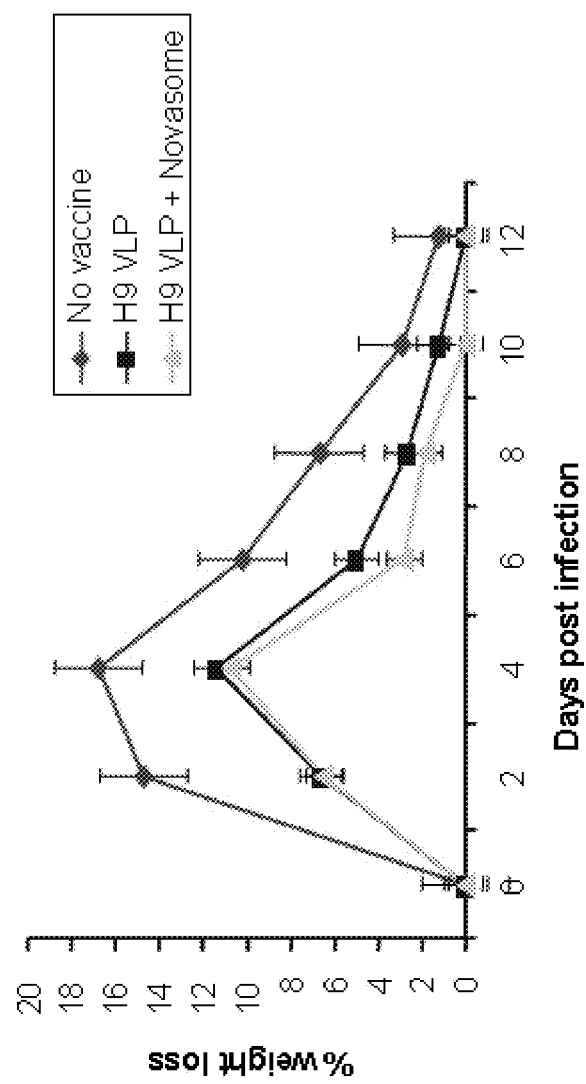
FIG. 15 depicts weight loss (%) in BALB/c mice challenged with H9N2 influenza.

In addition, weight loss was significantly less in the mice immunized with H9N2 VLPs or with VLPs plus adjuvant compared to unvaccinated control animals (FIG. 15). There was no statistical difference in weight loss in the groups immunized with H9N2 VLPs and H9N2 VLPs plus Novasome adjuvant.

Figure 16:
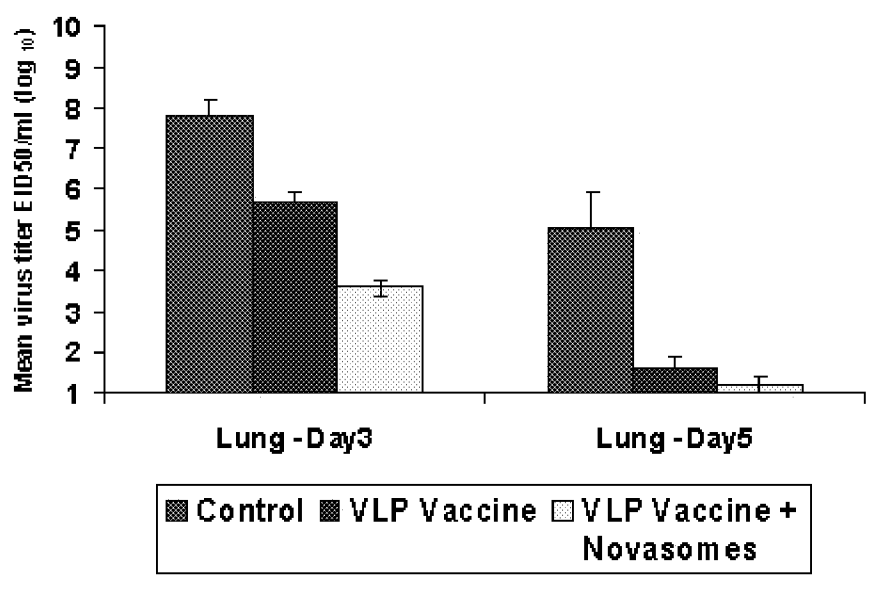

Likewise, lung virus titers at 3 and 5 days post challenge with H9N2 virus were significantly reduced in mice immunized with H9N2 VLPs (FIG. 16). At day 3 when the influenza virus titers peak in the lung tissues, mice immunized with H9N2 VLPs plus Novasomes® had a significantly greater reduction in virus titer compared to mice immunized with VLPs alone and the unvaccinated control mice.

Example 16

Figure 17A:
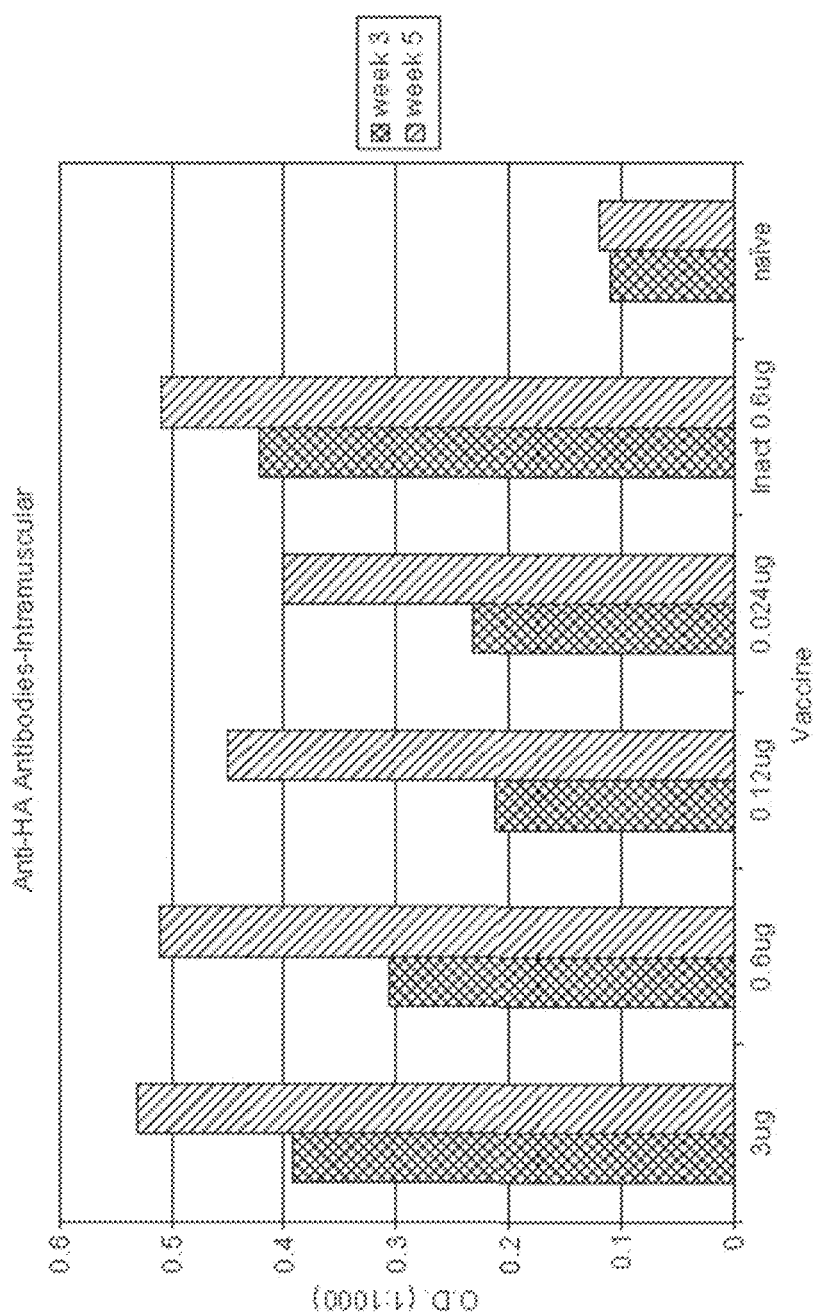
Figure 17B:
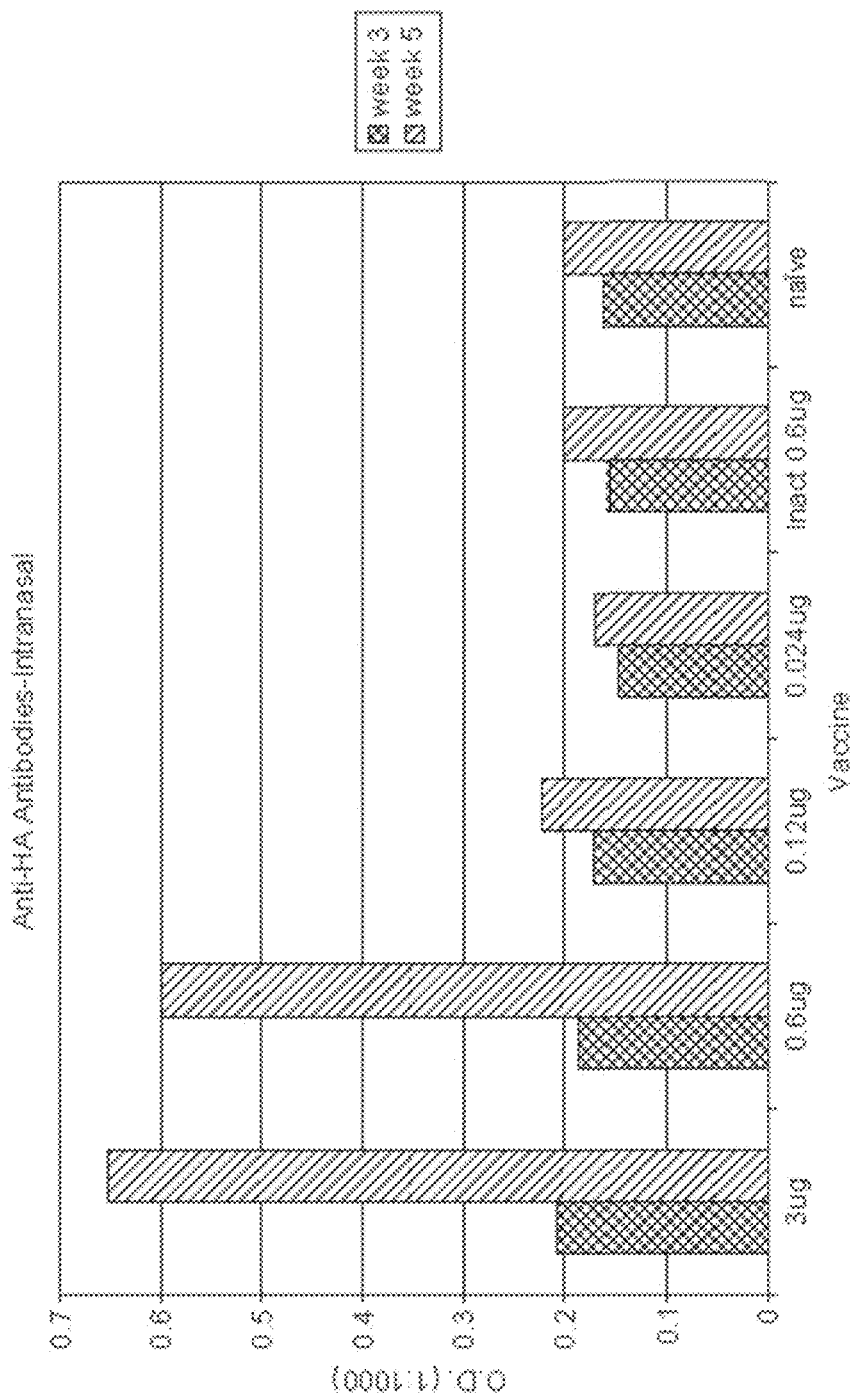

A/Fujian/411/2002 (H3N2) VLP Immunogenicity and Cross Reactivity Between Several Influenza Strains BALB/c mice were immunized with A/Fujian/411/2002 VLPs (3.0, 0.6, 0.12 and 0.24 µg HA/dose), twice IM and IN. Mice were bled on days 0 and 35. The serum was then assayed for anti-HA antibodies by the hemagglutination inhibition assay (HI) using turkey RBCs, and for anti-influenza antibodies by ELISA. Results of this study are shown on FIGS. 17A, 17B and 17C. These results indicate that an immune response was mounted both IM and IN against HA and NA.

Example 17

Determination of the IgG Isotypes in Mouse after Inoculation with H3N2 VLPs

Mice were inoculated with VLPs intramuscularly and intranasal. At week 5 sera was collected and assayed to distinguish between IgG isotypes.

Figure 18A:
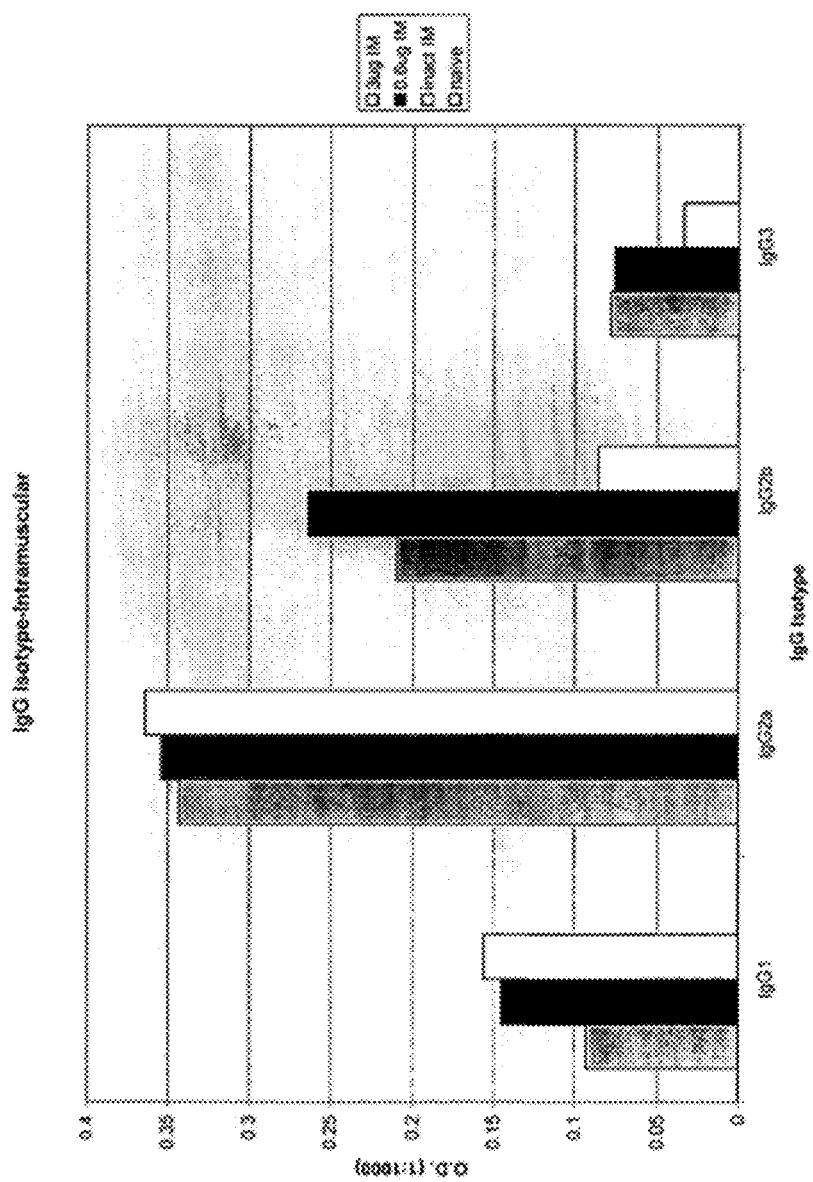

Sera was tested on plates coated with purified HA (Protein Sciences) A/Wyoming/3/2003 using an ELISA assay. Serial five-fold dilutions of sera was added to the wells and the plates were incubated. Next, the biotinylated goat anti-mouse Ig, or anti-mouse IgG1, anti-mouse IgG2a, anti-mouse IgG2b and anti-mouse IgG3. Then, streptavidine-peroxidase was added to the wells. Bound conjugates were detected. Results are illustrated on FIGS. 18A and B. These results illustrate that IgG2a are the most abundant isotype in an immune response against VLPs in mouse.

Example 18

A/Hong Kong/1073/99 (H9N2) VLP Dose-Ranging Study in SD Rats

Figure 19:
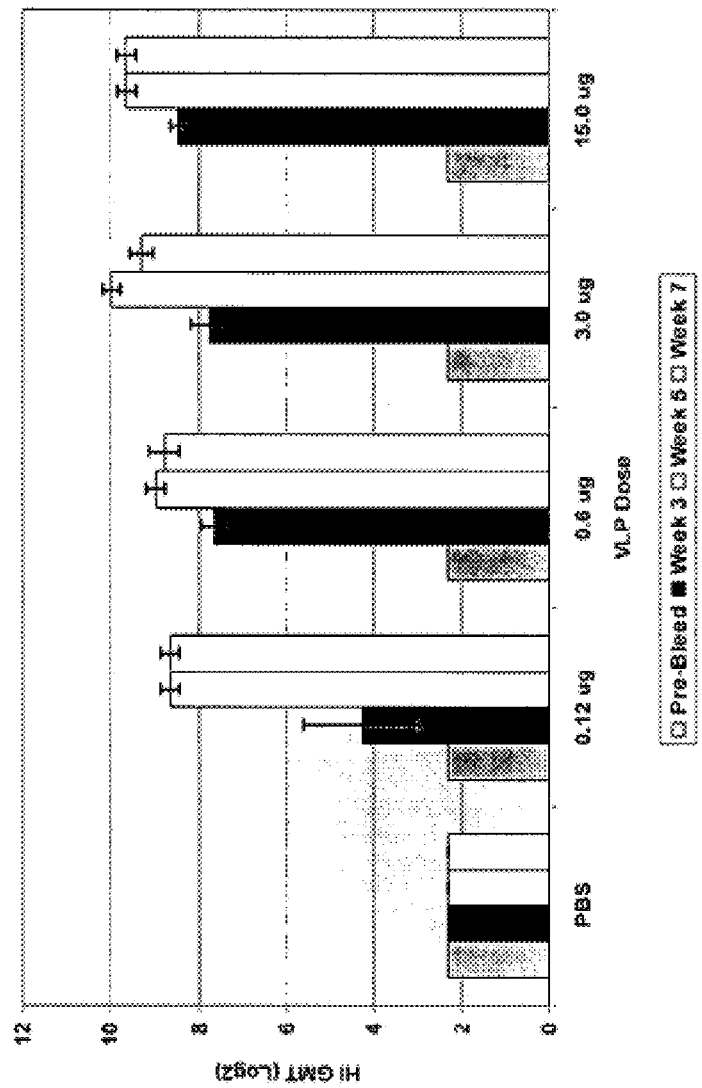
FIG. 19 hemagglutinin inhibition (HI) antibody responses in SD Rats immunized with H9N2 VLP vaccine.

SD rats (n=6 per dose) were immunized on day 0 and day 21 with purified A/Hong Kong/1073/99 (H9N2) VLPs diluted with PBS at neutral pH to 0.12, 0.6, 3.0, and 15.0 µg HA or with PBS alone. Blood samples were taken from the animals on day 0, day 21, day 35 and day 49 and the serum assayed for hemagglutination inhibition assay (HI) to detect functional antibodies able to inhibit the binding function of the HA. The dosage was based on HA content as measured using SDS-PAGE and scanning densitometry of purified H9N2 VLPs. Hemagglutinin inhibition assay titer results are depicted in FIG. 19. A single 0.6 µg HA dose of H9N2 VLPs or two doses of 0.12 µg HA produced protective levels of HI antibodies in rats. These data indicate that a lower amount of HA can induce a protective response when said HA is part of a VLP.

Example 19

Kong/1073/99 (H9N2) VLP Immunogenicity

Figure 20A:
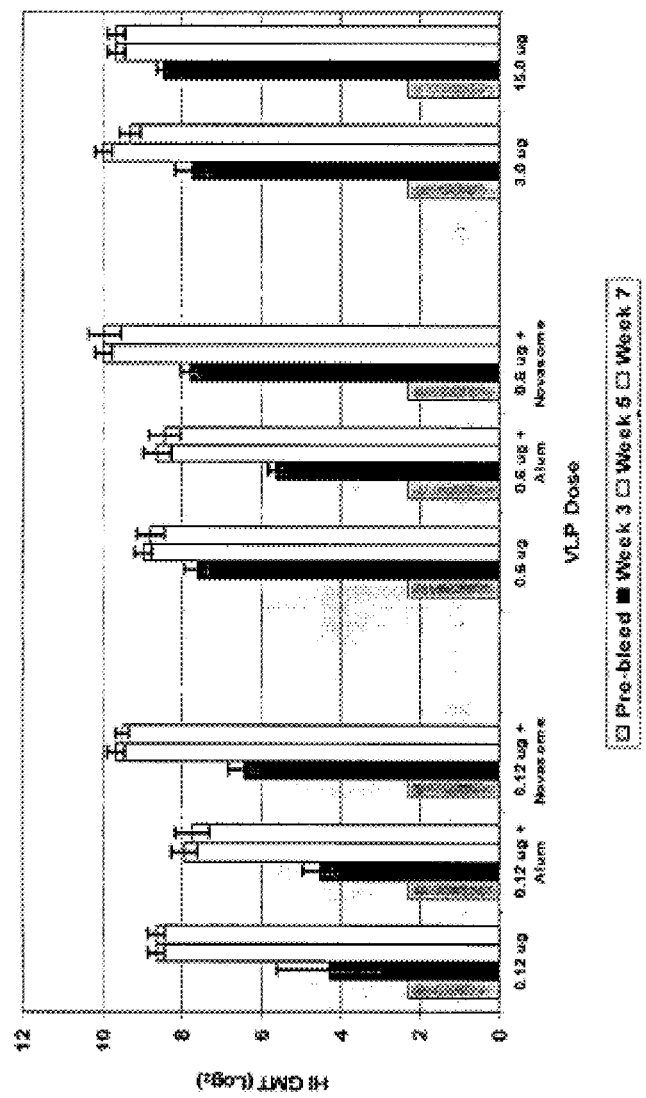
FIGS. 20A and 20B depict hemagglutinin inhibition (HI) antibody responses to different doses of H9N2 VLPs with and without adjuvant in BALB/c mice.

BALB/C mice were immunized with H9N2 VLPs (0.12, 0.6 µg HA/dose), with or without 100 µg Novasome and Alum adjuvant, on day 0 and day 21 and challenged with homologous infectious virus IN on day 57. Mice were also immunized with 3.0 and 15.0 µg HA/dose (no adjuvant). Mice were bled on days 0, 21, 35 and 49 with the serum assayed for anti-HA antibodies by the hemagglutination inhibition assay (HI) using turkey RBCs, and influenza by ELISA. Results of this study are shown in FIGS. 20 A and B.

The results indicate that a more robust overall immune response was observed when the VLPs were administered with an adjuvant. However, a protective response was elicited with 0.12 µg HA/dose at week 3 when compared to the VLPs formulation with Alum and VLPs with no adjuvant. Also in week 7, the VLPs comprising Novasomes had about 2 log increase in HI titer as compared to the VLP with Alum. The robustness of the response was similar to VLPs administered at 3.0 and 15.0 µg HA/dose without an adjuvant. These results indicate that Novasomes elicit a more robust response as compared to Alum. In addition, a protective immune response can be achieved with 25× less VLPs when said VLPs are administered in a formulation comprising Novasomes.

Also, in the 0.6 µg HA/dose data, the Novasome formulation had an about 1.5 log greater response than compared to Alum. The immune responses were similar in magnitude to VLPs administered in 3.0 and 15.0 µg HA/dose without adjuvant. These results indicate that with an adjuvant, approximately 5× less VLPs are needed to be administered to achieve a protective response.

Figure 20B:
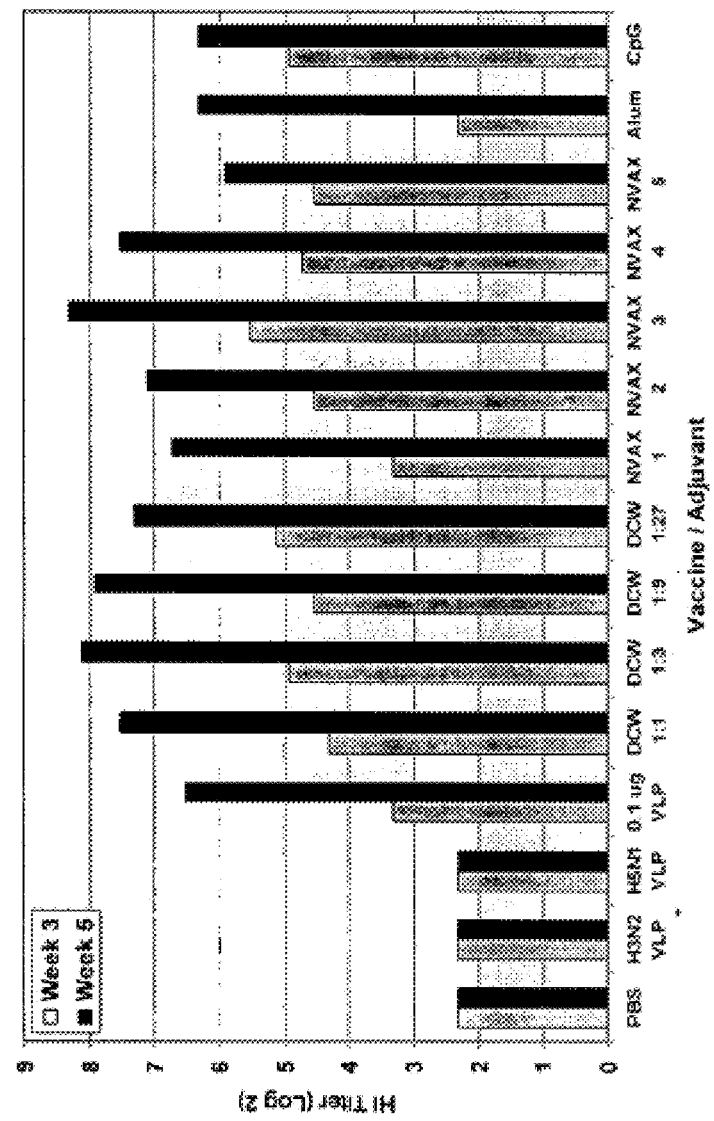
Figure 21:
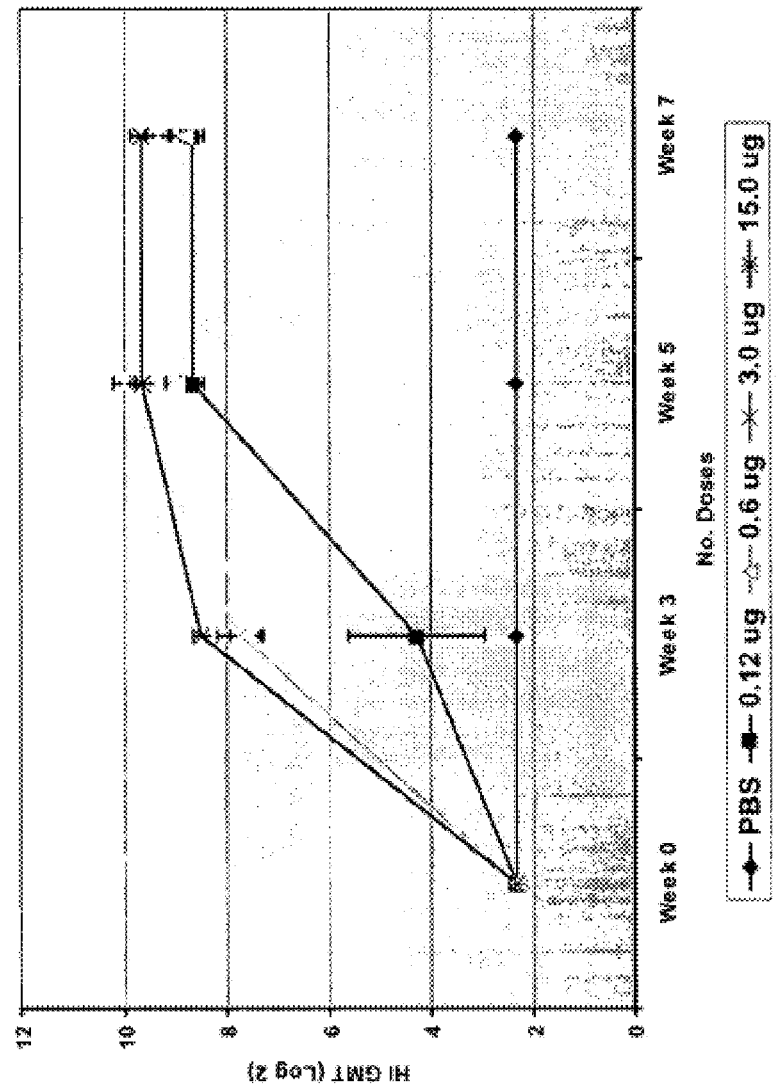
FIG. 21 depicts serum hemagglutinin inhibition (HI) responses in BALB/c mice between different doses of VLPs.

Also, FIG. 20B depicts the HI titer of H9N2 VLPs using different formulations of Novasomes. The following are the formulas used in the experiment:
Group 1: H9N2 VLP (0.1 µg) (n=5)
Group 2: H9N2 VLP (0.1 µg) w/DCW neat) (n=5)
Group 3: H9N2 VLP (0.1 μg) w/DCW 1:3) (n=5)
Group 4: H9N2 VLP (0.1 μg) w/DCW 1:9) (n=5)
Group 5: H9N2 VLP (0.1 μg) w/DCW 1:27) (n=5)
Group 6: H9N2 VLP (0.1 μg) w/NVAX 1) (n=5)
Group 7: H9N2 VLP (0.1 μg) w/NVAX 2) (n=5)
Group 8: H9N2 VLP (0.1 μg) w/NVAX 3) (n=5)
Group 9: H9N2 VLP (0.1 μg) w/NVAX 4) (n=5)
Group 10: H9N2 VLP (0.1 μg) w/NVAX 5) (n=5)
Group 11: H9N2 VLP (0.1 μg) w/Alum-OH) (n=5)
Group 12: H9N2 VLP (0.1 μg) w/CpG) (n=5)
Group 13: PBS (0.6 μg) (n=5)
Group 14: H3 VLPs (0.6 μg) (n=5)
Group 15: H5 VLPs (0.6 μg) (n=8)

H9: (Lot#11005)

DCW: Novasomes (Lot#121505-2, Polyoxyethylene-2-cetyl ether, Cholesterol, Superfined soybean oil, and Cetylpridinium chloride)

NVAX 1: B35P83, MF-59 replica (Squalene, Polysorbate, and Span)

NVAX 2: B35P87 (Soybean Oil, Brij, Cholesterol, Pluronic F-68)

NVAX 3: B35P88 (Soybean Oil, Brij, Cholesterol, Pluronic F-68, and Polyethyleneimine)

NVAX 4: B31P60 (Squalene, Brij, Cholesterol, Oleic acid)

NVAX 5: B31P63 (Soybean oil, Glyceryl monostearate, Cholesterol, Polysorbate)

CpG: (Lot#1026004)

H5: (Lot#22406)

FIG. 21 depicts and H9N2 VLP dose response curve. This data indicates that a dose of VLPs at 0.6 μg HA/dose is the minimum to elicit a protective immune response in mice after 3 weeks.

Example 20

Materials and Methods for Ferret Studies

Ferrets were purchased from Triple F Farms (FFF, Sayre, Pa.). All ferrets purchased has an HAI titer of less that 10 hemagglutination units. Approximately two days prior to vaccination, animals were implanted with a temperature transponder (BioMedic Data Systems, Inc.). Animal (6 animals/group) were vaccinated on day 0 either with (1) PBS (negative control, group one), (2) H3N2 influenza VLPs @ 15 μg of H3 (group 2), (3) H3N2 influenza VLPs @ 3 μg of H3 (group 2), (4) H3N2 influenza VLPs @ 0.6 μg of H3 (group 3), (5) H3N2 influenza VLPs @ 0.12 μg of H3 (group 5), or (6) rH3HA @ 15 μg (group 6). On day 21 animals were boosted with vaccine. Animals were bled on days 0 (prior to vaccination), day 21 (prior to vaccine boost), and day 42. Animals were assessed for clinical signs of adverse vaccine effects once weekly throughout the study period. Similar studies were performed with other influenza VLPs.

HAI Levels in Ferret Sera

Ferret sera were obtained from FFF, treated with Receptor Destroying Enzyme (RDE) and tested in a hemagglutination inhibition (HAI) assay by standard procedures (Kendal et al. (1982)). All ferrets that were chosen for the study tested negative (HAI 10) for pre-existing antibodies to currently circulating human influenza virus (A/New Caledonia/20/99 (H1N1), A panama/2007/99 (H3N2), A/Wellington/01/04 (H2N3) and B/Sichuan/379/99 and H5N1).

Ferrets

Approximately 8 month-old, influenza naïve, castrated and descented, male Fitch ferrets (*Mustela putorius* furo) were purchased form FFF. Animals were housed in stainless steel rabbit cages (Shor-line, KS) containing Sani-chips Laboratory Animal Bedding (P.J. Murphy Forest Products, NJ). Ferrets were provided with Teklad Global Ferret Diet (Harlan Teklad, Wis.) and fresh water ad libitum. Pans were changed three times each week, and cages were cleaned biweekly.

Vaccinations and Blood Collection of Ferrets

The vaccine, H3N2 influenza VLPs or H9N2 influenza VLPs and controls, for example, rH3NA (A/Wyoming/3/2003) and PBS (negative control) were stored at 4° C. prior to use. For most studies, six groups of ferrets (N-6/group) were vaccinated intramuscularly with either concentration of vaccine or control in a volume of 0.5 ml.

Prior to blood collection and vaccination, animals were anesthetized by intramuscular injection into the inner thigh with a solution of Katamine (25 mg/kg, Atropine (0.05 mg/kg) and Xylazine (2.0 mg/kg) "KAX." Once under anesthesia, ferrets were positioned in dorsal recumbency and blood was collected (volume between 0.5 and 1.0 ml) from the anterior vena cava using a 23 gauge 1" needle connected to a 1 cc tuberculin syringe. Blood was transferred to a tube containing a serum separator and clot activator and allowed to clot at room temperature. Tubes were centrifuged and sera was removed and frozen at −80° C. Blood was collected prior to vaccination (day 0), prior to boost (day 21) and day 42 and tested by HAI assay.

Monitoring of Ferrets

Temperatures were measured weekly at approximately the same time throughout the study period. Pre-vaccination values were averaged to obtain a baseline temperature for each ferret. The change in temperature (in degrees Fahrenheit) was calculated at each time point for each animal. Ferrets were examined weekly for clinical signs of adverse vaccine effects, including temperature, weight loss, loss of activity, nasal discharge, sneezing and diarrhea. A scoring system bases on that described by Reuman et al. (1989) was used to assess activity level where 0=alert and playful; 1=alert but playful only when stimulated; 2=alert by not playful when stimulated; 3=neither alert not playful when stimulated. Based on the scores for each animal in a group, a relative inactivity index was calculated as Σ(day 0-Day 42)[activity score+1]/Σ(day 0-Day 42), where n equals the total number of observations. A value of 1 was added to each base score so that a score of "0" could be divided by a denominator, resulting in an index value of 1.0.

Serum Preparations

Sera generally have low levels of non-specific inhibitors on hemagglutination. To inactivate these non-specific inhibitors, sera were treated with (RDE) prior to being tested. Briefly, three part RDE was added to one part sera and incubated overnight at 37° C. RDE was inactivated by incubation at 56° C. for approximately 30 minutes. Following inactivation of RDE, PBS was added to the sample for a final serum dilution of 1:10 (RDE-Tx). The diluted RDE-Tx sera was stored at 4° C. prior to testing (for 7 days) or stored at −20° C.

Preparation Turkey Erythrocytes:

Human influenza viruses bind to sialic acid receptors containing N-acetylneuraminic acid a 2,6-galactose linkages. Avian influenza viruses bind to sialic acid receptors containing N-acetylneuraminic acid a 2,3 galactose (a 2,3 linkages) and express both a 2,3 and a 2,6 linkages. Turkey erythrocytes (TRBC) are used for the HAI assay since A/Fujian is a human influenza virus. The TRBCs adjusted with PBS to achieve a 0.5% vol/vol suspension. The cells are kept at 4° C. and used within 72 hours of preparation.

HAI Assay

The HAI assay was adapted from the CDC laboratory-based influenza surveillance manual (Kendal et al. (1982) Concepts and procedures for laboratory based influenza surveillance, U.S. Department of Health and Human Services, Public Health Service, Centers for Disease Control, Atlanta, Ga., herein incorporated by reference in its entirety for all purposes). RDE-Tx sera was serially two-fold diluted in v-bottom microtiter plates. An equal volume of virus adjusted, adjusted to approximately 8 HAU/50 ul was added to each well. The plates were covered and incubated at room temperature for 15 minutes followed by the addition of 0.5% TRBC. The plates were mixed by agitation, covered, and the TRBC were allowed to settle for 30 minutes at room temperature. The HAI titer was determined by the reciprocal dilution of the last row which contained non-agglutinated TRBC. Positive and negative serum controls were included for each plate.

Example 21

A/Hong Kong/1073/99 (H9N2) VLP dose-ranging study in Ferrets

Figure 22:
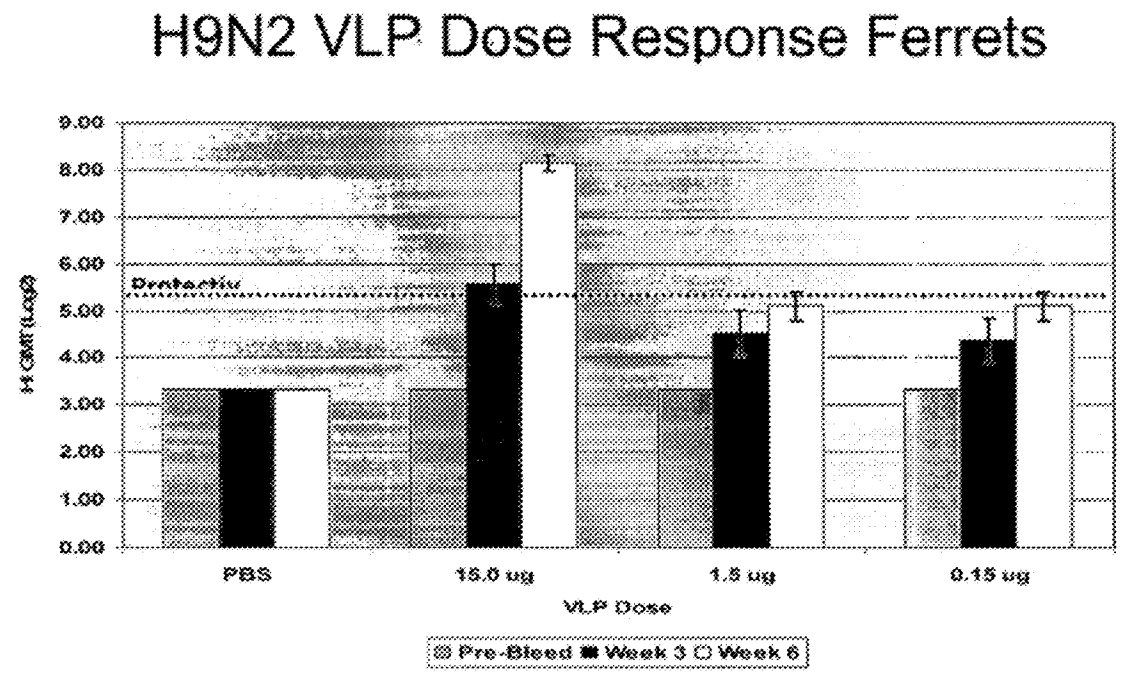

Ferrets, serologically negative by hemagglutination inhibition for influenza viruses, were used to assess the antibody and HI titer after an inoculation with H9N2 VLPs. Ferrets were bled on days 0, and 21 days with the serum assayed for anti-HA antibodies by the hemagglutination inhibition assay (HI) using turkey RBCs, and for anti-influenza antibodies by ELISA. Results are illustrated in FIG. 22. These results show HI titers corresponding to protective antibody levels at VLP doses of 1.5 and 15 µg.

Example 21

Vaccination of H3N2 VLPs in Ferrets

Ferrets were vaccinated at day 0, and given a boost on day 21 with different strains of H3N2 VLPs at different dosages (HA dosages of 0.12, 0.6, 3.0, 15.0 µg). The positive control was rH3HA at 15 µg and PBS alone is the negative control. Sera, as described above, were taken from the ferrets on day 0 prior to vaccination, day 21 (prior to boost) and day 42. An HI assay was conducted on the serum samples to determine if there was an immune response against the VLPs. These data are illustration on FIG. 23. These data indicate that H3N2 VLPs, when introduced into ferrets, do induce an immune response. Thus, the H3N2 VLPs are immunogenic in ferrets.

Example 22

RT-PCR and Cloning of HA, NA, and M1 Genes of Influenza A/Indonesia/5/05 (H5N1) Virus Clade 2 influenza virus, strain A/Indonesia/5/05 (H5N1) viral RNA was extracted using Trizol LS (Invitrogen, Carlsbad, Calif.) under BSL-3 containment conditions. Reverse transcription (RT) and PCR were performed on extracted viral RNA using the One-Step RT-PCR system (Invitrogen) with gene-specific oligonucleotide primers. The following primer pairs were used for the synthesis of the H5N1 hemagglutinin (HA), neuraminidase (NA), and matrix (M1) genes, respectively:

```
                                                     (SEQ ID NO: 4)
   5'-AACGGTCCGATGGAGAAAATAGTGCTTCTTC-3'
   and (HA)
                                                     (SEQ ID NO: 5)
   5'-AAAGCTTTTAAATGCAAATTCTGCATTGTAACG-3';

(SEQ ID NO: 6)
   5'-AACGGTCCGATGAATCCAAATCAGAAGATAAT-3'
   and (NA)
                                                     (SEQ ID NO: 7)
   5'-AAAGCTTCTACTTGTCAATGGTGAATGGCAAC-3';
   and (SEQ ID NO: 8)
   5'-AACGGTCCGATGAGTCTTCTAACCGAGGTC-3'
   and (M1) (ATG codons are underlined)
                                                     (SEQ ID NO: 9)
   5'-AAAGCTTTCACTTGAATCGCTGCATCTGCAC-3'.
```

Following RT-PCR, cDNA fragments containing influenza HA, NA, and M1 genes with molecular weights of 1.7, 1.4, and 0.7 kB, respectively, were cloned into the pCR2.1-TOPO vector (Invitrogen). The nucleotide sequences of the HA, NA, and M1 genes were determined by DNA sequencing. A similar strategy was followed for cloning a clade 1 H5N1 influenza virus from Vietnam/1203/2003.

Example 23

Generation of recombinant baculoviruses comprising H5N1

The HA gene was cloned as a RsrII-HindIII DNA fragment (1.7 kb) downstream of the AcMNPV polyhedrin promoter within pFastBac1 bacmid transfer vector (Invitrogen) digested with RsrII and HindIII. Similarly, the NA and M1 genes were cloned as EcoRI-HindIII DNA fragments (1.4 and 0.8 kb, respectively) into EcoRI-HindIII-digested pFastBac1 plasmid DNA. The three resulting baculovirus transfer plasmids pHA, pNA, and pM1 containing influenza A/Indonesia/5/05 (H5N1)virus HA, NA, and M1 genes, respectively, were used to generate recombinant bacmids.

Bacmids were produced by site-specific homologous recombination following transformation of bacmid transfer plasmids containing influenza genes into E. coli DH10Bac competent cells, which contained the AcMNPV baculovirus genome (Invitrogen). The recombinant bacmid DNA was transfected into the Sf9 insect cells.

Nucleotide Sequences of the Indonesia/5/05 HA, NA, and M1 Genes.

HA
```
                                                    (SEQ ID NO: 10)
ATGGAGAAAATAGTGCTTCTTCTTGCAATAGTCAGTCTTGTTAAAAGTGA

TCAGATTTGCATTGGTTACCATGCAAACAATTCAACAGAGCAGGTTGACA

CAATCATGGAAAAGAACGTTACTGTTACACATGCCCAAGACATACTGGAA
```

-continued

AAGACACACAACGGGAAGCTCTGCGATCTAGATGGAGTGAAGCCTCTAAT

TTTAAGAGATTGTAGTGTAGCTGGATGGCTCCTCGGGAACCCAATGTGTG

ACGAATTCATCAATGTACCGGAATGGTCTTACATAGTGGAGAAGGCCAAT

CCAACCAATGACCTCTGTTACCCAGGGAGTTTCAACGACTATGAAGAACT

GAAACACCTATTGAGCAGAATAAACCATTTTGAGAAAATTCAAATCATCC

CCAAAAGTTCTTGGTCCGATCATGAAGCCTCATCAGGAGTGAGCTCAGCA

TGTCCATACCTGGGAAGTCCCTCCTTTTTTAGAAATGTGGTATGGCTTAT

CAAAAAGAACAGTACATACCCAACAATAAAGAAAAGCTACAATAATACCA

ACCAAGAAGATCTTTTGGTACTGTGGGGAATTCACCATCCTAATGATGCG

GCAGAGCAGACAAGGCTATATCAAAACCCAACCACCTATATTTCCATTGG

GACATCAACACTAAACCAGAGATTGGTACCAAAAATAGCTACTAGATCCA

AAGTAAACGGGCAAAGTGGAAGGATGGAGTTCTTCTGGACAATTTTAAAA

CCTAATGATGCAATCAACTTCGAGAGTAATGGAAATTTCATTGCTCCAGA

ATATGCATACAAAATTGTCAAGAAAGGGGACTCAGCAATTATGAAAAGTG

AATTGGAATATGGTAACTGCAACACCAAGTGTCAAACTCCAATGGGGGCG

ATAAACTCTAGTATGCCATTCCACAACATACACCCTCTCACCATCGGGGA

ATGCCCCAAATATGTGAAATCAAACAGATTAGTCCTTGCAACAGGGCTCA

GAAATAGCCCTCAAAGAGAGCAGAAGAAAAAAGAGAGGACTATTTGGA

GCTATAGCAGGTTTTATAGAGGGAGGATGGCAGGGAATGGTAGATGGTTG

GTATGGGTACCACCATAGCAATGAGCAGGGGAGTGGGTACGCTGCAGACA

AAGAATCCACTCAAAAGGCAATAGATGGAGTCACCAATAAGGTCAACTCA

ATCATTGACAAAATGAACACTCAGTTTGAGGCCGTTGGAAGGGAATTTAA

TAACTTAGAAAGGAGAATAGAGAATTTAAACAAGAAGATGGAAGACGGGT

TTCTAGATGTCTGGACTTATAATGCCGAACTTCTGGTTCTCATGGAAAAT

GAGAGAACTCTAGACTTTCATGACTCAAATGTTAAGAACCTCTACGACAA

GGTCCGACTACAGCTTAGGGATAATGCAAAGGAGCTGGGTAACGGTTGTT

TCGAGTTCTATCACAAATGTGATAATGATGTATGGAAAGTATAAGAAAC

GGAACGTACAACTATCCGCAGTATTCAGAAGAAGCAAGATTAAAAAGAGA

GGAAATAAGTGGGGTAAAATTGGAATCAATAGGAACTTACCAAATACTGT

CAATTTATTCAACAGTGGCGAGTTCCCTAGCACTGGCAATCATGATGGCT

GGTCTATCTTTATGGATGTGCTCCAATGGATCGTTACAATGCAGAATTTG

CATTTAA

NA
(SEQ ID NO: 11)
ATGAATCCAAATCAGAAGATAATAACCATTGGATCAATCTGTATGGTAAT

TGGAATAGTTAGCTTAATGTTACAAATTGGGAACATGATCTCAATATGGG

TCAGTCATTCAATTCAGACAGGGAATCAACACCAAGCTGAATCAATCAGC

AATACTAACCCTCTTACTGAGAAAGCTGTGGCTTCAGTAACATTAGCGGG

CAATTCATCTCTTTGCCCCATTAGAGGATGGGCTGTACACAGTAAGGACA

ACAATATAAGGATCGGTTCCAAGGGGGATGTGTTTGTTATTAGAGAGCCA

TTCATCTCATGCTCCCACCTGGAATGCAGAACTTTCTTCTTGACTCAGGG

AGCCTTGCTGAATGACAAGCACTCCAACGGGACTGTCAAAGACAGAAGCC

CTCACAGAACATTAATGAGTTGTCCTGTGGGTGAGGCTCCCTCTCCATAT

AACTCAAGGTTTGAGTCTGTTGCTTGGTCAGCAAGTGCTTGCCATGATGG

CACCAGTTGGTTGACAATTGGAATTTCTGGCCCAGACAATGAGGCTGTGG

CTGTATTGAAATACAATGGCATAATAACAGACACTATCAAGAGTTGGAGG

AACAACATACTGAGAACTCAAGAGTCTGAATGTGCATGTGTAAATGGCTC

TTGCTTTACTGTAATGACTGATGGACCAAGTGATGGGCAGGCATCATATA

AGATCTTCAAAATGGAAAAAGGAAAAGTGGTCAAATCAGTCGAATTGGAT

GCTCCTAATTATCACTATGAGGAATGCTCCTGTTATCCTGATGCCGGCGA

AATCACATGTGTTTGCAGGGATAATTGGCATGGCTCAAATAGGCCATGGG

TATCTTTCAATCAAAATTTGGAGTATCAAATAGGATATATATGCAGTGGA

GTTTTCGGAGACAATCCACGCCCCAATGATGGAACAGGTAGTTGTGGCCC

GATGTCCCCTAACGGGGCATATGGGGTAAAAGGGTTTTCATTTAAATACG

GCAATGGTGTTTGGATCGGGAGAACCAAAAGCACTAATTCCAGGAGCGGC

TTTGAAATGATTTGGGATCCAAATGGGTGGACTGGAACGGACAGTAGCTT

TTCAGTGAAACAAGATATAGTAGCAATAACTGATTGGTCAGGATATAGCG

GGAGTTTTGTCCAGCATCCAGAACTGACAGGATTAGATTGCATAAGACCT

TGTTTCTGGGTTGAGTTAATCAGAGGGCGGCCCAAAGAGAGCACAATTTG

GACTAGTGGGAGCAGCATATCTTTTTGTGGTGTAAATAGTGACACTGTGA

GTTGGTCTTGGCCAGACGGTGCTGAGTTGCCATTCACCATTGACAAGTAG

M1
(SEQ ID NO: 12)
ATGAGTCTTCTAACCGAGGTCGAAACGTACGTTCTCTCTATCATCCCGTC

AGGCCCCCTCAAAGCCGAGATCGCGCAGAAACTTGAAGATGTCTTTGCAG

GAAAGAACACCGATCTCGAGGCTCTCATGGAGTGGCTGAAGACAAGACCA

ATCCTGTCACCTCTGACTAAAGGGATTTTGGGATTTGTATTCACGCTCAC

CGTGCCCAGTGAGCGAGGACTGCAGCGTAGACGCTTTGTCCAGAATGCCC

TAAATGGAAATGGAGATCCAAATAATATGGATAGGGCAGTTAAGCTATAT

AAGAAGCTGAAAAGAGAAATAACATTCCATGGGGCTAAAGAGGTTTCACT

CAGCTACTCAACCGGTGCACTTGCCAGTTGCATGGGTCTCATATACAACA

GGATGGGAACGGTGACTACGGAAGTGGCTTTTGGCCTAGTGTGTGCCACT

TGTGAGCAGATTGCAGATTCACAGCATCGGTCTCACAGGCAGATGGCAAC

TATCACCAACCCACTAATCAGGCATGAAAACAGAATGGTGCTGGCCAGCA

CTACAGCTAAGGCTATGGAGCAGATGGCGGGATCAAGTGAGCAGGCAGCG

GAAGCCATGGAGGTCGCTAATCAGGCTAGGCAGATGGTGCAGGCAATGAG

GACAATTGGAACTCATCCTAACTCTAGTGCTGGTCTGAGAGATAATCTTC

TTGAAAATTTGCAGGCCTACCAGAAACGAATGGGAGTGCAGATGCAGCGA

TTCAAGTGA

One cloned HA gene, pHA5, contained two nucleotide changes, nt #1172 and nt #1508 (in the wt), as compared to the wild-type HA gene sequence. A similar strategy was followed for constructing and creating clade 1 H5N1 influenza virus from Vietnam/1203/2003 VLPs (see below). The alignments of pHA5 nucleotide and amino acid sequences follow.

```
wt         1 ....................ATGGAGAAAATAGTGCTTCTTCTTGCAATAG    31 SEQ ID NO: 10
                                 ||||||||||||||||||||||||||||||||
pHA5      51 ATTCGCCCTTAACGGTCCGATGGAGAAAATAGTGCTTCTTCTTGCAATAG   100 SEQ ID NO: 56

32 TCAGTCTTGTTAAAAGTGATCAGATTTGCATTGGTTACCATGCAAACAAT    81
             ||||||||||||||||||||||||||||||||||||||||||||||||||
         101 TCAGTCTTGTTAAAAGTGATCAGATTTGCATTGGTTACCATGCAAACAAT   150

82 TCAACAGAGCAGGTTGACACAATCATGGAAAAGAACGTTACTGTTACACA   131
             ||||||||||||||||||||||||||||||||||||||||||||||||||
         151 TCAACAGAGCAGGTTGACACAATCATGGAAAAGAACGTTACTGTTACACA   200

132 TGCCCAAGACATACTGGAAAAGACACACAACGGGAAGCTCTGCGATCTAG   181
             ||||||||||||||||||||||||||||||||||||||||||||||||||
         201 TGCCCAAGACATACTGGAAAAGACACACAACGGGAAGCTCTGCGATCTAG   250

182 ATGGAGTGAAGCCTCTAATTTTAAGAGATTGTAGTGTAGCTGGATGGCTC   231
             ||||||||||||||||||||||||||||||||||||||||||||||||||
         251 ATGGAGTGAAGCCTCTAATTTTAAGAGATTGTAGTGTAGCTGGATGGCTC   300

232 CTCGGGAACCCAATGTGTGACGAATTCATCAATGTACCGGAATGGTCTTA   281
             ||||||||||||||||||||||||||||||||||||||||||||||||||
         301 CTCGGGAACCCAATGTGTGACGAATTCATCAATGTACCGGAATGGTCTTA   350

282 CATAGTGGAGAAGGCCAATCCAACCAATGACCTCTGTTACCCAGGGAGTT   331
             ||||||||||||||||||||||||||||||||||||||||||||||||||
         351 CATAGTGGAGAAGGCCAATCCAACCAATGACCTCTGTTACCCAGGGAGTT   400

332 TCAACGACTATGAAGAACTGAAACACCTATTGAGCAGAATAAACCATTTT   381
             ||||||||||||||||||||||||||||||||||||||||||||||||||
         401 TCAACGACTATGAAGAACTGAAACACCTATTGAGCAGAATAAACCATTTT   450

382 GAGAAAATTCAAATCATCCCCAAAAGTTCTTGGTCCGATCATGAAGCCTC   431
             ||||||||||||||||||||||||||||||||||||||||||||||||||
         451 GAGAAAATTCAAATCATCCCCAAAAGTTCTTGGTCCGATCATGAAGCCTC   500

432 ATCAGGAGTGAGCTCAGCATGTCCATACCTGGGAAGTCCCTCCTTTTTTA   481
             ||||||||||||||||||||||||||||||||||||||||||||||||||
         501 ATCAGGAGTGAGCTCAGCATGTCCATACCTGGGAAGTCCCTCCTTTTTTA   550

482 GAAATGTGGTATGGCTTATCAAAAGAACAGTACATACCCAACAATAAAG    531
             ||||||||||||||||||||||||||||||||||||||||||||||||||
         551 GAAATGTGGTATGGCTTATCAAAAGAACAGTACATACCCAACAATAAAG    600

532 AAAAGCTACAATAATACCAACCAAGAAGATCTTTTGGTACTGTGGGAAT    581
             ||||||||||||||||||||||||||||||||||||||||||||||||||
         601 AAAAGCTACAATAATACCAACCAAGAAGATCTTTTGGTACTGTGGGAAT    650

582 TCACCATCCTAATGATGCGGCAGAGCAGACAAGGCTATATCAAAACCCAA   631
             ||||||||||||||||||||||||||||||||||||||||||||||||||
         651 TCACCATCCTAATGATGCGGCAGAGCAGACAAGGCTATATCAAAACCCAA   700

632 CCACCTATATTTCCATTGGGACATCAACACTAAACCAGAGATTGGTACCA   681
             ||||||||||||||||||||||||||||||||||||||||||||||||||
         701 CCACCTATATTTCCATTGGGACATCAACACTAAACCAGAGATTGGTACCA   750

682 AAAATAGCTACTAGATCCAAAGTAAACGGGCAAAGTGGAAGGATGGAGTT   731
             ||||||||||||||||||||||||||||||||||||||||||||||||||
         751 AAAATAGCTACTAGATCCAAAGTAAACGGGCAAAGTGGAAGGATGGAGTT   800

732 CTTCTGGACAATTTTAAAACCTAATGATGCAATCAACTTCGAGAGTAATG   781
             ||||||||||||||||||||||||||||||||||||||||||||||||||
         801 CTTCTGGACAATTTTAAAACCTAATGATGCAATCAACTTCGAGAGTAATG   850
```

-continued

```
 782 GAAATTTCATTGCTCCAGAATATGCATACAAAATTGTCAAGAAAGGGGAC  831
     ||||||||||||||||||||||||||||||||||||||||||||||||||
 851 GAAATTTCATTGCTCCAGAATATGCATACAAAATTGTCAAGAAAGGGGAC  900

832 TCAGCAATTATGAAAAGTGAATTGGAATATGGTAACTGCAACACCAAGTG  881
     ||||||||||||||||||||||||||||||||||||||||||||||||||
 901 TCAGCAATTATGAAAAGTGAATTGGAATATGGTAACTGCAACACCAAGTG  950

882 TCAAACTCCAATGGGGGCGATAAACTCTAGTATGCCATTCCACAACATAC  931
     ||||||||||||||||||||||||||||||||||||||||||||||||||
 951 TCAAACTCCAATGGGGGCGATAAACTCTAGTATGCCATTCCACAACATAC  1000

932 ACCCTCTCACCATCGGGGAATGCCCCAAATATGTGAAATCAAACAGATTA  981
     ||||||||||||||||||||||||||||||||||||||||||||||||||
1001 ACCCTCTCACCATCGGGGAATGCCCCAAATATGTGAAATCAAACAGATTA  1050

982 GTCCTTGCAACAGGGCTCAGAAATAGCCCTCAAAGAGAGCAGAAGAAA   1031
     ||||||||||||||||||||||||||||||||||||||||||||||||||
1051 GTCCTTGCAACAGGGCTCAGAAATAGCCCTCAAAGAGAGCAGAAGAAA   1100

1032 AAAGAGAGGACTATTTGGAGCTATAGCAGGTTTTATAGAGGGAGGATGGC  1081
     ||||||||||||||||||||||||||||||||||||||||||||||||||
1101 AAAGAGAGGACTATTTGGAGCTATAGCAGGTTTTATAGAGGGAGGATGGC  1150

1082 AGGGAATGGTAGATGGTTGGTATGGGTACCACCATAGCAATGAGCAGGGG  1131
     ||||||||||||||||||||||||||||||||||||||||||||||||||
1151 AGGGAATGGTAGATGGTTGGTATGGGTACCACCATAGCAATGAGCAGGGG  1200

1132 AGTGGGTACGCTGCAGACAAAGAATCCACTCAAAAGGCAATAGATGGAGT  1181
     |||||||||||||||||||||||||||||||||||||||| |||||||||
1201 AGTGGGTACGCTGCAGACAAAGAATCCACTCAAAAGGCAATGGATGGAGT  1250

1182 CACCAATAAGGTCAACTCAATCATTGACAAAATGAACACTCAGTTTGAGG  1231
     ||||||||||||||||||||||||||||||||||||||||||||||||||
1251 CACCAATAAGGTCAACTCAATCATTGACAAAATGAACACTCAGTTTGAGG  1300

1232 CCGTTGGAAGGGAATTTAATAACTTAGAAAGGAGAATAGAGAATTTAAAC  1281
     ||||||||||||||||||||||||||||||||||||||||||||||||||
1301 CCGTTGGAAGGGAATTTAATAACTTAGAAAGGAGAATAGAGAATTTAAAC  1350

1282 AAGAAGATGGAAGACGGGTTTCTAGATGTCTGGACTTATAATGCCGAACT  1331
     ||||||||||||||||||||||||||||||||||||||||||||||||||
1351 AAGAAGATGGAAGACGGGTTTCTAGATGTCTGGACTTATAATGCCGAACT  1400

1332 TCTGGTTCTCATGGAAAATGAGAGAACTCTAGACTTTCATGACTCAAATG  1381
     ||||||||||||||||||||||||||||||||||||||||||||||||||
1401 TCTGGTTCTCATGGAAAATGAGAGAACTCTAGACTTTCATGACTCAAATG  1450

1382 TTAAGAACCTCTACGACAAGGTCCGACTACAGCTTAGGGATAATGCAAAG  1431
     ||||||||||||||||||||||||||||||||||||||||||||||||||
1451 TTAAGAACCTCTACGACAAGGTCCGACTACAGCTTAGGGATAATGCAAAG  1500

1432 GAGCTGGGTAACGGTTGTTTCGAGTTCTATCACAAATGTGATAATGAATG  1481
     ||||||||||||||||||||||||||||||||||||||||||||||||||
1501 GAGCTGGGTAACGGTTGTTTCGAGTTCTATCACAAATGTGATAATGAATG  1550

1482 TATGGAAAGTATAAGAAACGGAACGTACAACTATCCGCAGTATTCAGAAG  1531
     |||||||||||||||||||||||||||| |||||||||||||||||||||
1551 TATGGAAAGTATAAGAAACGGAACGTGCAACTATCCGCAGTATTCAGAAG  1600

1532 AAGCAAGATTAAAAAGAGAGGAAATAAGTGGGGTAAAATTGGAATCAATA  1581
     ||||||||||||||||||||||||||||||||||||||||||||||||||
1601 AAGCAAGATTAAAAAGAGAGGAAATAAGTGGGGTAAAATTGGAATCAATA  1650
```

-continued

```
                  .         .         .         .         .
1582 GGAACTTACCAAATACTGTCAATTTATTCAACAGTGGCGAGTTCCCTAGC  1631
     ||||||||||||||||||||||||||||||||||||||||||||||||||
1651 GGAACTTACCAAATACTGTCAATTTATTCAACAGTGGCGAGTTCCCTAGC  1700

.         .         .         .         .
1632 ACTGGCAATCATGATGGCTGGTCTATCTTTATGGATGTGCTCCAATGGAT  1681
     ||||||||||||||||||||||||||||||||||||||||||||||||||
1701 ACTGGCAATCATGATGGCTGGTCTATCTTTATGGATGTGCTCCAATGGAT  1750

.         .         .         .         .
1682 CGTTACAATGCAGAATTTGCATtTAA........................  1707
     ||||||||||||||||||||||||||
1751 CGTTACAATGCAGAATTTGCATTTAAAAGCTTTAAGGGCGAATTCCAGCA  1800
                                .
```

Amino Acid Sequence Alignment of Hemagglutinin

```
pHA5    1 MEKIVLLLAIVSLVKSDQICIGYHANNSTEQVDTIMEKNVTVTHAQDILE   50 SEQ ID NO: 57
          ||||||||||||||||||||||||||||||||||||||||||||||||||
wt      1 MEKIVLLLAIVSLVKSDQICIGYHANNSTEQVDTIMEKNVTVTHAQDILE   50 SEQ ID NO: 58

.         .         .         .         .
         51 KTHNGKLCDLDGVKPLILRDCSVAGWLLGNPMCDEFINVPEWSYIVEKAN  100
            ||||||||||||||||||||||||||||||||||||||||||||||||||
         51 KTHNGKLCDLDGVKPLILRDCSVAGWLLGNPMCDEFINVPEWSYIVEKAN  100

.         .         .         .         .
        101 PTNDLCYPGSFNDYEELKHLLSRINHFEKIQIIPKSSWSDHEASSGVSSA  150
            ||||||||||||||||||||||||||||||||||||||||||||||||||
        101 PTNDLCYPGSFNDYEELKHLLSRINHFEKIQIIPKSSWSDHEASSGVSSA  150

.         .         .         .         .
        151 CPYLGSPSFFRNVVWLIKKNSTYPTIKKSYNNTNQEDLLVLWGIHHPNDA  200
            ||||||||||||||||||||||||||||||||||||||||||||||||||
        151 CPYLGSPSFFRNVVWLIKKNSTYPTIKKSYNNTNQEDLLVLWGIHHPNDA  200

.         .         .         .         .
        201 AEQTRLYQNPTTYISIGTSTLNQRLVPKIATRSKVNGQSGRMEFFWTILK  250
            ||||||||||||||||||||||||||||||||||||||||||||||||||
        201 AEQTRLYQNPTTYISIGTSTLNQRLVPKIATRSKVNGQSGRMEFFWTILK  250

.         .         .         .         .
        251 PNDAINFESNGNFIAPEYAYKIVKKGDSAIMKSELEYGNCNTKCQTPMGA  300
            ||||||||||||||||||||||||||||||||||||||||||||||||||
        251 PNDAINFESNGNFIAPEYAYKIVKKGDSAIMKSELEYGNCNTKCQTPMGA  300

.         .         .         .         .
        301 INSSMPFHNIHPLTIGECPKYVKSNRLVLATGLRNSPQRESRRKKRGLFG  350
            ||||||||||||||||||||||||||||||||||||||||||||||||||
        301 INSSMPFHNIHPLTIGECPKYVKSNRLVLATGLRNSPQRESRRKKRGLFG  350

.         .         .         .         .
        351 AIAGFIEGGWQGMVDGWYGYHHSNEQGSGYAADKESTQKAMDGVTNKVNS  400
            |||||||||||||||||||||||||||||||||||||||||.|||||||||
        351 AIAGFIEGGWQGMVDGWYGYHHSNEQGSGYAADKESTQKAIDGVTNKVNS  400

.         .         .         .         .
        401 IIDKMNTQFEAVGREFNNLERRIENLNKKMEDGFLDVWTYNAELLVLMEN  450
            ||||||||||||||||||||||||||||||||||||||||||||||||||
        401 IIDKMNTQFEAVGREFNNLERRIENLNKKMEDGFLDVWTYNAELLVLMEN  450

.         .         .         .         .
        451 ERTLDFHDSNVKNLYDKVRLQLRDNAKELGNGCFEFYHKCDNECMESIRN  500
            ||||||||||||||||||||||||||||||||||||||||||||||||||
        451 ERTLDFHDSNVKNLYDKVRLQLRDNAKELGNGCFEFYHKCDNECMESIRN  500

.         .         .         .         .
        501 GTCNYPQYSEEARLKREEISGVKLESIGTYQILSIYSTVASSLALAIMMA  550
            || |||||||||||||||||||||||||||||||||||||||||||||||
        501 GTYNYPQYSEEARLKREEISGVKLESIGTYQILSIYSTVASSLALAIMMA  550

.
        551 GLSLWMCSNGSLQCRICI.                                 568
            ||||||||||||||||||
        551 GLSLWMCSNGSLQCRICI*                                 569
```

Example 26

Generation of Influenza A/Indonesia/5/05 HA, NA, and M1 Genes Optimized for Efficient Expression in Sf9 Cells.

The following polypeptides were derived from codon-optimized nucleotides corresponding to the Indonesia/5/05 HA gene (see example 31). The codon-optimized nucleotides were designed and produced (Geneart GMBH, Regensburg, FRG) according to the methods disclosed in US patent publication 2005/0118191, herein incorporated by reference in its entirety for all proposes. See Example 31 for nucleic acid sequences

```
Vac2-hac-opt (unmodified aa sequence)
                                                       (SEQ ID NO: 27)
MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*

Vac2-hac-spc-opt
(modified, signal peptide from Chitinase, underlined)
                                                       (SEQ ID NO: 28)
Mplykllnvlwlvaysnaip DQICIGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*

Vac2-hac-sph9-opt (modified, signal peptide from H9, underlined)
                                                       (SEQ ID NO: 29)
METISLITIL LVVTASNA DQICIGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN
```

```
ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*

Vac2-hac-cs-opt (- is the modified cleavage site)
                                                (SEQ ID NO: 30)
MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE S----RGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI*
```

The following polypeptides corresponding to unmodified, codon-optimized NA and M1 genes where also synthesized.

```
Vac2-naj-opt (neuraminidase)
                                                (SEQ ID NO: 31)
MNPNQKIITI GSICMVIGIV SLMLQIGNMI SIWVSHSIQT GNQHQAESIS

NTNPLTEKAV ASVTLAGNSS LCPIRGWAVH SKDNNIRIGS KGDVFVIREP

FISCSHLECR TFFLTQGALL NDKHSNGTVK DRSPHRTLMS CPVGEAPSPY

NSRFESVAWS ASACHDGTSW LTIGISGPDN EAVAVLKYNG IITDTIKSWR

NNILRTQESE CACVNGSCFT VMTDGPSDGQ ASYKIFKMEK GKVVKSVELD

APNYHYEECS CYPDAGEITC VCRDNWHGSN RPWVSFNQNL EYQIGYICSG

VFGDNPRPND GTGSCGPMSP NGAYGVKGFS FKYGNGVWIG RTKSTNSRSG

FEMIWDPNGW TGTDSSFSVK QDIVAITDWS GYSGSFVQHP ELTGLDCIRP

CFWVELIRGR PKESTIWTSG SSISFCGVNS DTVSWSWPDG AELPFTIDK*

Vac2-mc-opt (matrix)
                                                (SEQ ID NO: 32)
MSLLTEVETY VLSIIPSGPL KAEIAQKLED VFAGKNTDLE ALMEWLKTRP

ILSPLTKGIL GFVFTLTVPS ERGLQRRRFV QNALNGNGDP NNMDRAVKLY

KKLKREITFH GAKEVSLSYS TGALASCMGL IYNRMGTVTT EVAFGLVCAT

CEQIADSQHR SHRQMATITN PLIRHENRMV LASTTAKAME QMAGSSEQAA

EAMEVANQAR QMVQAMRTIG THPNSSAGLR DNLLENLQAY QKRMGVQMQR

FK*
```

The synthetic, codon-optimized HA, NA, and M1 genes were subcloned into pFastBac1 transfer plasmid using BamHI and HindIII sites, as described above. Recombinant bacmids for expression in Sf9 cells of synthetic HA, NA, M1 genes were generated as described above, using *E. coli* strain DH10Bac (Invitrogen).

Example 24

Cloning of Clade 1 A/Viet Nam/1203/04 (H5N1) Influenza Virus by RT-PCR

The HA, NA and M1 genes were cloned by RT-PCR according to the above describes method. The below sequences are comparisons of the published gene compared to the cloned genes.

The HA Gene for Clade 1 A/Viet Nam/1203/04 (H5N1)

(SEQ ID NO: 36)
Upper Lane: Acc #AY818135 HA gene (SEQ ID NO: 37)
Lower Lane: Novavax's A/Vietnam/1203/2004 (H5N1) HA gene

```
   1 ......................................ATGGAGAAAA     10
                                            ||||||||||
 301 AGTGTGATGGATATCTGCAGAATTCGCCCTTAGGCGCGCCATGGAGAAAA    350

11 TAGTGCTTCTTTTTGCAATAGTCAGTCTTGTTAAAAGTGATCAGATTTGC     60
     ||||||||||||||||||||||||||||||||||||||||||||||||||
 351 TAGTGCTTCTTTTTGCAATAGTCAGTCTTGTTAAAAGTGATCAGATTTGC    400

61 ATTGGTTACCATGCAAACAACTCGACAGAGCAGGTTGACACAATAATGGA    110
     ||||||||||||||||||||||||||||||||||||||||||||||||||
 401 ATTGGTTACCATGCAAACAACTCGACAGAGCAGGTTGACACAATAATGGA    450

111 AAAGAACGTTACTGTTACACATGCCCAAGACATACTGGAAAAGAAACACA    160
     ||||||||||||||||||||||||||||||||||||||||||||||||||
 451 AAAGAACGTTACTGTTACACATGCCCAAGACATACTGGAAAAGAAACACA    500

161 ACGGGAAGCTCTGCGATCTAGATGGAGTGAAGCCTCTAATTTTGAGAGAT    210
     ||||||||||||||||||||||||||||||||||||||||||||||||||
 501 ACGGGAAGCTCTGCGATCTAGATGGAGTGAAGCCTCTAATTTTGAGAGAT    550

211 TGTAGCGTAGCTGGATGGCTCCTCGGAAACCCAATGTGTGACGAATTCAT    260
     ||||||||||||||||||||||||||||||||||||||||||||||||||
 551 TGTAGCGTAGCTGGATGGCTCCTCGGAAACCCAATGTGTGACGAATTCAT    600

261 CAATGTGCCGGAATGGTCTTACATAGTGGAGAAGGCCAATCCAGTCAATG    310
     ||||||||||||||||||||||||||||||||||||||||||||||||||
 601 CAATGTGCCGGAATGGTCTTACATAGTGGAGAAGGCCAATCCAGTCAATG    650

311 ACCTCTGTTACCCAGGGGATTTCAATGACTATGAAGAATTGAAACACCTA    360
     ||||||||||||||||||||||||||||||||||||||||||||||||||
 651 ACCTCTGTTACCCAGGGGATTTCAATGACTATGAAGAATTGAAACACCTA    700

361 TTGAGCAGAATAAACCATTTTGAGAAAATTCAGATCATCCCCAAAAGTTC    410
     ||||||||||||||||||||||||||||||||||||||||||||||||||
 701 TTGAGCAGAATAAACCATTTTGAGAAAATTCAGATCATCCCCAAAAGTTC    750

411 TTGGTCCAGTCATGAAGCCTCATTAGGGGTGAGCTCAGCATGTCCATACC    460
     ||||||||||||||||||||||||||||||||||||||||||||||||||
 751 TTGGTCCAGTCATGAAGCCTCATTAGGGGTGAGCTCAGCATGTCCATACC    800

461 AGGGAAAGTCCTCCTTTTTCAGAAATGTGGTATGGCTTATCAAAAAGAAC    510
     ||||||||||||||||||||||||||||||||||||||||||||||||||
 801 AGGGAAAGTCCTCCTTTTTCAGAAATGTGGTATGGCTTATCAAAAAGAAC    850

511 AGTACATACCCAACAATAAAGAGGAGCTACAATAATACCAACCAAGAAGA    560
     ||||||||||||||||||||||||||||||||||||||||||||||||||
 851 AGTACATACCCAACAATAAAGAGGAGCTACAATAATACCAACCAAGAAGA    900

561 TCTTTTGGTACTGTGGGGGATTCACCATCCTAATGATGCGGCAGAGCAGA    610
     ||||||||||||||||||||||||||||||||||||||||||||||||||
 901 TCTTTTGGTACTGTGGGGGATTCACCATCCTAATGATGCGGCAGAGCAGA    950

611 CAAAGCTCTATCAAAACCCAACCACCTATATTTCCGTTGGGACATCAACA    660
     ||||||||||||||||||||||||||||||||||||||||||||||||||
 951 CAAAGCTCTATCAAAACCCAACCACCTATATTTCCGTTGGGACATCAACA    1000

661 CTAAACCAGAGATTGGTACCAAGAATAGCTACTAGATCCAAAGTAAACGG    710
     ||||||||||||||||||||||||||||||||||||||||||||||||||
1001 CTAAACCAGAGATTGGTACCAAGAATAGCTACTAGATCCAAAGTAAACGG    1050
```

```
 711 GCAAAGTGGAAGGATGGAGTTCTTCTGGACAATTTTAAAGCCGAATGATG   760
     ||||||||||||||||||||||||||||||||||||||||||||||||||
1051 GCAAAGTGGAAGGATGGAGTTCTTCTGGACAATTTTAAAGCCGAATGATG  1100

761 CAATCAACTTCGAGAGTAATGGAAATTTCATTGCTCCAGAATATGCATAC   810
     ||||||||||||||||||||||||||||||||||||||||||||||||||
1101 CAATCAACTTCGAGAGTAATGGAAATTTCATTGCTCCAGAATATGCATAC  1150

811 AAAATTGTCAAGAAAGGGGACTCAACAATTATGAAAAGTGAATTGGAATA   860
     ||||||||||||||||||||||||||||||||||||||||||||||||||
1151 AAAATTGTCAAGAAAGGGGACTCAACAATTATGAAAAGTGAATTGGAATA  1200

861 TGGTAACTGCAACACCAAGTGTCAAACTCCAATGGGGCGATAAACTCTA    910
     ||||||||||||||||||||||||||||||||||||||||||||||||||
1201 TGGTAACTGCAACACCAAGTGTCAAACTCCAATGGGGCGATAAACTCTA   1250

911 GCATGCCATTCCACAATATACACCCTCTCACCATTGGGGAATGCCCCAAA   960
     ||||||||||||||||||||||||||||||||||||||||||||||||||
1251 GCATGCCATTCCACAATATACACCCTCTCACCATTGGGGAATGCCCCAAA  1300

961 TATGTGAAATCAAACAGATTAGTCCTTGCGACTGGGCTCAGAAATAGCCC  1010
     ||||||||||||||||||||||||||||||||||||||||||||||||||
1301 TATGTGAAATCAAACAGATTAGTCCTTGCGACTGGGCTCAGAAATAGCCC  1350

1011 TCAAAGAGAGAAGAAGAAAAAAGAGAGGATTATTTGGAGCTATAGCAG    1060
     ||||||||||||||||||||||||||||||||||||||||||||||||||
1351 TCAAAGAGAGAAGAAGAAAAAAGAGAGGATTATTTGGAGCTATAGCAG    1400

1061 GTTTTATAGAGGGAGGATGGCAGGGAATGGTAGATGGTTGGTATGGGTAC  1110
     ||||||||||||||||||||||||||||||||||||||||||||||||||
1401 GTTTTATAGAGGGAGGATGGCAGGGAATGGTAGATGGTTGGTATGGGTAC  1450

1111 CACCATAGCAATGAGCAGGGGAGTGGGTACGCTGCAGACAAAGAATCCAC  1160
     ||||||||||||||||||||||||||||||||||||||||||||||||||
1451 CACCATAGCAATGAGCAGGGGAGTGGGTACGCTGCAGACAAAGAATCCAC  1500

1161 TCAAAAGGCAATAGATGGAGTCACCAATAAGGTCAACTCGATCATTGACA  1210
     ||||||||||||||||||||||||||||||||||||||||||||||||||
1501 TCAAAAGGCAATAGATGGAGTCACCAATAAGGTCAACTCGATCATTGACA  1550

1211 AAATGAACACTCAGTTTGAGGCCGTTGGAAGGGAATTTAACAACTTAGAA  1260
     ||||||||||||||||||||||||||||||||||||||||||||||||||
1551 AAATGAACACTCAGTTTGAGGCCGTTGGAAGGGAATTTAACAACTTAGAA  1600

1261 AGGAGAATAGAGAATTTAAACAAGAAGATGGAAGACGGGTTCCTAGATGT  1310
     ||||||||||||||||||||||||||||||||||||||||||||||||||
1601 AGGAGAATAGAGAATTTAAACAAGAAGATGGAAGACGGGTTCCTAGATGT  1650

1311 CTGGACTTATAATGCTGAACTTCTGGTTCTCATGGAAAATGAGAGAACTC  1360
     ||||||||||||||||||||||||||||||||||||||||||||||||||
1651 CTGGACTTATAATGCTGAACTTCTGGTTCTCATGGAAAATGAGAGAACTC  1700

1361 TAGACTTTCATGACTCAAATGTCAAGAACCTTTACGACAAGGTCCGACTA  1410
     ||||||||||||||||||||||||||||||||||||||||||||||||||
1701 TAGACTTTCATGACTCAAATGTCAAGAACCTTTACGACAAGGTCCGACTA  1750

1411 CAGCTTAGGGATAATGCAAAGGAGCTGGGTAACGGTTGTTTCGAGTTCTA  1460
     ||||||||||||||||||||||||||||||||||||||||||||||||||
1751 CAGCTTAGGGATAATGCAAAGGAGCTGGGTAACGGTTGTTTCGAGTTCTA  1800

1461 TCATAAATGTGATAATGAATGTATGGAAAGTGTAAGAAATGGAACGTATG  1510
     ||||||||||||||||||||||||||||||||||||||||||||||||||
1801 TCATAAATGTGATAATGAATGTATGGAAAGTGTAAGAAATGGAACGTATG  1850
```

-continued

```
1511 ACTACCCGCAGTATTCAGAAGAAGCGAGACTAAAAAGAGAGGAAATAAGT 1560
     ||||||||||||||||||||||||||||||||||||||||||||||||||
1851 ACTACCCGCAGTATTCAGAAGAAGCGAGACTAAAAAGAGAGGAAATAAGT 1900

1561 GGAGTAAAATTGGAATCAATAGGAATTTACCAAATACTGTCAATTTATTC 1610
     ||||||||||||||||||||||||||||||||||||||||||||||||||
1901 GGAGTAAAATTGGAATCAATAGGAATTTACCAAATACTGTCAATTTATTC 1950

1611 TACAGTGGCGAGTTCCCTAGCACTGGCAATCATGGTAGCTGGTCTATCCT 1660
     ||||||||||||||||||||||||||||||||||||||||||||||||||
1951 TACAGTGGCGAGTTCCCTAGCACTGGCAATCATGGTAGCTGGTCTATCCT 2000

1661 TATGGATGTGCTCCAATGGATCGTTACAATGCAGAATTTGCATTTAA... 1707
     ||||||||||||||||||||||| ||||||||||||||||||||||
2001 TATGGATGTGCTCCAATGGGTCGTTACAATGCAGAATTTGCATTTAAGCG 2050
```

Comparison of the NA Genes.

```
                                                   (SEQ ID NO: 39)
The NA gene for Clade 1 A/Viet Nam/1203/04 (H5N1)

(SEQ ID NO: 38)
H5N1naLANL ISDN 38704 x NA_Viet1203_Lark(NVAX)

1 .....ATGAATCCAAATCAGAAGATAATAACCATCGGATCAATCTGTATG 45
          |||||||||||||||||||||||||||||||||||||||||||||
 451 CCGGGATGAATCCAAATCAGAAGATAATAACCATCGGATCAATCTGTATG 500

46 GTAACTGGAATAGTTAGCTTAATGTTACAAATTGGGAACATGATCTCAAT 95
     ||||||||||||||||||||||||||||||||||||||||||||||||||
 501 GTAACTGGAATAGTTAGCTTAATGTTACAAATTGGGAACATGATCTCAAT 550

96 ATGGGTCAGTCATTCAATTCACACAGGGAATCAACACCAATCTGAACCAA 145
     ||||||||||||||||||||||||||||||||||||||||||||||||||
 551 ATGGGTCAGTCATTCAATTCACACAGGGAATCAACACCAATCTGAACCAA 600

146 TCAGCAATACTAATTTTCTTACTGAGAAAGCTGTGGCTTCAGTAAAATTA 195
     ||||||||||||||||||||||||||||||||||||||||||||||||||
 601 TCAGCAATACTAATTTTCTTACTGAGAAAGCTGTGGCTTCAGTAAAATTA 650

196 GCGGGCAATTCATCTCTTTGCCCCATTAACGGATGGGCTGTATACAGTAA 245
     ||||||||||||||||||||||||||||||||||||||||||||||||||
 651 GCGGGCAATTCATCTCTTTGCCCCATTAACGGATGGGCTGTATACAGTAA 700

246 GGACAACAGTATAAGGATCGGTTCCAAGGGGGATGTGTTTGTTATAAGAG 295
     ||||||||||||||||||||||||||||||||||||||||||||||||||
 701 GGACAACAGTATAAGGATCGGTTCCAAGGGGGATGTGTTTGTTATAAGAG 750

296 AGCCGTTCATCTCATGCTCCCACTTGGAATGCAGAACTTTCTTTTTGACT 345
     ||||||||||||||||||||||||||||||||||||||||||||||||||
 751 AGCCGTTCATCTCATGCTCCCACTTGGAATGCAGAACTTTCTTTTTGACT 800

346 CAGGGAGCCTTGCTGAATGACAAGCACTCCAATGGGACTGTCAAAGACAG 395
     |||||||||| |||||||||||||||||||||||||||||||||||||||
 801 CAGGGAGCCTCGCTGAATGACAAGCACTCCAATGGGACTGTCAAAGACAG 850

396 AAGCCCTCACAGAACATTAATGAGTTGTCCTGTGGGTGAGGCTCCCTCCC 445
     ||||||||||||||||||||||||||||||||||||||||||||||||||
 851 AAGCCCTCACAGAACATTAATGAGTTGTCCTGTGGGTGAGGCTCCCTCCC 900

446 CATATAACTCAAGGTTTGAGTCTGTTGCTTGGTCAGCAAGTGCTTGCCAT 495
     ||||||||||||||||||||||||||||||||||||||||||||||||||
 901 CATATAACTCAAGGTTTGAGTCTGTTGCTTGGTCAGCAAGTGCTTGCCAT 950
```

-continued

```
 496 GATGGCACCAGTTGGTTGACGATTGGAATTTCTGGCCCAGACAATGGGGC  545
     ||||||||||||||||||||||||||||||||||||||||||||||||||
 951 GATGGCACCAGTTGGTTGACGATTGGAATTTCTGGCCCAGACAATGGGGC 1000

546 TGTGGCTGTATTGAAATACAATGGCATAATAACAGACACTATCAAGAGTT  595
     ||||||||||||||||||||||||||||||||||||||||||||||||||
1001 TGTGGCTGTATTGAAATACAATGGCATAATAACAGACACTATCAAGAGTT 1050

596 GGAGGAACAACATACTGAGAACTCAAGAGTCTGAATGTGCATGTGTAAAT  645
     ||||||||||||||||||||||||||||||||||||||||||||||||||
1051 GGAGGAACAACATACTGAGAACTCAAGAGTCTGAATGTGCATGTGTAAAT 1100

646 GGCTCTTGCTTTACTGTAATGACTGACGGACCAAGTAATGGTCAGGCATC  695
     ||||||||||||||||||||||||||||||||||||||||||||||||||
1101 GGCTCTTGCTTTACTGTAATGACTGACGGACCAAGTAATGGTCAGGCATC 1150

696 ACATAAGATCTTCAAAATGGAAAAAGGGAAAGTGGTTAAATCAGTCGAAT  745
     ||||||||||||||||||||||||||||||||||||||||||||||||||
1151 ACATAAGATCTTCAAAATGGAAAAAGGGAAAGTGGTTAAATCAGTCGAAT 1200

746 TGGATGCTCCTAATTATCACTATGAGGAATGCTCCTGTTATCCTAATGCC  795
     ||||||||||||||||||||||||||||||||||||||||||||||||||
1201 TGGATGCTCCTAATTATCACTATGAGGAATGCTCCTGTTATCCTAATGCC 1250

796 GGAGAAATCACATGTGTGTGCAGGGATAATTGGCATGGCTCAAATCGGCC  845
     ||||||||||||||||||||||||||||||||||||||||||||||||||
1251 GGAGAAATCACATGTGTGTGCAGGGATAATTGGCATGGCTCAAATCGGCC 1300

846 ATGGGTATCTTTCAATCAAAATTTGGAGTATCAAATAGGATATATATGCA  895
     ||||||||||||||||||||||||||||||||||||||||||||||||||
1301 ATGGGTATCTTTCAATCAAAATTTGGAGTATCAAATAGGATATATATGCA 1350

896 GTGGAGTTTTCGGAGACAATCCACGCCCCAATGATGGAACAGGTAGTTGT  945
     ||||||||||||||||||||||||||||||||||||||||||||||||||
1351 GTGGAGTTTTCGGAGACAATCCACGCCCCAATGATGGAACAGGTAGTTGT 1400

946 GGTCCGGTGTCCTCTAACGGGGCATATGGGGTAAAAGGGTTTTCATTTAA  995
     ||||||||||||||||||||||||||||||||||||||||||||||||||
1401 GGTCCGGTGTCCTCTAACGGGGCATATGGGGTAAAAGGGTTTTCATTTAA 1450

996 ATACGGCAATGGTGTCTGGATCGGGAGAACCAAAAGCACTAATTCCAGGA 1045
     ||||||||||||||||||||||||||||||||||||||||||||||||||
1451 ATACGGCAATGGTGTCTGGATCGGGAGAACCAAAAGCACTAATTCCAGGA 1500

1046 GCGGCTTTGAAATGATTTGGGATCCAAATGGGTGGACTGAAACGGACAGT 1095
     ||||||||||||||||||||||||||||||||||||||||||||||||||
1501 GCGGCTTTGAAATGATTTGGGATCCAAATGGGTGGACTGAAACGGACAGT 1550

1096 AGCTTTTCAGTGAAACAAGATATCGTAGCAATAACTGATTGGTCAGGATA 1145
     ||||||||||||||||||||||||||||||||||||||||||||||||||
1551 AGCTTTTCAGTGAAACAAGATATCGTAGCAATAACTGATTGGTCAGGATA 1600

1146 TAGCGGGAGTTTTGTCCAGCATCCAGAACTGACAGGACTAGATTGCATAA 1195
     ||||||||||||||||||||||||||||||||||||||||||||||||||
1601 TAGCGGGAGTTTTGTCCAGCATCCAGAACTGACAGGACTAGATTGCATAA 1650

1196 GACCTTGTTTCTGGGTTGAGTTGATCAGAGGGCGGCCCAAAGAGAGCACA 1245
     ||||||||||||||||||||||||||||||||||||||||||||||||||
1651 GACCTTGTTTCTGGGTTGAGTTGATCAGAGGGCGGCCCAAAGAGAGCACA 1700

1246 ATTTGGACTAGTGGGAGCAGCATATCTTTTTGTGGTGTAAATAGTGACAC 1295
     ||||||||||||||||||||||||||||||||||||||||||||||||||
1701 ATTTGGACTAGTGGGAGCAGCATATCTTTTTGTGGTGTAAATAGTGACAC 1750
```

```
1296 TGTGGGTTGGTCTTGGCCAGACGGTGCCGAGTTGCCATTCACCATTGACA 1345
     |||||||||||||||||||||||||||||| |||||||||||||||||||
1751 TGTGGGTTGGTCTTGGCCAGACGGTGCTGAGTTGCCATTCACCATTGACA 1800

1346 AGTAG............................................. 1350
     |||||
1801 AGTAGGGGCCCTCGAGTAAGGGCGAATTCCAGCACACTGGCGGCCGTTAC 1850
```

Comparisons of the M1 Genes.

```
                                                    (SEQ ID NO: 40)
The M1 gene for Clade 1 A/Viet Nam/1203/04 (H5N1)

(SEQ ID NO: 41)
H5N1m1Lanl ISDN39958 x M1_Viet1203_Lark(NVAX)

1 ................................ATGAGTCTTCTAACCG   16
                                    ||||||||||||||||
301 ATATCTGCAGAATTCGCCCTTAGAATTCGACGTCATGAGTCTTCTAACCG  350

17 AGGTCGAAACGTACGTTCTCTCTATCATCCCGTCAGGCCCCCTCAAAGCC   66
    ||||||||||||||||||||||||||||||||||||||||||||||||||
351 AGGTCGAAACGTACGTTCTCTCTATCATCCCGTCAGGCCCCCTCAAAGCC  400

67 GAGATCGCACAGAAACTTGAAGATGTCTTTGCAGGAAAGAACACCGATCT  116
    ||||||||||||||||||||||||||||||||||||||||||||||||||
401 GAGATCGCACAGAAACTTGAAGATGTCTTTGCAGGAAAGAACACCGATCT  450

117 CGAGGCTCTCATGGAGTGGCTAAAGACAAGACCAATCCTGTCACCTCTGA  166
    ||||||||||||||||||||||||||||||||||||||||||||||||||
451 CGAGGCTCTCATGGAGTGGCTAAAGACAAGACCAATCCTGTCACCTCTGA  500

167 CTAAAGGGATTTTGGGATTTGTATTCACGCTCACCGTGCCCAGTGAGCGA  216
    ||||||||||||||||||||||||||||||||||||||||||||||||||
501 CTAAAGGGATTTTGGGATTTGTATTCACGCTCACCGTGCCCAGTGAGCGA  550

217 GGACTGCAGCGTAGACGCTTTGTCCAGAATGCCCTAAATGGAAATGGAGA  266
    ||||||||||||||||||||||||||||||||||||||||||||||||||
551 GGACTGCAGCGTAGACGCTTTGTCCAGAATGCCCTAAATGGAAATGGAGA  600

267 TCCAAATAATATGGATAGGGCAGTTAAGCTATATAAGAAGCTGAAAAGAG  316
    ||||||||||||||||||||||||||||||||||||||||||||||||||
601 TCCAAATAATATGGATAGGGCAGTTAAGCTATATAAGAAGCTGAAAAGAG  650

317 AAATAACATTCCATGGGCTAAGGAGGTCGCACTCAGCTACTCAACCGGT   366
    ||||||||||||||||||||||||||||||||||||||||||||||||
651 AAATAACATTCCATGGGCTAAGGAGGTCGCACTCAGCTACTCAACCGGT   700

367 GCACTTGCCAGTTGCATGGGTCTCATATACAACAGGATGGGAACGGTGAC  416
    ||||||||||||||||||||||||||||||||||||||||||||||||||
701 GCACTTGCCAGTTGCATGGGTCTCATATACAACAGGATGGGAACGGTGAC  750

417 TACGGAAGTGGCTTTTGGCCTAGTGTGTGCCACTTGTGAGCAGATTGCAG  466
    ||||||||||||||||||||||||||||||||||||||||||||||||||
751 TACGGAAGTGGCTTTTGGCCTAGTGTGTGCCACTTGTGAGCAGATTGCAG  800

467 ATTCACAGCATCGGTCTCACAGACAGATGGCAACTATCACCAACCCACTA  516
    ||||||||||||||||||||||||||||||||||||||||||||||||||
801 ATTCACAGCATCGGTCTCACAGACAGATGGCAACTATCACCAACCCACTA  850

517 ATCAGACATGAGAACAGAATGGTGCTGGCCAGCACTACAGCTAAGGCTAT  566
    ||||||||||||||||||||||||||||||||||||||||||||||||||
851 ATCAGACATGAGAACAGAATGGTGCTGGCCAGCACTACAGCTAAGGCTAT  900
```

```
567 GGAGCAGATGGCGGGATCAAGTGAGCAGGCAGCGGAAGCCATGGAGATCG    616
    ||||||||||||||||||||||||||||||||||||||||||||||||||
901 GGAGCAGATGGCGGGATCAAGTGAGCAGGCAGCGGAAGCCATGGAGATCG    950

617 CTAATCAGGCTAGGCAGATGGTGCAGGCAATGAGGACAATTGGGACTCAT    666
    ||||||||||||||||||||||||||||||||||||||||||||||||||
951 CTAATCAGGCTAGGCAGATGGTGCAGGCAATGAGGACAATTGGGACTCAT   1000

667 CCTAACTCTAGTGCTGGTCTGAGAGATAATCTTCTTGAAAATTTGCAGGC    716
     ||||||||||||||||||||||||||||||||||||||||||||||||||
1001 CCTAACTCTAGTGCTGGTCTGAGAGATAATCTTCTTGAAAATTTGCAGGC   1050

717 CTACCAGAAACGAATGGGAGTGCAGATGCAGCGATTCAAGTGA
     |||||||||||||||||||||||||||||||||||||||||||
1051 CTACCAGAAACGAATGGGAGTGCAGATGCAGCGATTCAAGTGA
```

All the sequences were cloned and analyzed according to the dislcosed methods above.

Example 25

Generation of Clade 1 H5N1 Influenza A/Viet Nam/1203/04 HA, NA, and M1 Genes Optimized for Efficient Expression in Sf9 Cells The following polypeptides were derived from codon-optimized nucleotides corresponding to A/Viet Nam/1203/04. The nucleotides were designed and synthesized (Geneart GMBH, Regensburg, FRG) as disclosed above (see Example 24).

```
VN1203-ha-cs-opt (modified cleavage site,
underlined)
                                       (SEQ ID NO: 33)
MEKIVLLFAIVSLVKSDQICIGYHANNSTEQVDTIMEKNVTVTHAQDILE

KTHNGKLCDLDGVKPLILRDCSVAGWLLGNPMCDEFINVPEWSYIVEKAN

PANDLCYPGDFNDYEELKHLLSRINHFEKIQIIPKNSWSSHEASLGVSSA

CPYQGKSSFFRNVVWLIKKNNAYPTIKRSYNNTNQEDLLVLWGIHHPNDA

AEQTRLYQNPTTYISVGTSTLNQRLVPKIATRSKVNGQNGRMEFFWTILK

PNDAINFESNGNFIAPEYAYKIVKKGDSAIMKSELEYGNCNTKCQTPMGA

INSSMPFHNIHPLTIGECPKYVKSNRLVLATGLRNSPQRET----RGLFG

AIAGFIEGGWQGMVDGWYGYHHSNEQGSGYAADKESTQKAIDGVTNKVNS

IIDKMNTQFEAVGREFNNLERRIENLNKKMEDGFLDVWTYNAELLVLMEN

ERTLDFHDSNVKNLYDKVRLQLRDNAKELGNGCFEFYHKCDNECMESVRN

GTYDYPQYSEEARLKREEISGVKLESIGTYQILSIYSTVASSLALAIMVA

GLSLWMCSNGSLQCRICI*

VN1203-ha-spc-opt (modified signal peptide,
underlined)
                                       (SEQ ID NO: 34)
Mplykllnvlwlvavsnaip DQICIGYHANNSTEQVDTIMEKNVTVTHA

QDILEKTHNGKLCDLDGVKPLILRDCSVAGWLLGNPMCDEFINVPEWSYI

VEKANPANDLCYPGDFNDYEELKHLLSRINHFEKIQIIPKNSWSSHEASL

GVSSACPYQGKSSFFRNVVWLIKKNNAYPTIKRSYNNTNQEDLLVLWGIH

HPNDAAEQTRLYQNPTTYISVGTSTLNQRLVPKIATRSKVNGQNGRMEFF

WTILKPNDAINFESNGNFIAPEYAYKIVKKGDSAIMKSELEYGNCNTKCQ

TPMGAINSSMPFHNIHPLTIGECPKYVKSNRLVLATGLRNSPQRERRRKK

RGLFGAIAGFIEGGWQGMVDGWYGYHHSNEQGSGYAADKESTQKAIDGVT

NKVNSIIDKMNTQFEAVGREFNNLERRIENLNKKMEDGFLDVWTYNAELL

VLMENERTLDFHDSNVKNLYDKVRLQLRDNAKELGNGCFEFYHKCDNECM

ESVRNGTYDYPQYSEEARLKREEISGVKLESIGTYQILSIYSTVASSLAL

AIMVAGLSLWMCSNGSLQCRICI*

VN1203-ha-sph9-opt (The signal peptide and
cleavage site are italicized)
                                       (SEQ ID NO: 35)
METISLITIL LVVTASNA DQICIGYHANNSTEQVDTIMEKNVTVTHAQ

DILEKTHNGKLCDLDGVKPLILRDCSVAGWLLGNPMCDEFINVPEWSYIV

EKANPANDLCYPGDFNDYEELKHLLSRINHFEKIQIIPKNSWSSHEASLG

VSSACPYQGKSSFFRNVVWLIKKNNAYPTIKRSYNNTNQEDLLVLWGIHH

PNDAAEQTRLYQNPTTYISVGTSTLNQRLVPKIATRSKVNGQNGRMEFFW

TILKPNDAINFESNGNFIAPEYAYKIVKKGDSAIMKSELEYGNCNTKCQT

PMGAINSSMPFHNIHPLTIGECPKYVKSNRLVLATGLRNSPQRERRRKKR

GLFGAIAGFIEGGWQGMVDGWYGYHHSNEQGSGYAADKESTQKAIDGVTN

KVNSIIDKMNTQFEAVGREFNNLERRIENLNKKMEDGFLDVWTYNAELLV

LMENERTLDFHDSNVKNLYDKVRLQLRDNAKELGNGCFEFYHKCDNECME

SVRNGTYDYPQYSEEARLKREEISGVKLESIGTYQILSIYSTVASSLALA

IMVAGLSLWMCSNGSLQCRICI*
```

Example 26

H5N1 Vietnam/1203/2003 VLP Immunogenicity (Extreme Dose Sparing)

Figure 24:
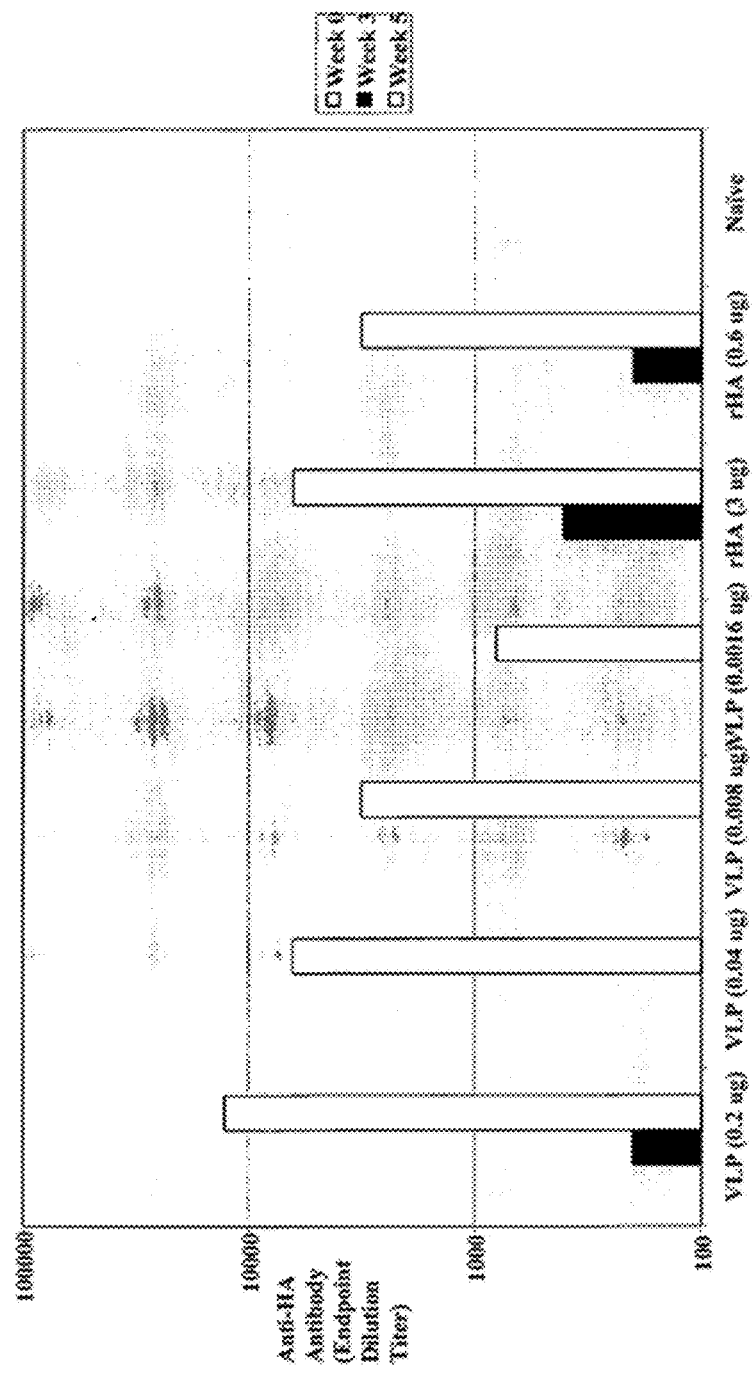
FIG. 24 depicts anti-HA Antibody (Endpoint Dilution Titer) of mice inoculated intramuscularly with H5N1 (Vietnam/1203/2003) VLPs at low doses.
Figure 25:
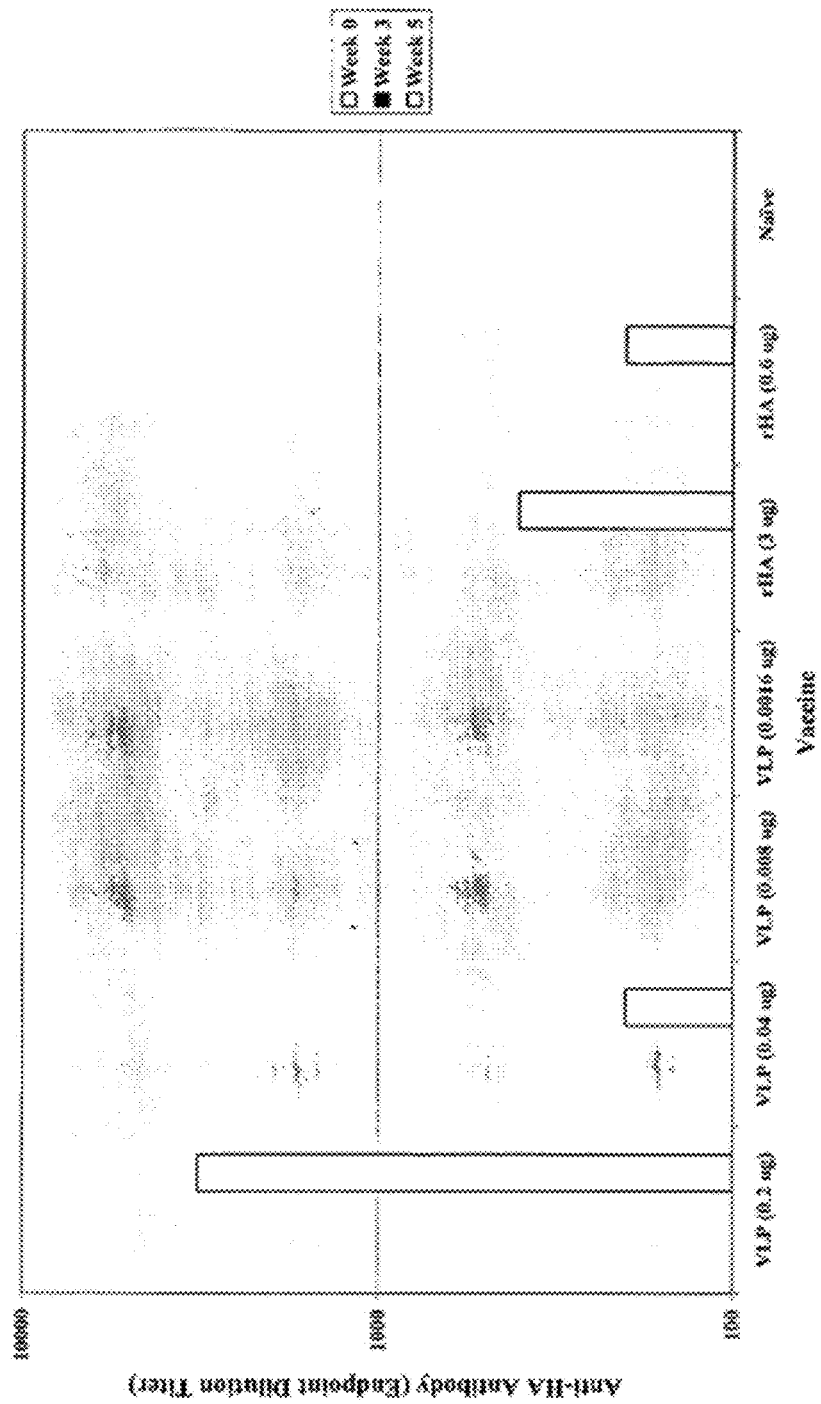
FIG. 25 depicts anti-HA Antibody (Endpoint Dilution Titer) of mice inoculated intranasally with H5N1 (Vietnam/1203/2003) VLPs at low doses.
Figure 26:
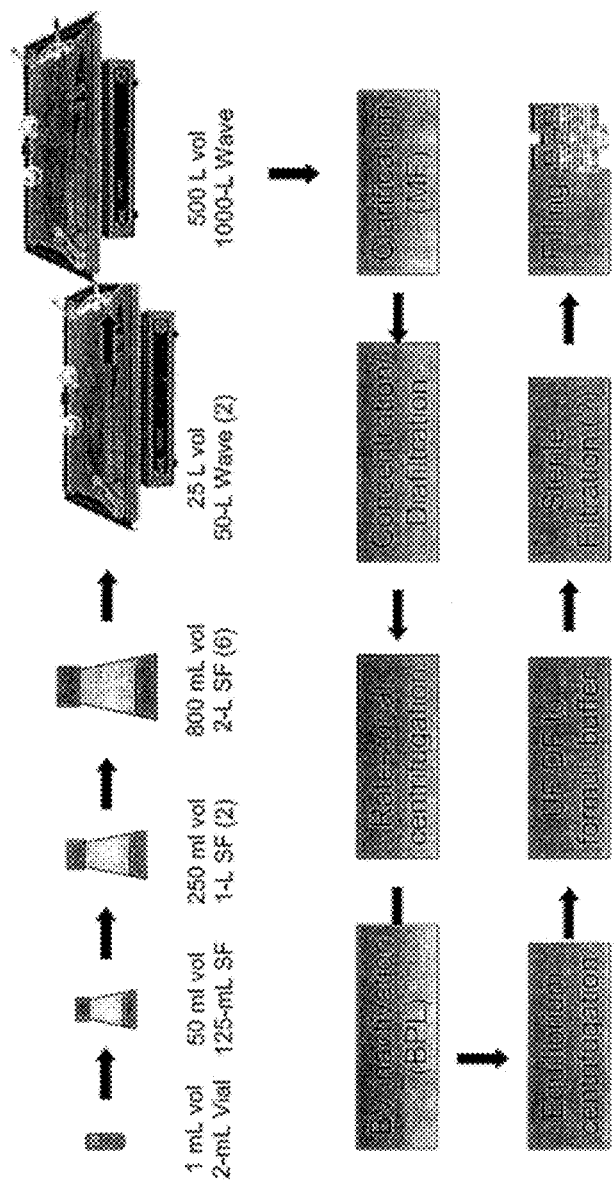
FIG. 26 depicts an example for manufacturing, isolating and purifying VLPs of the invention.

BALB/C mice were immunized intramuscularly and intranasally with H5N1 VLPs at very low doses of VLPs (0.2, 0.04, 0.008, 0.0016 ng HA/dose), Mice were bled on days 0, 21 and 35. The mice were given a boost on day 21. The serum was assayed for anti-HA antibodies by the hemagglutination inhibition assay (HI) using turkey RBCs and influenza virus using an ELISA. Results of this study are shown in FIGS. 24 and 25.

The results indicate that a robust overall immune response was observed when the VLPs were administered intramuscularly at very lose doses. The robustness of the response was similar to control at 3.0 and 0.6 µg HA/dose. These data show see a true dose response and the antibody response to 0.2 µg of VLP is greater than 3.0 µg of rHA protein. Although the response was not as robust for the intranasal administration, a dose of VLPs at 0.2 µg HA/dose did induce a robust response. The ELISA titer with the 0.2 µg dose in this experiment is similar to the 0.12 µg dose of the H3N2 VLP vaccine in previous experiments, see above.

Example 27

Challenge Studies

Figure 27:
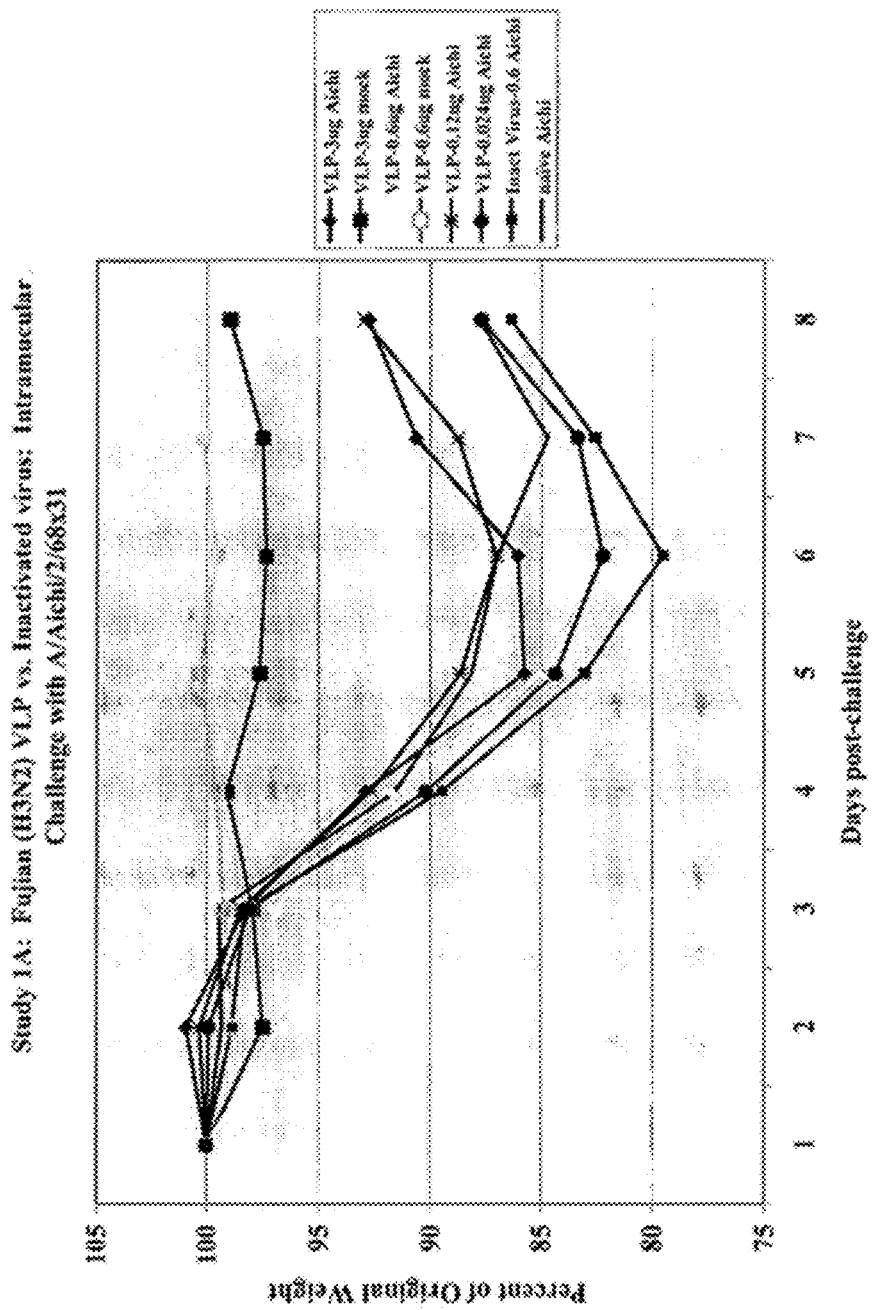
FIG. 27 depicts mice inoculated with H3N2 VLPs given intramuscularly and subsequently challenged intranasally with A/Aichi/2/68x31 (H3N2) virus.
Figure 28:
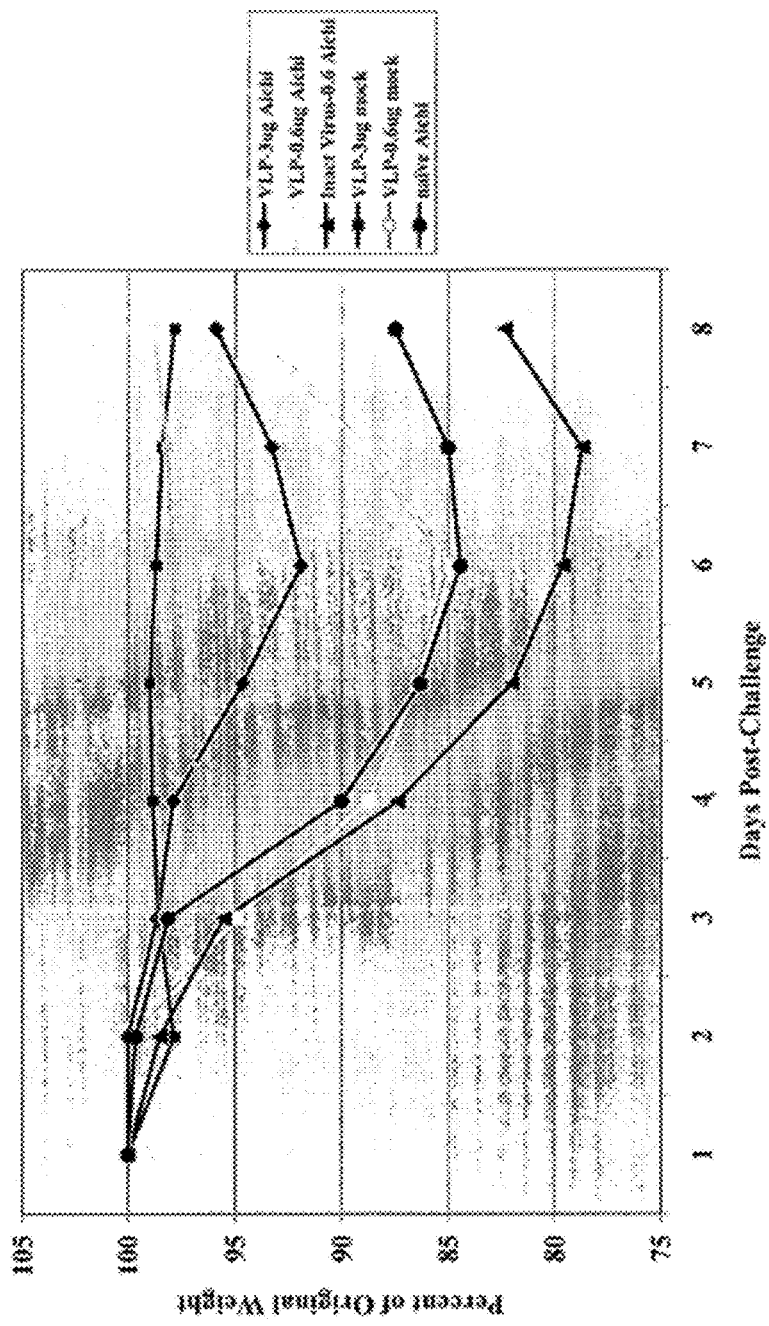
FIG. 28 depicts mice inoculated with H3N2 VLPs given intranasally and subsequently challenged intranasally with A/Aichi/2/68x31 (H3N2) virus.
Figure 30A:
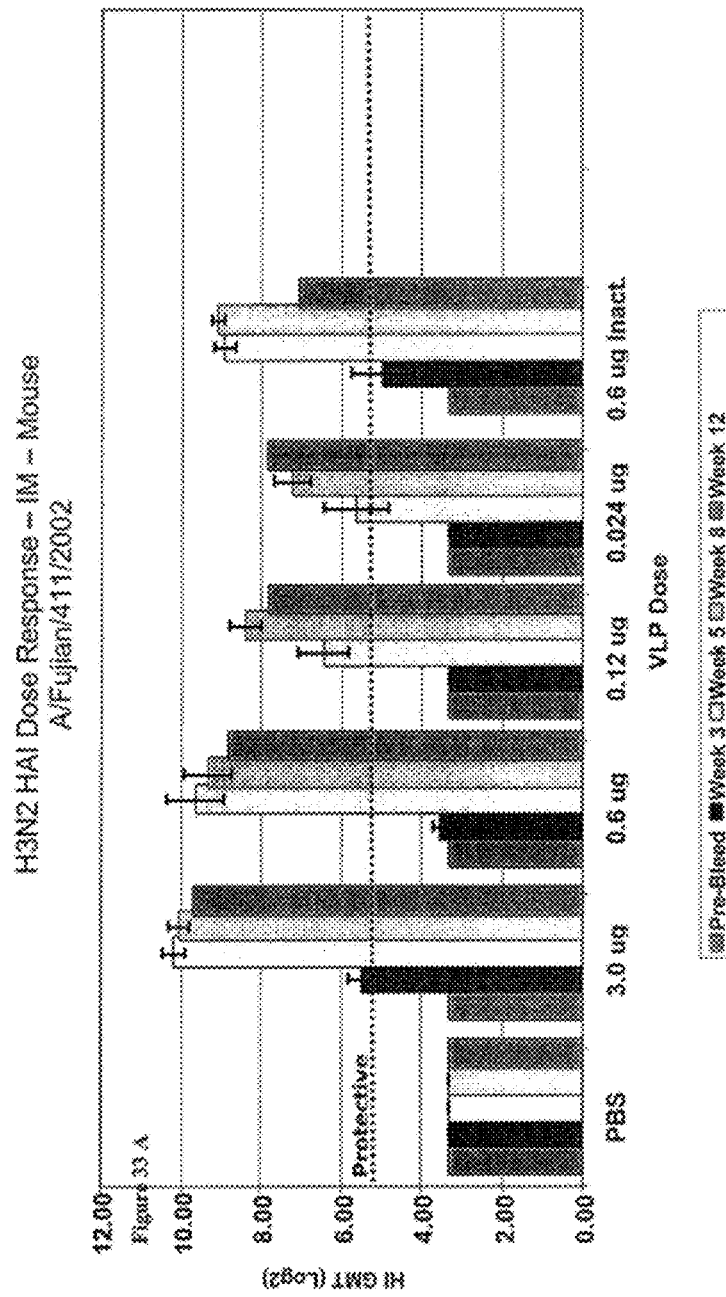
Figure 30B:
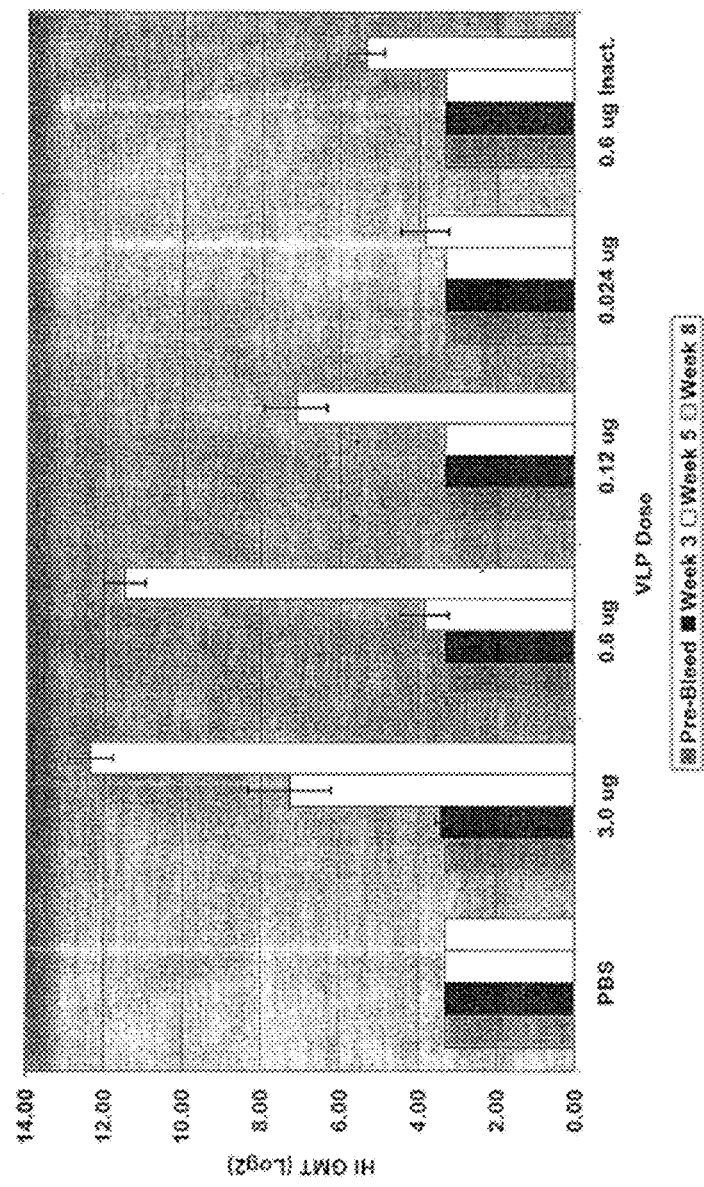
Figure 30E:
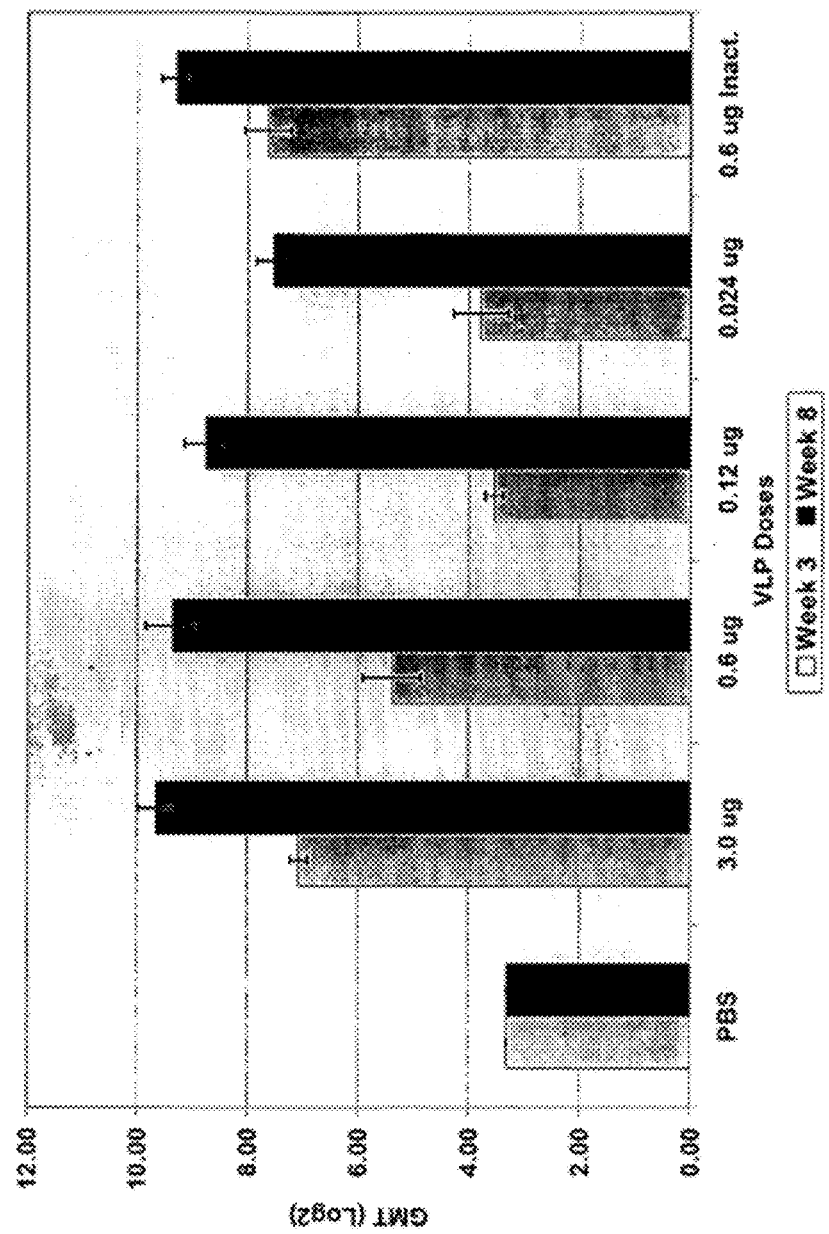
Figure 30H:
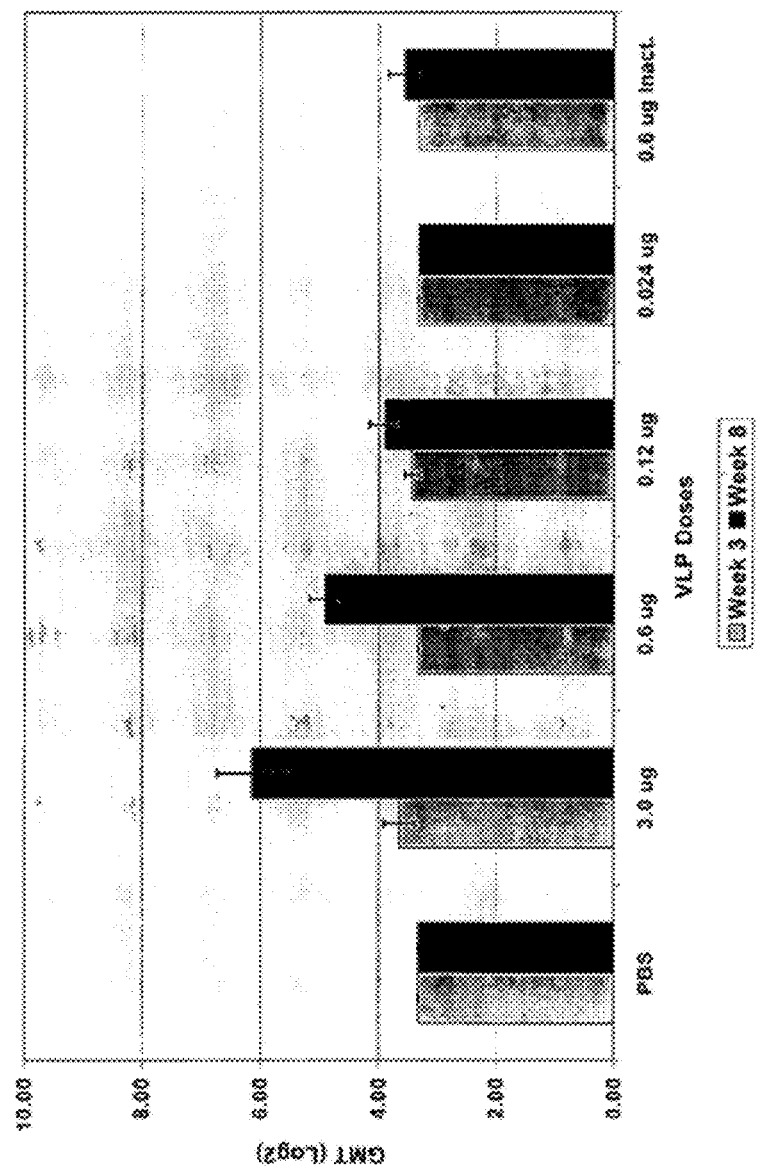

The results indic After inoculating BALB/c mice with VLPs at concentrations of 3 µg, 0.6 µg 0.12 µg and 0.02 µg of H3N2 VLPs intramuscularly and intranasally (total HA dose), mice were challenged with influenza virus A/Aichi/268x31. The results of this study are shown on FIGS. 27 and 28. These data show that there is a decrease in weight in all vaccinated animals, however the animals that were vaccinated with 3.0 µg and 0.12 µg of VLPs recovered quicker than the other animals in both intramuscular and intranasal vaccinations. The intranasal doses provided enhanced protection.

Example 28

Challenge Studies (Ferrets)

In this study, ferrets were vaccinated with H9N2 VLPs. There were a total of 18 ferrets in the challenge study: 6 mock vaccinated, 6 vaccinated with medium dose (1.5 µg), and 6 vaccinated with high dose (15.0 µg) intramuscularly. Next, ferrets were challenged with $10^6$ $EID_{50}$ of A/HK/1073/99 intranasally. Nasal washes were collected on days 1, 3, 5 and 7. The virus in the nasal washes was titered on days 3, 5 and 7 for all animals. These data are represented on Table 2 and in FIG. 29. These data show that by day 7, all of the vaccinated animals had no detectable virus in nasal washes while the mock group had detectable viral titers.

TABLE 2

Wild Type Virus Titers (log 10/ml) in Ferrets after viral challenge

| Ferret | Day 3 | Day 5 | Day 7 |
|---|---|---|---|
| Group: Placebo Mock Control (n = 6) | | | |
| 4512 | 7 | 5.5 | 3.5 |
| 4524 | 6.5 | 6.75 | 1.98 |
| 4525 | 7.5 | 6.5 | 6.75 |
| 4526 | 7.5 | 7.25 | 3.5 |
| 4527 | 6.75 | 7.25 | 2.5 |
| 4528 | 7.5 | 6.25 | 2.75 |
| Mean | 7.125 | 6.583333 | 3.496667 |
| Std. Dev. | 0.44017 | 0.66458 | 1.699137 |
| Group: Low Dose | | | |
| 3916 | 6.75 | 2.75 | 1.5 |
| 3917 | 7.5 | 5.5 | 1.5 |
| 3918 | 7.5 | 6.5 | 1.5 |
| 3919 | 5.5 | 3 | 1.5 |
| 3920 | 6.75 | 2.25 | 1.5 |
| 3921 | 6.5 | 3.5 | 1.5 |

TABLE 2-continued

Wild Type Virus Titers (log 10/ml) in Ferrets after viral challenge

| Ferret | Day 3 | Day 5 | Day 7 |
|---|---|---|---|
| Avg | 6.75 | 3.916667 | 1.5 |
| Std Dev | 0.74162 | 1.693123 | 0 |
| Group: High Dose | | | |
| 3922 | 6.5 | 2.75 | 1.5 |
| 3923 | 6.25 | 3.75 | 1.5 |
| 3924 | 5.75 | 1.5 | 1.5 |
| 3925 | 6.5 | 4.75 | 1.5 |
| 3926 | 6.25 | 3.5 | 1.5 |
| 3927 | 5.75 | 1.5 | 1.5 |
| Avg. | 6.166667 | 2.958333 | 1.5 |
| Std Dev | 0.341565 | 1.298236 | 0 |

Example 29

Mice Intramuscular and Intranasal Inoculation Studies

Mice were inoculated with A/Fujian/411/2002 (H3N2) VLPs at concentrations of 3 µg, 0.6 µg 0.12 µg or 0.024 µg (total HA dose) intramuscularly or intranasally at day 0 and were boosted 3 weeks later. Control mice were inoculated with formalin inactivated A/Wyoming (Fujian-Like, vaccine strain) or PBS. Sera were collected from the inoculated mice at weeks 0, 3, 5 and 8. The collected sera were assayed for anti-HA antibodies by the hemagglutination inhibition assay (HI) for anti-influenza antibodies by ELISA. The assay was conducted using A/Fujian/411/2002, A/Panama/2007/99, A/Wyoming/3/03 and A/New York/55/2004 influenza virus strains of H3N2. Results of this study are shown on FIGS. 30 A-H. These data indicate the H3N2 VLPs induced antibodies against the parent A/Fujian/411/2002 strains of influenza virus and against other H3N2 strains. These data also indicate that the titers in intranasally inoculated mice rise later than intramuscularly inoculated mice. However, the intranasal titers are higher than intramuscular titers after about 8 weeks. In addition, titers to the inactivated virus antigen appear to be comparable to the VLP at equivalent doses following intramuscular inoculation. However, the inactivated antigen does not appear to be as immunogenic following intranasal inoculation, nor is it as broadly protective following intranasal inoculation.

Example 30

Generation of Clade 2 H5N1 Influenza HA, NA, and M1 Genes Optimized for Efficient Expression in Sf9 Cells The following optimized nucleotides and polypeptides corresponding to HA, NA and M1 of Clade 2 H5N1 viruses, A A/Indonesia/5/05, A/Bar headed goose/Qinghai/1A/2005 and A/Anhui/1/2005, were designed and synthesized (Geneart GMBH, Regensburg, FRG) as disclosed above. The optimized nucleotides and polypeptides are listed below. In order to make VLPs, A/Anhui HA can be expressed with A/Indonesia NA and M1. For VLPs comprising A/Quinghai HA and NA, A/Indonesia M1 gene can be co-expressed with A/Quinghai HA and NA.

A/INDONESIA/5/05
A/INDONESIA Optimized HA (Start and stop codon are underlined)

(SEQ ID NO: 42)

GGTACCGGATCCGCCACC<u>ATG</u>GAGAAGATCGTGCTGCTGCTGGCTATCGTGTCCCTGGTG

AAGTCCGACCAGATCTGCATCGGTTACCACGCTAACAACTCCACCGAGCAGGTGGACACC

-continued

```
ATCATGGAGAAGAACGTCACCGTGACCCACGCTCAGGACATCCTCGAAAAGACCCACAAC

GGCAAGCTGTGCGACCTGGACGGTGTCAAGCCCCTGATCCTGCGTGACTGCTCCGTGGCT

GGTTGGCTGCTGGGTAACCCCATGTGCGACGAGTTCATCAACGTGCCCGAGTGGTCCTAC

ATCGTGGAGAAGGCTAACCCCACCAACGACCTGTGCTACCCCGGTTCCTTCAACGACTAC

GAGGAGCTGAAGCACCTGCTGTCCCGTATCAACCACTTCGAGAAGATCCAGATCATCCCC

AAGTCCTCTTGGTCCGACCACGAGGCTTCCTCCGGTGTCTCCTCCGCTTGCCCCTACCTG

GGTTCCCCCTCCTTCTTCCGTAACGTGGTGTGGCTGATCAAGAAGAACTCCACCTACCCC

ACCATCAAGAAGTCCTACAACAACACCAACCAGGAGGACCTGCTGGTCCTGTGGGGTATC

CACCACCCCAACGACGCTGCCGAGCAGACCCGTCTGTACCAGAACCCCACCACCTACATC

TCCATCGGCACCTCCACCCTGAACCAGCGTCTGGTGCCCAAGATCGCTACCCGTTCCAAG

GTGAACGGCCAGTCCGGTCGTATGGAGTTCTTCTGGACCATCCTGAAGCCTAACGACGCT

ATCAACTTCGAGTCCAACGGCAACTTCATCGCTCCCGAGTACGCTTACAAGATCGTGAAG

AAGGGCGACTCCGCTATCATGAAGTCCGAGCTGGAGTACGGTAACTGCAACACCAAGTGC

CAGACCCCCATGGGTGCTATCAACTCCTCCATGCCCTTCCACAACATCCACCCCCTGACC

ATCGGCGAGTGCCCCAAGTACGTGAAGTCCAACCGTCTGGTGCTGGCTACCGGTCTGCGT

AACTCCCCCCAGCGCGAGTCCCGTCGTAAGAAGCGTGGTCTGTTCGGCGCTATCGCTGGT

TTCATCGAGGGCGGTTGGCAGGGCATGGTGGACGGATGGTACGGTTACCACCACTCTAAC

GAGCAGGGTTCCGGTTACGCTGCTGACAAGGAGTCCACCCAGAAGGCTATCGACGGCGTC

ACCAACAAGGTGAACTCCATCATCGACAAGATGAACACCCAGTTCGAGGCTGTGGGTCGT

GAGTTCAACAACCTCGAGCGTCGTATCGAGAACCTGAACAAGAAGATGGAGGACGGTTTC

CTGGACGTGTGGACCTACAACGCCGAGCTGCTGGTGCTGATGGAGAACGAGCGTACCCTG

GACTTCCACGACTCCAACGTGAAGAACCTGTACGACAAGGTCCGCCTGCAGCTGCGTGAC

AACGCTAAGGAGCTGGGTAACGGTTGCTTCGAGTTCTACCACAAGTGCGACAACGAGTGC

ATGGAGTCCATCCGTAACGGCACCTACAACTACCCCCAGTACTCCGAGGAGGCTCGTCTG

AAGCGTGAGGAGATCTCCGGCGTGAAGCTCGAGTCCATCGGAACCTACCAGATCCTGTCC

ATCTACTCCACCGTGGCTTCCTCCCTGGCTCTGGCTATCATGATGGCTGGTCTGTCCCTG

TGGATGTGCTCCAACGGTTCCCTGCAGTGCCGTATCTGCATCTAATGAAAGCTTGAGCTC
```

A/INDONESIA HA Protein Sequence
(SEQ ID NO: 43)

```
MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRRKKRGLFG

AIAGFIEGGW QGMVDGWYGY HHSNEQGSGY AADKESTQKA IDGVTNKVNS

IIDKMNTQFE AVGREFNNLE RRIENLNKKM EDGFLDVWTY NAELLVLMEN

ERTLDFHDSN VKNLYDKVRL QLRDNAKELG NGCFEFYHKC DNECMESIRN

GTYNYPQYSE EARLKREEIS GVKLESIGTY QILSIYSTVA SSLALAIMMA

GLSLWMCSNG SLQCRICI
```

-continued

A/INDONESIA Optimized HA (cleavage site deleted)
(Start and stop codon are underlined)

(SEQ ID NO: 44)

GGATCCGCCACC<u>ATG</u>GAGAAGATCGTGCTGCTGCTGGCTATCGTGTCCCTGGTGAAGTCC

GACCAGATCTGCATCGGTTACCACGCTAACAACTCCACCGAGCAGGTGGACACCATCATG

GAGAAGAACGTCACCGTGACCCACGCTCAGGACATCCTCGAAAAGACCCACAACGGCAAG

CTGTGCGACCTGGACGGTGTCAAGCCCCTGATCCTGCGTGACTGCTCCGTGGCTGGTTGG

CTGCTGGGTAACCCCATGTGCGACGAGTTCATCAACGTGCCCGAGTGGTCCTACATCGTG

GAGAAGGCTAACCCCACCAACGACCTGTGCTACCCCGGTTCCTTCAACGACTACGAGGAG

CTGAAGCACCTGCTGTCCCGTATCAACCACTTCGAGAAGATCCAGATCATCCCCAAGTCC

TCTTGGTCCGACCACGAGGCTTCCTCCGGTGTCTCCTCCGCTTGCCCCTACCTGGGTTCC

CCCTCCTTCTTCCGTAACGTGGTGTGGCTGATCAAGAAGAACTCCACCTACCCCACCATC

AAGAAGTCCTACAACAACACCAACCAGGAGGACCTGCTGGTCCTGTGGGGTATCCACCAC

CCCAACGACGCTGCCGAGCAGACCCGTCTGTACCAGAACCCCACCACCTACATCTCCATC

GGCACCTCCACCCTGAACCAGCGTCTGGTGCCCAAGATCGCTACCCGTTCCAAGGTGAAC

GGCCAGTCCGGTCGTATGGAGTTCTTCTGGACCATCCTGAAGCCTAACGACGCTATCAAC

TTCGAGTCCAACGGCAACTTCATCGCTCCCGAGTACGCTTACAAGATCGTGAAGAAGGGC

GACTCCGCTATCATGAAGTCCGAGCTGGAGTACGGTAACTGCAACACCAAGTGCCAGACC

CCCATGGGTGCTATCAACTCCTCCATGCCCTTCCACAACATCCACCCCCTGACCATCGGC

GAGTGCCCCAAGTACGTGAAGTCCAACCGTCTGGTGCTGGCTACCGGTCTGCGTAACTCC

CCCCAGCGCGAGTCCCGTGGTCTGTTCGGCGCTATCGCTGGTTTCATCGAGGGCGGTTGG

CAGGGCATGGTGGACGGATGGTACGGTTACCACCACTCTAACGAGCAGGGTTCCGGTTAC

GCTGCTGACAAGGAGTCCACCCAGAAGGCTATCGACGGCGTCACCAACAAGGTGAACTCC

ATCATCGACAAGATGAACACCCAGTTCGAGGCTGTGGGTCGTGAGTTCAACAACCTCGAG

CGTCGTATCGAGAACCTGAACAAGAAGATGGAGGACGGTTTCCTGGACGTGTGGACCTAC

AACGCCGAGCTGCTGGTGCTGATGGAGAACGAGCGTACCCTGGACTTCCACGACTCCAAC

GTGAAGAACCTGTACGACAAGGTCCGCCTGCAGCTGCGTGACAACGCTAAGGAGCTGGGT

AACGGTTGCTTCGAGTTCTACCACAAGTGCGACAACGAGTGCATGGAGTCCATCCGTAAC

GGCACCTACAACTACCCCCAGTACTCCGAGGAGGCTCGTCTGAAGCGTGAGGAGATCTCC

GGCGTGAAGCTCGAGTCCATCGGAACCTACCAGATCCTGTCCATCTACTCCACCGTGGCT

TCCTCCCTGGCTCTGGCTATCATGATGGCTGGTCTGTCCCTGTGGATGTGCTCCAACGGT

TCCCTGCAGTGCCGTATCTGCATC<u>TAA</u>TGAAAGCTT

A/INDONESIA HA Protein sequence (SEQ ID NO: 45)

MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PTNDLCYPGS FNDYEELKHL LSRINHFEKI QIIPKSSWSD HEASSGVSSA

CPYLGSPSFF RNVVWLIKKN STYPTIKKSY NNTNQEDLLV LWGIHHPNDA

AEQTRLYQNP TTYISIGTST LNQRLVPKIA TRSKVNGQSG RMEFFWTILK

PNDAINFESN GNFIAPEYAY KIVKKGDSAI MKSELEYGNC NTKCQTPMGA

INSSMPFHNI HPLTIGECPK YVKSNRLVLA TGLRNSPQRE SRGLFGAIAG

FIEGGWQGMV DGWYGYHHSN EQGSGYAADK ESTQKAIDGV TNKVNSIIDK

MNTQFEAVGR EFNNLERRIE NLKKMEDGF LDVWTYNAEL LVLMENERTL

DFHDSNVKNL YDKVRLQLRD NAKELGNGCF EFYHKCDNEC MESIRNGTYN

YPQYSEEARL KREEISGVKL ESIGTYQILS IYSTVASSLA LAIMMAGLSL

WMCSNGSLQC RICI

A/INDONESIA Optimized NA (Start and stop codon are underlined)

(SEQ ID NO: 46)

GGTACCGGATCCGCCACCATGAACCCCAACCAGAAGATCATCACCATCGGCTCCATCTGC

ATGGTGATCGGTATCGTGTCCCTGATGCTGCAGATCGGTAACATGATCTCCATCTGGGTG

TCCCACTCCATCCAGACCGGTAACCAGCACCAGGCTGAGTCCATCTCCAACACCAACCCC

CTGACCGAGAAGGCTGTGGCTTCCGTGACCCTGGCTGGTAACTCCTCCCTGTGCCCCATC

CGTGGTTGGGCTGTGCACTCCAAGGACAACAACATCCGCATCGGTTCCAAGGGTGACGTG

TTCGTGATCCGTGAGCCCTTCATCTCCTGCTCCCACCTCGAGTGCCGTACCTTCTTCCTG

ACCCAAGGTGCTCTGCTGAACGACAAGCACTCCAACGGCACCGTGAAGGACCGTTCCCCC

CACCGTACCCTGATGTCCTGCCCCGTGGGCGAGGCTCCCTCCCCCTACAACTCCCGTTTC

GAGTCCGTGGCTTGGTCCGCTTCCGCTTGCCACGACGGCACCTCTTGGCTGACCATCGGT

ATCTCCGGTCCCGACAACGAGGCTGTCGCTGTGCTGAAGTACAACGGCATCATCACCGAC

ACCATCAAGTCCTGGCGTAACAACATCCTGCGTACCCAGGAGTCCGAGTGCGCTTGCGTG

AACGGTTCCTGCTTCACCGTGATGACCGACGGTCCCTCCGACGGCCAGGCTTCCTACAAG

ATCTTCAAGATGGAGAAGGGCAAGGTGGTGAAGTCCGTGGAGCTGGACGCTCCCAACTAC

CACTACGAGGAGTGCTCTTGCTACCCCGACGCTGGCGAGATCACCTGCGTGTGCCGTGAC

AACTGGCACGGTTCCAACCGTCCCTGGGTGTCCTTCAACCAGAACCTCGAGTACCAGATC

GGTTACATCTGCTCCGGCGTGTTCGGTGACAACCCCCGTCCCAACGACGGAACCGGTTCC

TGCGGTCCCATGTCCCCCAACGGTGCTTACGGTGTCAAGGGCTTCTCCTTCAAGTACGGT

AACGGTGTCTGGATCGGTCGTACCAAGTCCACCAACTCCCGCTCCGGTTTCGAGATGATC

TGGGACCCCAACGGTTGGACCGGCACCGACTCTTCCTTCTCCGTGAAGCAGGACATCGTG

GCTATCACCGACTGGTCCGGTTACTCCGGTTCCTTCGTGCAGCACCCCGAGCTGACCGGT

CTGGACTGCATTCGTCCCTGCTTCTGGGTGGAGCTGATCCGTGGTCGTCCCAAGGAGTCC

ACCATCTGGACCTCCGGCTCCTCCATCTCTTTCTGCGGTGTGAACTCCGACACCGTGTCC

TGGTCCTGGCCCGACGGTGCCGAGCTGCCCTTCACCATCGACAAGTAATGAAAGCTTGAG

CTC

A/INDONESIA NA Protein sequence (SEQ ID NO: 47)

MNPNQKIITI GSICMVIGIV SLMLQIGNMI SIWVSHSIQT GNQHQAESIS

NTNPLTEKAV ASVTLAGNSS LCPIRGWAVH SKDNNIRIGS KGDVFVIREP

FISCSHLECR TFFLTQGALL NDKHSNGTVK DRSPHRTLMS CPVGEAPSPY

NSRFESVAWS ASACHDGTSW LTIGISGPDN EAVAVLKYNG IITDTIKSWR

NNILRTQESE CACVNGSCFT VMTDGPSDGQ ASYKIFKMEK GKVVKSVELD

APNYHYEECS CYPDAGEITC VCRDNWHGSN RPWVSFNQNL EYQIGYICSG

VFGDNPRPND GTGSCGPMSP NGAYGVKGFS FKYGNGVWIG RTKSTNSRSG

FEMIWDPNGW TGTDSSFSVK QDIVAITDWS GYSGSFVQHP ELTGLDCIRP

CFWVELIRGR PKESTIWTSG SSISFCGVNS DTVSWSWPDG AELPFTIDK

A/INDONESIA Optimized M1

(SEQ ID NO: 48)

GGTACCGGATCCGCCACCATGTCCCTGCTGACCGAGGTGGAGACCTACGTGCTGTCCATC

ATCCCCTCCGGTCCTCTGAAGGCTGAGATCGCTCAGAAGCTCGAGGACGTTTTCGCTGGC

-continued

AAGAACACCGACCTCGAGGCTCTGATGGAGTGGCTCAAGACCCGTCCCATCCTGTCCCCC

CTGACCAAGGGTATCCTGGGTTTCGTGTTCACCCTGACCGTGCCCTCCGAGCGTGGTCTG

CAGCGTCGTCGTTTCGTGCAGAACGCTCTGAACGGTAACGGTGACCCCAACAACATGGAC

CGTGCTGTGAAGCTGTACAAGAAGCTGAAGCGCGAGATCACCTTCCACGGTGCTAAGGAG

GTGTCCCTGTCCTACTCCACCGGTGCTCTGGCTAGCTGCATGGGCCTGATCTACAACCGT

ATGGGCACCGTGACCACCGAGGTGGCCTTCGGTCTGGTCTGCGCTACCTGCGAGCAGATC

GCTGACTCCCAGCACCGTTCCCACCGTCAGATGGCTACCATCACCAACCCCCTGATCCGT

CACGAGAACCGTATGGTGCTGGCTTCCACCACCGCTAAGGCTATGGAGCAGATGGCTGGT

TCCTCCGAGCAGGCTGCTGAGGCCATGGAGGTGGCCAACCAGGCTCGTCAGATGGTGCAG

GCTATGCGTACCATCGGCACCCACCCCAACTCCTCCGCTGGTCTGCGTGACAACCTGCTC

GAGAACCTGCAGGCTTACCAGAAGCGTATGGGAGTCCAGATGCAGCGCTTCAAG<u>TAA</u>TGA

AAGCTTGAGCTC

A/INDONESIA M1 Protein sequence
(SEQ ID NO: 49)

MSLLTEVETY VLSIIPSGPL KAEIAQKLED VFAGKNTDLE ALMEWLKTRP

ILSPLTKGIL GFVFTLTVPS ERGLQRRRFV QNALNGNGDP NNMDRAVKLY

KKLKREITFH GAKEVSLSYS TGALASCMGL IYNRMGTVTT EVAFGLVCAT

CEQIADSQHR SHRQMATITN PLIRHENRMV LASTTAKAME QMAGSSEQAA

EAMEVANQAR QMVQAMRTIG THPNSSAGLR DNLLENLQAY QKRMGVQMQR

FK

A/Anhui/1/2005
A/Anhui Optimized HA (Start and stop codon are underlined)
(SEQ ID NO: 50)

GGTACCGGATCCCTCGAG<u>ATG</u>GAGAAGATCGTGCTGCTGCTGGCTATCGTGTCCCTGGTG

AAGTCCGACCAGATCTGCATCGGTTACCACGCTAACAACTCCACCGAGCAGGTGGACACC

ATCATGGAGAAGAACGTCACCGTGACCCACGCTCAGGACATCCTGGAAAAGACCCACAAC

GGCAAGCTGTGCGACCTGGACGGTGTCAAGCCCCTGATCCTGCGTGACTGCTCCGTGGCT

GGTTGGCTGCTGGGTAACCCCATGTGCGACGAGTTCATCAACGTGCCCGAGTGGTCCTAC

ATCGTGGAGAAGGCTAACCCCGCTAACGACCTGTGCTACCCCGGTAACTTCAACGACTAC

GAGGAGCTGAAGCACCTGCTGTCCCGTATCAACCACTTCGAGAAGATCCAGATCATCCCC

AAGTCCTCTTGGTCCGACCACGAGGCTTCCTCCGGTGTCTCCTCCGCTTGCCCATACCAG

GGCACCCCATCTTTCTTCCGTAACGTGGTGTGGCTGATCAAGAAGAACAACACCTACCCC

ACCATCAAGCGTTCCTACAACAACACCAACCAGGAGGACCTGCTGATCCTGTGGGGTATC

CACCACTCCAACGACGCTGCCGAGCAGACCAAGCTGTACCAGAACCCCACCACCTACATC

TCCGTGGGCACCTCCACCCTGAACCAGCGTCTGGTGCCCAAGATCGCTACCCGTTCCAAG

GTGAACGGCCAGTCCGGTCGTATGGACTTCTTCTGGACCATCCTGAAGCCTAACGACGCT

ATCAACTTCGAGTCCAACGGCAACTTCATCGCTCCCGAGTACGCTTACAAGATCGTGAAG

AAGGGCGACTCCGCTATCGTCAAGTCCGAGGTGGAGTACGGTAACTGCAACACCAAGTGC

CAGACCCCCATCGGTGCTATCAACTCCTCCATGCCCTTCCACAACATCCACCCCCTGACC

ATCGGCGAGTGCCCCAAGTACGTGAAGTCCAACAAGCTGGTGCTGGCTACCGGTCTGCGT

AACTCCCCCCTGCGTGAGCGTGGTCTGTTCGGCGCTATCGCTGGTTTCATCGAGGGCGGT

TGGCAGGGCATGGTGGACGGTTGGTACGGTTACCACCACAGCAACGAGCAGGGTTCCGGT

TACGCTGCTGACAAGGAGTCCACCCAGAAGGCTATCGACGGCGTCACCAACAAGGTGAAC

```
TCCATCATCGACAAGATGAACACCCAGTTCGAGGCTGTGGGTCGTGAGTTCAACAACCTG

GAGCGTCGTATCGAGAACCTGAACAAGAAGATGGAGGACGGTTTCCTGGACGTGTGGACC

TACAACGCCGAGCTGCTGGTGCTGATGGAGAACGAGCGTACCCTGGACTTCCACGACTCT

AACGTGAAGAACCTGTACGACAAGGTCCGCCTGCAGCTGCGTGACAACGCTAAGGAGCTG

GGTAACGGTTGCTTCGAGTTCTACCACAAGTGCGACAACGAGTGCATGGAGTCCGTGCGT

AACGGCACCTACGACTACCCCCAGTACTCCGAGGAGGCTCGTCTGAAGCGTGAGGAGATC

TCCGGCGTGAAGCTGGAGTCCATCGGCACCTACCAGATCCTGTCCATCTACTCCACCGTG

GCTTCCTCCCTGGCTCTGGCTATCATGGTGGCTGGTCTGTCCCTGTGGATGTGCTCCAAC

GGTTCCCTGCAGTGCCGTATCTGCATCTAATAATGAGGCGCGCCAAGCTTGAGCTC
```

A/Anhui HA Protein sequence (SEQ ID NO: 51)

```
MEKIVLLLAI VSLVKSDQIC IGYHANNSTE QVDTIMEKNV TVTHAQDILE

KTHNGKLCDL DGVKPLILRD CSVAGWLLGN PMCDEFINVP EWSYIVEKAN

PANDLCYPGN FNDYEELKHL LSRINHFEKI QIIPKSSWSD HEASSGVSSA

CPYQGTPSFF RNVVWLIKKN NTYPTIKRSY NNTNQEDLLI LWGIHHSNDA

AEQTKLYQNP TTYISVGTST LNQRLVPKIA TRSKVNGQSG RMDFFWTILK

PNDAINFESN GNFIAPEYAY KIVKKGDSAI VKSEVEYGNC NTKCQTPIGA

INSSMPFHNI HPLTIGECPK YVKSNKLVLA TGLRNSPLRE RGLFGAIAGF

IEGGWQGMVD GWYGYHHSNE QGSGYAADKE STQKAIDGVT NKVNSIIDKM

NTQFEAVGRE FNNLERRIEN LNKKMEDGFL DVWTYNAELL VLMENERTLD

FHDSNVKNLY DKVRLQLRDN AKELGNGCFE FYHKCDNECM ESVRNGTYDY

PQYSEEARLK REEISGVKLE SIGTYQILSI YSTVASSLAL AIMVAGLSLW

MCSNGSLQCR ICI
```

A/Bar headed goose/Qinghai/1A/2005
A/Qinghai Optimized HA (Start and stop codon are underlined)

(SEQ ID NO: 52)

```
CGGGCGCGGAGCGGCCGCATGGAGAAGATCGTGCTGCTGCTGGCTATCGTGTCTCTGGTCAAGTCCGACCAGATCTGCA

TCGGTTACCACGCTAACAACTCCACCGAGCAGGTGGACACCATCATGGAGAAGAACGTCACCGTGACCCACGCTCAGGA

CATCCTCGAAAAGACCCACAACGGCAAGCTGTGCGACCTGGACGGCGTGAAGCCCCTGATCCTGCGTGACTGCTCCGTG

GCTGGTTGGCTGCTGGGTAACCCCATGTGCGACGAGTTCCTCAACGTGCCCGAGTGGTCCTACATCGTGGAGAAGATCA

ACCCCGCTAACGACCTGTGCTACCCCGGTAACTTCAACGACTACGAGGAGCTGAAGCACCTGCTGTCCCGTATCAACCA

CTTCGAGAAGATCCAGATCATCCCCAAGTCCTCTTGGTCCGACCACGAGGCTTCCTCCGGTGTCTCCTCCGCTTGCCCA

TACCAGGGCCGTTCTTCCTTCTTCCGCAACGTGGTGTGGCTGATCAAGAAGAACAACGCCTACCCCACCATCAAGCGTT

CCTACAACAACACCAACCAGGAGGACCTGCTGGTCCTGTGGGGTATCCACCACCCCAACGACGCTGCCGAGCAGACCCG

TCTGTACCAGAACCCCACCACCTACATCTCCGTGGGCACCTCTACCCTGAACCAGCGTCTGGTGCCCAAGATCGCTACC

CGTTCCAAGGTGAACGGCCAGTCCGGTCGTATGGAGTTCTTCTGGACCATCCTGAAGCCTAACGACGCTATCAACTTCG

AGTCCAACGGCAACTTCATCGCTCCCGAGAACGCTTACAAGATCGTGAAGAAGGGCGACTCCACCATCATGAAGTCCGA

GCTGGAGTACGGCAACTGCAACACTAAGTGCCAGACCCCCATCGGTGCTATCAACTCCTCCATGCCCTTCCACAACATC

CACCCCCTGACTATCGGCGAGTGCCCCAAGTACGTGAAGTCCAACCGTCTGGTGCTGGCTACCGGTCTGCGTAACTCCC

CCCAGATCGAGACTCGTGGTCTGTTCGGCGCTATCGCTGGTTTCATCGAGGGCGGTTGGCAGGGCATGGTGGACGGTTG

GTACGGTTACCACCACTCTAACGAGCAGGGTTCCGGTTACGCTGCTGACAAGGAGTCTACCCAGAAGGCTATCGACGGC

GTCACCAACAAGGTGAACTCCATCATCGACAAGATGAACACCCAGTTCGAGGCTGTGGGTCGTGAGTTCAACAACCTCG

AACGTCGTATCGAGAACCTGAACAAGAAGATGGAGGACGGTTTCCTGGACGTGTGGACCTACAACGCCGAGCTGCTGGT
```

-continued

GCTGATGGAGAACGAGCGTACCCTGGACTTCCACGACTCCAACGTGAAGAACCTGTACGACAAGGTCCGCCTGCAGCTG

CGTGACAACGCTAAGGAGCTGGGTAACGGTTGCTTCGAGTTCTACCACCGTTGCGACAACGAGTGCATGGAGTCCGTGC

GTAACGGCACCTACGACTACCCCAGTACTCCGAGGAGGCTCGTCTGAAGCGTGAGGAGATCTCCGGTGTCAAGCTCGA

ATCCATCGGAACCTACCAGATCCTGTCCATCTACTCCACCGTGGCTTCCTCCCTGGCTCTGGCTATCATGGTGGCTGGT

CTGTCCCTGTGGATGTGCTCCAACGGTTCCCTGCAGTGCCGTATCTGCATC<u>TAA</u>TAATGAGGCGCGCCAAGCTTGTCGA

A/Qinghai HA Protein sequence (SEQ ID NO: 53)

ME

-continued

```
FISCSHLECR TFFLTQGALL NDKHSNGTVK DRSPHRTLMS CPVGEAPSPY

NSRFESVAWS ASACHDGTSW LTIGISGPDN GAVAVLKYNG IITDTIKSWR

NNILRTQESE CACVNGSCFT VMTDGPSNGQ ASYKIFKMEK GKVVKSVELD

APNYHYEECS CYPDAGEITC VCRDNWHGSN RPWVSFNQNL EYQIGYICSG

VFGDNPRPND GTGSCGPVSP NGAYGVKGFS FKYGNGVWIG RTKSTNSRSG

FEMIWDPNGW TGTDSSFSVK QDIVAITDWS GYSGSFVQHP ELTGLDCIRP

CFWVELIRGR PKESTIWTSG SSISFCGVNS DTVSWSWPDG AELPFTIDK
```

Example 31

Human Administration of H5N1 VLPs Vaccines

The purpose of this double-blind, placebo-controlled study was to evaluate the reactogenicity and immunogenicity of H5N1 VLP influenza vaccine (H5N1 VLP) in healthy adults 18 to 40 years of age. The study design evaluates approximately 230 subjects.

Approximately 70 subjects received two doses of a vaccine comprising H5N1 VLPs at a dosage of either 15 μg or 45 μg (or placebo). Of the 70 subjects who were enrolled in this study, 20 subjects where in the 15 μg arm and 50 subjects were in the 45 μg arm. Dosing commenced at 15 μg, which is approximately one third of the total HA antigen content targeted for most seasonal influenza vaccines. Subjects were randomly assigned to receive either two doses (day 0 and day 28) of vaccine or placebo in a 7:3 ratio.

The H5N1 VLP vaccine (H5N1 VLP) used in this study was comprised of virus-like particles (VLPs) containing the hemagglutinin (HA), neuraminidase (NA), and matrix 1 (M1) proteins derived from A/Indonesia/05/2005 (H5N1) influenza virus, which had been extracted and purified from *Spodoptera frugiperda* (Sf9) insect cells infected with a recombinant baculovirus containing the influenza virus genes for HA, NA, and M1. The 45 μg dosages were packaged in single-dose vials, with 0.5 mL dose of the vaccine formulated to contain 45 μg of HA in phosphate buffered saline with 0.5M NaCl at neutral pH. The 15 μg dose was prepared by the clinical site pharmacist by 5:1 dilution of placebo (phosphate buffered saline with 0.5M NaCl at neutral pH) and 180 μg/ml vaccine according to a standard procedure. The H5N1 VLP vaccine was administered by IM injection in the deltoid muscle.

Blood samples for the evaluation were collected at baseline (pre dose 1), approximately 4 weeks later (post dose 1/pre dose 2), approximately 4 weeks post dose 2 and approximately 6 months post dose two. Hemagglutination-inhibition titers and viral neutralization titers were measured utilizing the assays described above. The viruses used for the neutralization studies were wild type, egg-adapted, A/Indo/5/2005 and A/Vietnam/1203/04. Results from this study are shown in the tables below.

TABLE 3

Subject Accounting for Immunogenicity Analyses

| Status | 15 μg HAI & Neut (N = 14) n (%) | 45 μg HAI (N = 35) n (%) | 45 μg Neut (N = 35) n (%) |
|---|---|---|---|
| Randomized | 14 (100) | 35 (100) | 35 (100) |
| Discontinued | 1 (7.1) | 2 (5.7) | 2 (5.7) |
| Samples/results missing | 1 (7.1) | 2 (5.7) | 3 (8.6) |
| Evaluable samples | 12 (85.7) | 31 (88.6) | 30 (85.7) |

Table 4 summarizes the data of neutralizing antibody titers against A/Indo/5/2005 among subjects who received two doses of the H5N1 VLP vaccine at a dose of 15 μg. Three values for neutralizing antibody titers were available for each subject.

TABLE 4

Neutralizing Antibody Titers Against A/Indo/5/2005 (15 μg)

| Subject # | Run #1* | Run #2* | Run #3* | GMT |
|---|---|---|---|---|
| 1 | 5 | 10 | 10 | 7.9 |
| 2 | 20 | 20 | 10 | 15.9 |
| 3 | 10 | 10 | 10 | 10.0 |
| 4 | 20 | 10 | 10 | 12.6 |
| 5 | 10 | 10 | 10 | 10.0 |
| 6 | 10 | 10 | 10 | 10.0 |
| 7 | 5 | 5 | 5 | 5.0 |
| 8 | 40 | 80 | 40 | 50.4 |
| 9 | 10 | 5 | 10 | 7.9 |
| 10 | 40 | 40 | 20 | 31.7 |
| 11 | 5 | 5 | 5 | 5.0 |
| 12 | 5 | 5 | 5 | 5.0 |
| Group GMT | 11.2 | 11.2 | 10.0 | 10.8 |

*Run 1 - passed; Run 2 - plate failure and $TCID_{50}$ titer for Indonesia virus was outside of set range; Run 3 - controls failed but $TCID_{50}$ titer within range; Results for all 3 runs were consistent (within 2-fold)

Table 5 summarizes hemagglutination inhibition (HAI) from individuals who received two doses of the of the H5N1 VLP vaccine at a dose of 45 μg.

TABLE 5

HAI Responses* (VLP Vaccine at 45 μg)

| | n (%) | |
|---|---|---|
| Immunologic Parameter | HAI against A/Indo/5/05 N = 31 | HAI against A/VN/1203/04 N = 31 |
| Titer ≥ 1:10 | 17 (55) | 4 (13) |
| Titer ≥ 1:20 | 15 (48) | 3 (10) |
| Titer ≥ 1:40 | 10 (32) | 2 (7) |

TABLE 5-continued

HAI Responses* (VLP Vaccine at 45 µg)

n (%)

| Immunologic Parameter | HAI against A/Indo/5/05 N = 31 | HAI against A/VN/1203/04 N = 31 |
|---|---|---|
| 4-fold rise from baseline | 15 (48) | 3 (10) |
| GMT (95% CI) | 14.6 (9.8, 21.9) | 6.4 (4.9, 8.4) |

*No subjects had detectable antibody at baseline
No placebo recipients had detectable antibody Table 6 summarizes neutralizing antibody responses among subjects who received two doses of the H5N1 VLP vaccine at a dose of 45 µg.

TABLE 6

Neutralizing Antibody Responses* n (%)

| Immunologic Parameter | Neut. Antibody against A/Indo/5/05 N = 30 | Neut. Antibody against A/VN/1203/04 N = 30 |
|---|---|---|
| Titer ≥ 1:10 | 25 (83) | 5 (17) |
| Titer ≥ 1:20 | 19 (63) | 0 (0) |
| Titer ≥ 1:40 | 14 (47) | 0 (0) |
| 4-fold rise from baseline | 19 (63) | 0 (0) |
| GMT (95% CI) | 32.8 (21.3, 50.6) | 5.7 (5.1, 6.4) |

*No subjects had detectable antibody at baseline.
No placebo recipients had detectable antibody.

These data show that among healthy adults who received two injections of H5N1 VLP influenza vaccine at a dose of 15 µg, there was an induction immunologic activity (neutralizing antibody) against the homologous A/Indo/5/05 influenza strain (Table 4). In addition, a vaccine dose of 45 µg was immunogenic with respect to HAI and neutralizing antibody responses against the homologous A/Indo/5/05 influenza strain (Tables 5 and 6). Moreover, antibody responses against the A/Viet Nam/1203/04 strain were observed in a limited number of subjects. Thus, these data show that administering influenza VLPs of the invention to a human can induce a protective (HAI Titer ≥1:40) immune response.

Example 32

Expressing Seasonal and Avian VLPs from Two Baculovirus Vectors

Seasonal and avian influenza M1 and HA proteins were cloned and expressed in a baculovirus expression system. In this example, the A/Indonesia/5/05 was cloned into a one baculovirus and the HA and/or NA was cloned in another baculovirus vector. Both viruses were co infected into Sf9 insect cells and grown under conditions that allow VLP formation. Cells comprising either seasonal HA and M1, avian HA and M1 or a combination of seasonal and avian HA and M1 were grown under conditions that allow formation of VLPs. The seasonal influenza strains used for these experiments were A/Fujian/411/2002 and A/Wisconsin/67/2005 and the avian influenza strain used was A/Indonesia/5/05.

Next, the VLPs were harvested and isolated from the supernatant by centrifugation and by a discontinuous sucrose step gradient. The fraction comprising the VLPs was collected from the top of the gradient. The VLPs isolated from the sucrose gradient were analyzed by SDS-PAGE and western immunoblot. These data are on illustrated on FIGS. 1 and 2.

Figure 31:
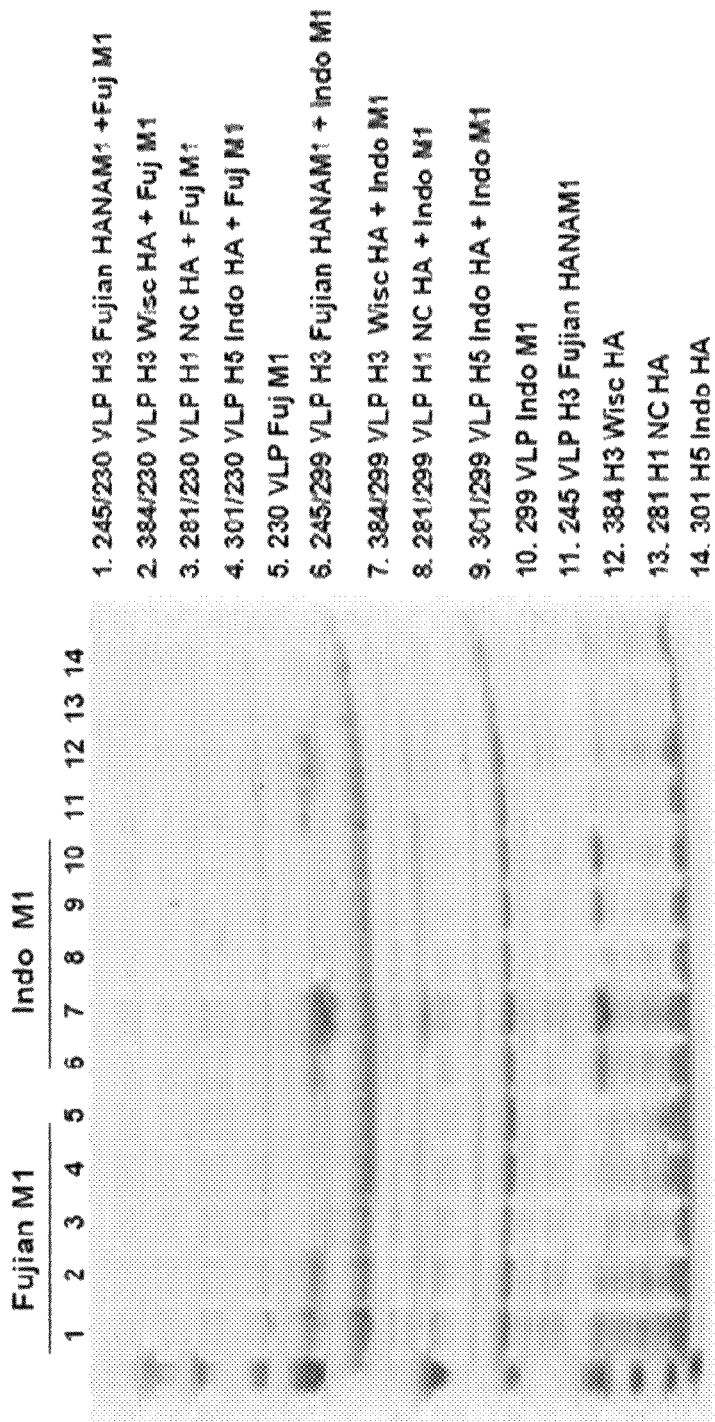
FIG. 31 depicts a stained SDS-PAGE gel derived from VLPs made from different constructs after isolation from a sucrose gradient.

FIG. 31 is a stained SDS-PAGE gel. The lanes in the gel comprise the following: 1 to 5, A/Fujian M1 with 4 different HAs or alone; 6 to 10, A/Indo/M1 with 4 different HAs or alone; 11 to 14, various controls.

Comparing the bands on the gel, the lanes that comprise VLPs comprising avian M1 have stronger bands of M1 and HA in the same lanes, while the lanes that comprise seasonal influenza do not. M1 and HA bands in the same lane is indicative of HA associating with M1. This association is indicative of VLP formation comprising HA and M1. These data provide evidence that avian influenza proteins form VLPs more efficiently than seasonal influenza M1 either with homologous or heterologous envelopes. These data also show that M1 from avian influenza is strongly expressed and stable when compared to seasonal influenza M1.

Figure 32:
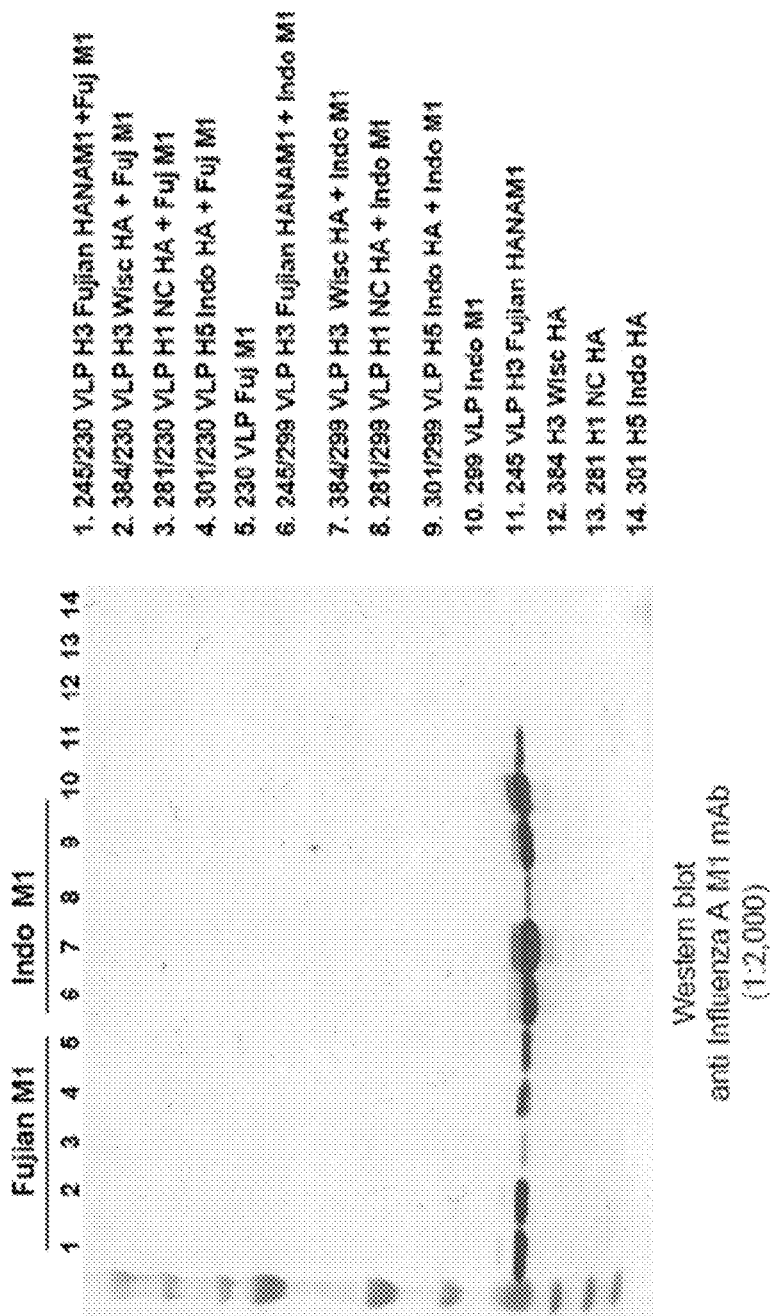
FIG. 32 depicts a stained western blot derived from VLPs made from different constructs after isolation from a sucrose gradient.

FIG. 32 is a western blot showing M1 expression. This blot shows that avian influenza M1 is strongly expressed as compared to seasonal M1. The intensity of the bands indicate that there is more M1, and thus, more VLPs.

Example 33

Expressing Seasonal and Avian VLPs from One Baculovirus Vector

Seasonal and avian influenza M1 and HA proteins were cloned and expressed in a baculovirus expression system. This example, the A/Indonesia/5/05 M1 and A/Fujian/411/2002 HA and NA was cloned into a one baculovirus vector. The recombinant virus was infected into Sf9 insect cells and grown under conditions that allow VLP formation. Cells comprising either seasonal HA and M1, avian HA and M1 or a combination of seasonal and avian HA and M1 were grown under conditions that allow formation of VLPs. The seasonal influenza strains used for these experiments were A/Fujian/411/2002 and A/Wisconsin/67/2005 and the avian influenza strain used was A/Indonesia/5/05.

Next, VLPs were harvested and isolated from the supernatant by centrifugation and by a discontinuous sucrose step gradient. The fraction comprising the VLPs was collected from the top of the gradient. The VLPs isolated from the sucrose gradient were analyzed by SDS-PAGE and western immunoblot. These data are on illustrated on FIGS. 3 and 4.

Figure 33:
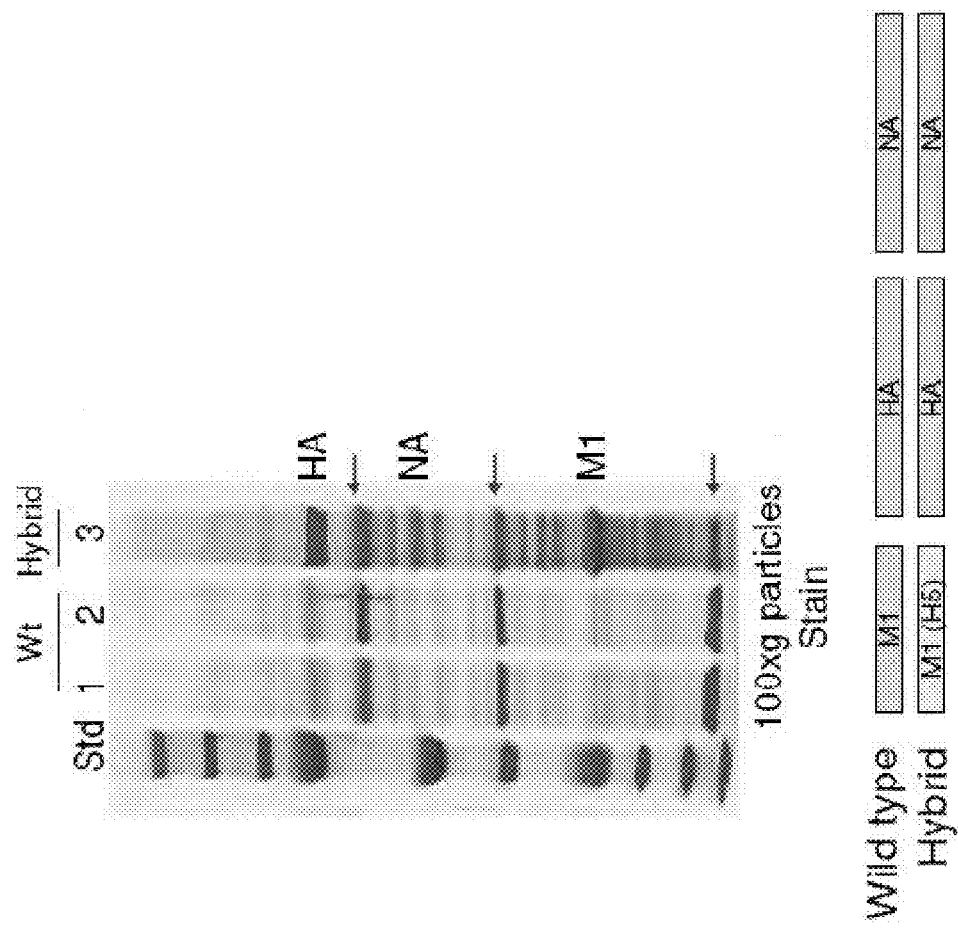
FIG. 33 is a stained SDS-PAGE gel derived from VLPs made from wild type or hybrids of A/Indonesia/5/05 M1 and A/Fujian/411/2002 HA and NA.

FIG. 33 is a stained SDS-PAGE gel. The lanes in the gel comprise the following: 1 and 2 is A/Fujian VLPS (M1, HA and NA) and lane 3 comprises, A/Indo/M1 with A/Fujian HA and NA.

Comparing the bands on the gel, the lane that comprise VLPs from A/Indo/M1 has stronger bands of M1 and HA in the same lanes, while the lanes that comprise A/Fujian do not. M1, HA and NA bands in the same lane is indicative of HA and NA associating with M1. This association is indicative of VLP formation comprising HA, NA, and M1. These data provide evidence that avian influenza proteins form VLPs with greater efficiency than seasonal M1 influenza based VLPs. These data also show that M1 from avian influenza is strongly expressed and stable when compared to seasonal influenza M1.

Figure 34:
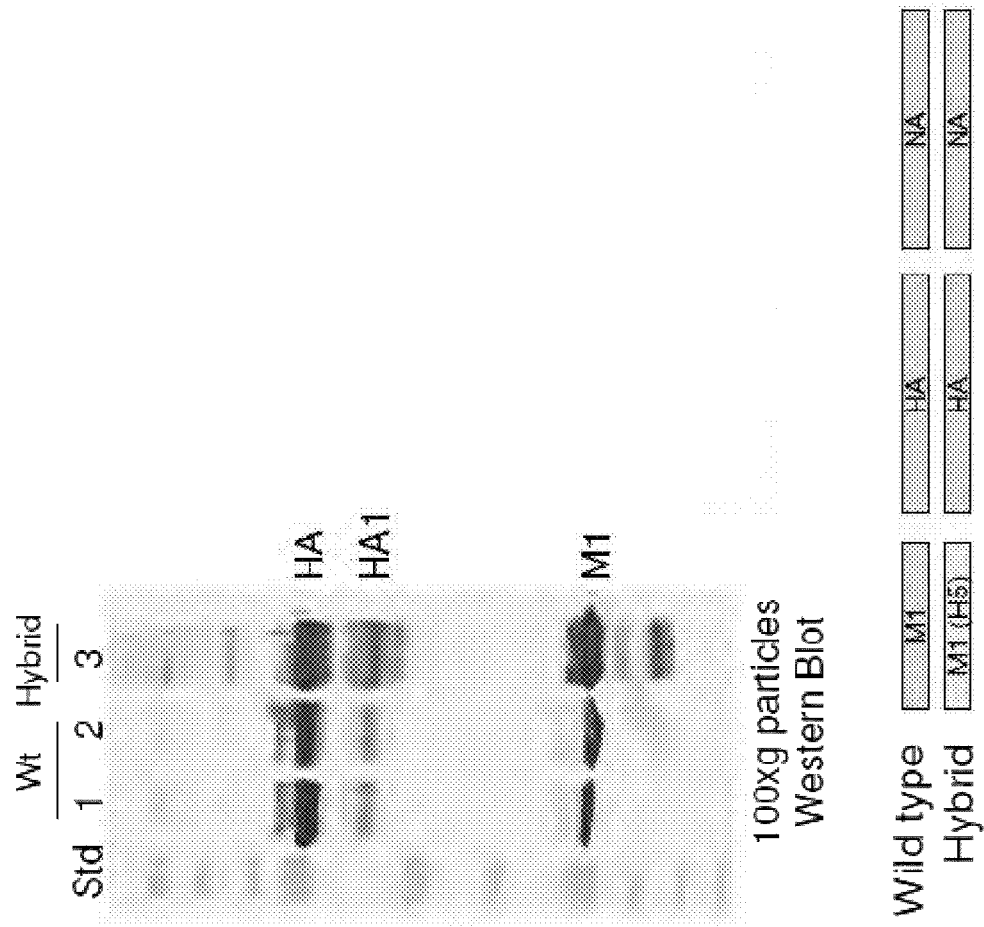
FIG. 34 depicts a stained western blot derived from VLPs made from wild type or hybrids of A/Indonesia/5/05 M1 and A/Fujian/411/2002 HA and NA.

FIG. 34 is a western blot showing M1 expression. This blot shows that VLPs comprising endo A/Indo/M1 and A/Fujian HA, NA are strongly expressed as compared to A/Fujian VLPs. The intensity of the bands indicate that there is more M1, HA and NA in lanes with avian M1 VLPs, and thus, more VLPs.

Example 34

Expressing Chimeric Influenza B HA and NA Constructs Using Common A/Indonesia/5/05 Matrix Protein to Assemble VLPs The sequences below depict the transmembrane and terminal sequences derived from A/Indonesia/5/05 HA and NA (underlined). The transmembrane and terminal sequences of HA and NA molecules can be determined using software prediction by GCG/Accelrys or similar software, as well as by other methods. The exact location of junctions for Indonesia/5/05 sequences can vary.

The sequences below are examples of a chimeric B strain HA with an A/Indonesia/5/05 HA end as well as a chimeric B strain NA with an A/Indo NA substitution of the endodomain and transmembrane regions. These sequences are co-expressed in a baculovirus expression system with an avian influenza M1 protein to produce chimeric VLPs that express influenza B antigens on the surface of VLPs.

Example 35

Making Chimeric VLPs with Coronavirus S Protein
Materials and Methods

*Spodoptera frugiperda* Sf9 insect cells (ATCC CRL-1711) were maintained as suspension in HyQ-SFX insect serum free medium (HyClone, Logan, Utah) at 28° C. A Bac-to-Bac baculovirus expression system (Invitrogen, Carlsbad, Calif.) was used with pFastBac 1 transfer vector in *E. coli* DH10Bac cells for the generation of recombinant baculovirus vectors expressing SARS S and Influenza M1 genes.

SARS coronavirus (SARS-CoV) Urbani strain spike (S) protein amino acids sequence was obtained from NCBI access number AAP13441. The hemagglutinin amino acids sequence of influenza A virus (A/Indonesia/5/05(H5N1)) was obtained from NCBI access number ABP51969. To construct the chimeric SARS S protein, the transmembrane and carboxyl terminal domain (TM/CT) of S protein (aa 1196-1255) was removed, and the TM/CT from Indonesia

```
Hemagglutinin, HA, from Influenza B virus (B/Hong Kong/557/2000) ABL76892
                                                               (SEQ ID NO: 78)
    1  mkaiivllmv vtsnadrict gitssnsphv vktatqgevn vtgviplttt ptkshfanlk 61  gtrtrgklcp dclnctdldv algrpmcvgt tpsakasilh evrpvtsgcf pimhdrtkir 121  qlpnllrgye nirlstqnvi daekapggpy rlgtsgscpn atsksgffat mawavpkdnn 181  knatnpltve vpyvcteged qitvwgfhsd nktqmknlyg dsnpqkftss angvtthyvs 241  qiggfpdqte dgglpqsgri vvdymvqkpg ktgtivyqrg vllpqkvwca sgrskvikgs 301  lpligeadcl hekygglnks kpyytgehak aigncpiwvk tplklangtk yrppakllke 361  rgffgaiagf leggwegmia gwhgytshga hgvavaadlk stqeainkit knlnslsele 421  vknlqrlsga mdelhneile ldekvddlra dtissqiela vllsnegiin sedehllale 481  rklkkmlgps avdigngcfe tkhkcnqtcl driaagtfna gefslptfds lnitaaslnd 541  dgldnhtQIL SIYSTVASSL ALAIMMAGLS LWMCSNGSLQ CRICI Neuraminidase, NA, from Flu B/Shanghai/361/02 ISDN129538
                                                               (SEQ ID NO: 79)
MNPNQKIITIGSICMVIGIVSLMLQIGNMISSDILLKFSTTEITAPTMPLDCANASNVQAVNRSATKGVTLLLPE

PEWTYPRLSCPGSTFQKALLISPHRFGETKGNSAPLIIREPFIACGPKECKHFALTHYAAQPGGYYNGTREDRNK

LRHLISVKLGKIPTVENSIFHMAAWSGSACHDGKEWTYIGVDGPDSNALLKIKYGEAYTDTYHSYANNILRTQES

ACNCIGGNCYLMITDGSASGISECRFLKIREGRIIKEIFPTGRVKHTEECTCGFASNKTIECACRDNSYTAKRPF

VKLNVETDTAEIRLMCTETYLDTPRPDDGSITGPCESNGNKGSGGIKGGFVHQRMASKIGRWYSRTMSKTKRMGM

GLYVKYDGDPWIDSDALALSGVMVSMEEPGWYSFGFEIKDKKCDVPCIGIEMVHDGGKETWHSAATAIYCLMGSG

QLLWDTVTGVDMAL

M1 from A/Indonesia
                                                               (SEQ ID NO: 49)
MSLLTEVETY VLSIIPSGPL KAEIAQKLED VFAGKNTDLE ALMEWLKTRP

ILSPLTKGIL GFVFTLTVPS ERGLQRRRFV QNALNGNGDP NNMDRAVKLY

KKLKREITFH GAKEVSLSYS TGALASCMGL IYNRMGTVTT EVAFGLVCAT

CEQIADSQHR SHRQMATITN PLIRHENRMV LASTTAKAME QMAGSSEQAA

EAMEVANQAR QMVQAMRTIG THPNSSAGLR DNLLENLQAY QKRMGVQMQR

FK
```

H5N1 HA (aa 531-568) was added after amino acid 1195 of S protein. The amino acids sequence of the chimeric S-HA protein is shown in FIG. 35 (SEQ ID NO: 62). The matrix protein 1 (M1) amino acids sequence of influenza Indonesia H5N1 was obtained from NCBI access number ABW06359 (FIG. 36).

Figure 37:
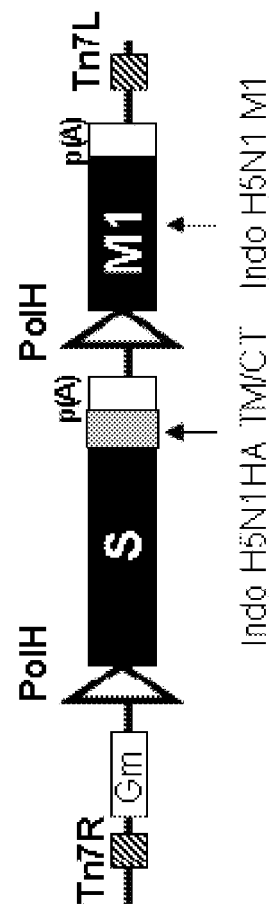
FIG. 37 depicts pFastBac 1 vector containing coding sequences for SARS S with Indonesia H5N1 HA TM/CT domain and Indonesia H5N1 M1 protein.

The codon optimized DNA sequences of M1 and chimeric S for expression in insect cells were synthesized by Geneart (Germany) and subcloned into BamHI and HindIII sites of pFastBac 1 individually. The SnaBI/PuvI fragment containing M1 coding sequence of pFastBac1-M1 was cut and inserted into the HpaI/PvuI fragment containing S coding sequence from pFastBac1-S. The result tandem vector that expresses two proteins is shown in FIG. 37. This vector was used to transform DH10Bac to obtain the bacmid which was tranfected into Sf9 cell to obtain the recombinant baculovirus.

VLPs Expression, Purification and Characterizations

Sf9 insect cells were infected for 64 hours at a cell density of $2\times10^6$ cells/ml with recombinant baculoviruses that express both chimeric SARS S and Indo M1 at a MOI=1. Culture supernatants were harvest by centrifuge at 4000 g. The cell free supernatants were concentrated by ultrafiltration (UF) with a 500 kDa MWCO hollow fiber filter (GE healthcare). The retentate was buffer exchanged with diafiltration (DF) to 25 mM TrisCl pH 8.0, 300 mM NaCl. The UF/DF retentate was loaded on an ion exchange column (Fractogel TMAE, EMD) equilibrium in the same buffer. VLPs passed through from the column while baculovirus and DNA bound to the column. The flow through fractions containing VLPs were further concentrated with ultrafiltration before load to a Sephacryl S500 size exclusion column (GE healthcare).

The pool of VLPs peak from size exclusion column was analyzed with SDS-PAGE (4-12% Bis-Tris NuPage, Invitrogen) and densitometry for purity. The VLPs were also analyzed with particle size analyzer (Malvern Zetasizer NanoSeries NanoZS) and electron microscopy. The antibodies used in this study were from the following vendors: rabbit anti-SARS S and normal anti-rabbit IgG (IMGNEX), rabbit anti-SARS M (Abgent), mouse anti-influenza M1 (Serotec).

Results

Figure 38:
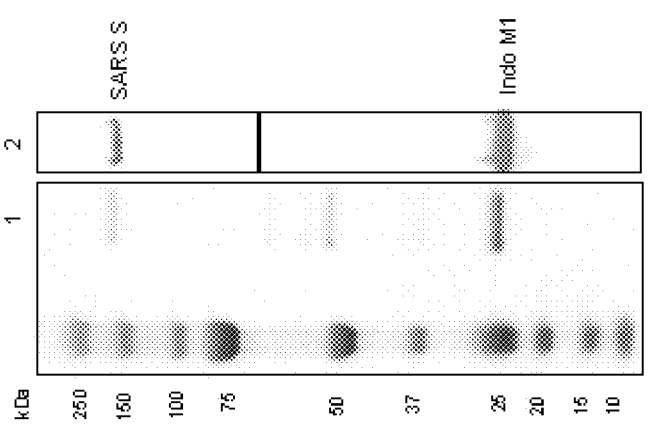
FIG. 38 depicts the purified SARS S/Indo M1 chimeric VLPs. Lane 1 is coomassie blue stain. Lane 2 is western blot, top panel: anti SARS S; bottom panel: anti influenza M1.

Purified SARS S/Indo M1 chimeric VLPs were analyzed by SDS-PAGE, densitometry and western blot (FIG. 38). The purity for SARS S protein was 13.7% and purity for Indo M1 protein was 67.6%. The combined purity for the S and M1 is 81.3%. The western blot confirmed the identity of S and M1 (FIG. 38, lane 2).

Figure 39:
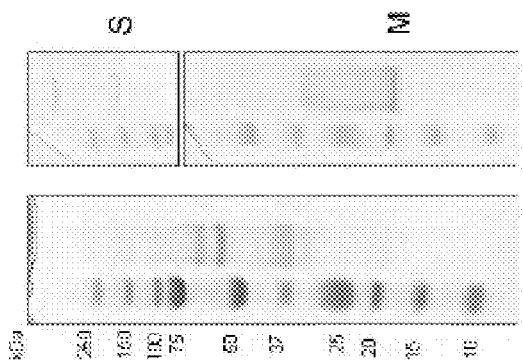
FIGS. 39A and 39B depict purified wild type SARS VLPs composed of SARS S, M and E proteins.

Recombinant baculovirus that expressed SARS spike (S), membrane (M) and envelope (E) proteins in a tandem manner were also expressed. We expressed and purified the wild type SARS VLPs with the same protocol that was used to purify chimeric VLPs. The purity of wild type SARS VLPs (no influenza proteins) were analyzed by SDS-PAGE and western blot (FIG. 39). The S and M proteins can hardly be seen in the Coomassie-stained gel and the contaminant proteins were much more prominent. The data indicate that wild type SARS VLPs are insufficient to form in the baculovirus insect cell expression system while the SARS S/Indo M1 chimeric VLPs an greatly improve the yield and purity of the product VLPs.

Figure 40:
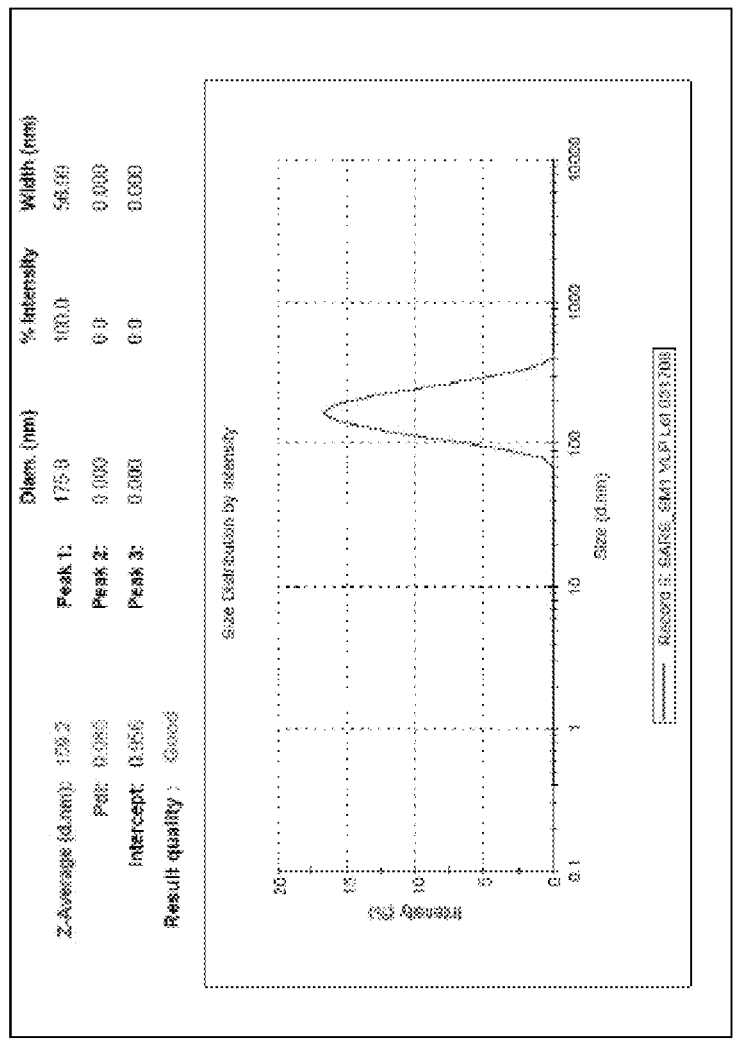
FIG. 40 depicts particle size analysis result for SARS S/Indo M1 chimeric VLPs with Malvern Zetasizer.
Figure 41B:
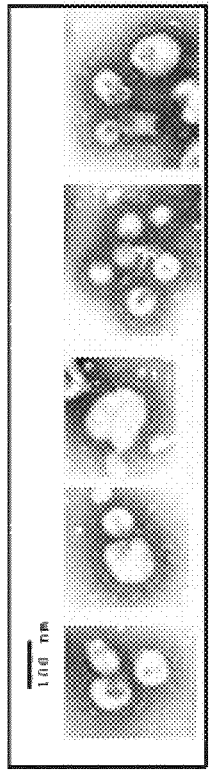
FIGS. 41A, 41B, and 41C depict electron microscope (EM) negative stain of SARS S/Indo M1 chimeric VLPs.
Figure 41A:
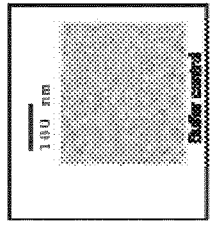
Figure 41C:
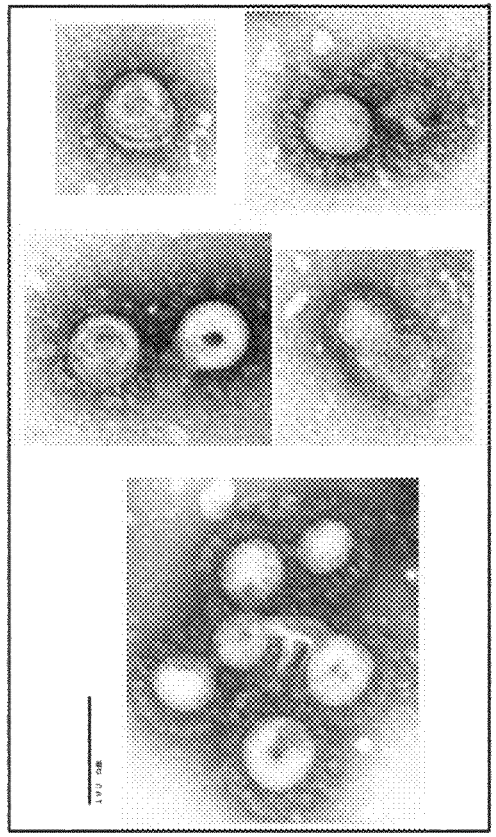
Figure 42:
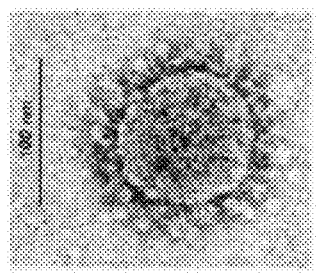
FIGS. 42A, 42B, and 42C depict Published EM images for SARS-CoV and coronavirus.
Figure 42:
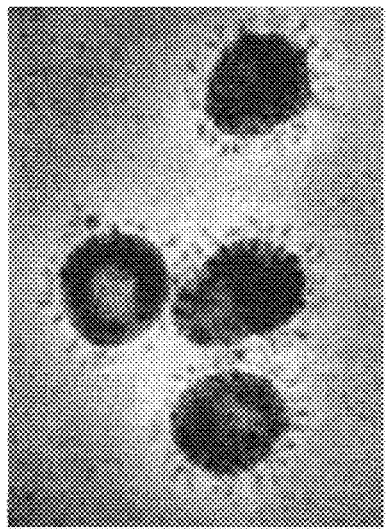
Figure 42:
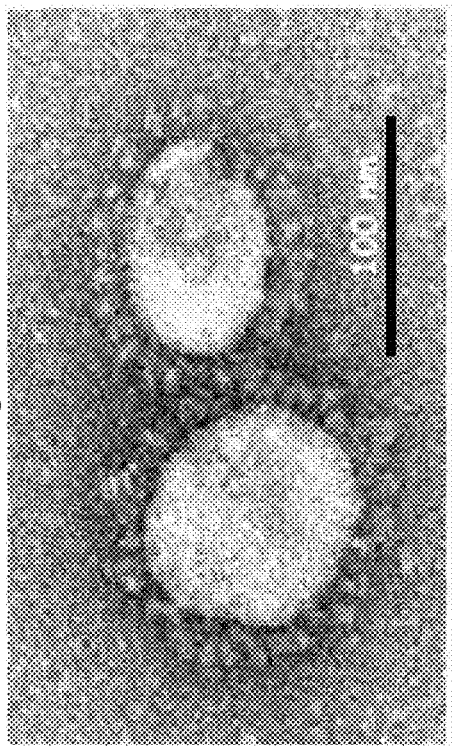

Next, we analyzed the average particle size of purified chimeric VLPs to be 159.2 nm (FIG. 40). The chimeric VLPs were imaged with electron microscopy (EM) negative stain (FIG. 41). The size and morphology of chimeric VLPs are very similar to the published EM images of SARS coronavirus (FIG. 42). They are about 100 nm diameter with corona structure on the outer rim. The immuno-gold EM with anti-SARS S antibody confirmed that SARS S proteins were located on the surface of chimeric VLPs (FIG. 12).

The inventors have engineered a chimeric VLP comprising the major spike (S) gene of coronavirus (CoV) that causes SARS. A CoV S chimeric envelope glycoprotein was made by replacing the transmembrane and C-terminus (endodomain) with analogous sequences from the avian influenza HA (A/Indonesia/5/05 H5N1 strain). Unexpected high levels of SARS VLPs were produced in Sf9 insect cells infected with a baculovirus expressing the chimeric SARS S glycoprotein and the avian M1 matrix protein. Chimeric VLPs comprising S protein have the morphology that is nearly identical to the wild type CoV with the recombinant, chimeric S spike protein forming a corona (crown)—envelope in a lipid envelope on spherical particles with an avian influenza M1 core. These recombinant chimeric SARS-avian flu VLPs are efficiently produced in insect cells and were purified as described above.

These data provide an excellent example that avian M1, e.g. Indonesia H5N1 M1 protein, can form chimeric VLPs with surface antigen from other virus such as SARS-CoV. The chimeric VLPs with avian influenza protein as backbone can be purified through a manufacturing friendly procedure that requires only two steps of chromatography. The size and morphology of the chimeric VLPs are similar to the wild type viruses that carry the same surface antigen.

Example 36

Chimeric Influenza B VLPs

Influenza B virus antigen is an important component of seasonal influenza vaccines. The expression levels of influenza B antigen are critically important for ensuring timely delivery of sufficient number of influenza vaccine doses, otherwise vaccine shortages can occur. Influenza B VLPs for B/Florida/4/06 consist of three proteins, HA (SEQ ID NO: 73), NA (SEQ ID NO: 68), and M1 (SEQ ID NO: 77), which are assembled into VLP structure. HA and NA genes where obtained by RT-PCR from the influenza B/Florida/4/06 virus. In order to improve expression levels of influenza B VLPs, VLPs using three different M1 proteins were made. One M1 protein is derived from the B/Florida/4/06 virus. The second M1 gene is derived from influenza B/Ann Arbor/1/1986 strain, which is often used for preparation of live reassortant influenza B viruses in current influenza vaccine industry. The third M1 is derived from avian influenza A/Indonesia/5/05 (H5N1) virus. Thus, three types of influenza B/Florida/4/06 VLPs have been produced in Sf9 cells, and expression levels have been compared.

Methods.

Figure 43:
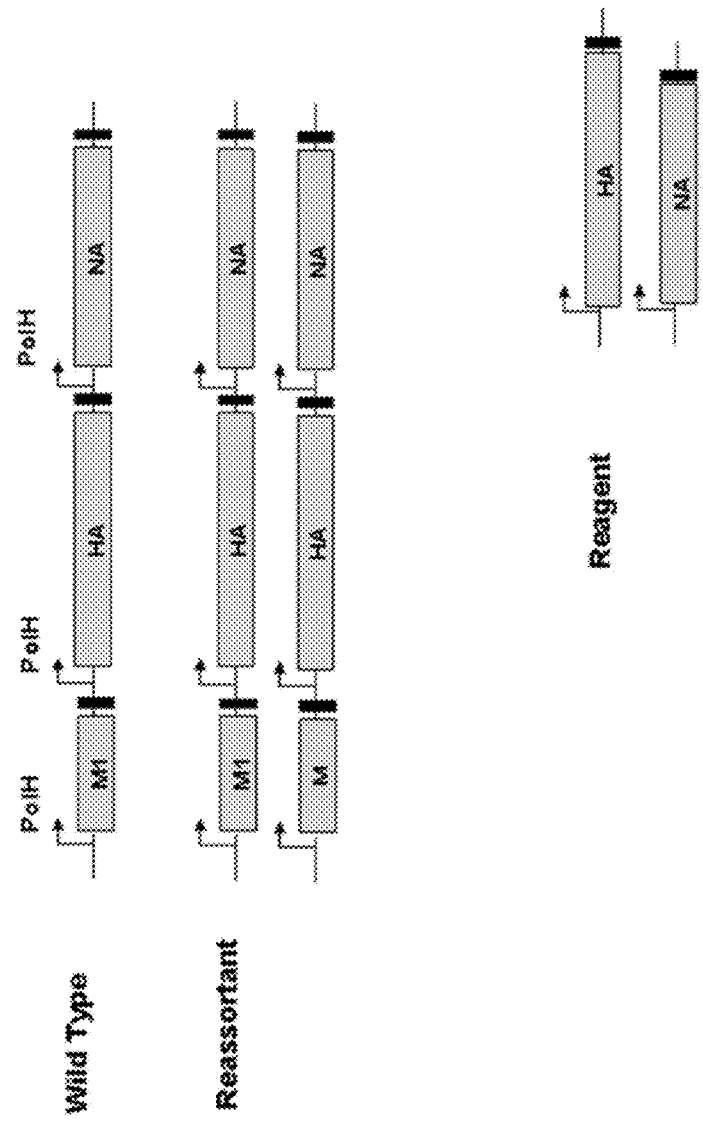
FIG. 43 depicts expression constructs for production of B/Florida/4/06 VLPs in Sf9 insect cells. Shown are the location of HA, NA, and M1 genes, as well as locations of polyhedron promoter. Also shown are the constructs for individual expression of HA and NA genes for reagent purposes.

Baculoviruses were engineered to express full length HA, NA, and M1 genes of influenza. HA and NA genes where obtained by RT-PCR from the influenza B/Florida/4/06 virus. M1 gene has been also generated by RT-PCR from the influenza B/Florida/4/06 virus. Alternatively, M1 gene of B/Ann Arbor/1/1986 was synthesized (GeneArt, Germany) and M1 gene of influenza A/Indonesia/5/05 (H5N1) was also synthesized (GeneArt, Germany). Each gene was cloned into a pFastBac1 vector under the control of the baculovirus polyhedrin promoter (Invitrogen). Then, HA, NA, and M1 genes were combined into tandem vectors as shown on FIG. 43. Then, tandem gene constructs were transferred to an AcMNPV baculovirus bacmid vectors (Invitrogen), the Bacmid DNAs were purified and used to transfect Sf9 insect cells. The resulting recombinant baculoviruses were plaque-purified and virus stocks prepared in Sf9 cells.

Figure 44:
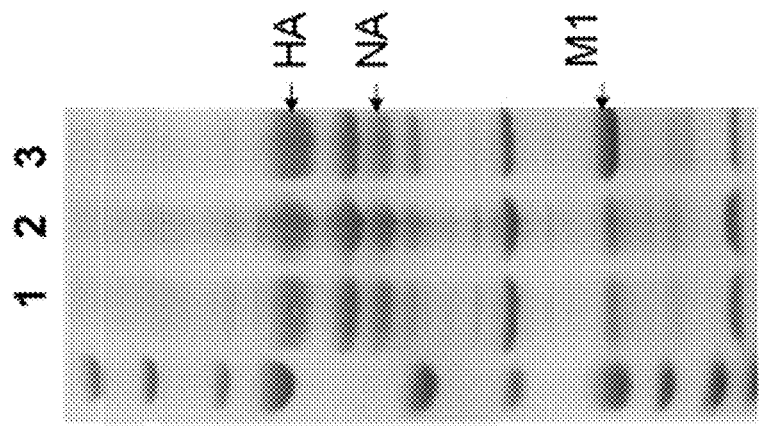
FIG. 44 depicts expression levels of influenza B/Florida/4/06 VLPs by Coomassie staining (left panel) and HA/NA assays (right panel). Lane 1. Sample of B/Florida/4/06 VLPs containing B/Florida/4/06 M1, Lane 2. Sample of B/Florida/4/06 VLPs containing B/Ann Arbor/1/1986 M1, Lane 3 Sample of B/Florida/4/06 VLPs containing A/Indonesia/5/05 (H5N1) M1. The right panels shows HA and NA activity by the hemagglutination and neuraminidase enzyme activity essays.

About 30 ml of Sf9 cells, at about $2 \times 10^6$ cells/ml in a 125 ml shaker flasks, were infected with recombinant baculoviruses expressing HA, NA, and M1 genes at a multiplicity of infection (MOI) of 1-3 infectious particles per ml (pfu), incubated at 27° C. with constant shaking, then harvested at 66-72 hours post infection. The media was removed by low speed centrifugation. Then, media were clarified using filtration through 0.45 µM filters and the media were subjected to ultracentrifugation for 1 hour at 26,000 rpm through 30% sucrose layer. Pellets were resuspended in 200 ml of PBS and analyzed by SDS-PAGE and western blot (FIG. 14). Resuspended pellets were also analyzed for ability to agglutinate guinea pig red blood cells in vitro. The data are shown on FIG. 44. The resuspended pellets have been also analyzed by negative staining transmission electron microscopy.

Results.

Figure 45:
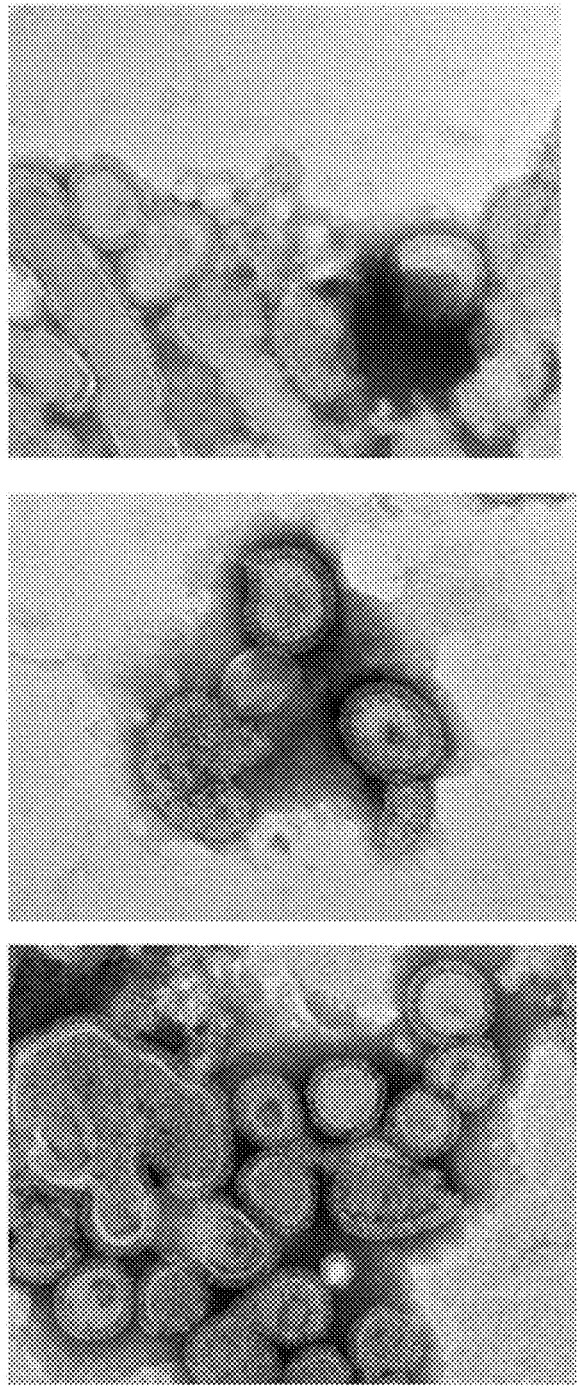
FIG. 45 depicts Electron microscopy of purified VLPs. Negative staining transmission electron microscopy of influenza B/Florida/4/06 VLPs containing M1 from A/Indonesia/5/05 (H5N1) (left), B/Ann Arbor/1/1986 (middle), and B/Florida/4/06 (right).

M1 derived from influenza A/Indonesia/5/05 (H5N1) showed significantly higher expression levels by Coomassie gel staining (FIG. 44, lane 3) compared to VLPs made using B/Florida/4/06 M1 or B/Ann Arbor/1/1986 M1. Also, HA titers of VLPs containing influenza A/Indonesia/5/05 (H5N1) M1, were 4-8 times higher as compared to the other two VLP types. Electron microscopy of VLPs containing influenza A/Indonesia/5/05 (H5N1) M1 had higher concentration of VLP and more regular spherical shape as compared to the other two VLPs (FIG. 45).

Example 37

Making Chimeric VLPs with RSV F1 Protein

*Spodoptera frugiperda* Sf9 insect cells are maintained and grown as essentially described above. The codon optimized DNA sequences of influenza M1 (SEQ ID NO: 48) and chimeric RSV F1 (HA TM/CY (SEQ ID NO: 80) for expression in insect cells are synthesized and subcloned into pFastBac 1. The result vector expresses both proteins. This vector is used to transform DH10Bac to obtain the bacmid which is transfected into Sf9 cell to obtain the recombinant baculovirus.

Sf9 insect cells are infected for 64 hours at a cell density of $2 \times 10^6$ cells/ml with recombinant baculoviruses that express both chimeric RSV F1 and Indo M1 at a M01=1. Culture supernatants are harvest by centrifuge at 4000 g. The cell free supernatants are concentrated by ultrafiltration (UF) with a 500 kDa MWCO hollow fiber filter (GE Healthcare). The retentate is buffer exchanged with diafiltration (DF) to 25 mM TrisCl pH 8.0, 300 mM NaCl. The UF/DF retentate is loaded on an ion exchange column (Fractogel TMAE, EMD). VLPs pass through from the column while baculovirus and DNA binds to the column. The flow through fractions containing VLPs are further concentrated with ultrafiltration before loading onto a Sephacryl S500 size exclusion column (GE Healthcare).

The pool of VLPs peak from size exclusion column is analyzed with SDS-PAGE (4-12% Bis-Tris NuPage, Invitrogen) and densitometry for purity. The VLPs are also analyzed with particle size analyzer (Malvern Zetasizer NanoSeries NanoZS), SDS PAGE, western blot analysis, and electron microscopy.

Example 38

Figure 46:
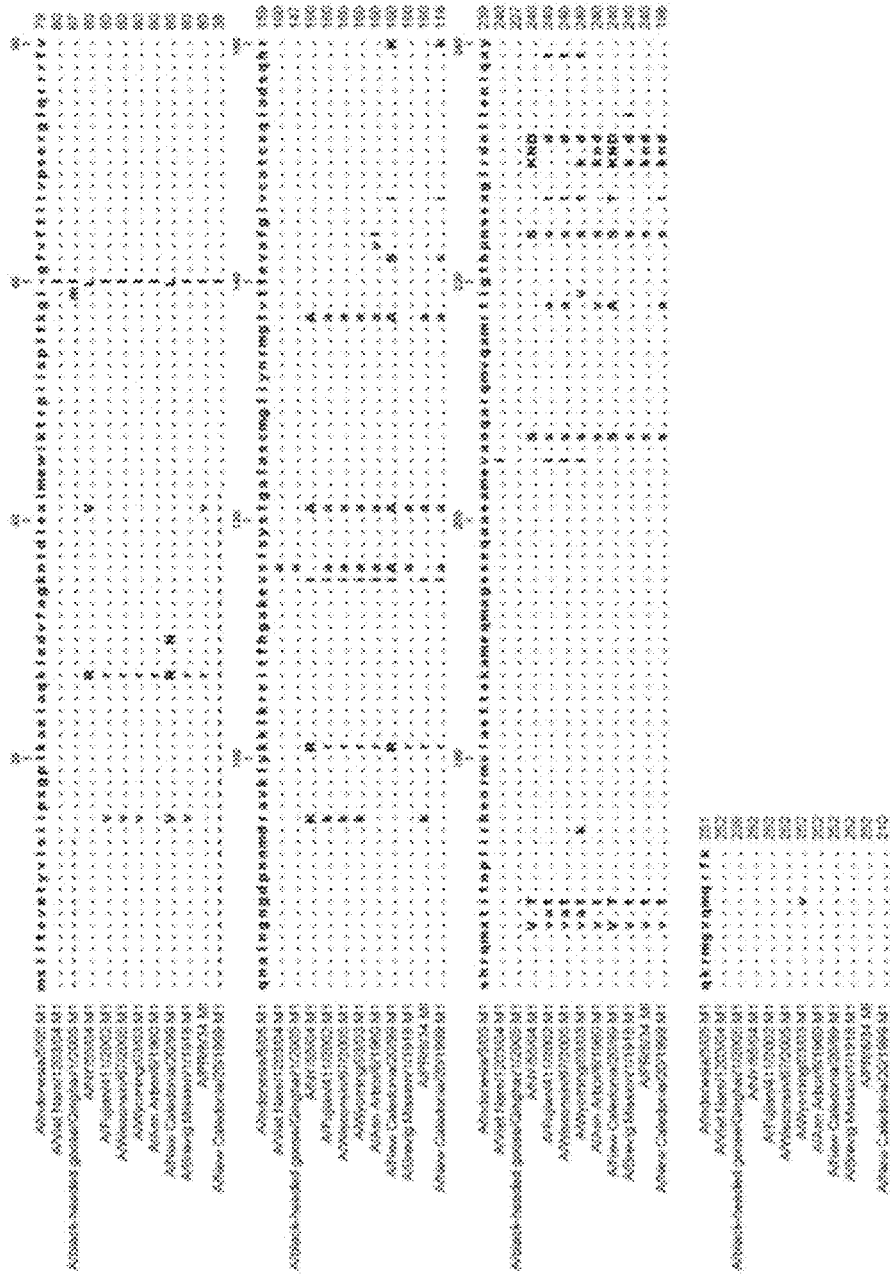
FIG. 46 depicts the M1 amino acid sequences of three avian influenza strains and a variety of seasonal and pandemic human influenza strains. A/Indonesia/5/05 M1 (SEQ ID NO: 49).

Avian Influenza Proteins Comprise an L Domain Sequence Conferring Highly Efficient VLP Production To identify the key structural elements responsible for the VLP-forming efficiency of avian M1 proteins, the M1 amino acid sequences of three avian influenza strains were aligned with the M1 sequences from a variety of seasonal and pandemic human influenza strains (FIG. 46). The alignments revealed that avian influenza virus strains contain the sequence "YKKL" at amino acids 100-103 of the M1 protein. In contrast, human influenza M1 proteins, which exhibit poor VLP-forming capacity, harbor "YRKL" at amino acids 100-103 of the M1 protein. These four amino acids represent a motif called the late domain (L-domain) which is important in recruiting host components required for budding and release of virus particles.

Figure 47:
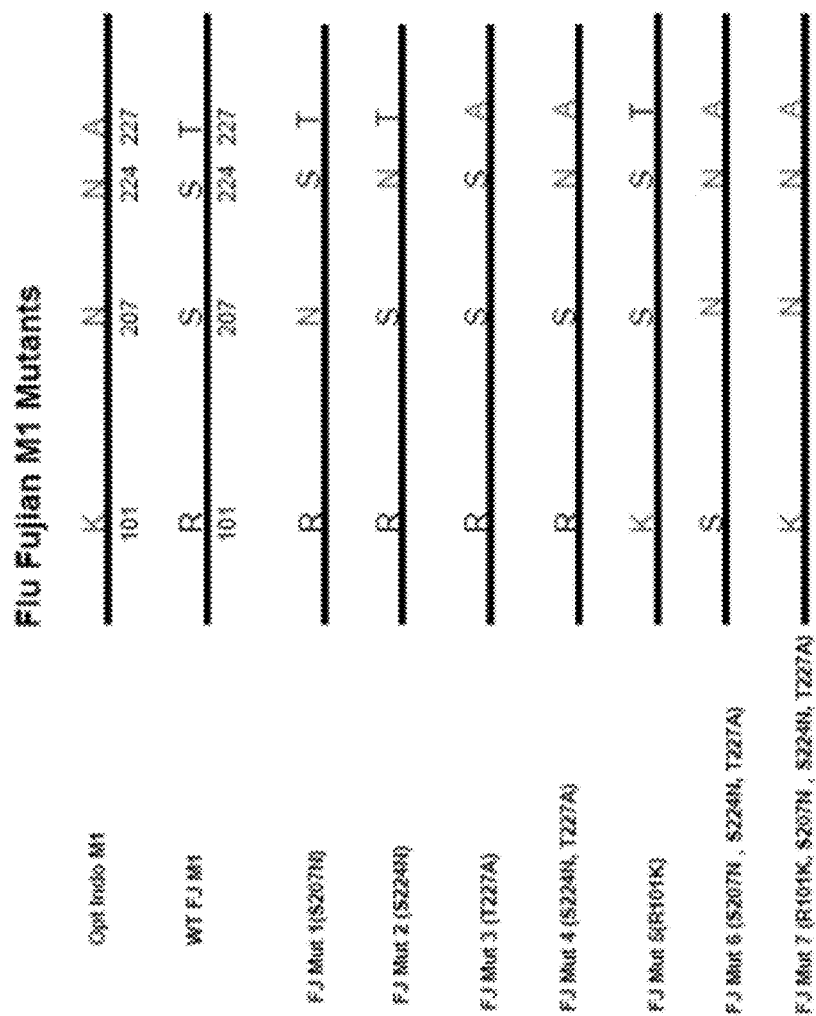
FIG. 47 depicts the amino acid changes in seven A/Fujian mutants generated by site-directed mutagenesis.

To evaluate the significance of the YKKL L-domain, site-directed mutagenesis experiments were performed using the human seasonal strain A/Fujian/411/02 containing the YRKL L-domain sequence. FIG. 47 shows the amino acid changes in seven A/Fujian mutants generated by site-directed mutagenesis. Four mutants have only a single point mutation introduced: FJ Mutant 1 (S207N), FJ Mutant 2 (S224N), FJ Mutant 3, (T227A) and FJ Mutant 5 (R101K) and three mutants have combined two, three or four mutations introduced: FJ Mutant 4 (S224N, T227A), FJ Mutant 6 (S207N, S224N, T227A), FJ Mutant 7 (R101K, S207N, S224N, T227A).

Figure 48:
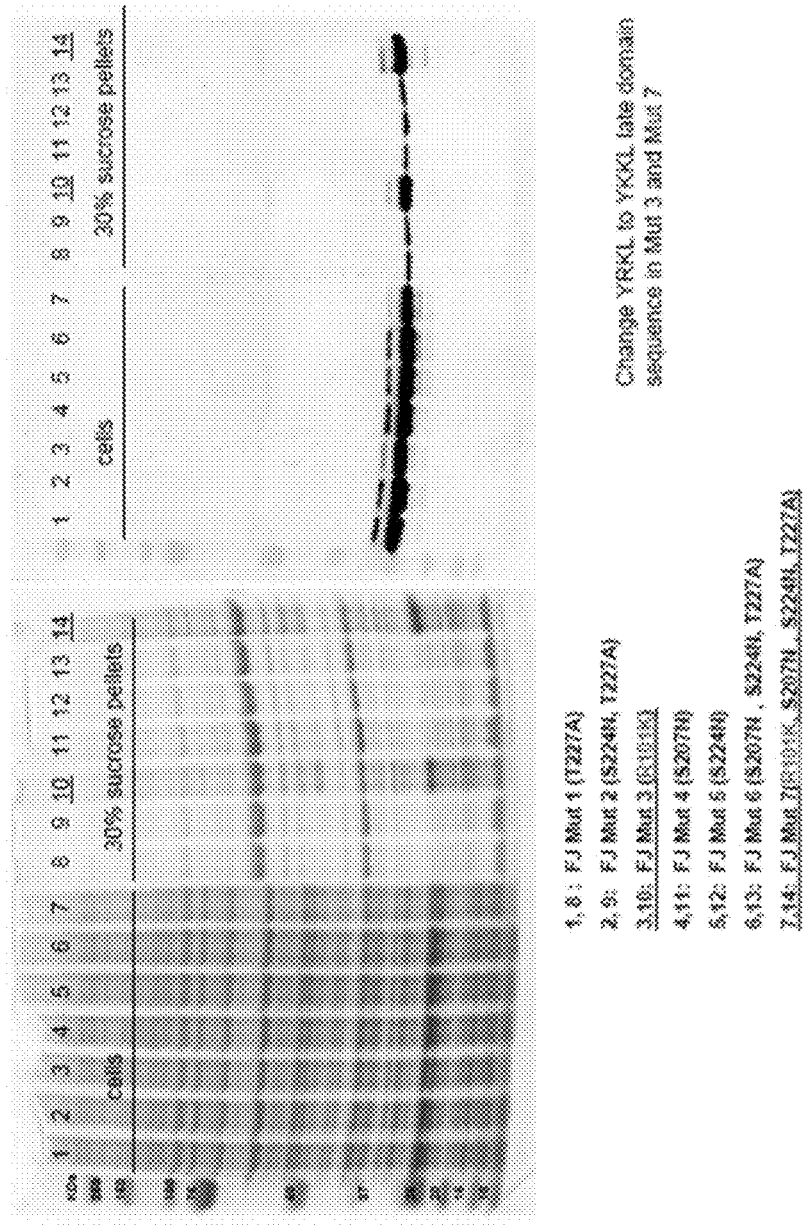
FIG. 48 depicts a SDS-PAGE gel derived from the expression of Influenza Fujian M1 Mutants. The left panel is stained for total proteins with Coomassie blue, the right panel is stained for influenza M protein by western blot.

Mutants 3 and 7 with an R101K mutation (and thus harboring the avian-like M1 YKKL L-domain sequence) were able to secrete significantly larger amounts of M1 from infected cells compared to strains possessing the seasonal-like M1 YRKL L-domain sequence (FIG. 48). Sf9 cells were infected with recombinant baculovirus expressing different Fujian M1 genes at a multiplicity of infection (MOI) of 1 ffu/cell. Infected sf9 cells and supernatants were harvested at 67 hr post-infection. Infection supernatants were filtered through a 0.45 micron filter and pelleted by centrifugation at 26,000 rpm/min through a 30% sucrose cushion, and resuspended at 50× concentration. Cells and pellets were analyzed by SDS-PAGE, stained for total proteins by Coomassie blue, and stained for influenza M protein by Western blot using an anti-influenza antibody. Lanes 1 to 7 are the intracellular expression of the seven M1 mutants from infected Sf9 cell lysates, lanes 8 to 14 are 50× concentrated 26K pellets of the seven Fujian M1 mutants. Intracellular M1 (28 KDa) of all seven mutants are strongly visible on Coomassie blue stained gel and confirmed by Western blot. Fujian M1 mutant 3 (R101K, lane 10) and mutant 7 (R101K, 5207N, 2224N, T227A, lane 14) are able to release large amounts of M1 particles from infected cells (comparing the bands on the gels, mutant 3 (lanes 3 and 10) and mutant 7 (lanes 7 and 14) show stronger bands in the 30% sucrose pellets than the other mutants, indicating an increased amount of M1 available for association in a VLP, while showing equal amounts of intracellular M1 across all mutants (lanes 1-7). These data demonstrate that mutants harboring the R101K mutation (and thus possessing the avian-like YKKL L-domain) show higher levels of M1 present in the pellet (secreted) fraction than mutants containing the YRKL (seasonal-like) domain.

Figure 49:
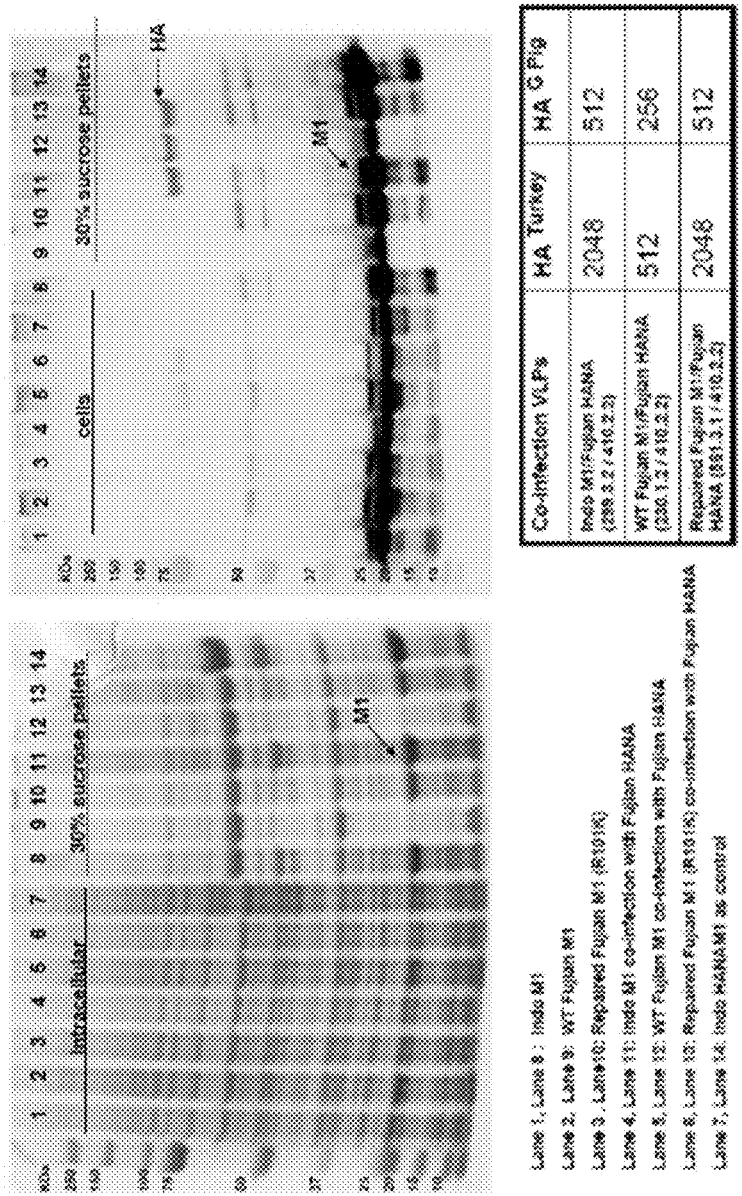
FIG. 49 depicts a SDS-PAGE gel derived from VLPs made from Influenza Fujian M1 Mutants. The left panel is stained for total proteins with Coomassie blue, the right panel is stained for influenza M protein by western blot.

The role of the avian YKKL L-domain sequence in increased VLP formation was confirmed using co-infection experiments (FIG. 49). Sf9 cells were co-infected with baculovirus expressing A/Fujian hemagglutinin (HA) and neuraminidase (NA), in conjunction with recombinant baculovirus expressing either the avian influenza strain A/Indonesia M1, the wild-type human influenza strain A/Fujian M1, or the "repaired" Fujian M1 mutant, A/Fujian mutant (R101K) which was mutated to mimic the avian YKKL L-domain sequence. As a control, Sf9 cells were infected individually with each recombinant construct in the absence of A/Fujian HA and NA. Infected sf9 cells and supernatants were harvested at 68 hr post-infection, filtered through a 0.45 micron filter and pelleted by ultracentrifugation at 26,000 rpm/min over a 30% sucrose cushion. The resulting pellets were analyzed by SDS-PAGE, stained for total proteins by Coomassie blue, and stained for influenza M1 protein by western blot using anti-A/Fujian/411/03 antibody. Lanes 1 to 7 are the total cell lysates from each culture and lanes 8 to 14 are 50× concentrated 26K supernatant pellets. Each 26K supernatant pellet was assayed for hemagglutination (HA) activity using turkey and guinea pig red blood cells (RBCs) The table shows the HA titer for each VLP sample.

The intracellular levels of A/Indonesia/5/05 M1, wild-type A Fujian/411/02 M1, and A Fujian/411/02 Mutant (R101K) appear to be very similar by Coomassie staining (FIG. 49A). Higher levels of M1 were found in the pellet fraction from strains harboring the YKKL L-domain M1 sequence (see the stronger bands of YKKL-containing A/Indonesia in lanes 8, 11, 14 and YKKL-containing A/Fujian (R101K) in lanes 10 and 13) as compared to the YRKL-containing wild-type A/Fujian strain (see lanes 9 and 12). These results were confirmed with a western immunoblot (see FIG. 49B). The increased intensity of the bands indicate that there is more M1, and thus, more VLPs. Furthermore, strains harboring the YKKL L-domain M1 sequence (A/Indonesia and the repaired A/Fujian mutant (R101K)) showed higher levels of hemagglutination activity than the YRKL-containing wild-type (WT) A/Fujian/411/02 strain using turkey and guinea pig RBCs (table in FIG. 49).

Example 39

Generation of Influenza Reassortant Virus-Like Particles (rVLPs): Residue $K^{101}$ of M1 Protein Improves rVLP Budding The present inventors have generated rVLPs, in which the HA and NA proteins were derived from either A/Brisbane/59/07 (H1N1), A/Brisbane/10/07 (H3N2), or B/Florida/4/06 strains, whereas M1 was derived from A/PR/8/34 (H1N1), A/Indonesia/5/05 (H5N1), or from B/Ann Arbor/1/66 virus. The efficiencies of VLP formation for (i) rVLPs containing different M1 proteins, (ii) native VLPs containing the homologous M1 from the same strain as HA and NA, and (iii) M1-deficient VLPs were compared. It was found that the use of M1 protein derived from H5N1 strain improved budding and yields for both influenza type A and type B rVLPs. As described above in example 38, site-directed mutagenesis has shown that budding efficacy was affected by amino acid residue 101 within the M1 protein. The effects of mutations and the role M1 protein in VLP formation are discussed below. These findings clarify the function of M1 and can lead to the improvement of influenza vaccines.

Materials and Methods

Viruses, constructs and cells. Influenza A/Brisbane/59/07 (H1N1), A/Brisbane/10/07 (H3N2), and B/Florida/4/06 viruses grown in Madine-Darby canine kidney (MDCK) were obtained from the Centers for Disease Control and Prevention (CDC, Atlanta, Ga.). Viral RNAs were extracted from each virus using Trizol LS reagent (Invitrogen, Carlsbad, Calif.). RT-PCR was conducted using specific oligonucleotide primers and One-Step RT-PCR system (Invitrogen) to generate cDNA for HA, NA, and M1 genes of 1.7, 1.4, and 0.7 kB in length, respectively, from each virus. For A/Brisbane/59/07 (H1N1), the HA and NA primers were designed according to GenBank ISDN282676 and ISDN285099 sequences, respectively. For A/Brisbane/10/07 (H3N2), the HA and NA primers were according to GenBank EU199366 and EU199420, respectively. For both viruses, the M1 genes were generated by using forward and reverse primers: 5'-ATGagtcttttaaccgaggtcgaa-3' and: 5'-TCActtgaatcgttgcatctgcac-3' (start and stop codons are capitalized). For B/Florida/4/06, the HA and NA primers were generated according to GenBank ISDN285778 and ISDN261650, respectively, whereas M1 gene was generated using primers 5'-ATGtcgctgtttggagacacaattgcctacc-3' and 5'-TTAtagatatttcttcacaagagctgaat-3'. For reassortant VLPs, the M1 genes of A/PR/8/34 (H1N1, GenBank AF389121), A/Udorn/72 (H3N2, GenBank CY009637), A/Indonesia/5/05 (H5N1, GenBank CY014173), and B/Ann Arbor/1/66 (GenBank M20176) were synthesized at GeneArt AG (Regensburg, Germany). Similarly, A/Fujian/411/02 (H3N2) HA, NA, and M1 genes were synthesized at GeneArt. Site-directed mutagenesis of M1 genes was carried out using QuikChange site-directed mutagenesis kit (Stratagene, La Jolla, Calif.).

The HA, NA, or M1 genes were cloned into a pFastBac1 baculovirus transfer vector downstream of the AcMNPV polyhedrin promoter between BamHI-HindIII sites. Genes were combined within a pFastBac1-based transfer vector in a tandem fashion as described previously (Pushko et al., 2005).

Spodoptera frugiperda Sf9 insect cells (ATCC CRL-1711) were maintained as suspension cultures in HyQ-SFX insect serum free medium (HyClone, Logan, Utah) at 27±2° C. Recombinant baculoviruses (rBVs) expressing influenza genes were generated using a Bac-to-Bac baculovirus expression system (Invitrogen). Briefly, rBV bacmid DNAs were generated by site-specific homologous recombination following transformation of pFastBac1-based transfer plasmids containing influenza genes into E. coli DH10Bac competent cells (Invitrogen), which contained the AcMNPV baculovirus genome. The recombinant bacmid DNA was extracted from E. coli cells and transfected into Sf9 cells using CellFectin reagent (Invitrogen). The rBVs were recovered, plaque-purified, amplified, and the titers of rBV stocks were determined by using BacPak Baculovirus Rapid Titer Kit (Clontech, Mountain View, Calif.) or by agarose plaque assay using Sf9 cell monolayers.

Purification and detection of influenza VLPs. For purification of VLPs, Sf9 cells were infected at a multiplicity of infection (MOI) of 3.0 for 66-72 hr at a cell density of $2 \times 10^6$ cells/ml with rBVs encoding influenza proteins. VLPs were concentrated and partially purified from the Sf9 media by ultracentrifugation at 100 000×g for 1 hr through a 30% sucrose cushion and resuspended in phosphate buffered saline (PBS), pH7.2. Alternatively, SF9 culture supernatants containing VLPs were concentrated by tangential flow filtration with a 500,000 molecular weight hollow fiber filter (GE HealthCare), and the purification of influenza VLPs was carried out using a combination of gel filtration and ion exchange chromatography.

Influenza proteins were analyzed by SDS-PAGE using 4-12% gradient polyacrylamide gels (Invitrogen), and stained with GelCode Blue Stain reagent (Pierce, Rockford, Ill.) and quantified by scanning densitometry using OneDscan system (BD Biosciences, Rockville, Md.). Western blot was carried out using antisera specific for influenza viruses. After electrophoretic protein transfer, membranes were blocked for 1 hr at 25° C. in blocking solution (Invitrogen), rinsed 3 times (5 min each) with PBS, pH7.2, and incubated for 16 hr with indicated influenza protein-specific antisera at 1:1,000 dilution. Following PBS rinsing step as indicated above, membranes were incubated at 25° C. for 1 hr with alkaline phosphatase conjugated goat IgG (H+L) secondary antibodies. Membranes were rinsed again with PBS, pH7.2 as indicated above, and protein bands were developed using the one-component BCIP/NBT phosphatase substrate (Kirkegaard and Perry, Gaithersburg, Md.).

Hemagglutination and neuraminidase enzyme activity assays. Serial dilutions of VLPs were prepared in 96-well microtiter plates, followed by the addition of 1.5% guinea pig or 1% turkey red blood cells (RBC) (Lampire Biologicals, Pipersville, Pa.) in PBS. RBC were stored at 4° C. and used within 72 hours of preparation. The plates were mixed by agitation, covered, the RBCs were allowed to settle for 30-60 min at room temperature, and the HA titer was determined by visual inspection.

For NA enzyme activity essay, VLP samples (25 μl) were transferred to a black 96-well plate and 75 μl of 20 μM methyl-umbelliferyl-N-acetyl neuraminic acid was added. After incubation of the plate at 37° C. for 1 hr, 100 μl stop solution (0.1 M glycine, pH 10.7-25% ethanol) was added to each well and fluorescence was read on a fluorometer (Turner BioSystems, Sunnyvale, Calif.) with excitation and emission filters of 365 nm and 450 nm, respectively.

Negative staining electron microscopy. VLP samples were adsorbed by flotation for 2 min onto a freshly discharged 400 mesh carbon parlodion-coated copper grid (PolySciences, Warrington, Pa.). The grid was rinsed with buffer containing 20 mM Tris, pH 7.4, and 120 mM KCl and negatively stained with 1% phosphotungstic acid, then dried by aspiration. VLPs were visualized on a Hitachi H-7600 transmission electron microscope (Hitachi High Technologies America, Schaumburg, Ill.) operating at 80 kV and digitally captured with a CCD camera at 1K×1K resolution (Advanced Microscopy Techniques Corp., Danvers, Mass.).

Results

Figure 50:
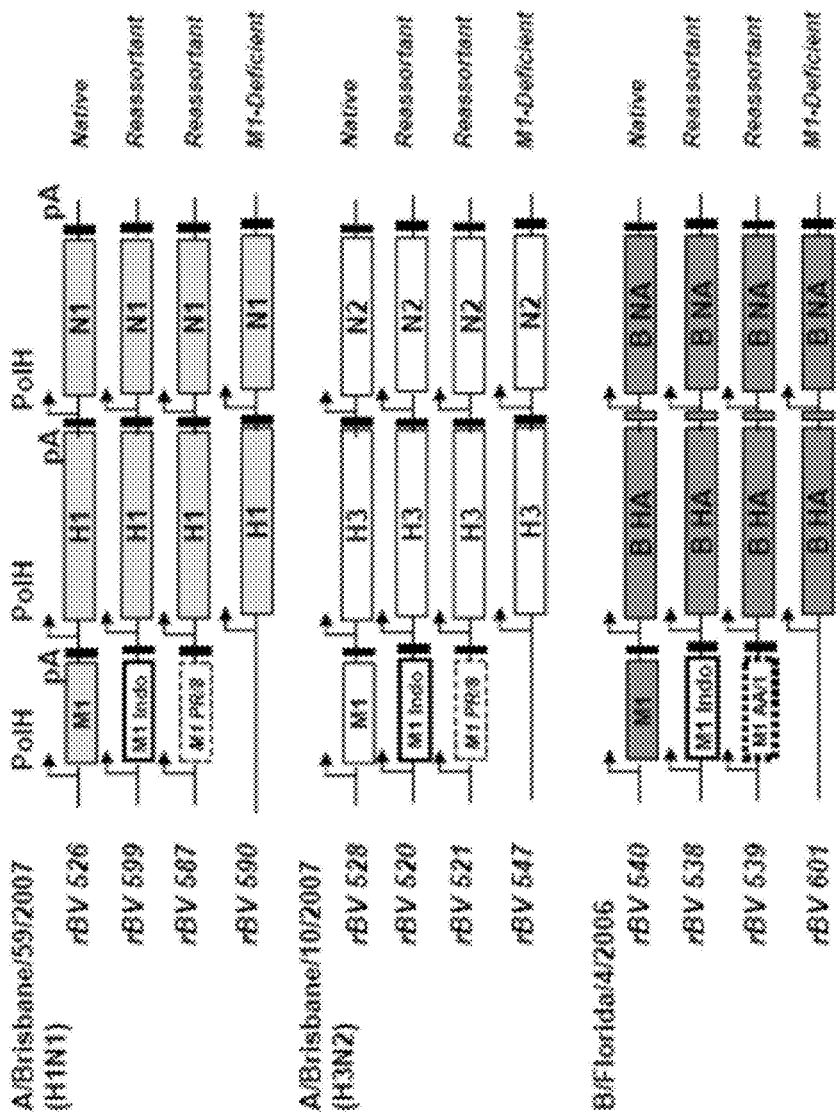
FIG. 50 depicts recombinant baculovirus (rBV) constructs for expression of native, reassortant, and M1-deficient VLPs in Sf9 cells. Influenza HA, NA, and M1 genes were generated for each indicated strain by RT-PCR using extracted viral RNA. Additionally, the M1 Indo, M1 PR/8, and M1 AA/1 genes for A/Indonesia/5/05 (H5N1), A/PR/8/34 (H1N1), B/Ann Arbor/1/66, respectively, were used in reassortant VLPs. The HA, NA, and M1 genes were combined within each rBV in a tandem fashion so that each gene was expressed from its own expression cassette that included polyhedrin promoter (PolH) and SV40 polyadenylation signal (pA).

Constructs for expression of native, reassortant, and M1-deficient VLPs. The rBV constructs for expression of A/Brisbane/59/07 (H1N1), A/Brisbane/10/07 (H3N2), and B/Florida/4/06 VLPs are shown on FIG. 50. These three strains were recommended by WHO/CDC for 2008-09 influenza season vaccine development (FDA, 2008). Influenza HA, NA, and M1 cDNA genes were generated from each strain by RT-PCR using extracted viral RNAs as templates. The HA, NA, and M1 genes were combined within an rBV in a tandem fashion so that each gene was expressed from its own expression cassette that included polyhedrin promoter and SV40 polyadenylation signal. For generation of native (wild type) VLPs, the M1, HA, and NA genes were derived from the same virus. In the reassortant VLPs (rVLPs), the HA and NA genes were derived from the same virus, whereas M1 gene was derived from either A/Indonesia/5/05 (H5N1), A/PR/8/34 (H1N1), or B/Ann Arbor/1/66 viruses (FIG. 50). Thus, M1 from A/PR/8/34 has been used to generate A/Brisbane/59/07 (H1N1) and A/Brisbane/10/07 (H3N2) rVLPs, whereas M1 protein from B/Ann Arbor/1/66 has been used to generate B/Florida/4/06 rVLPs. The M1 from A/Indonesia/5/05 has been used to generate rVLPs for all three seasonal influenza strains including B/Florida/4/06 (FIG. 1). In summary, for each influenza strain, a native as well as two rVLP constructs have been made. In addition, for each strain, we have made the M1-deficient construct that expressed the HA and NA proteins only, with no M1 protein (FIG. 50). The rBVs expressing native, reassortant, and M1-deficient VLPs were prepared using homologous recombination with baculovirus genome in E. coli DH10Bac cells followed by transformation into Sf9 cells, as described in the Materials and Methods.

Expression of native, reassortant and M1-deficient VLPs. Sf9 cells were infected with rBVs, which contained gene cassettes for expression of native, reassortant, and M1-deficient VLPs for N1N1, H3N2, and influenza B strains (FIG. 50). After incubation for 72 hr, VLPs from the media were concentrated and partially purified by ultracentrifugation. Expression of influenza proteins in VLPs was determined by SDS-PAGE and western blot (FIG. 51), as well as by hemagglutination and NA enzyme activity assays (Table 7).

TABLE 7

Expression and Functional Activity of Native, Reassortant, and M1-deficient VLPs derived from 2008-2009 influenza vaccine strains.

| VLP | M1 Source | rBV* | Total Protein, mg/ml | HA Titer** | NA activity, mU/ml |
|---|---|---|---|---|---|
| A/Brisbane/59/07 (H1N1) | | | | | |
| Native | A/Brisbane/59/07 (H1N1) | 526 | 0.91 ± 0.02 | 16 384 | 702.7 ± 18.9 |
| Reassortant | A/Indonesia/5/05 (H5N1) | 599 | 1.07 ± 0.01 | 65 536 | 1 223.1 ± 46.6 |
| Reassortant | A/PR/8/34 (H1N1) | 587 | 1.11 ± 0.03 | 16 384 | 1 142.2 ± 26.6 |
| M1-deficient | — | 590 | 0.69 ± 0.01 | 128 | 477.9 ± 24.2 |
| A/Brisbane/10/07 (H3N2) | | | | | |
| Native | A/Brisbane/10/07 (H3N2) | 528 | 0.73 ± 0.02 | 16 384 | 545.7 ± 9.2 |
| Reassortant | A/Indonesia/5/05 (H5N1) | 520 | 0.86 ± 0.00 | 65 536 | 950.2 ± 7.6 |
| Reassortant | A/PR/8/34 (H1N1) | 521 | 0.69 ± 0.02 | 32 768 | 877.0 ± 9.1 |
| M1-deficient | — | 547 | 0.49 ± 0.01 | 4 096 | 376.6 ± 18.3 |
| B/Florida/4/06 | | | | | |
| Native | B/Florida/4/06 | 540 | 0.92 ± 0.01 | 32 768 | 249.5 ± 0.0 |
| Reassortant | A/Indonesia/5/05 (H5N1) | 538 | 0.88 ± 0.01 | 262 144 | 696.5 ± 9.3 |
| Reassortant | B/Ann Arbor/1/66 | 539 | 0.83 ± 0.01 | 32 768 | 397.2 ± 1.3 |
| M1-deficient | — | 601 | 0.85 ± 0.04 | 32 768 | 160.9 ± 4.8 |

*The rBV designations are according to FIG. 50.
**HA titers were determined using guinea pig red blood cells.

Figure 51:
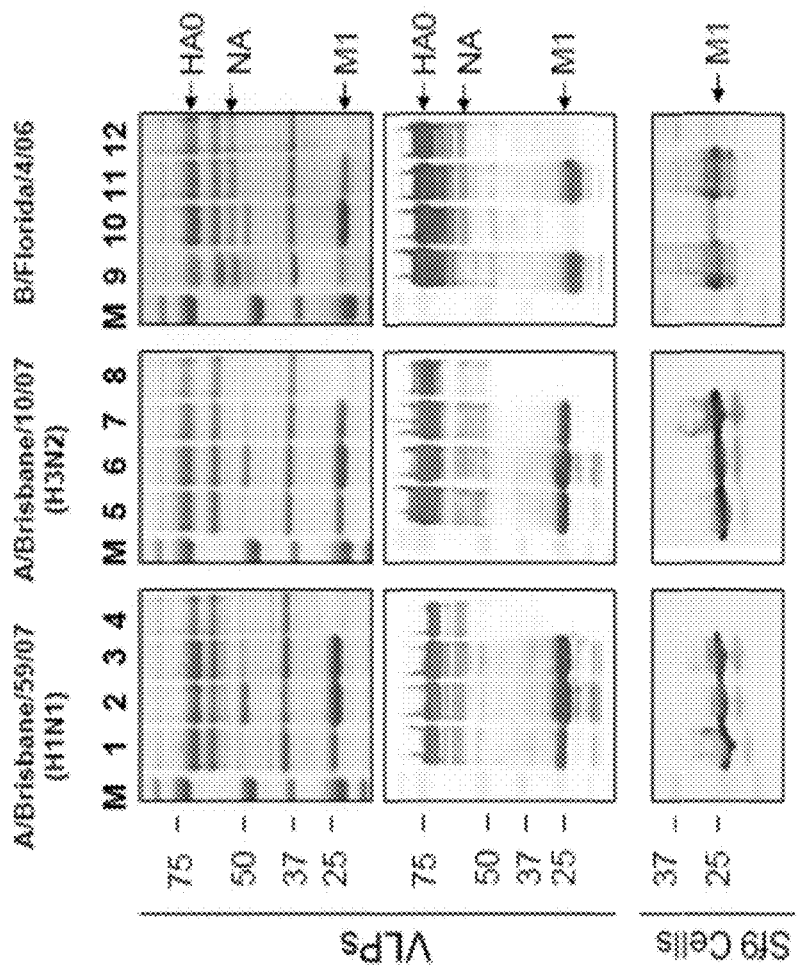
FIG. 51 depicts expression of influenza proteins in the native, reassortant and M1-deficient VLPs, by coomassie staining and western blot. Sf9 cells were infected with rBVs (FIG. 50) for 72 hr, and VLPs were concentrated and partially purified from culture media by ultracentrifugation at 10 000×g for 1 hr through a 30% sucrose cushion. Pellets were resuspended in PBS. Lanes 1-4, A/Brisbane/59/07 (H1N1) VLPs generated using rBVs 526, 599, 587, and 590, respectively (FIG. 50); lanes 5-8, A/Brisbane/10/07 (H3N2) VLPs generated using rBVs 528, 520, 521, and 547, respectively (FIG. 50); lanes 9-12, B/Florida/4/06 VLPs generated using rBVs 540, 538, 539, and 601, respectively (FIG. 50). M, Precision Plus protein molecular weight marker (Bio-Rad, Hercules, Calif.). Locations of influenza proteins are indicated on the left. Western blots were done using sheep antisera raised against H1N1, H3N2, and influenza B viruses, followed by alkaline phosphatase-conjugated anti-sheep IgG (H+L) (Kirkegaard and Perry, Gaithersburg, Md.). Also shown is expression of M1 proteins in the infected Sf9 cells (bottom panel) by western blot using the same antisera.

Expression of HA and NA was detected in all native, reassortant, and M1-deficient VLP preparations derived from the three strains (FIG. 51). By SDS-PAGE and western blot, the rVLPs contained the HA and NA proteins at the levels equivalent or greater to those of the native VLPs or M1-deficient VLPs. Consistent with previous observations (Pushko et al., 2005), the HA was expressed in Sf9 cells as HA0 polypeptide of 65-74 kDa, with no significant cleavage into HA1 and HA2 detected. The NA was found as a polypeptide of approximately 50 kDa. As expected, the M1 band of approximately 26 kDa was observed in the native VLPs and in rVLPs, but not in M1-deficient VLPs (FIG. 51, lanes 4, 8, 12). The levels of expression of M1 in the VLPs varied, with the highest expression observed in rVLPs that contained the A/Indonesia/5/05 (H5N1) M1 (FIG. 51, lanes 2, 6, 10). Interestingly, intracellular levels of M1 proteins including A/Indonesia/5/05 M1 were comparable in Sf9 cells (FIG. 51, lines 1-7, bottom panel). Surprisingly, significant amounts of A/Indonesia/5/05 M1 were also detected in B/Florida/4 VLPs (lane 10), suggesting effective formation of the heterotypic rVLPs. In all rVLP preparations containing A/Indonesia/5/05 M1, a prominent protein band with apparent molecular weight of 52 kDa was also detected, which corresponded to the predicted molecular weight of a dimeric M1. The presence of M1 protein in this band was confirmed by liquid chromatography/mass spectrometry method (data not shown).

The expression levels of M1 correlated with the expression levels and functional activity of HA and NA. In all three strains, the lowest levels of HA and NA proteins were detected in M1-deficient VLP preparations (FIG. 51, lanes 4, 8, 12), indicating that the absence of M1 protein adversely affected generation of VLPs. In order to assess the levels of HA and NA quantitatively, hemagglutination and neuraminidase activity assays were conducted. The highest HA and NA titers were observed in rVLPs containing A/Indonesia/5/05 M1, whereas the lowest titers were detected in M1-deficient VLPs (Table 7).

Purification and electron microscopy of native, reassortant and M1-deficient VLPs. In the next experiment, the rVLPs were purified using a gel filtration and ion exchange chromatography. By using this method, the majority of contaminants including rBV were removed. The HA, NA, and M1 co-purified during the process confirming that these proteins are associated into rVLPs. The example of purified rVLPs, as well as of native and M1-deficient H3N2 VLPs is shown on FIG. 52. Similarly to the previous results (Table 7), the levels of HA and NA activity in the purified VLPs correlated with the M1 content (Table 8).

TABLE 8

Hemagglutinin and Neuraminidase Enzyme Activity of Purified A/Brisbane/10/07 (H3N2) VLPs.

| H3N2 VLP | M1 Source | rBV* | M1, %** | HA Titer*** | NA activity, mU/ml |
|---|---|---|---|---|---|
| Native | A/Brisbane/59/2007 (H1N1) | 528 | 19.3 ± 0.6 | 512 | 4 941 |
| Reassortant | A/Indonesia/5/05 (H5N1) | 521 | 38.1 ± 0.2 | 1 024 | 18 002.6 |
| Reassortant | A/PR/8/34 (H1N1) | 520 | 40.1 ± 0.6 | 512 | 16 290.1 |
| M1-deficient | — | 547 | NA | 216 | 4 325.8 |

*The rBV designations are according to FIG. 50.
**M1 content determined by SDS-PAGE followed by scanning densitometry.
***HA titers were dtermined using guinea pig red blood cells.

The highest HA and NA activity was observed in rVLPs containing A/Indonesia/5/05 M1, whereas the lowest activity was observed in M1-deficient VLPs. The band corresponding to the dimeric form of M1 was apparent in the rVLPs containing M1 derived from A/Indonesia/5/05 (H5N1) virus.

Ultrastructure of VLPs was analyzed by negative staining transmission electron microscopy (FIG. 52B). Influenza-like pleomorphic particles with diameter of approximately 100 nm were detected in all four H3N2 VLPs including rVLPs and M1-deficient VLPs. In spite of the differences in the levels of expression of M1 (FIG. 51, 52A), no significant amounts of M1-only VLPs were detected. Most of the M1-deficient VLPs had electron-dense inner areas, possibly reflecting the enhanced infiltration of stain inside the "empty" M1-deficient particles. In the M1-deficient VLPs, particles were also observed, which contained core structures surrounded by influenza-like envelope with characteristic spikes of HA (FIG. 52B, panel 4). It is believed that the absence of M1 in the M1-deficient VLPs may have lead to incorporation of unrelated proteins derived from Sf9 cells or baculovirus, into VLPs in place of the M1 protein.

Figure 53A:
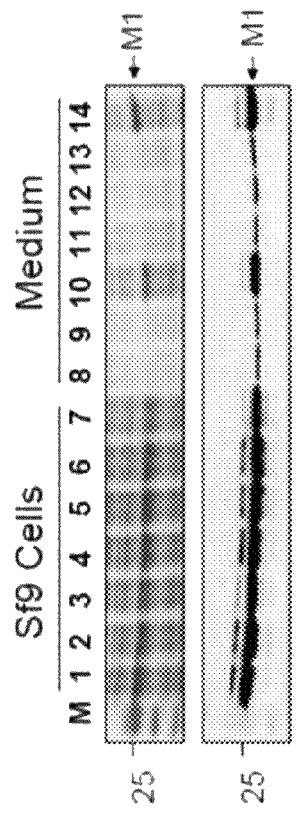
FIGS. 53A and 53B depict the effect of the $K^{101}$ residue on expression of M1-only VLPs.

$K^{101}$ residue within M1 protein is important for budding of M1 particles. The data suggested that the presence of M1 derived from A/Indonesia/5/05 (H5N1) virus correlated with the improved budding of rVLPs (Tables 7, 8). In order to elucidate amino acid residues within the M1 that affected budding, site-directed mutagenesis of M1 was conducted. It has been reported previously that M1 alone can form particles released into the medium (Gomez-Puertas et al., 2000). This provides a convenient assay for determination of the effect of mutations. In the first set of experiments, A/Fujian/411/02 M1 was mutated. Out of eighteen amino acid differences between the M1 proteins of A/Fujian/411/02 and A/Indonesia/5/05, $R^{101}$, $S^{207}$, $S^{224}$, or $T^{227}$ were altered in A/Fujian/411/02 to corresponding residues $K^{101}$, $N^{207}$, $N^{224}$, or $A^{227}$ of A/Indonesia/5/05 M1. Residues at these positions are not conserved among different strains and may affect M1 polypeptide folding, according to computer predictions (data not shown). Individual mutations or combinations of these mutations were made, rBVs generated, and expression of mutant M1 proteins was determined in Sf9 cells (FIG. 53A, lanes 1-7), as well as in the media (FIG. 53A, lanes 8-14). All mutants were expressed at equivalent levels in the cells. However, the only proteins that were detected at high levels in the media were A/Fujian/411/02 M1 containing $K^{101}$, as well as quadruple mutant containing $K^{101}$, $N^{207}$, $N^{224}$, and $A^{227}$ residues derived from A/Indonesia/5/05 M1 (FIG. 53A, lanes 10 and 14). This result suggests the importance of $K^{101}$ residue for budding of M1-only VLPs.

Figure 53B:
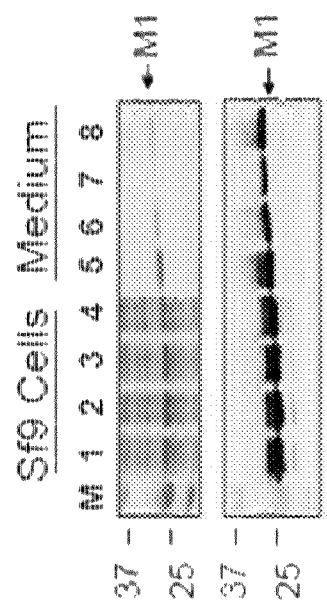
Figures 54A, 54B:
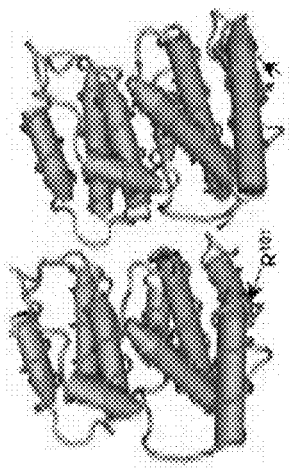
FIGS. 54A and 54B depict the 3-D structure of M1 and alignment of residues within the α-helix 6.

In order to confirm the role of $K^{101}$ on budding of M1, residue 101 was mutated within the M1 genes of A/Indonesia/5/05 (H5N1) and A/Udorn/72 (H3N2) and the effects of mutations on budding of M1-only particles was determined (FIG. 53B). According to X-ray crystallography of the N-terminal portion of M1 (Arzt et al., 2001), the amino acid residue 101 is located within the sixth α-helix of M1 (FIG. 54A) and may be involved in the intramolecular interactions between the M1 subunits (Harris et al., 2001). Alternatively, residue $K^{101}$ can be a part of nuclear localization sequence 101-RKLKR-105 (residues 101-105 of SEQ ID NO: 75) (Ye et al., 1995) or a part of YXXL-type late (L) domain spanning residues 100-103. In the human influenza A isolates A/PR/8/34, A/Udorn/72, A/Fujian/411/02, and 2008-09 influenza A vaccine strains, residue 101 corresponds to $R^{101}$, whereas avian isolates including A/Indonesia/5/05 (H5N1) have $K^{101}$ at this position (FIG. 54B).

In order to elucidate if $R/K^{101}$ residue affects budding of M1-only particles, two mutations were made: the $K^{101}$ in A/Indonesia/5/05 was changed to $R^{101}$, whereas $R^{101}$ in A/Udorn/72 was changed to $K^{101}$. Corresponding rBVs that encoded the wild type and mutant M1 proteins of A/Indonesia/5/05 and A/Udorn/72 were constructed and used to infect Sf9 cells. The expression of M1 was analyzed in infected Sf9 cells and media by SDS-PAGE and western blot. All four M1 proteins were expressed at similar levels within the Sf9 cells (FIG. 53B, lanes 1-4). Efficient release of M1 particles of A/Indonesia/5/05 wild type M1-$K^{101}$ was detected in the medium, suggesting effective budding from the cells (lane 5). However, when $K^{101}$ in Indonesia/5/05 was changed to $R^{101}$, budding was suppressed approximately 4-fold, according to stained SDS-PAGE gel (lane 6) and densitometry analysis. Likewise, the wild type M1 of A/Udorn/72 had low budding efficacy (lane 7), but when $R^{101}$ in the wild type A/Udorn/72 M1 was changed to $K^{101}$, budding improved 4-fold (lane 8) confirming the role of $K^{101}$ in budding.

Figure 55A:
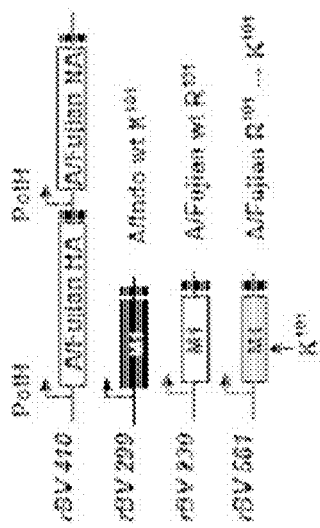
FIGS. 55A and 55B depict the effect of engineered KEN residue within M1 on expression of H3N2 VLPs.

Engineered M1 protein with $K^{101}$ residue improves budding of influenza rVLPs. The data showed that $K^{101}$ residue affects budding of M1-only particles. The present inventors further evaluated if the introduction of $K^{101}$ in place of $R^{101}$ can also improve budding of VLPs comprised of HA, NA, and M1 proteins. For this purpose, the present inventors constructed rBV that co-expressed A/Fujian/411/02 (H3N2) HA and NA, as well as two rBVs encoding either the wild type A/Fujian/411/02 M1 containing $R^{101}$, or the mutant M1 containing $K^{101}$ (FIG. 55A). The M1 proteins were expressed in Sf9 cells either alone, or they were co-expressed along with A/Fujian/411/02 HA and NA proteins following co-infection with two rBVs. As a control, we used rBV that expressed A/Indonesia/5/05 M1 protein. Infected cells and media were evaluated for the expression of influenza proteins.

Figure 55B:
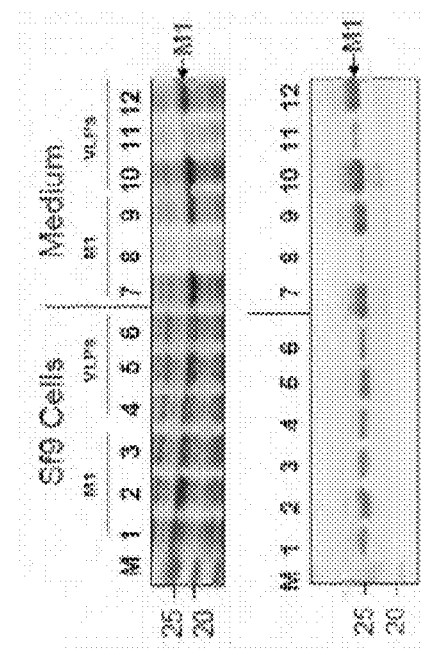

When expressed alone or co-expressed along with HA and NA, intracellular expression of the A/Fujian/411/02 wild type M1-$R^{101}$ (FIG. 55B, lanes 2, 5) was equivalent to expression of A/Indonesia/5/05 M1-$K^{101}$ (lanes 1, 4) or mutant A/Fujian/411/02 M1-$K^{101}$ (lanes 3, 6). However, release of A/Fujian/411/02 wild type M1-$K^{101}$ into the medium from infected Sf9 cells (lanes 8, 12) was reduced up to 12 times compared to mutant M1-$K^{101}$ (lanes 9, 12) or A/Indonesia/5/05 M1-$K^{101}$ (lanes 7, 10). Budding efficacy of M1-only particles correlated with that of the VLPs. Thus, a single $K^{101}$ mutation improved budding of VLPs containing A/Fujian/411/02 M1 to the levels similar to rVLPs containing A/Indonesia/5/05 M1.

In order to confirm the improved budding of the VLPs containing engineered A/Fujian/411/02 M1-$K^{101}$ protein, hemagglutination and NA enzyme activity assays were carried out on the VLP preparations (Table 9).

TABLE 9

Effect of $K^{101}$ Mutation in the M1 Protein on Budding of A/Fujian/411/02 (H3N2) VLPs

| H3N2 VLP | M1 Source | rBV* | Residue 101 | HA Titer** |
|---|---|---|---|---|
| Native | A/Fujian/411/02 (H3N2) | 230 | $R^{101}$ | 512 |
| Native, $K^{101}$ | A/Fujian/411/02 with $K^{101}$ | 561 | $K^{101}$ | 2 048 |
| Reassortant | A/Indonesia/5/05 (H5N1) | 299 | $K^{101}$ | 2 048 |

*The rBV designations are according to FIG. 50.
**HA titers were determined using guinea pig red blood cells.

In these assays, VLPs that contained A/Indonesia/5/05 M1-$K^{101}$ or A/Fujian/411/02 M1-$K^{101}$ proteins demonstrated 4-fold improvement of HA titers and 2-fold improvement of the NA enzyme activity titers, as compared to A/Fujian/411/02 wild type M1-$R^{101}$. These results have shown that engineering of M1 by introduction of a single $R^{101}K$ mutation improves budding and the yields of influenza VLPs.

CONCLUSIONS

In this Example, the present inventors provide evidence that trivalent rVLP-based vaccine can be efficiently made for all three 2008-09 influenza strains, including influenza B, by using a single high-yield influenza M1 protein, such as A/Indonesia/5/05 (H5N1). The efficient generation of heterotypic A/B VLPs comprised of type A M1 and type B HA and NA proteins is somewhat unexpected. Phenotypic mixing of proteins from different enveloped viruses has been previously described, for example between SV5, a paramyxovirus, and vesicular stomatitis virus, a rhabdovirus (Choppin et al., 1970). However, phenotypic mixing of influenza A and B viruses is less studied. In the currently licensed vaccines, different donor strains are used for type A and type B vaccines, such as A/PR/8/34 (H1N1) or B/Ann Arbor/1/66 (Chen et al., 2008).

The data presented herein shows that M1 proteins derived from various strains had varying capabilities for budding, which in turn affected budding of VLPs from Sf9 cells. Among rVLPs, the highest yields were observed when VLPs were made in the presence of A/Indonesia/5/05 (H5N1) M1 protein. The present inventors found that the $K^{101}$ residue, characteristic for M1 of avian influenza viruses, improves budding of seasonal strains of VLPs if introduced in the M1 protein. Although reasons for improvement of budding are not clear, it is believed that the $K^{101}$ residue represents the "molecular switch" that triggers formation of stable M1 dimers. Indeed, a major band corresponding to a dimeric M1 was consistently detected in rVLP preparations that contained A/Indonesia/5/05 M1-$K^{101}$, but not A/PR/8/34 M1-$K^{101}$ or B/Florida/4/06 M1 (FIG. 51, 52). Formation of stable dimers between the M1 subunits may stabilize M1 lattice and result in improved stability and budding of VLPs. However, additional viral or/and cellular factors may also contribute to the formation of VLPs. For example, $K^{101}$ residue, which is located within 100-YKKL-103 sequence of A/Indonesia/5/05 M1 protein may be the part of an YXXL-type viral L-domain that could facilitate budding. In other viruses, such as retroviruses, the L-domains recruit host proteins that are necessary for budding and release of virus particles (Demirov and Freed, 2004). Another possibility is that $K^{101}$ interferes with nuclear localization sequence 101-RKLKR-105, which may affect intracellular distribution of M1 (Ye et al., 1995).

The results reported here can be useful for the development of other influenza vaccine approaches, for example for co-expression of influenza genes from DNA constructs or from viral vectors, as well as for manufacturing of current influenza vaccines.

The following references are incorporated herein by reference:

Berglund, P., Fleeton, M. N., Smerdou, C., and Liljestrom, P. (1999). Immunization with recombinant Semliki Forest virus induces protection against influenza challenge in mice. Vaccine 17, 497-507.

Cox, J. C., and Coulter, A. R. (1997). Adjuvants—a classification and review of their modes of action. Vaccine 15, 248-256.

Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. Vaccine 17, 2265-2274.

Crowther R A, Kiselev N A, Bottcher B, Berriman J A, Borisova G P, Ose V, Pumpens P. (1994). Three-dimensional structure of hepatitis B virus core particles determined by electron cryomicroscopy. Cell 17, 943-50.

Gomez-Puertas, P., Mena, I., Castillo, M., Vivo, A., Perez-Pastrana, E., and Portela, A. (1999). Efficient formation of influenza virus-like particles: dependence on the expression levels of viral proteins. J. Gen. Virol. 80, 1635-1645.

Johansson, B. E. (1999). Immunization with influenza A virus hemagglutinin and neuraminidase produced in recombinant baculovirus results in a balanced and broadened immune response superior to conventional vaccine. Vaccine 17, 2073-2080.

Lakey, D. L., Treanor, J. J., Betts, B. F., Smith, G. E., Thompson, J., Sannella, E., Reed, G., Wilkinson, B. E., and Wright, P. E. (1996) Recombinant baculovirus influenza A hemagglutinin vaccines are well tolerated and immunogenic in healthy adults. J. Infect. Dis. 174, 838-841.

Latham, T., and Galarza, J. M. (2001). Formation of wild-type and chimeric influenza virus-like particles following simultaneous expression of only four structural proteins. J. Virol. 75, 6154-6165.

Mena, I., Vivo, A., Perez, E., and Portela, A (1996). Rescue of a synthetic chloramphenicol acetyltransferase RNA into influenza-like particles obtained from recombinant plasmids. J. Virol. 70, 5016-5024.

Murphy, B. R., and Webster, R. G. (1996). Orthomyxoviruses. In "Virology" (D. M. K. B. N. Fields, P. M. Howley, Eds.) Vol. 1, pp. 1397-1445. Lippincott-Raven, Philadelphia.

Neumann, G., Watanabe, T., and Kawaoka, Y. (2000). Plasmid-driven formation of influenza virus-like particles. J. Virol. 74, 547-551.

Olsen, C. W., McGregor, M. W., Dybdahl-Sissoko, N., Schram, B. R., Nelson, K. M., Lunn, D. P., Macklin, M. D., and Swain, W. F. (1997). Immunogenicity and efficacy of baculovirus-expressed and DNA-based equine influenza virus hemagglutinin vaccines in mice. Vaccine 15, 1149-1156.

Peiris, J. S., Guan, Y., Markwell, D., Ghose, P., Webster, R. G., and Shortridge, K. F. (2001). Cocirculation of avian H9N2 and contemporary "human" H3N2 influenza A viruses in pigs in southwestern China: potential for genetic reassortment? J. Virol. 75, 9679-9686.

Pumpens, P., and Grens, E. (2003). Artificial genes for chimeric virus-like particles. In: "Artificial DNA" (Khudyakov, Y. E, and Fields, H. A., Eds.) pp. 249-327. CRC Press, New York.

Pushko, P., Parker, M., Ludwig, G. V., Davis, N. L., Johnston, R. E., and Smith, J. F. (1997). Replicon-helper systems from attenuated Venezuelan equine encephalitis virus: expression of heterologous genes in vitro and immunization against heterologous pathogens in vivo. Virology 239, 389-401.

Slepushkin, V. A., Katz, J. M., Black, R. A., Gamble, W. C., Rota, P. A., and Cox, N. J. (1995). Protection of mice against influenza A virus challenged by vaccination with baculovirus-expressed M2 protein. Vaccine 13, 1399-1402.

Treanor, J. J., Betts, R. F., Smith, G. E., Anderson, E. L., Hackett, C. S., Wilkinson, B. E., Belshe, R. B., and Powers, D. C. (1996). Evaluation of a recombinant hemagglutinin expressed in insect cells as an influenza vaccine in young and elderly adults. J. Infect. Dis. 173, 1467-1470.

Tsuji, M., et al. (1998). Recombinant Sindbis viruses expressing a cytotoxic T-lymphocyte epitope of a malaria parasite or of influenza virus elicit protection against the corresponding pathogen in mice. J. Virol. 72, 6907-6910.

Ulmer, J. B., et al. (1993). Heterologous protection against influenza by injection of DNA encoding a viral protein. Science 259, 1745-1749.

Ulmer, J. B., et al. (1998). Protective CD4+ and CD8+ T cells against influenza virus induced by vaccination with nucleoprotein DNA. J. Virol. 72, 5648-5653.

Watanabe, T., Watanabe, S., Neumann, G., and Kawaoka, Y. (2002) Immunogenicity and protective efficacy of replication-incompetent influenza virus-like particles. J. Virol. 76, 767-773.

Zhou, X., et al. (1995). Generation of cytotoxic and humoral immune responses by non-replicative recombinant Semliki Forest virus. Proc. Natl. Acad. Sci. USA 92, 3009-3013.

OTHER EMBODIMENTS

Those skilled in the art will recognize, or be able to ascertain using no more than routine experimentation, many equivalents to the specific embodiments of the invention described herein. Such equivalents are intended to be encompassed by the claims provided herein.

We claim:

1. A virus-like particle (VLP) comprising influenza proteins, wherein the influenza proteins consist of an influenza M1 protein and an influenza hemagglutinin (HA) protein, wherein said M1 protein comprises the amino acid residues YKKL at the positions corresponding to positions 100-103 of SEQ ID NO: 49.

2. The VLP of claim 1, wherein said influenza M1 protein is derived from an avian influenza virus strain.

3. The VLP of claim 2, wherein said avian influenza virus strain is A/Indonesia/5/05.

4. The VLP of claim 1, wherein the HA protein is from a different influenza strain than the M1 protein.

5. The VLP of claim 4, wherein said HA protein is derived from an avian influenza virus.

6. The VLP of claim 5, wherein said avian influenza virus is H5N1.

7. The VLP of claim 5, wherein said avian influenza virus is H9N2.

8. The VLP of claim 4, wherein said HA protein is derived from a seasonal influenza virus.

9. The VLP of claim 8, wherein said seasonal influenza virus is a type A influenza virus.

10. The VLP of claim 8, wherein said seasonal influenza virus is a type B influenza virus.

11. The VLP of claim 4, wherein said HA protein exhibits hemagglutinin activity.

12. The VLP of claim 4, wherein said HA protein is a chimeric protein.

13. The VLP of claim 12, wherein said chimeric proteins comprise external domains of non-avian influenza HA protein sequences fused to the transmembrane and/or cytoplasmic terminal domains of the avian HA.

14. The VLP of claim 13, wherein said non-avian influenza HA is from influenza strain A/Wisconsin/67/2005 and said avian influenza HA is from influenza strain A/Indonesia/5/05.

15. A method of increasing the efficiency of VLP production comprising expressing an influenza M1 protein and an influenza hemagglutinin (HA) protein in an insect host cell, wherein said M1 protein comprises the amino acid residues YKKL at the positions corresponding to positions 100-103 of SEQ ID NO: 49, wherein the influenza proteins consist of an influenza M1 protein and an influenza hemagglutinin (HA) protein.

16. The method of claim 15, wherein said influenza M1 protein is derived from an avian influenza virus strain.

17. The method of claim 16, wherein said avian influenza virus strain is A/Indonesia/5/05.

18. The method of claim 15, wherein the HA protein is from a different influenza strain than the M1 protein.

19. The VLP of claim 18, wherein said HA protein is derived from a seasonal influenza virus.

20. A vaccine comprising the VLP of claim 1.

* * * * *